(12) United States Patent
Zhan et al.

(10) Patent No.: US 12,297,272 B2
(45) Date of Patent: May 13, 2025

(54) IgG Fc VARIANTS FOR VETERINARY USE

(71) Applicant: Elanco US Inc., Greenfield, IN (US)

(72) Inventors: Hangjun Zhan, Foster City, CA (US); Lam Nguyen, Union City, CA (US); Yongzhong Li, Rockville, MD (US); Fawn Qian, Burlingame, CA (US); Shyr Jiann Li, Millbrae, CA (US)

(73) Assignee: Eianco US inc., Greenfield, IN (US)

( * ) Notice: Subject to any disclaimer, the term of this patent is extended or adjusted under 35 U.S.C. 154(b) by 337 days.

(21) Appl. No.: 16/638,402

(22) PCT Filed: Aug. 15, 2018

(86) PCT No.: PCT/IB2018/056142
§ 371 (c)(1),
(2) Date: Feb. 11, 2020

(87) PCT Pub. No.: WO2019/035010
PCT Pub. Date: Feb. 21, 2019

(65) Prior Publication Data
US 2020/0362034 A1 Nov. 19, 2020

Related U.S. Application Data

(60) Provisional application No. 62/545,858, filed on Aug. 15, 2017.

(51) Int. Cl.
*C07K 16/28* (2006.01)
*A61K 9/00* (2006.01)
*A61K 39/395* (2006.01)
*A61P 3/04* (2006.01)
*C07K 14/605* (2006.01)
*A61K 38/00* (2006.01)
*A61K 45/06* (2006.01)

(52) U.S. Cl.
CPC .......... *C07K 16/283* (2013.01); *A61K 9/0019* (2013.01); *A61P 3/04* (2018.01); *C07K 14/605* (2013.01); *A61K 38/00* (2013.01); *A61K 39/395* (2013.01); *A61K 45/06* (2013.01); *C07K 2317/31* (2013.01); *C07K 2317/53* (2013.01); *C07K 2317/71* (2013.01); *C07K 2317/92* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,194,551 B1 | 2/2001 | Idusogie et al. | |
| 7,083,784 B2 | 8/2006 | Dall'Acqua et al. | |
| 7,658,921 B2 | 2/2010 | Dall'Acqua et al. | |
| 8,273,854 B2 | 9/2012 | Glaesner et al. | |
| 8,658,174 B2 | 2/2014 | Wang et al. | |
| 8,852,586 B2 | 10/2014 | Chamberlain et al. | |
| 9,731,007 B2 * | 8/2017 | Drew | A61P 29/00 |
| 10,538,569 B2 | 1/2020 | Sung et al. | |
| 10,851,147 B2 | 12/2020 | Lancaster et al. | |
| 10,870,686 B2 | 12/2020 | Lancaster et al. | |
| 10,947,292 B2 | 3/2021 | Lancaster et al. | |
| 10,961,294 B2 | 3/2021 | Lancaster et al. | |
| 11,186,623 B2 | 11/2021 | Lancaster et al. | |
| 2001/0034024 A1 * | 10/2001 | Keating | C07K 14/705 435/7.1 |
| 2003/0224412 A1 * | 12/2003 | Anderson | C12Q 1/6897 506/10 |

(Continued)

FOREIGN PATENT DOCUMENTS

| | | |
|---|---|---|
| CN | 101802197 A | 8/2010 |
| CN | 102633880 A | 8/2012 |

(Continued)

OTHER PUBLICATIONS

Borrok et al., "An 'Fc-Silenced' IgG1 Format With Extended Half-Life Designed for Improved Stability," Journal of Pharmaceutical Sciences, 2017, 106:1008-1017.
Butler et al., "Porcine IgG: structure, genetics, and evolution," Immunogenetics, 2009, 61:209-230.
Carter, "Potent antibody therapeutics by design," Nature Reviews | Immunology, 2006, 6:343-357.
Lazanovich et al., "Intraveneous Immunoglobulins: Mechanisms of Therapeutic Effects," Medical Immunology, 2014, 16(4):311-322 (English Abstract at p. 321).
Lewis et al., "The different effector function capabilities of the seven equine IgG subclasses have implications for vaccine strategies, " Molecular Immunology, 2008, 45:818-827.

(Continued)

*Primary Examiner* — Marianne P Allen
(74) *Attorney, Agent, or Firm* — McBee, Moore & Vanik IP, LLC

(57) ABSTRACT

Provided are various embodiments relating to variant IgG Fc polypeptides of companion animals having increased Protein A binding for ease of purification, decreased C1q binding for reduced complement-mediated immune responses, decreased CD16 binding (e.g., for reduced antibody-dependent cellular cytotoxicity (ADCC) induction, increased stability, and/or the ability to form heterodimeric proteins. In addition, various embodiments relating to antibodies and fusion proteins comprising such variant IgG Fc polypeptides are provided. Also provided are various embodiments relating to contiguous polypeptides comprising one or more variant GLP1 polypeptide(s) having improved serum half-life. Further provided are various embodiments relating to contiguous polypeptides or heterodimeric polypeptides comprising a GLP1 polypeptide and a glucagon polypeptide as a dual GLP1 receptor and glucagon receptor agonist. In various embodiments, such polypeptides may be used to treat, for example, diabetes, obesity, or related indications, in companion animals, such as canines, felines, and equines.

31 Claims, 6 Drawing Sheets
Specification includes a Sequence Listing.

(56) References Cited

U.S. PATENT DOCUMENTS

| | | | |
|---|---|---|---|
| 2003/0237101 A1* | 12/2003 | Wehrle-Haller | A61P 17/06 514/21.7 |
| 2009/0181912 A1 | 7/2009 | Wang et al. | |
| 2009/0232807 A1 | 9/2009 | Glaesner et al. | |
| 2010/0105877 A1 | 4/2010 | Song et al. | |
| 2011/0021755 A1 | 1/2011 | Lazar et al. | |
| 2011/0123440 A1 | 5/2011 | Hansen et al. | |
| 2012/0093814 A1 | 4/2012 | Canada et al. | |
| 2012/0251531 A1 | 10/2012 | Baehner et al. | |
| 2014/0037621 A1 | 2/2014 | Tsurushita et al. | |
| 2014/0170136 A1 | 6/2014 | Gearing | |
| 2014/0255407 A1 | 9/2014 | Koenig | |
| 2014/0328838 A1 | 11/2014 | Gearing | |
| 2015/0025022 A1 | 1/2015 | Aharoni et al. | |
| 2016/0185837 A1 | 6/2016 | Bednarek et al. | |
| 2016/0193295 A1 | 7/2016 | Kannan et al. | |
| 2017/0000895 A1 | 1/2017 | Nordkild et al. | |
| 2017/0158756 A1 | 6/2017 | Bergeron et al. | |
| 2017/0362293 A1 | 12/2017 | Sung et al. | |
| 2018/0009869 A1 | 1/2018 | Lu et al. | |
| 2018/0258178 A1 | 9/2018 | Tsui et al. | |
| 2019/0111107 A1 | 4/2019 | Nordkild et al. | |
| 2020/0031948 A1 | 1/2020 | Ober et al. | |
| 2020/0181258 A1 | 6/2020 | Eger et al. | |
| 2020/0199216 A1 | 6/2020 | Li et al. | |
| 2020/0216536 A1 | 7/2020 | Brondyk et al. | |
| 2020/0362034 A1 | 11/2020 | Zhan et al. | |
| 2020/0362035 A1 | 11/2020 | Brondyk et al. | |
| 2021/0347854 A1 | 11/2021 | Brondyk et al. | |
| 2021/0388053 A1 | 12/2021 | Zhan et al. | |
| 2021/0395340 A1 | 12/2021 | Zhan et al. | |
| 2022/0009990 A1 | 1/2022 | Lancaster et al. | |
| 2022/0009994 A1 | 1/2022 | Brondyk et al. | |
| 2022/0017590 A1 | 1/2022 | Lancaster et al. | |
| 2022/0025005 A1 | 1/2022 | Zhan et al. | |
| 2022/0048981 A1 | 2/2022 | Nakao et al. | |
| 2022/0049002 A1 | 2/2022 | Li et al. | |
| 2022/0169740 A1 | 6/2022 | Zhan et al. | |

FOREIGN PATENT DOCUMENTS

| | | |
|---|---|---|
| CN | 102971340 A | 3/2013 |
| CN | 104080811 A | 10/2014 |
| CN | 107074966 A | 8/2017 |
| CN | 108699152 A | 10/2018 |
| EP | 3407905 B1 | 2/2021 |
| EP | 3655006 B1 | 11/2021 |
| JP | 2004321100 A | 11/2004 |
| JP | 2010533197 A | 10/2010 |
| RU | 2571923 C2 | 12/2015 |
| WO | 2009009562 A2 | 1/2009 |
| WO | 2010117448 A2 | 10/2010 |
| WO | 2010117760 A2 | 10/2010 |
| WO | 2012020096 A1 | 2/2012 |
| WO | 2012130831 A1 | 10/2012 |
| WO | 2012175751 A2 | 12/2012 |
| WO | 2013011368 A2 | 1/2013 |
| WO | 2013063186 A2 | 5/2013 |
| WO | 2013100702 A1 | 7/2013 |
| WO | 2014093387 A1 | 6/2014 |
| WO | 2015017548 A2 | 2/2015 |
| WO | 2015091910 A2 | 6/2015 |
| WO | 2015120790 A1 | 8/2015 |
| WO | 2016044189 A1 | 3/2016 |
| WO | 2016050721 A1 | 4/2016 |
| WO | 2016108654 A | 7/2016 |
| WO | 2016154177 A2 | 9/2016 |
| WO | 2017068472 A1 | 4/2017 |
| WO | 2017102920 A1 | 6/2017 |
| WO | 2017201527 A2 | 11/2017 |
| WO | 2018009921 A1 | 1/2018 |
| WO | 2018073185 A1 | 4/2018 |
| WO | WO 2018/195388 * | 10/2018 |
| WO | 2018236728 A1 | 12/2018 |
| WO | 2019035010 A1 | 2/2019 |
| WO | 2020056393 A1 | 3/2020 |
| WO | 2020082048 A1 | 4/2020 |
| WO | 2020086886 A1 | 4/2020 |
| WO | 2020123849 A1 | 6/2020 |
| WO | 2020139984 A1 | 7/2020 |
| WO | 2020142625 A2 | 7/2020 |
| WO | 2020191289 A1 | 9/2020 |
| WO | 2021035177 A2 | 2/2021 |
| WO | 2021212081 A1 | 10/2021 |
| WO | 2021212084 A1 | 10/2021 |
| WO | 2021216810 A1 | 10/2021 |
| WO | 2021216899 A1 | 10/2021 |
| WO | 2021043127 A1 | 11/2021 |
| WO | 2021251438 A1 | 12/2021 |
| WO | 2022005883 A1 | 1/2022 |
| WO | 2022046941 A1 | 3/2022 |

OTHER PUBLICATIONS

Strietzel et al., "In Vitro functional characterization of feline IgGs," Veterinary Immunology and Immunopathology, 2014, 158:214-223.

Strohl, "Fusion Proteins for Half-Life Extension of Biologics as a Strategy to Make Biobetters," BioDrugs, 2015, 29:215-239.

Bergeron et al., "Comparative functional characterization of canine IgG subclasses," Vet Immunol Immunopathol., 2014, 157(1):31-41.

Chen et al., "Stabilizing the CH2 Domain of an Antibody by Engineering in an Enhanced Aromatic Sequon," ACS Chemical Biology, 2016, 11(7): 1852-1861.

International Search Report and Written Opinion for PCT/US2019/068629 dated Jun. 2, 2020, 14 pages.

Nagaoka et al., "Single Amino Acid Substitution in the Mouse IgG1 Fc Region Induces Drastic Enhancement of the Affinity to Protein A," Protein Eng., 2003, 16(4):243-245.

Ridgway et al., "Knobs-into-holes' engineering of antibody Ch3 domains for heavy chain heterodimerization," Protein Eng., 1996, 9(7):617-621.

Saunders, "Conceptual Approaches to Modulating Antibody Effector Functions and Circulation Half-Life," Front. Immunol., 2019, 10:1296.

Schlothauer et al., "Novel human IgG1 and IgG4 Fc-engineered antibodies with completely abolished immune effector functions," Protein Eng Des Sel, 2016, 29(10):457-466.

Wang et al., "IgG Fc engineering to modulate antibody effector functions," Protein Cell, 2018, 9(1):63-73.

International Search Report and Written Opinion in PCT/US2019/057093, dated Feb. 11, 2020, 10 pages.

Kraft et al., "Heparin chromatography as an in vitro predictor for antibody clearance rate through pinocytosis," MABS, vol. 12, No. 01, e1683432, (9 pages) 2020.

Mackness et al., "Antibody Fc engineering for enhanced neonatal Fc receptor binding and prolonged circulation half life," MABS, https://doi.org/10.1080/19420862.2019.1633883, pp. 1-13, 2019.

Oganesyan et al., "Structural Insights into Neonatal Fc Receptor-based Recycling Mechanisms," The Journal of Biological Chemistry, vol. 289, No. 11, pp. 7812-7824, 2014.

Pyzik et al., "The Neonatal Fc Receptor {FcRn): A Misnomer?," Frontiers in Immunology, vol. 10, Article 1540, pp. 1-24, 2019.

Vacarro et al., "Engineering the Fc region of immunoglobulin G to modulate in vivo antibody levels," Nature Biotechnology, vol. 23, No. 10, pp. 1283-1288, 2005.

West et al., "Crystal Structure and Immunoglobulin G Binding Properties of the Human Major Histocompatibility Complex-Related Fc Receptor," Biochemistry, vol. 39, No. 32, pp. 9698-9708, 2000.

Chen et al., "Fusion Protein Linkers: Property, Design and Functionality," Advanced Drug Delivery Reviews, 2013, vol. 55, No. 10, pp. 1357-1369.

Colman, "Effects of amino acid sequence changes on antibody-antigen interactions," Research in Immunology, 1994, V. 145, No. 1, pp. 33-36.

(56) References Cited

OTHER PUBLICATIONS

Glaesner et al., "Engineering and characterization of the long-acting glucagon-like peptide-1 analogue LY2189265, a re fusion protein," Diabetes/Metabolism Research and Reviews, 2010, vol. 26, No. 4, pp. 287-296.

Maeda et al., "Engineering of Functional Chimeric Protein G-Vargula Luciferase," Analytical Biochemistry, 1997, vol. J49, No. 2, pp. 147-152.

Safdari et al., "Antibody humanization methods—a review and update," Biotechnology and Genetic Engineering Reviews, 2013, vol. 29, No. 2, pp. 175-186.

Shen et al., "Single Variable Domain-IgG Fusion: A Novel Recombinant Approach to Fe Domain-Containing Bispecific Antibodies," Journal of Biological Chemistry, 2006, vol. 281, No. 16, pp. 10706-10714.

Torres et al., "The immunoglobulin constant region contributes to affinity and specificity," Trends in immunology, 2008, vol. 29, No. 2, pp. 91-97.

Muller et al., "Spliceosomal Peptide P140 for Immunotherapy of Systemic Lupus Erythematosus: Results of an Early Phase II Clinical Trial," Arthritis & Rheumatism: Official Journal of the American College of Rheumatology, 2008, vol. 58, No. 12, pp. 3873-3883.

International Search Report and Written Opinion in PCT/US2019/068629, mailed Jun. 2, 2020, 14 pages.

International Search Report and Written Opinion in PCT/IB2018/056142, dated Jan. 28, 2019, 17 pages.

International Search Report and Written Opinion in PCT/US2018/038033, dated Sep. 13, 2018, 16 pages.

Supplementary European search report in EP 19874587, PCT/US2019057093, dated Jun. 15, 2022, 12 pages.

Supplementary European Search Report in EP 18845242, PCT/IB2018/056142, dated Apr. 28, 2021, 12 pages.

Canadian Office Action issued in related Canadian Application No. 3,071,337 (mailed Aug. 25, 2023).

Notice of Preliminary Rejection issued in Korean Patent Application No. 10-2020-7005513, with brief summary translation.

Japanese Office Action issued in related Japanese Patent Application No. 2020-507675, with English translation (8 pages) (Mar. 28, 2023).

El-Amine M. et al., "In vivo induction of tolerance by an Ig peptide is not affected by the deletion of FcR or a mutated IgG Fc fragment," International immunology, v. 14, n. 7, p. 761-766 (2002).

Jonnalagadda M. et al., "Chimeric antigen receptors with mutated IgG4 Fc spacer avoid fc receptor binding and improve T cell persistence and antitumor efficacy," Molecular Therapy, v. 23, n. 4, p. 757-768 (2015).

Keskin O. et al., "A new, structurally nonredundant, diverse data set of protein-protein interfaces and its implications," Protein Sci., v.13, n.4, p. 1043-1055 (2004).

Zhiqiang An et al., "IgG2m4, an engineered antibody isotype with reduced Fc function," MAbs, v.1, issue 6, p. 572-579 (2009).

Jendeberg, et al., "Engineering of Fc1 and Fc3 from human immunoglobulin G to analyse subclass specificity for staphylococcal protein A," Journal of Immunological Methods, vol. 201, No. 1 (Feb. 14, 1997).

Li Jinjing, "Cloning and Expression of IFN-α and Human LgG Fc Fusion Protein with Longer Serum Half-life," China Master's Theses Full-text Database (Medicine & Health Series), No. 09 (2011) English Abstract provided—Resubmission (see IDS filed Nov. 17, 2023).

\* cited by examiner

```
IgG-A  PVPEPLGGPSVLIFPPKPKDILRITRTPEVTCVVLDLGREDPEVQISWFVDGKEVHTAKT
IgG-D  PVPESLGGPSVFIFPPKPKDILRITRTPEITCVVLDLGREDPEVQISWFVDGKEVHTAKT
IgG-B  PAPEMLGGPSVFIFPPKPKDTLLIARTPEVTCVVVDLDPEDPEVQISWFVDGKQMQTAKT
IgG-C  PGCGLLGGPSVFIFPPKPKDILVTARTPTVTCVVVDLDPENPEVQISWFVDSKQVQTANT
        *  *******:*******: ::* **:*:**** **** *******.*:: :  ***:*

IgG-A  QSREQQFNGTYRVVSVLPIEHQDWLTGKEFKCRVNHIDLPSPIERTISKARGRAHKPSVY
IgG-D  QPREQQFNSTYRVVSVLPIEHQDWLTGKEFKCRVNHIGLPSPIERTISKARGQAHQPSVY
IgG-B  QPREEQFNGTYRVVSVLPIGHQDWLKGKQFTCKVNNKALPSPIERTISKARGQAHQPSVY
IgG-C  QPREEQSNGTYRVVSVLPIGHQDWLSGKQFKCKVNNKALPSPIEEIISKTPGQAHQPNVY
        .**:* *.************ ****.**:* *:**:  *****. ***:  *:: *.**

IgG-A  VLPPSPKELSSSDTVSITCLIKDFYPPDIDVEWQSNGQQEPERKHRMTPPQLDEDGSYFL
IgG-D  VLPPSPKELSSSDTVTLTCLIKDFYPPEIDVEWQSNGQQEPEPESKYHTTAPQLDEDGSYFL
IgG-B  VLPPSREELS-KNTVSLTCLIKDFFPPDIDVEWQSNGQQEPEPESKYRTTPPQLDEDGSYFL
IgG-C  VLPPSRDEMS-KNTVTLTCLVKDFFPPEIDVEWQSNGQQEPEPESKYRMTPPQLDEDGSYFL
        *****.:*:* .:**::***:***:**:*************** *:: :*..*********

IgG-A  YSKLSVDKSRWQQGDPFTCAVMHETLQNHYTDLSLSHSPGK
IgG-D  YSKLSVDKSRWQQGDTFTCAVMHEALQNHYTDLSLSHSPGK
IgG-B  YSKLSVDKSRWQRGDTFICAVMHEALHNHYTQESLSHSPGK
IgG-C  YSKLSVDKSRWQRGDTFICAVMHEALHNHYTQISLSHSPGK
       ************:**.*:*******:*:*** :*******

IgG-A  SEQ ID NO: 1
IgG-D  SEQ ID NO: 4
IgG-B  SEQ ID NO: 2
IgG-C  SEQ ID NO: 3
```

Fig. 1

SEQUENCE LISTING

```
<160> NUMBER OF SEQ ID NOS: 199

<210> SEQ ID NO 1
<211> LENGTH: 221
<212> TYPE: PRT
<213> ORGANISM: Unknown
<220> FEATURE:
<223> OTHER INFORMATION: Wild-type canine IgG-A Fc , Protein A -, C1q -,
      CD16

<400> SEQUENCE: 1

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Ser Arg Glu
    50                  55                  60

Gln Gln Phe Asn Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
            100                 105                 110

Arg Ala His Lys Pro Ser Val Tyr Val Leu Pro Pro Ser Pro Lys Glu
        115                 120                 125

Leu Ser Ser Ser Asp Thr Val Ser Ile Thr Cys Leu Ile Lys Asp Phe
    130                 135                 140

Tyr Pro Pro Asp Ile Asp Val Glu Trp Gln Ser Asn Gly Gln Gln Glu
145                 150                 155                 160

Pro Glu Arg Lys His Arg Met Thr Pro Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Pro Phe Thr Cys Ala Val Met His Glu Thr Leu Gln Asn
        195                 200                 205

His Tyr Thr Asp Leu Ser Leu Ser His Ser Pro Gly Lys
    210                 215                 220

<210> SEQ ID NO 2
<211> LENGTH: 220
<212> TYPE: PRT
<213> ORGANISM: Unknown
<220> FEATURE:
<223> OTHER INFORMATION: Wild-type canine IgG-B Fc , Protein A +, C1q +,
      CD16 +

<400> SEQUENCE: 2

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30
```

```
Val Val Val Asp Leu Asp Pro Glu Pro Glu Val Gln Ile Ser Trp
            35                  40                  45

Phe Val Asp Gly Lys Gln Met Gln Thr Ala Lys Thr Gln Pro Arg Glu
 50                  55                  60

Glu Gln Phe Asn Gly Thr Tyr Arg Val Val Ser Val Leu Pro Ile Gly
 65                  70                  75                  80

His Gln Asp Trp Leu Lys Gly Lys Gln Phe Thr Cys Lys Val Asn Asn
                 85                  90                  95

Lys Ala Leu Pro Ser Pro Ile Glu Arg Thr Ile Ser Lys Ala Arg Gly
                100                 105                 110

Gln Ala His Gln Pro Ser Val Tyr Val Leu Pro Pro Ser Arg Glu Glu
                115                 120                 125

Leu Ser Lys Asn Thr Val Ser Leu Thr Cys Leu Ile Lys Asp Phe Phe
                130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
                195                 200                 205

Tyr Thr Gln Glu Ser Leu Ser His Ser Pro Gly Lys
                210                 215                 220

<210> SEQ ID NO 3
<211> LENGTH: 220
<212> TYPE: PRT
<213> ORGANISM: Unknown
<220> FEATURE:
<223> OTHER INFORMATION: Wild-type canine IgG-C Fc , Protein A - ,
      C1q +, CD16 +

<400> SEQUENCE: 3

Pro Gly Cys Gly Leu Leu Gly Gly Pro Ser Val Phe Ile Phe Pro Pro
  1               5                  10                  15

Lys Pro Lys Asp Ile Leu Val Thr Ala Arg Thr Pro Thr Val Thr Cys
                 20                  25                  30

Val Val Val Asp Leu Asp Pro Glu Asn Pro Glu Val Gln Ile Ser Trp
            35                  40                  45

Phe Val Asp Ser Lys Gln Val Gln Thr Ala Asn Thr Gln Pro Arg Glu
 50                  55                  60

Glu Gln Ser Asn Gly Thr Tyr Arg Val Val Ser Val Leu Pro Ile Gly
 65                  70                  75                  80

His Gln Asp Trp Leu Ser Gly Lys Gln Phe Lys Cys Lys Val Asn Asn
                 85                  90                  95

Lys Ala Leu Pro Ser Pro Ile Glu Glu Ile Ile Ser Lys Thr Pro Gly
                100                 105                 110

Gln Ala His Gln Pro Asn Val Tyr Val Leu Pro Pro Ser Arg Asp Glu
                115                 120                 125

Met Ser Lys Asn Thr Val Thr Leu Thr Cys Leu Val Lys Asp Phe Phe
                130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
```

-continued

```
                  165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
        210                 215                 220

<210> SEQ ID NO 4
<211> LENGTH: 221
<212> TYPE: PRT
<213> ORGANISM: Unknown
<220> FEATURE:
<223> OTHER INFORMATION: Wild-type canine IgG-D Fc , Protein A -, C1q -,
      CD16

<400> SEQUENCE: 4

Pro Val Pro Glu Ser Leu Gly Gly Pro Ser Val Phe Ile Phe Pro Pro
1               5                   10                  15

Lys Pro Lys Asp Ile Leu Arg Ile Thr Arg Thr Pro Glu Ile Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Pro Arg Glu
    50                  55                  60

Gln Gln Phe Asn Ser Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Thr Cys Leu Ile Lys Asp Phe
    130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Thr Phe Thr Cys Ala Val Met His Glu Ala Leu Gln Asn
        195                 200                 205

His Tyr Thr Asp Leu Ser Leu Ser His Ser Pro Gly Lys
    210                 215                 220

<210> SEQ ID NO 5
<211> LENGTH: 221
<212> TYPE: PRT
<213> ORGANISM: Artificial Sequence
<220> FEATURE:
<223> OTHER INFORMATION: Synthetic: Variant canine IgG-A Fc , C1q -,
      Protein A +, I(21)T, R(23)L, T(25)A, E(80)G, T(205)A, Q(207)H

<400> SEQUENCE: 5

Pro Val Pro Glu Pro Leu Gly Gly Pro Ser Val Leu Ile Phe Pro Pro
1               5                   10                  15

Lys Pro Lys Asp Thr Leu Leu Ile Ala Arg Thr Pro Glu Val Thr Cys
```

```
            20                  25                  30
Val Val Leu Asp Leu Gly Arg Glu Asp Pro Glu Val Gln Ile Ser Trp
        35                  40                  45
Phe Val Asp Gly Lys Glu Val His Thr Ala Lys Thr Gln Ser Arg Glu
    50                  55                  60
Gln Gln Phe Asn Gly Thr Tyr Arg Val Val Ser Val Leu Pro Ile Gly
65                  70                  75                  80
His Gln Asp Trp Leu Thr Gly Lys Glu Phe Lys Cys Arg Val Asn His
                85                  90                  95
Ile Asp Leu Pro Ser Pro Ile Glu Arg Thr Ile Ser Lys Ala Arg Gly
            100                 105                 110
Arg Ala His Lys Pro Ser Val Tyr Val Leu Pro Pro Ser Pro Lys Glu
        115                 120                 125
Leu Ser Ser Ser Asp Thr Val Ser Ile Thr Cys Leu Ile Lys Asp Phe
    130                 135                 140
Tyr Pro Pro Asp Ile Asp Val Glu Trp Gln Ser Asn Gly Gln Gln Glu
145                 150                 155                 160
Pro Glu Arg Lys His Arg Met Thr Pro Pro Gln Leu Asp Glu Asp Gly
                165                 170                 175
Ser Tyr Phe Leu Tyr Ser Lys Leu Ser Val Asp Lys Ser Arg Trp Gln
            180                 185                 190
Gln Gly Asp Pro Phe Thr Cys Ala Val Met His Glu Ala Leu His Asn
        195                 200                 205
His Tyr Thr Asp Leu Ser Leu Ser His Ser Pro Gly Lys
    210                 215                 220

<210> SEQ ID NO 6
<211> LENGTH: 220
<212> TYPE: PRT
<213> ORGANISM: Artificial Sequence
<220> FEATURE:
<223> OTHER INFORMATION: Synthetic: Variant canine IgG-C Fc , C1q +,
      Protein A +, I(21)T, V(23)L, T(24)I

<400> SEQUENCE: 6

Pro Gly Cys Gly Leu Leu Gly Gly Pro Ser Val Phe Ile Phe Pro Pro
1               5                   10                  15
Lys Pro Lys Asp Thr Leu Leu Ile Ala Arg Thr Pro Thr Val Thr Cys
            20                  25                  30
Val Val Val Asp Leu Asp Pro Glu Asn Pro Glu Val Gln Ile Ser Trp
        35                  40                  45
Phe Val Asp Ser Lys Gln Val Gln Thr Ala Asn Thr Gln Pro Arg Glu
    50                  55                  60
Glu Gln Ser Asn Gly Thr Tyr Arg Val Val Ser Val Leu Pro Ile Gly
65                  70                  75                  80
His Gln Asp Trp Leu Ser Gly Lys Gln Phe Lys Cys Lys Val Asn Asn
                85                  90                  95
Lys Ala Leu Pro Ser Pro Ile Glu Glu Ile Ile Ser Lys Thr Pro Gly
            100                 105                 110
Gln Ala His Gln Pro Asn Val Tyr Val Leu Pro Pro Ser Arg Asp Glu
        115                 120                 125
Met Ser Lys Asn Thr Val Thr Leu Thr Cys Leu Val Lys Asp Phe Phe
    130                 135                 140
Pro Pro Glu Ile Asp Val Glu Trp Gln Ser Asn Gly Gln Gln Glu Pro
145                 150                 155                 160
```

```
Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Ile Ser Leu Ser His Ser Pro Gly Lys
    210                 215                 220
```

<210> SEQ ID NO 7
<211> LENGTH: 221
<212> TYPE: PRT
<213> ORGANISM: Artificial Sequence
<220> FEATURE:
<223> OTHER INFORMATION: Synthetic: Variant canine IgG-D Fc , C1q -,
      Protein A +, I(21)T, R(23)L, T(25)A, E(80)G, Q(207)H

<400> SEQUENCE: 7

```
Pro Val Pro Glu Ser Leu Gly Gly Pro Ser Val Phe Ile Phe Pro Pro
1               5                   10                  15

Lys Pro Lys Asp Thr Leu Leu Ile Ala Arg Thr Pro Glu Ile Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Pro Arg Glu
    50                  55                  60

Gln Gln Phe Asn Ser Thr Tyr Arg Val Val Ser Val Leu Pro Ile Gly
65                  70                  75                  80

His Gln Asp Trp Leu Thr Gly Lys Glu Phe Lys Cys Arg Val Asn His
                85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Thr Cys Leu Ile Lys Asp Phe
    130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Thr Phe Thr Cys Ala Val Met His Glu Ala Leu His Asn
        195                 200                 205

His Tyr Thr Asp Leu Ser Leu Ser His Ser Pro Gly Lys
    210                 215                 220
```

<210> SEQ ID NO 8
<211> LENGTH: 221
<212> TYPE: PRT
<213> ORGANISM: Artificial Sequence
<220> FEATURE:
<223> OTHER INFORMATION: Synthetic: Variant canine IgG-A Fc ,
      Heterodimer chain 1 T(138)Y

<400> SEQUENCE: 8

```
Pro Val Pro Glu Pro Leu Gly Gly Pro Ser Val Leu Ile Phe Pro Pro
1               5                   10                  15
```

```
Lys Pro Lys Asp Ile Leu Arg Ile Thr Arg Thr Pro Glu Val Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Ser Arg Glu
    50                  55                  60

Gln Gln Phe Asn Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
            100                 105                 110

Arg Ala His Lys Pro Ser Val Tyr Val Leu Pro Pro Ser Pro Lys Glu
        115                 120                 125

Leu Ser Ser Ser Asp Thr Val Ser Ile Tyr Cys Leu Ile Lys Asp Phe
    130                 135                 140

Tyr Pro Pro Asp Ile Asp Val Glu Trp Gln Ser Asn Gly Gln Gln Glu
145                 150                 155                 160

Pro Glu Arg Lys His Arg Met Thr Pro Gln Leu Asp Glu Asp Gly
                165                 170                 175

Ser Tyr Phe Leu Tyr Ser Lys Leu Ser Val Asp Lys Ser Arg Trp Gln
                180                 185                 190

Gln Gly Asp Pro Phe Thr Cys Ala Val Met His Glu Thr Leu Gln Asn
            195                 200                 205

His Tyr Thr Asp Leu Ser Leu Ser His Ser Pro Gly Lys
        210                 215                 220

<210> SEQ ID NO 9
<211> LENGTH: 221
<212> TYPE: PRT
<213> ORGANISM: Artificial Sequence
<220> FEATURE:
<223> OTHER INFORMATION: Synthetic: Variant canine IgG-A Fc ,
      Heterodimer chain 2, Y(181)T

<400> SEQUENCE: 9

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Ser Arg Glu
    50                  55                  60

Gln Gln Phe Asn Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
            100                 105                 110

Arg Ala His Lys Pro Ser Val Tyr Val Leu Pro Pro Ser Pro Lys Glu
        115                 120                 125

Leu Ser Ser Ser Asp Thr Val Ser Ile Thr Cys Leu Ile Lys Asp Phe
    130                 135                 140

Tyr Pro Pro Asp Ile Asp Val Glu Trp Gln Ser Asn Gly Gln Gln Glu
145                 150                 155                 160
```

```
Pro Glu Arg Lys His Arg Met Thr Pro Pro Gln Leu Asp Glu Asp Gly
                165                 170                 175

Ser Tyr Phe Leu Thr Ser Lys Leu Ser Val Asp Lys Ser Arg Trp Gln
            180                 185                 190

Gln Gly Asp Pro Phe Thr Cys Ala Val Met His Glu Thr Leu Gln Asn
        195                 200                 205

His Tyr Thr Asp Leu Ser Leu Ser His Ser Pro Gly Lys
    210                 215                 220

<210> SEQ ID NO 10
<211> LENGTH: 220
<212> TYPE: PRT
<213> ORGANISM: Artificial Sequence
<220> FEATURE:
<223> OTHER INFORMATION: Synthetic: Variant canine IgG-B Fc ,
      Heterodimer chain 1 T(137)Y

<400> SEQUENCE: 10

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Tyr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 11
<211> LENGTH: 220
<212> TYPE: PRT
<213> ORGANISM: Artificial Sequence
<220> FEATURE:
<223> OTHER INFORMATION: Synthetic: Variant canine IgG-B Fc ,
      Heterodimer chain 2, Y(180)T

<400> SEQUENCE: 11

Pro Ala Pro Glu Met Leu Gly Gly Pro Ser Val Phe Ile Phe Pro Pro
1               5                   10                  15
```

Lys Pro Lys Asp Thr Leu Leu Ile Ala Arg Thr Pro Glu Val Thr Cys
                20                  25                  30

Val Val Val Asp Leu Asp Pro Glu Asp Pro Glu Val Gln Ile Ser Trp
            35                  40                  45

Phe Val Asp Gly Lys Gln Met Gln Thr Ala Lys Thr Gln Pro Arg Glu
 50                  55                  60

Glu Gln Phe Asn Gly Thr Tyr Arg Val Val Ser Val Leu Pro Ile Gly
 65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
            115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Thr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Glu Ser Leu Ser His Ser Pro Gly Lys
            210                 215                 220

<210> SEQ ID NO 12
<211> LENGTH: 220
<212> TYPE: PRT
<213> ORGANISM: Artificial Sequence
<220> FEATURE:
<223> OTHER INFORMATION: Synthetic: Variant canine IgG-C Fc ,
      Heterodimer chain 1 T(137)Y

<400> SEQUENCE: 12

Pro Gly Cys Gly Leu Leu Gly Gly Pro Ser Val Phe Ile Phe Pro Pro
 1               5                  10                  15

Lys Pro Lys Asp Ile Leu Val Thr Ala Arg Thr Pro Thr Val Thr Cys
                20                  25                  30

Val Val Val Asp Leu Asp Pro Glu Asn Pro Glu Val Gln Ile Ser Trp
            35                  40                  45

Phe Val Asp Ser Lys Gln Val Gln Thr Ala Asn Thr Gln Pro Arg Glu
 50                  55                  60

Glu Gln Ser Asn Gly Thr Tyr Arg Val Val Ser Val Leu Pro Ile Gly
 65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
            115                 120                 125

Met Ser Lys Asn Thr Val Thr Leu Tyr Cys Leu Val Lys Asp Phe Phe
130                 135                 140

Pro Pro Glu Ile Asp Val Glu Trp Gln Ser Asn Gly Gln Gln Glu Pro

```
145                 150                 155                 160
Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
                195                 200                 205

Tyr Thr Gln Ile Ser Leu Ser His Ser Pro Gly Lys
                210                 215                 220

<210> SEQ ID NO 13
<211> LENGTH: 220
<212> TYPE: PRT
<213> ORGANISM: Artificial Sequence
<220> FEATURE:
<223> OTHER INFORMATION: Synthetic: Variant canine IgG-C Fc ,
      Heterodimer chain 2, Y(180)T

<400> SEQUENCE: 13

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
                20                  25                  30

Val Val Val Asp Leu Asp Pro Glu Asn Pro Glu Val Gln Ile Ser Trp
            35                  40                  45

Phe Val Asp Ser Lys Gln Val Gln Thr Ala Asn Thr Gln Pro Arg Glu
        50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
                100                 105                 110

Gln Ala His Gln Pro Asn Val Tyr Val Leu Pro Pro Ser Arg Asp Glu
                115                 120                 125

Met Ser Lys Asn Thr Val Thr Leu Thr Cys Leu Val Lys Asp Phe Phe
                130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Thr Ser Lys Leu Ser Val Asp Lys Ser Arg Trp Gln Arg
                180                 185                 190

Gly Asp Thr Phe Ile Cys Ala Val Met His Glu Ala Leu His Asn His
                195                 200                 205

Tyr Thr Gln Ile Ser Leu Ser His Ser Pro Gly Lys
                210                 215                 220

<210> SEQ ID NO 14
<211> LENGTH: 221
<212> TYPE: PRT
<213> ORGANISM: Artificial Sequence
<220> FEATURE:
<223> OTHER INFORMATION: Synthetic: Variant canine IgG-D Fc ,
      Heterodimer chain 1 T(138)Y

<400> SEQUENCE: 14

Pro Val Pro Glu Ser Leu Gly Gly Pro Ser Val Phe Ile Phe Pro Pro
```

```
                1               5              10               15
            Lys Pro Lys Asp Ile Leu Arg Ile Thr Arg Thr Pro Glu Ile Thr Cys
                            20                  25                  30

Val Val Leu Asp Leu Gly Arg Glu Asp Pro Glu Val Gln Ile Ser Trp
                            35                  40                  45

Phe Val Asp Gly Lys Glu Val His Thr Ala Lys Thr Gln Pro Arg Glu
                50                  55                  60

Gln Gln Phe Asn Ser Thr Tyr Arg Val Val Ser Val Leu Pro Ile Glu
             65                  70                  75                  80

His Gln Asp Trp Leu Thr Gly Lys Glu Phe Lys Cys Arg Val Asn His
                            85                  90                  95

Ile Gly Leu Pro Ser Pro Ile Glu Arg Thr Ile Ser Lys Ala Arg Gly
                            100                 105                 110

Gln Ala His Gln Pro Ser Val Tyr Val Leu Pro Pro Ser Pro Lys Glu
                            115                 120                 125

Leu Ser Ser Ser Asp Thr Val Thr Leu Tyr Cys Leu Ile Lys Asp Phe
                130                 135                 140

Phe Pro Pro Glu Ile Asp Val Glu Trp Gln Ser Asn Gly Gln Pro Glu
            145                 150                 155                 160

Pro Glu Ser Lys Tyr His Thr Thr Ala Pro Gln Leu Asp Glu Asp Gly
                            165                 170                 175

Ser Tyr Phe Leu Tyr Ser Lys Leu Ser Val Asp Lys Ser Arg Trp Gln
                            180                 185                 190

Gln Gly Asp Thr Phe Thr Cys Ala Val Met His Glu Ala Leu Gln Asn
                            195                 200                 205

His Tyr Thr Asp Leu Ser Leu Ser His Ser Pro Gly Lys
                            210                 215                 220

<210> SEQ ID NO 15
            <211> LENGTH: 221
            <212> TYPE: PRT
            <213> ORGANISM: Artificial Sequence
            <220> FEATURE:
            <223> OTHER INFORMATION: Synthetic: Variant canine IgG-D Fc ,
                  Heterodimer chain 2, Y(181)T

<400> SEQUENCE: 15

Pro Val Pro Glu Ser Leu Gly Gly Pro Ser Val Phe Ile Phe Pro Pro
            1               5                  10                  15

Lys Pro Lys Asp Ile Leu Arg Ile Thr Arg Thr Pro Glu Ile Thr Cys
                            20                  25                  30

Val Val Leu Asp Leu Gly Arg Glu Asp Pro Glu Val Gln Ile Ser Trp
                            35                  40                  45

Phe Val Asp Gly Lys Glu Val His Thr Ala Lys Thr Gln Pro Arg Glu
                50                  55                  60

Gln Gln Phe Asn Ser Thr Tyr Arg Val Val Ser Val Leu Pro Ile Glu
             65                  70                  75                  80

His Gln Asp Trp Leu Thr Gly Lys Glu Phe Lys Cys Arg Val Asn His
                            85                  90                  95

Ile Gly Leu Pro Ser Pro Ile Glu Arg Thr Ile Ser Lys Ala Arg Gly
                            100                 105                 110

Gln Ala His Gln Pro Ser Val Tyr Val Leu Pro Pro Ser Pro Lys Glu
                            115                 120                 125

Leu Ser Ser Ser Asp Thr Val Thr Leu Thr Cys Leu Ile Lys Asp Phe
                130                 135                 140
```

```
Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
            165                 170                 175

Ser Tyr Phe Leu Thr Ser Lys Leu Ser Val Asp Lys Ser Arg Trp Gln
            180                 185                 190

Gln Gly Asp Thr Phe Thr Cys Ala Val Met His Glu Ala Leu Gln Asn
            195                 200                 205

His Tyr Thr Asp Leu Ser Leu Ser His Ser Pro Gly Lys
            210                 215                 220
```

<210> SEQ ID NO 16
<211> LENGTH: 237
<212> TYPE: PRT
<213> ORGANISM: Unknown
<220> FEATURE:
<223> OTHER INFORMATION: Wild-type feline IgG2 Fc, Protein A +, C1q -

<400> SEQUENCE: 16

```
Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asn Val Gln Ile Thr
        50                  55                  60

Trp Phe Val Asp Asn Thr Glu Met His Thr Ala Lys Thr Arg Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
    130                 135                 140

Glu Leu Ser Glu Asn Lys Val Ser Val Thr Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235
```

<210> SEQ ID NO 17
<211> LENGTH: 237
<212> TYPE: PRT
<213> ORGANISM: Artificial Sequence
<220> FEATURE:
<223> OTHER INFORMATION: Synthetic: Variant feline IgG2 Fc , Hinge Cys,
      G(14)C

```
<400> SEQUENCE: 17

Pro Lys Thr Ala Ser Thr Ile Glu Ser Lys Thr Gly Glu Cys Pro Lys
1               5                   10                  15

Cys Pro Val Pro Glu Ile Pro Gly Ala Pro Ser Val Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Ser Asn Val Gln Ile Thr
50                  55                  60

Trp Phe Val Asp Asn Thr Glu Met His Thr Ala Lys Thr Arg Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
    130                 135                 140

Glu Leu Ser Glu Asn Lys Val Ser Val Thr Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 18
<211> LENGTH: 228
<212> TYPE: PRT
<213> ORGANISM: Artificial Sequence
<220> FEATURE:
<223> OTHER INFORMATION: Synthetic: Variant equine Fc IgG2 (with equine
      IgG1 hinge), Protein A - , C1q -

<400> SEQUENCE: 18

Asp Met Ser Lys Cys Pro Lys Cys Pro Ala Pro Glu Leu Leu Gly Gly
1               5                   10                  15

Pro Ser Val Phe Ile Phe Pro Pro Asn Pro Lys Asp Ala Leu Met Ile
            20                  25                  30

Ser Arg Thr Pro Val Val Thr Cys Val Val Val Asn Leu Ser Asp Gln
        35                  40                  45

Tyr Pro Asp Val Gln Phe Ser Trp Tyr Val Asp Asn Thr Glu Val His
50                  55                  60

Ser Ala Ile Thr Lys Gln Arg Glu Ala Gln Phe Asn Ser Thr Tyr Arg
65                  70                  75                  80

Val Val Ser Val Leu Pro Ile Gln His Gln Asp Trp Leu Ser Gly Lys
                85                  90                  95

Glu Phe Lys Cys Ser Val Thr Asn Val Gly Val Pro Gln Pro Ile Ser
            100                 105                 110
```

Arg Ala Ile Ser Arg Gly Lys Gly Pro Ser Arg Val Pro Gln Val Tyr
            115                 120                 125

Val Leu Pro Pro His Pro Asp Glu Leu Ala Lys Ser Lys Val Ser Val
    130                 135                 140

Thr Cys Leu Val Lys Asp Phe Tyr Pro Pro Asp Ile Ser Val Glu Trp
145                 150                 155                 160

Gln Ser Asn Arg Trp Pro Glu Leu Glu Gly Lys Tyr Ser Thr Thr Pro
                165                 170                 175

Ala Gln Leu Asp Gly Asp Gly Ser Tyr Phe Leu Tyr Ser Lys Leu Ser
            180                 185                 190

Leu Glu Thr Ser Arg Trp Gln Gln Val Glu Ser Phe Thr Cys Ala Val
        195                 200                 205

Met His Glu Ala Leu His Asn His Phe Thr Lys Thr Asp Ile Ser Glu
    210                 215                 220

Ser Leu Gly Lys
225

<210> SEQ ID NO 19
<211> LENGTH: 228
<212> TYPE: PRT
<213> ORGANISM: Artificial Sequence
<220> FEATURE:
<223> OTHER INFORMATION: Synthetic: Variant equine IgG2 Fc (with equine
      IgG1 hinge), C1q -, Protein A +, A(29)T, F(217)Y

<400> SEQUENCE: 19

Asp Met Ser Lys Cys Pro Lys Cys Pro Ala Pro Glu Leu Leu Gly Gly
1               5                   10                  15

Pro Ser Val Phe Ile Phe Pro Pro Asn Pro Lys Asp Thr Leu Met Ile
            20                  25                  30

Ser Arg Thr Pro Val Val Thr Cys Val Val Val Asn Leu Ser Asp Gln
        35                  40                  45

Tyr Pro Asp Val Gln Phe Ser Trp Tyr Val Asp Asn Thr Glu Val His
    50                  55                  60

Ser Ala Ile Thr Lys Gln Arg Glu Ala Gln Phe Asn Ser Thr Tyr Arg
65                  70                  75                  80

Val Val Ser Val Leu Pro Ile Gln His Gln Asp Trp Leu Ser Gly Lys
                85                  90                  95

Glu Phe Lys Cys Ser Val Thr Asn Val Gly Val Pro Gln Pro Ile Ser
            100                 105                 110

Arg Ala Ile Ser Arg Gly Lys Gly Pro Ser Arg Val Pro Gln Val Tyr
            115                 120                 125

Val Leu Pro Pro His Pro Asp Glu Leu Ala Lys Ser Lys Val Ser Val
    130                 135                 140

Thr Cys Leu Val Lys Asp Phe Tyr Pro Pro Asp Ile Ser Val Glu Trp
145                 150                 155                 160

Gln Ser Asn Arg Trp Pro Glu Leu Glu Gly Lys Tyr Ser Thr Thr Pro
                165                 170                 175

Ala Gln Leu Asp Gly Asp Gly Ser Tyr Phe Leu Tyr Ser Lys Leu Ser
            180                 185                 190

Leu Glu Thr Ser Arg Trp Gln Gln Val Glu Ser Phe Thr Cys Ala Val
        195                 200                 205

Met His Glu Ala Leu His Asn His Tyr Thr Lys Thr Asp Ile Ser Glu
    210                 215                 220

Ser Leu Gly Lys
225

<210> SEQ ID NO 20
<211> LENGTH: 29
<212> TYPE: PRT
<213> ORGANISM: Artificial Sequence
<220> FEATURE:
<223> OTHER INFORMATION: Synthetic: Variant GLP1 (7-35)
<220> FEATURE:
<221> NAME/KEY: misc_feature
<222> LOCATION: (2)..(2)
<223> OTHER INFORMATION: X may be G or S

<400> SEQUENCE: 20

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic: Glucagon (Gluc)

<400> SEQUENCE: 21

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 22
<211> LENGTH: 39
<212> TYPE: PRT
<213> ORGANISM: Artificial Sequence
<220> FEATURE:
<223> OTHER INFORMATION: Synthetic: Extendin-4

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 23
<211> LENGTH: 325
<212> TYPE: PRT
<213> ORGANISM: Artificial Sequence
<220> FEATURE:
<223> OTHER INFORMATION: Synthetic: GLP1-G8/GLP-2G_III_ WTfeIgG2

<400> SEQUENCE: 23

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Ser Gly Gly Gly Gly Ser
        35                  40                  45

Pro Lys Thr Ala Ser Thr Ile Glu Ser Lys Thr Gly Glu Gly Pro Lys
    50                  55                  60

Cys Pro Val Pro Glu Ile Pro Gly Ala Pro Ser Val Phe Ile Phe Pro

```
                65                  70                  75                  80
Pro Lys Pro Lys Asp Thr Leu Ser Ile Ser Arg Thr Pro Glu Val Thr
                    85                  90                  95

Cys Leu Val Val Asp Leu Gly Pro Asp Asp Ser Asn Val Gln Ile Thr
                    100                 105                 110

Trp Phe Val Asp Asn Thr Glu Met His Thr Ala Lys Thr Arg Pro Arg
                    115                 120                 125

Glu Glu Gln Phe Asn Ser Thr Tyr Arg Val Val Ser Val Leu Pro Ile
                130                 135                 140

Leu His Gln Asp Trp Leu Lys Gly Lys Glu Phe Lys Cys Lys Val Asn
145                 150                 155                 160

Ser Lys Ser Leu Pro Ser Ala Met Glu Arg Thr Ile Ser Lys Ala Lys
                    165                 170                 175

Gly Gln Pro His Glu Pro Gln Val Tyr Val Leu Pro Pro Thr Gln Glu
                    180                 185                 190

Glu Leu Ser Glu Asn Lys Val Ser Val Thr Cys Leu Ile Lys Gly Phe
                    195                 200                 205

His Pro Pro Asp Ile Ala Val Glu Trp Glu Ile Thr Gly Gln Pro Glu
                    210                 215                 220

Pro Glu Asn Asn Tyr Gln Thr Thr Pro Pro Gln Leu Asp Ser Asp Gly
225                 230                 235                 240

Thr Tyr Phe Leu Tyr Ser Arg Leu Ser Val Asp Arg Ser His Trp Gln
                    245                 250                 255

Arg Gly Asn Thr Tyr Thr Cys Ser Val Ser His Glu Ala Leu His Ser
                    260                 265                 270

His His Thr Gln Lys Ser Leu Thr Gln Ser Pro Gly Lys Gly Gly Gly
                    275                 280                 285

Gly Ser Gly Gly Gly Gly His Ala Glu Gly Thr Phe Thr Ser Asp Val
                290                 295                 300

Ser Ser Tyr Leu Glu Gly Gln Ala Ala Lys Glu Phe Ile Ala Trp Leu
305                 310                 315                 320

Val Lys Gly Gly Gly
                325

<210> SEQ ID NO 24
<211> LENGTH: 285
<212> TYPE: PRT
<213> ORGANISM: Artificial Sequence
<220> FEATURE:
<223> OTHER INFORMATION: Synthetic: GLP1-G8_I_WTfeIgG2

<400> SEQUENCE: 24

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
                20                  25                  30

Ser Gly Gly Gly Gly Ser Gly Gly Gly Ser Gly Gly Gly Gly Ser
            35                  40                  45

Pro Lys Thr Ala Ser Thr Ile Glu Ser Lys Thr Gly Glu Gly Pro Lys
            50                  55                  60

Cys Pro Val Pro Glu Ile Pro Gly Ala Pro Ser Val Phe Ile Phe Pro
65                  70                  75                  80

Pro Lys Pro Lys Asp Thr Leu Ser Ile Ser Arg Thr Pro Glu Val Thr
                    85                  90                  95

Cys Leu Val Val Asp Leu Gly Pro Asp Asp Ser Asn Val Gln Ile Thr
```

```
                100                 105                 110
Trp Phe Val Asp Asn Thr Glu Met His Thr Ala Lys Thr Arg Pro Arg
            115                 120                 125
Glu Glu Gln Phe Asn Ser Thr Tyr Arg Val Val Ser Val Leu Pro Ile
            130                 135                 140
Leu His Gln Asp Trp Leu Lys Gly Lys Glu Phe Lys Cys Lys Val Asn
145                 150                 155                 160
Ser Lys Ser Leu Pro Ser Ala Met Glu Arg Thr Ile Ser Lys Ala Lys
            165                 170                 175
Gly Gln Pro His Glu Pro Gln Val Tyr Val Leu Pro Pro Thr Gln Glu
            180                 185                 190
Glu Leu Ser Glu Asn Lys Val Ser Val Thr Cys Leu Ile Lys Gly Phe
            195                 200                 205
His Pro Pro Asp Ile Ala Val Glu Trp Glu Ile Thr Gly Gln Pro Glu
            210                 215                 220
Pro Glu Asn Asn Tyr Gln Thr Thr Pro Pro Gln Leu Asp Ser Asp Gly
225                 230                 235                 240
Thr Tyr Phe Leu Tyr Ser Arg Leu Ser Val Asp Arg Ser His Trp Gln
            245                 250                 255
Arg Gly Asn Thr Tyr Thr Cys Ser Val Ser His Glu Ala Leu His Ser
            260                 265                 270
His His Thr Gln Lys Ser Leu Thr Gln Ser Pro Gly Lys
            275                 280                 285

<210> SEQ ID NO 25
<211> LENGTH: 325
<212> TYPE: PRT
<213> ORGANISM: Artificial Sequence
<220> FEATURE:
<223> OTHER INFORMATION: Synthetic: GLP1-G8/GLP1-2G_III_ VARfeIgG2

<400> SEQUENCE: 25

His Gly Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Gly Gly Gly
            20                  25                  30
Ser Gly Gly Gly Gly Ser Gly Gly Gly Gly Ser Gly Gly Gly Gly Ser
            35                  40                  45
Pro Lys Thr Ala Ser Thr Ile Glu Ser Lys Thr Gly Glu Cys Pro Lys
        50                  55                  60
Cys Pro Val Pro Glu Ile Pro Gly Ala Pro Ser Val Phe Ile Phe Pro
65                  70                  75                  80
Pro Lys Pro Lys Asp Thr Leu Ser Ile Ser Arg Thr Pro Glu Val Thr
            85                  90                  95
Cys Leu Val Val Asp Leu Gly Pro Asp Asp Ser Asn Val Gln Ile Thr
            100                 105                 110
Trp Phe Val Asp Asn Thr Glu Met His Thr Ala Lys Thr Arg Pro Arg
            115                 120                 125
Glu Glu Gln Phe Asn Ser Thr Tyr Arg Val Val Ser Val Leu Pro Ile
            130                 135                 140
Leu His Gln Asp Trp Leu Lys Gly Lys Glu Phe Lys Cys Lys Val Asn
145                 150                 155                 160
Ser Lys Ser Leu Pro Ser Ala Met Glu Arg Thr Ile Ser Lys Ala Lys
            165                 170                 175
Gly Gln Pro His Glu Pro Gln Val Tyr Val Leu Pro Pro Thr Gln Glu
```

```
            180                 185                 190
Glu Leu Ser Glu Asn Lys Val Ser Val Thr Cys Leu Ile Lys Gly Phe
            195                 200                 205

His Pro Pro Asp Ile Ala Val Glu Trp Glu Ile Thr Gly Gln Pro Glu
            210                 215                 220

Pro Glu Asn Asn Tyr Gln Thr Thr Pro Pro Gln Leu Asp Ser Asp Gly
225                 230                 235                 240

Thr Tyr Phe Leu Tyr Ser Arg Leu Ser Val Asp Arg Ser His Trp Gln
            245                 250                 255

Arg Gly Asn Thr Tyr Thr Cys Ser Val Ser His Glu Ala Leu His Ser
            260                 265                 270

His His Thr Gln Lys Ser Leu Thr Gln Ser Pro Gly Lys Gly Gly Gly
            275                 280                 285

Gly Ser Gly Gly Gly Gly His Ala Glu Gly Thr Phe Thr Ser Asp Val
            290                 295                 300

Ser Ser Tyr Leu Glu Gly Gln Ala Ala Lys Glu Phe Ile Ala Trp Leu
305                 310                 315                 320

Val Lys Gly Gly Gly
            325

<210> SEQ ID NO 26
<211> LENGTH: 285
<212> TYPE: PRT
<213> ORGANISM: Artificial Sequence
<220> FEATURE:
<223> OTHER INFORMATION: Synthetic: GLP1-G8_I_VARfeIgG2

<400> SEQUENCE: 26

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Gly Ser Gly Gly Gly Gly Ser
            35                  40                  45

Pro Lys Thr Ala Ser Thr Ile Glu Ser Lys Thr Gly Glu Cys Pro Lys
50                  55                  60

Cys Pro Val Pro Glu Ile Pro Gly Ala Pro Ser Val Phe Ile Phe Pro
65                  70                  75                  80

Pro Lys Pro Lys Asp Thr Leu Ser Ile Ser Arg Thr Pro Glu Val Thr
            85                  90                  95

Cys Leu Val Val Asp Leu Gly Pro Asp Asp Ser Asn Val Gln Ile Thr
            100                 105                 110

Trp Phe Val Asp Asn Thr Glu Met His Thr Ala Lys Thr Arg Pro Arg
            115                 120                 125

Glu Glu Gln Phe Asn Ser Thr Tyr Arg Val Val Ser Val Leu Pro Ile
            130                 135                 140

Leu His Gln Asp Trp Leu Lys Gly Lys Glu Phe Lys Cys Lys Val Asn
145                 150                 155                 160

Ser Lys Ser Leu Pro Ser Ala Met Glu Arg Thr Ile Ser Lys Ala Lys
            165                 170                 175

Gly Gln Pro His Glu Pro Gln Val Tyr Val Leu Pro Pro Thr Gln Glu
            180                 185                 190

Glu Leu Ser Glu Asn Lys Val Ser Val Thr Cys Leu Ile Lys Gly Phe
            195                 200                 205

His Pro Pro Asp Ile Ala Val Glu Trp Glu Ile Thr Gly Gln Pro Glu
```

```
                210                 215                 220
Pro Glu Asn Asn Tyr Gln Thr Thr Pro Pro Gln Leu Asp Ser Asp Gly
225                 230                 235                 240

Thr Tyr Phe Leu Tyr Ser Arg Leu Ser Val Asp Arg Ser His Trp Gln
                245                 250                 255

Arg Gly Asn Thr Tyr Thr Cys Ser Val Ser His Glu Ala Leu His Ser
                260                 265                 270

His His Thr Gln Lys Ser Leu Thr Gln Ser Pro Gly Lys
                275                 280                 285

<210> SEQ ID NO 27
<211> LENGTH: 327
<212> TYPE: PRT
<213> ORGANISM: Artificial Sequence
<220> FEATURE:
<223> OTHER INFORMATION: Synthetic: GLP1-S8/GLP1-3G_III_ WTfeIgG2

<400> SEQUENCE: 27

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
                20                  25                  30

Gly Gly Gly Gly Ser Gly Gly Ser Gly Gly Ser Gly Gly Gly
                35                  40                  45

Ser Pro Lys Thr Ala Ser Thr Ile Glu Ser Lys Thr Gly Glu Gly Pro
50                  55                  60

Lys Cys Pro Val Pro Glu Ile Pro Gly Ala Pro Ser Val Phe Ile Phe
65                  70                  75                  80

Pro Pro Lys Pro Lys Asp Thr Leu Ser Ile Ser Arg Thr Pro Glu Val
                85                  90                  95

Thr Cys Leu Val Val Asp Leu Gly Pro Asp Asp Ser Asn Val Gln Ile
                100                 105                 110

Thr Trp Phe Val Asp Asn Thr Glu Met His Thr Ala Lys Thr Arg Pro
                115                 120                 125

Arg Glu Glu Gln Phe Asn Ser Thr Tyr Arg Val Val Ser Val Leu Pro
130                 135                 140

Ile Leu His Gln Asp Trp Leu Lys Gly Lys Glu Phe Lys Cys Lys Val
145                 150                 155                 160

Asn Ser Lys Ser Leu Pro Ser Ala Met Glu Arg Thr Ile Ser Lys Ala
                165                 170                 175

Lys Gly Gln Pro His Glu Pro Gln Val Tyr Val Leu Pro Pro Thr Gln
                180                 185                 190

Glu Glu Leu Ser Glu Asn Lys Val Ser Val Thr Cys Leu Ile Lys Gly
                195                 200                 205

Phe His Pro Pro Asp Ile Ala Val Glu Trp Glu Ile Thr Gly Gln Pro
210                 215                 220

Glu Pro Glu Asn Asn Tyr Gln Thr Thr Pro Pro Gln Leu Asp Ser Asp
225                 230                 235                 240

Gly Thr Tyr Phe Leu Tyr Ser Arg Leu Ser Val Asp Arg Ser His Trp
                245                 250                 255

Gln Arg Gly Asn Thr Tyr Thr Cys Ser Val Ser His Glu Ala Leu His
                260                 265                 270

Ser His His Thr Gln Lys Ser Leu Thr Gln Ser Pro Gly Lys Gly Gly
                275                 280                 285

Gly Gly Ser Gly Gly Gly Gly His Ala Glu Gly Thr Phe Thr Ser Asp
```

```
                290                 295                 300
Val Ser Ser Tyr Leu Glu Gly Gln Ala Ala Lys Glu Phe Ile Ala Trp
305                 310                 315                 320

Leu Val Lys Gly Gly Gly
                325

<210> SEQ ID NO 28
<211> LENGTH: 286
<212> TYPE: PRT
<213> ORGANISM: Artificial Sequence
<220> FEATURE:
<223> OTHER INFORMATION: Synthetic: GLP1-S8_I_WTfeIgG2

<400> SEQUENCE: 28

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
                20                  25                  30

Gly Gly Gly Gly Ser Gly Gly Ser Gly Gly Ser Gly Gly Gly
            35                  40                  45

Ser Pro Lys Thr Ala Ser Thr Ile Glu Ser Lys Thr Gly Glu Gly Pro
50                  55                  60

Lys Cys Pro Val Pro Glu Ile Pro Gly Ala Pro Ser Val Phe Ile Phe
65                  70                  75                  80

Pro Pro Lys Pro Lys Asp Thr Leu Ser Ile Ser Arg Thr Pro Glu Val
                85                  90                  95

Thr Cys Leu Val Val Asp Leu Gly Pro Asp Asp Ser Asn Val Gln Ile
            100                 105                 110

Thr Trp Phe Val Asp Asn Thr Glu Met His Thr Ala Lys Thr Arg Pro
        115                 120                 125

Arg Glu Glu Gln Phe Asn Ser Thr Tyr Arg Val Val Ser Val Leu Pro
130                 135                 140

Ile Leu His Gln Asp Trp Leu Lys Gly Lys Glu Phe Lys Cys Lys Val
145                 150                 155                 160

Asn Ser Lys Ser Leu Pro Ser Ala Met Glu Arg Thr Ile Ser Lys Ala
                165                 170                 175

Lys Gly Gln Pro His Glu Pro Gln Val Tyr Val Leu Pro Pro Thr Gln
            180                 185                 190

Glu Glu Leu Ser Glu Asn Lys Val Ser Val Thr Cys Leu Ile Lys Gly
        195                 200                 205

Phe His Pro Pro Asp Ile Ala Val Glu Trp Glu Ile Thr Gly Gln Pro
210                 215                 220

Glu Pro Glu Asn Asn Tyr Gln Thr Thr Pro Pro Gln Leu Asp Ser Asp
225                 230                 235                 240

Gly Thr Tyr Phe Leu Tyr Ser Arg Leu Ser Val Asp Arg Ser His Trp
                245                 250                 255

Gln Arg Gly Asn Thr Tyr Thr Cys Ser Val Ser His Glu Ala Leu His
            260                 265                 270

Ser His His Thr Gln Lys Ser Leu Thr Gln Ser Pro Gly Lys
        275                 280                 285

<210> SEQ ID NO 29
<211> LENGTH: 323
<212> TYPE: PRT
<213> ORGANISM: Artificial Sequence
<220> FEATURE:
<223> OTHER INFORMATION: Synthetic: GLP1-G8/GLP1-3G_III_ VARcaIgGD
```

<400> SEQUENCE: 29

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
            20                  25                  30

Gly Gly Gly Gly Ser Gly Gly Ser Gly Gly Ser Gly Gly Gly
            35                  40                  45

Ser Pro Lys Glu Ser Thr Ser Lys Cys Ile Ser Pro Cys Pro Val Pro
50                  55                  60

Glu Ser Leu Gly Gly Pro Ser Val Phe Ile Phe Pro Pro Lys Pro Lys
65                  70                  75                  80

Asp Thr Leu Leu Ile Ala Arg Thr Pro Glu Ile Thr Cys Val Val Leu
                85                  90                  95

Asp Leu Gly Arg Glu Asp Pro Glu Val Gln Ile Ser Trp Phe Val Asp
                100                 105                 110

Gly Lys Glu Val His Thr Ala Lys Thr Gln Pro Arg Glu Gln Gln Phe
            115                 120                 125

Asn Ser Thr Tyr Arg Val Val Ser Val Leu Pro Ile Gly His Gln Asp
130                 135                 140

Trp Leu Thr Gly Lys Glu Phe Lys Cys Arg Val Asn His Ile Gly Leu
145                 150                 155                 160

Pro Ser Pro Ile Glu Arg Thr Ile Ser Lys Ala Arg Gly Gln Ala His
                165                 170                 175

Gln Pro Ser Val Tyr Val Leu Pro Pro Ser Pro Lys Glu Leu Ser Ser
            180                 185                 190

Ser Asp Thr Val Thr Leu Thr Cys Leu Ile Lys Asp Phe Phe Pro Pro
        195                 200                 205

Glu Ile Asp Val Glu Trp Gln Ser Asn Gly Gln Pro Glu Pro Glu Ser
210                 215                 220

Lys Tyr His Thr Thr Ala Pro Gln Leu Asp Glu Asp Gly Ser Tyr Phe
225                 230                 235                 240

Leu Tyr Ser Lys Leu Ser Val Asp Lys Ser Arg Trp Gln Gln Gly Asp
                245                 250                 255

Thr Phe Thr Cys Ala Val Met His Glu Ala Leu His Asn His Tyr Thr
            260                 265                 270

Asp Leu Ser Leu Ser His Ser Pro Gly Lys Gly Gly Gly Ser Gly
            275                 280                 285

Gly Gly Gly His Ala Glu Gly Thr Phe Thr Ser Asp Val Ser Ser Tyr
        290                 295                 300

Leu Glu Gly Gln Ala Ala Lys Glu Phe Ile Ala Trp Leu Val Lys Gly
305                 310                 315                 320

Gly Gly Gly

<210> SEQ ID NO 30
<211> LENGTH: 282
<212> TYPE: PRT
<213> ORGANISM: Artificial Sequence
<220> FEATURE:
<223> OTHER INFORMATION: Synthetic: GLP1-G8_I_VARcaIgGD

<400> SEQUENCE: 30

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly

```
            20                  25                  30
Gly Gly Gly Gly Ser Gly Gly Ser Gly Gly Gly Ser Gly Gly Gly
            35                  40                  45

Ser Pro Lys Glu Ser Thr Cys Lys Cys Ile Ser Pro Cys Val Pro
            50                  55                  60

Glu Ser Leu Gly Gly Pro Ser Val Phe Ile Phe Pro Pro Lys Pro Lys
 65                  70                  75                  80

Asp Thr Leu Leu Ile Ala Arg Thr Pro Glu Ile Thr Cys Val Val Leu
                    85                  90                  95

Asp Leu Gly Arg Glu Asp Pro Glu Val Gln Ile Ser Trp Phe Val Asp
                    100                 105                 110

Gly Lys Glu Val His Thr Ala Lys Thr Gln Pro Arg Glu Gln Gln Phe
                    115                 120                 125

Asn Ser Thr Tyr Arg Val Val Ser Val Leu Pro Ile Gly His Gln Asp
                    130                 135                 140

Trp Leu Thr Gly Lys Glu Phe Lys Cys Arg Val Asn His Ile Gly Leu
145                 150                 155                 160

Pro Ser Pro Ile Glu Arg Thr Ile Ser Lys Ala Arg Gly Gln Ala His
                    165                 170                 175

Gln Pro Ser Val Tyr Val Leu Pro Pro Ser Pro Lys Glu Leu Ser Ser
                    180                 185                 190

Ser Asp Thr Val Thr Leu Thr Cys Leu Ile Lys Asp Phe Phe Pro Pro
                    195                 200                 205

Glu Ile Asp Val Glu Trp Gln Ser Asn Gly Gln Pro Glu Pro Glu Ser
                    210                 215                 220

Lys Tyr His Thr Thr Ala Pro Gln Leu Asp Glu Asp Gly Ser Tyr Phe
225                 230                 235                 240

Leu Tyr Ser Lys Leu Ser Val Asp Lys Ser Arg Trp Gln Gln Gly Asp
                    245                 250                 255

Thr Phe Thr Cys Ala Val Met His Glu Ala Leu His Asn His Tyr Thr
                    260                 265                 270

Asp Leu Ser Leu Ser His Ser Pro Gly Lys
                    275                 280

<210> SEQ ID NO 31
<211> LENGTH: 323
<212> TYPE: PRT
<213> ORGANISM: Artificial Sequence
<220> FEATURE:
<223> OTHER INFORMATION: Synthetic: GLP1-S8/GLP1-3G_III_ VARcaIgGD

<400> SEQUENCE: 31

His Ser Glu Gly Thr Phe Thr Ser Asp Val Ser Ser Tyr Leu Glu Gly
 1                   5                  10                  15

Gln Ala Ala Lys Glu Phe Ile Ala Trp Leu Val Lys Gly Gly Ala Gly
                    20                  25                  30

Gly Gly Gly Gly Ser Gly Gly Ser Gly Gly Gly Ser Gly Gly Gly
            35                  40                  45

Ser Pro Lys Glu Ser Thr Ser Lys Cys Ile Ser Pro Cys Val Pro
            50                  55                  60

Glu Ser Leu Gly Gly Pro Ser Val Phe Ile Phe Pro Pro Lys Pro Lys
 65                  70                  75                  80

Asp Thr Leu Leu Ile Ala Arg Thr Pro Glu Ile Thr Cys Val Val Leu
                    85                  90                  95

Asp Leu Gly Arg Glu Asp Pro Glu Val Gln Ile Ser Trp Phe Val Asp
```

```
                    100                 105                 110
Gly Lys Glu Val His Thr Ala Lys Thr Gln Pro Arg Glu Gln Gln Phe
            115                 120                 125

Asn Ser Thr Tyr Arg Val Val Ser Val Leu Pro Ile Gly His Gln Asp
        130                 135                 140

Trp Leu Thr Gly Lys Glu Phe Lys Cys Arg Val Asn His Ile Gly Leu
145                 150                 155                 160

Pro Ser Pro Ile Glu Arg Thr Ile Ser Lys Ala Arg Gly Gln Ala His
                165                 170                 175

Gln Pro Ser Val Tyr Val Leu Pro Ser Pro Lys Glu Leu Ser Ser
            180                 185                 190

Ser Asp Thr Val Thr Leu Thr Cys Leu Ile Lys Asp Phe Phe Pro Pro
        195                 200                 205

Glu Ile Asp Val Glu Trp Gln Ser Asn Gly Gln Pro Glu Pro Glu Ser
210                 215                 220

Lys Tyr His Thr Thr Ala Pro Gln Leu Asp Glu Asp Gly Ser Tyr Phe
225                 230                 235                 240

Leu Tyr Ser Lys Leu Ser Val Asp Lys Ser Arg Trp Gln Gln Gly Asp
                245                 250                 255

Thr Phe Thr Cys Ala Val Met His Glu Ala Leu His Asn His Tyr Thr
            260                 265                 270

Asp Leu Ser Leu Ser His Ser Pro Gly Lys Gly Gly Gly Gly Ser Gly
        275                 280                 285

Gly Gly Gly His Ala Glu Gly Thr Phe Thr Ser Asp Val Ser Ser Tyr
    290                 295                 300

Leu Glu Gly Gln Ala Ala Lys Glu Phe Ile Ala Trp Leu Val Lys Gly
305                 310                 315                 320

Gly Gly Gly

<210> SEQ ID NO 32
<211> LENGTH: 282
<212> TYPE: PRT
<213> ORGANISM: Artificial Sequence
<220> FEATURE:
<223> OTHER INFORMATION: Synthetic: GLP1-S8_I_VARcaIgGD

<400> SEQUENCE: 32

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
            20                  25                  30

Gly Gly Gly Gly Ser Gly Gly Gly Ser Gly Gly Gly Ser Gly Gly Gly
        35                  40                  45

Ser Pro Lys Glu Ser Thr Cys Lys Cys Ile Ser Pro Cys Pro Val Pro
    50                  55                  60

Glu Ser Leu Gly Gly Pro Ser Val Phe Ile Phe Pro Pro Lys Pro Lys
65                  70                  75                  80

Asp Thr Leu Leu Ile Ala Arg Thr Pro Glu Ile Thr Cys Val Val Leu
                85                  90                  95

Asp Leu Gly Arg Glu Asp Pro Glu Val Gln Ile Ser Trp Phe Val Asp
            100                 105                 110

Gly Lys Glu Val His Thr Ala Lys Thr Gln Pro Arg Glu Gln Gln Phe
        115                 120                 125

Asn Ser Thr Tyr Arg Val Val Ser Val Leu Pro Ile Gly His Gln Asp
    130                 135                 140
```

```
Trp Leu Thr Gly Lys Glu Phe Lys Cys Arg Val Asn His Ile Gly Leu
145                 150                 155                 160

Pro Ser Pro Ile Glu Arg Thr Ile Ser Lys Ala Arg Gly Gln Ala His
            165                 170                 175

Gln Pro Ser Val Tyr Val Leu Pro Pro Ser Pro Lys Glu Leu Ser Ser
            180                 185                 190

Ser Asp Thr Val Thr Leu Thr Cys Leu Ile Lys Asp Phe Phe Pro Pro
            195                 200                 205

Glu Ile Asp Val Glu Trp Gln Ser Asn Gly Gln Pro Glu Pro Glu Ser
            210                 215                 220

Lys Tyr His Thr Thr Ala Pro Gln Leu Asp Glu Asp Gly Ser Tyr Phe
225                 230                 235                 240

Leu Tyr Ser Lys Leu Ser Val Asp Lys Ser Arg Trp Gln Gln Gly Asp
            245                 250                 255

Thr Phe Thr Cys Ala Val Met His Glu Ala Leu His Asn His Tyr Thr
            260                 265                 270

Asp Leu Ser Leu Ser His Ser Pro Gly Lys
            275                 280

<210> SEQ ID NO 33
<211> LENGTH: 318
<212> TYPE: PRT
<213> ORGANISM: Artificial Sequence
<220> FEATURE:
<223> OTHER INFORMATION: Synthetic: GLP1-G8/GLPL1-3G_III_ VAReqIgG2

<400> SEQUENCE: 33

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
            20                  25                  30

Gly Gly Gly Gly Ser Gly Gly Gly Ser Gly Gly Gly Ser Gly Gly Gly
            35                  40                  45

Ser Asp Met Ser Lys Cys Pro Lys Cys Pro Ala Pro Glu Leu Leu Gly
50                  55                  60

Gly Pro Ser Val Phe Ile Phe Pro Pro Asn Pro Lys Asp Thr Leu Met
65                  70                  75                  80

Ile Ser Arg Thr Pro Val Val Thr Cys Val Val Asn Leu Ser Asp
            85                  90                  95

Gln Tyr Pro Asp Val Gln Phe Ser Trp Tyr Val Asp Asn Thr Glu Val
            100                 105                 110

His Ser Ala Ile Thr Lys Gln Arg Glu Ala Gln Phe Asn Ser Thr Tyr
            115                 120                 125

Arg Val Val Ser Val Leu Pro Ile Gln His Gln Asp Trp Leu Ser Gly
            130                 135                 140

Lys Glu Phe Lys Cys Ser Val Thr Asn Val Gly Val Pro Gln Pro Ile
145                 150                 155                 160

Ser Arg Ala Ile Ser Arg Gly Lys Gly Pro Ser Arg Val Pro Gln Val
            165                 170                 175

Tyr Val Leu Pro Pro His Pro Asp Glu Leu Ala Lys Ser Lys Val Ser
            180                 185                 190

Val Thr Cys Leu Val Lys Asp Phe Tyr Pro Pro Asp Ile Ser Val Glu
            195                 200                 205

Trp Gln Ser Asn Arg Trp Pro Glu Leu Glu Gly Lys Tyr Ser Thr Thr
            210                 215                 220
```

```
Pro Ala Gln Leu Asp Gly Asp Gly Ser Tyr Phe Leu Tyr Ser Lys Leu
225                 230                 235                 240

Ser Leu Glu Thr Ser Arg Trp Gln Gln Val Glu Ser Phe Thr Cys Ala
            245                 250                 255

Val Met His Glu Ala Leu His Asn His Tyr Thr Lys Thr Asp Ile Ser
        260                 265                 270

Glu Ser Leu Gly Lys Gly Gly Gly Ser Gly Gly Gly Gly His Ala
            275                 280                 285

Glu Gly Thr Phe Thr Ser Asp Val Ser Ser Tyr Leu Glu Gly Gln Ala
        290                 295                 300

Ala Lys Glu Phe Ile Ala Trp Leu Val Lys Gly Gly Gly
305                 310                 315

<210> SEQ ID NO 34
<211> LENGTH: 277
<212> TYPE: PRT
<213> ORGANISM: Artificial Sequence
<220> FEATURE:
<223> OTHER INFORMATION: Synthetic: GLP1-G8_I_VAReqIgG2

<400> SEQUENCE: 34

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
            20                  25                  30

Gly Gly Gly Gly Ser Gly Gly Gly Ser Gly Gly Gly Ser Gly Gly Gly
        35                  40                  45

Ser Asp Met Ser Lys Cys Pro Lys Cys Pro Ala Pro Glu Leu Leu Gly
50                  55                  60

Gly Pro Ser Val Phe Ile Phe Pro Pro Asn Pro Lys Asp Thr Leu Met
65                  70                  75                  80

Ile Ser Arg Thr Pro Val Val Thr Cys Val Val Val Asn Leu Ser Asp
            85                  90                  95

Gln Tyr Pro Asp Val Gln Phe Ser Trp Tyr Val Asp Asn Thr Glu Val
            100                 105                 110

His Ser Ala Ile Thr Lys Gln Arg Glu Ala Gln Phe Asn Ser Thr Tyr
        115                 120                 125

Arg Val Val Ser Val Leu Pro Ile Gln His Gln Asp Trp Leu Ser Gly
    130                 135                 140

Lys Glu Phe Lys Cys Ser Val Thr Asn Val Gly Val Pro Gln Pro Ile
145                 150                 155                 160

Ser Arg Ala Ile Ser Arg Gly Lys Gly Pro Ser Arg Val Pro Gln Val
                165                 170                 175

Tyr Val Leu Pro Pro His Pro Asp Glu Leu Ala Lys Ser Lys Val Ser
            180                 185                 190

Val Thr Cys Leu Val Lys Asp Phe Tyr Pro Pro Asp Ile Ser Val Glu
        195                 200                 205

Trp Gln Ser Asn Arg Trp Pro Glu Leu Glu Gly Lys Tyr Ser Thr Thr
    210                 215                 220

Pro Ala Gln Leu Asp Gly Asp Gly Ser Tyr Phe Leu Tyr Ser Lys Leu
225                 230                 235                 240

Ser Leu Glu Thr Ser Arg Trp Gln Gln Val Glu Ser Phe Thr Cys Ala
                245                 250                 255

Val Met His Glu Ala Leu His Asn His Tyr Thr Lys Thr Asp Ile Ser
            260                 265                 270
```

```
Glu Ser Leu Gly Lys
        275

<210> SEQ ID NO 35
<211> LENGTH: 318
<212> TYPE: PRT
<213> ORGANISM: Artificial Sequence
<220> FEATURE:
<223> OTHER INFORMATION: Synthetic: GLP1-S8/GLP1-3G_III_ VAReqIgG2

<400> SEQUENCE: 35

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
            20                  25                  30

Gly Gly Gly Gly Ser Gly Gly Gly Ser Gly Gly Ser Gly Gly Gly Gly
        35                  40                  45

Ser Asp Met Ser Lys Cys Pro Lys Cys Pro Ala Pro Glu Leu Leu Gly
    50                  55                  60

Gly Pro Ser Val Phe Ile Phe Pro Pro Asn Pro Lys Asp Thr Leu Met
65                  70                  75                  80

Ile Ser Arg Thr Pro Val Val Thr Cys Val Val Asn Leu Ser Asp
                85                  90                  95

Gln Tyr Pro Asp Val Gln Phe Ser Trp Tyr Val Asp Asn Thr Glu Val
            100                 105                 110

His Ser Ala Ile Thr Lys Gln Arg Glu Ala Gln Phe Asn Ser Thr Tyr
        115                 120                 125

Arg Val Val Ser Val Leu Pro Ile Gln His Gln Asp Trp Leu Ser Gly
    130                 135                 140

Lys Glu Phe Lys Cys Ser Val Thr Asn Val Gly Val Pro Gln Pro Ile
145                 150                 155                 160

Ser Arg Ala Ile Ser Arg Gly Lys Gly Pro Ser Arg Val Pro Gln Val
                165                 170                 175

Tyr Val Leu Pro Pro His Pro Asp Glu Leu Ala Lys Ser Lys Val Ser
            180                 185                 190

Val Thr Cys Leu Val Lys Asp Phe Tyr Pro Asp Ile Ser Val Glu
        195                 200                 205

Trp Gln Ser Asn Arg Trp Pro Glu Leu Glu Gly Lys Tyr Ser Thr Thr
    210                 215                 220

Pro Ala Gln Leu Asp Gly Asp Gly Ser Tyr Phe Leu Tyr Ser Lys Leu
225                 230                 235                 240

Ser Leu Glu Thr Ser Arg Trp Gln Gln Val Glu Ser Phe Thr Cys Ala
                245                 250                 255

Val Met His Glu Ala Leu His Asn His Tyr Thr Lys Thr Asp Ile Ser
            260                 265                 270

Glu Ser Leu Gly Lys Gly Gly Gly Gly Ser Gly Gly Gly His Ala
        275                 280                 285

Glu Gly Thr Phe Thr Ser Asp Val Ser Ser Tyr Leu Glu Gly Gln Ala
    290                 295                 300

Ala Lys Glu Phe Ile Ala Trp Leu Val Lys Gly Gly Gly Gly
305                 310                 315

<210> SEQ ID NO 36
<211> LENGTH: 277
<212> TYPE: PRT
<213> ORGANISM: Artificial Sequence
```

```
<220> FEATURE:
<223> OTHER INFORMATION: Synthetic: GLP1-S8_I_VAReqIgG2

<400> SEQUENCE: 36

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
            20                  25                  30

Gly Gly Gly Gly Ser Gly Gly Ser Gly Gly Gly Ser Gly Gly Gly
        35                  40                  45

Ser Asp Met Ser Lys Cys Pro Lys Cys Pro Ala Pro Glu Leu Leu Gly
50                  55                  60

Gly Pro Ser Val Phe Ile Phe Pro Pro Asn Pro Lys Asp Thr Leu Met
65                  70                  75                  80

Ile Ser Arg Thr Pro Val Val Thr Cys Val Val Val Asn Leu Ser Asp
                85                  90                  95

Gln Tyr Pro Asp Val Gln Phe Ser Trp Tyr Val Asp Asn Thr Glu Val
            100                 105                 110

His Ser Ala Ile Thr Lys Gln Arg Glu Ala Gln Phe Asn Ser Thr Tyr
        115                 120                 125

Arg Val Val Ser Val Leu Pro Ile Gln His Gln Asp Trp Leu Ser Gly
    130                 135                 140

Lys Glu Phe Lys Cys Ser Val Thr Asn Val Gly Val Pro Gln Pro Ile
145                 150                 155                 160

Ser Arg Ala Ile Ser Arg Gly Lys Gly Pro Ser Arg Val Pro Gln Val
                165                 170                 175

Tyr Val Leu Pro Pro His Pro Asp Glu Leu Ala Lys Ser Lys Val Ser
            180                 185                 190

Val Thr Cys Leu Val Lys Asp Phe Tyr Pro Pro Asp Ile Ser Val Glu
        195                 200                 205

Trp Gln Ser Asn Arg Trp Pro Glu Leu Glu Gly Lys Tyr Ser Thr Thr
    210                 215                 220

Pro Ala Gln Leu Asp Gly Asp Gly Ser Tyr Phe Leu Tyr Ser Lys Leu
225                 230                 235                 240

Ser Leu Glu Thr Ser Arg Trp Gln Gln Val Glu Ser Phe Thr Cys Ala
                245                 250                 255

Val Met His Glu Ala Leu His Asn His Tyr Thr Lys Thr Asp Ile Ser
            260                 265                 270

Glu Ser Leu Gly Lys
        275

<210> SEQ ID NO 37
<211> LENGTH: 346
<212> TYPE: PRT
<213> ORGANISM: Artificial Sequence
<220> FEATURE:
<223> OTHER INFORMATION: Synthetic: ssGLP1-S8/GLP1-3G_III_ WTfeIgG2

<400> SEQUENCE: 37

Met Ala Val Leu Gly Leu Leu Phe Cys Leu Val Thr Phe Pro Ser Cys
1               5                   10                  15

Val Leu Ser His Ser Glu Gly Thr Phe Thr Ser Asp Val Ser Ser Tyr
            20                  25                  30

Leu Glu Gly Gln Ala Ala Lys Glu Phe Ile Ala Trp Leu Val Lys Gly
        35                  40                  45

Gly Ala Gly Gly Gly Gly Gly Ser Gly Gly Gly Ser Gly Gly Gly Ser
```

```
            50                  55                  60
Gly Gly Gly Ser Pro Lys Thr Ala Ser Thr Ile Glu Ser Lys Thr Gly
 65                  70                  75                  80

Glu Gly Pro Lys Cys Pro Val Pro Glu Ile Pro Gly Ala Pro Ser Val
                 85                  90                  95

Phe Ile Phe Pro Pro Lys Pro Lys Asp Thr Leu Ser Ile Ser Arg Thr
            100                 105                 110

Pro Glu Val Thr Cys Leu Val Val Asp Leu Gly Pro Asp Asp Ser Asn
        115                 120                 125

Val Gln Ile Thr Trp Phe Val Asp Asn Thr Glu Met His Thr Ala Lys
    130                 135                 140

Thr Arg Pro Arg Glu Glu Gln Phe Asn Ser Thr Tyr Arg Val Val Ser
145                 150                 155                 160

Val Leu Pro Ile Leu His Gln Asp Trp Leu Lys Gly Lys Glu Phe Lys
                165                 170                 175

Cys Lys Val Asn Ser Lys Ser Leu Pro Ser Ala Met Glu Arg Thr Ile
            180                 185                 190

Ser Lys Ala Lys Gly Gln Pro His Glu Pro Gln Val Tyr Val Leu Pro
        195                 200                 205

Pro Thr Gln Glu Glu Leu Ser Glu Asn Lys Val Ser Val Thr Cys Leu
    210                 215                 220

Ile Lys Gly Phe His Pro Pro Asp Ile Ala Val Glu Trp Glu Ile Thr
225                 230                 235                 240

Gly Gln Pro Glu Pro Glu Asn Asn Tyr Gln Thr Thr Pro Pro Gln Leu
                245                 250                 255

Asp Ser Asp Gly Thr Tyr Phe Leu Tyr Ser Arg Leu Ser Val Asp Arg
            260                 265                 270

Ser His Trp Gln Arg Gly Asn Thr Tyr Thr Cys Ser Val Ser His Glu
        275                 280                 285

Ala Leu His Ser His His Thr Gln Lys Ser Leu Thr Gln Ser Pro Gly
    290                 295                 300

Lys Gly Gly Gly Gly Ser Gly Gly Gly His Ala Glu Gly Thr Phe
305                 310                 315                 320

Thr Ser Asp Val Ser Ser Tyr Leu Glu Gly Gln Ala Ala Lys Glu Phe
                325                 330                 335

Ile Ala Trp Leu Val Lys Gly Gly Gly
            340                 345

<210> SEQ ID NO 38
<211> LENGTH: 344
<212> TYPE: PRT
<213> ORGANISM: Artificial Sequence
<220> FEATURE:
<223> OTHER INFORMATION: Synthetic: ssGLP1-G8/GLP1-2G_III_ VARfeIgG2

<400> SEQUENCE: 38

Met Ala Val Leu Gly Leu Leu Phe Cys Leu Val Thr Phe Pro Ser Cys
  1               5                  10                  15

Val Leu Ser His Gly Glu Gly Thr Phe Thr Ser Asp Val Ser Ser Tyr
                 20                  25                  30

Leu Glu Gly Gln Ala Ala Lys Glu Phe Ile Ala Trp Leu Val Lys Gly
             35                  40                  45

Gly Gly Gly Ser Gly Gly Gly Ser Gly Gly Gly Ser Gly Gly
         50                  55                  60

Gly Gly Ser Pro Lys Thr Ala Ser Thr Ile Glu Ser Lys Thr Gly Glu
```

```
                65                  70                  75                  80
Cys Pro Lys Cys Pro Val Pro Glu Ile Pro Gly Ala Pro Ser Val Phe
                    85                  90                  95
Ile Phe Pro Pro Lys Pro Lys Asp Thr Leu Ser Ile Ser Arg Thr Pro
            100                 105                 110
Glu Val Thr Cys Leu Val Val Asp Leu Gly Pro Asp Asp Ser Asn Val
            115                 120                 125
Gln Ile Thr Trp Phe Val Asp Asn Thr Glu Met His Thr Ala Lys Thr
        130                 135                 140
Arg Pro Arg Glu Glu Gln Phe Asn Ser Thr Tyr Arg Val Val Ser Val
145                 150                 155                 160
Leu Pro Ile Leu His Gln Asp Trp Leu Lys Gly Lys Glu Phe Lys Cys
                165                 170                 175
Lys Val Asn Ser Lys Ser Leu Pro Ser Ala Met Glu Arg Thr Ile Ser
            180                 185                 190
Lys Ala Lys Gly Gln Pro His Glu Pro Gln Val Tyr Val Leu Pro Pro
        195                 200                 205
Thr Gln Glu Glu Leu Ser Glu Asn Lys Val Ser Val Thr Cys Leu Ile
        210                 215                 220
Lys Gly Phe His Pro Pro Asp Ile Ala Val Glu Trp Glu Ile Thr Gly
225                 230                 235                 240
Gln Pro Glu Pro Glu Asn Asn Tyr Gln Thr Thr Pro Pro Gln Leu Asp
                245                 250                 255
Ser Asp Gly Thr Tyr Phe Leu Tyr Ser Arg Leu Ser Val Asp Arg Ser
            260                 265                 270
His Trp Gln Arg Gly Asn Thr Tyr Thr Cys Ser Val Ser His Glu Ala
        275                 280                 285
Leu His Ser His His Thr Gln Lys Ser Leu Thr Gln Ser Pro Gly Lys
        290                 295                 300
Gly Gly Gly Gly Ser Gly Gly Gly His Ala Glu Gly Thr Phe Thr
305                 310                 315                 320
Ser Asp Val Ser Ser Tyr Leu Glu Gly Gln Ala Ala Lys Glu Phe Ile
                325                 330                 335
Ala Trp Leu Val Lys Gly Gly Gly
                340

<210> SEQ ID NO 39
<211> LENGTH: 304
<212> TYPE: PRT
<213> ORGANISM: Artificial Sequence
<220> FEATURE:
<223> OTHER INFORMATION: Synthetic: ssGLP1-G8_I_VARfeIgG2

<400> SEQUENCE: 39

Met Ala Val Leu Gly Leu Leu Phe Cys Leu Val Thr Phe Pro Ser Cys
1               5                   10                  15
Val Leu Ser His Gly Glu Gly Thr Phe Thr Ser Asp Val Ser Ser Tyr
                20                  25                  30
Leu Glu Gly Gln Ala Ala Lys Glu Phe Ile Ala Trp Leu Val Lys Gly
        35                  40                  45
Gly Gly Gly Ser Gly Gly Gly Gly Ser Gly Gly Gly Gly Ser Gly Gly
    50                  55                  60
Gly Gly Ser Pro Lys Thr Ala Ser Thr Ile Glu Ser Lys Thr Gly Glu
65                  70                  75                  80
Cys Pro Lys Cys Pro Val Pro Glu Ile Pro Gly Ala Pro Ser Val Phe
```

```
                85                  90                  95
Ile Phe Pro Pro Lys Pro Lys Asp Thr Leu Ser Ile Ser Arg Thr Pro
            100                 105                 110

Glu Val Thr Cys Leu Val Val Asp Leu Gly Pro Asp Asp Ser Asn Val
            115                 120                 125

Gln Ile Thr Trp Phe Val Asp Asn Thr Glu Met His Thr Ala Lys Thr
        130                 135                 140

Arg Pro Arg Glu Glu Gln Phe Asn Ser Thr Tyr Arg Val Val Ser Val
145                 150                 155                 160

Leu Pro Ile Leu His Gln Asp Trp Leu Lys Gly Lys Glu Phe Lys Cys
                165                 170                 175

Lys Val Asn Ser Lys Ser Leu Pro Ser Ala Met Glu Arg Thr Ile Ser
            180                 185                 190

Lys Ala Lys Gly Gln Pro His Glu Pro Gln Val Tyr Val Leu Pro Pro
        195                 200                 205

Thr Gln Glu Glu Leu Ser Glu Asn Lys Val Ser Val Thr Cys Leu Ile
    210                 215                 220

Lys Gly Phe His Pro Pro Asp Ile Ala Val Glu Trp Glu Ile Thr Gly
225                 230                 235                 240

Gln Pro Glu Pro Glu Asn Asn Tyr Gln Thr Thr Pro Pro Gln Leu Asp
                245                 250                 255

Ser Asp Gly Thr Tyr Phe Leu Tyr Ser Arg Leu Ser Val Asp Arg Ser
            260                 265                 270

His Trp Gln Arg Gly Asn Thr Tyr Thr Cys Ser Val Ser His Glu Ala
        275                 280                 285

Leu His Ser His His Thr Gln Lys Ser Leu Thr Gln Ser Pro Gly Lys
    290                 295                 300

<210> SEQ ID NO 40
<211> LENGTH: 305
<212> TYPE: PRT
<213> ORGANISM: Artificial Sequence
<220> FEATURE:
<223> OTHER INFORMATION: Synthetic: ssGLP1-S8_I_WTfeIgG2

<400> SEQUENCE: 40

Met Ala Val Leu Gly Leu Leu Phe Cys Leu Val Thr Phe Pro Ser Cys
1               5                   10                  15

Val Leu Ser His Ser Glu Gly Thr Phe Thr Ser Asp Val Ser Ser Tyr
            20                  25                  30

Leu Glu Gly Gln Ala Ala Lys Glu Phe Ile Ala Trp Leu Val Lys Gly
        35                  40                  45

Gly Ala Gly Gly Gly Gly Ser Gly Gly Gly Ser Gly Gly Gly Gly Ser
    50                  55                  60

Gly Gly Gly Ser Pro Lys Thr Ala Ser Thr Ile Glu Ser Lys Thr Gly
65                  70                  75                  80

Glu Gly Pro Lys Cys Pro Val Pro Glu Ile Pro Gly Ala Pro Ser Val
                85                  90                  95

Phe Ile Phe Pro Pro Lys Pro Lys Asp Thr Leu Ser Ile Ser Arg Thr
            100                 105                 110

Pro Glu Val Thr Cys Leu Val Val Asp Leu Gly Pro Asp Asp Ser Asn
        115                 120                 125

Val Gln Ile Thr Trp Phe Val Asp Asn Thr Glu Met His Thr Ala Lys
    130                 135                 140

Thr Arg Pro Arg Glu Glu Gln Phe Asn Ser Thr Tyr Arg Val Val Ser
```

```
            145                 150                 155                 160
Val Leu Pro Ile Leu His Gln Asp Trp Leu Lys Gly Lys Glu Phe Lys
                165                 170                 175
Cys Lys Val Asn Ser Lys Ser Leu Pro Ser Ala Met Glu Arg Thr Ile
                180                 185                 190
Ser Lys Ala Lys Gly Gln Pro His Glu Pro Gln Val Tyr Val Leu Pro
                195                 200                 205
Pro Thr Gln Glu Glu Leu Ser Glu Asn Lys Val Ser Val Thr Cys Leu
                210                 215                 220
Ile Lys Gly Phe His Pro Pro Asp Ile Ala Val Glu Trp Glu Ile Thr
225                 230                 235                 240
Gly Gln Pro Glu Pro Glu Asn Asn Tyr Gln Thr Thr Pro Pro Gln Leu
                245                 250                 255
Asp Ser Asp Gly Thr Tyr Phe Leu Tyr Ser Arg Leu Ser Val Asp Arg
                260                 265                 270
Ser His Trp Gln Arg Gly Asn Thr Tyr Thr Cys Ser Val Ser His Glu
                275                 280                 285
Ala Leu His Ser His His Thr Gln Lys Ser Leu Thr Gln Ser Pro Gly
                290                 295                 300
Lys
305

<210> SEQ ID NO 41
<211> LENGTH: 340
<212> TYPE: PRT
<213> ORGANISM: Artificial Sequence
<220> FEATURE:
<223> OTHER INFORMATION: Synthetic: ssGLP1-G8/GLP1-2G_III_ VARcaIgGD

<400> SEQUENCE: 41

Met Ala Val Leu Gly Leu Leu Phe Cys Leu Val Thr Phe Pro Ser Cys
1               5                   10                  15
Val Leu Ser His Gly Glu Gly Thr Phe Thr Ser Asp Val Ser Ser Tyr
                20                  25                  30
Leu Glu Gly Gln Ala Ala Lys Glu Phe Ile Ala Trp Leu Val Lys Gly
                35                  40                  45
Gly Gly Gly Ser Gly Gly Gly Ser Gly Gly Gly Ser Gly Gly
            50                  55                  60
Gly Gly Ser Pro Lys Glu Ser Thr Cys Lys Cys Ile Ser Pro Cys Pro
65                  70                  75                  80
Val Pro Glu Ser Leu Gly Gly Pro Ser Val Phe Ile Phe Pro Pro Lys
                85                  90                  95
Pro Lys Asp Thr Leu Leu Ile Ala Arg Thr Pro Glu Ile Thr Cys Val
                100                 105                 110
Val Leu Asp Leu Gly Arg Glu Asp Pro Glu Val Gln Ile Ser Trp Phe
                115                 120                 125
Val Asp Gly Lys Glu Val His Thr Ala Lys Thr Gln Pro Arg Glu Gln
                130                 135                 140
Gln Phe Asn Ser Thr Tyr Arg Val Val Ser Val Leu Pro Ile Gly His
145                 150                 155                 160
Gln Asp Trp Leu Thr Gly Lys Glu Phe Lys Cys Arg Val Asn His Ile
                165                 170                 175
Gly Leu Pro Ser Pro Ile Glu Arg Thr Ile Ser Lys Ala Arg Gly Gln
                180                 185                 190
Ala His Gln Pro Ser Val Tyr Val Leu Pro Pro Ser Pro Lys Glu Leu
```

```
            195                 200                 205
Ser Ser Ser Asp Thr Val Thr Leu Thr Cys Leu Ile Lys Asp Phe Phe
    210                 215                 220

Pro Pro Glu Ile Asp Val Glu Trp Gln Ser Asn Gly Gln Pro Glu Pro
225                 230                 235                 240

Glu Ser Lys Tyr His Thr Thr Ala Pro Gln Leu Asp Glu Asp Gly Ser
                245                 250                 255

Tyr Phe Leu Tyr Ser Lys Leu Ser Val Asp Lys Ser Arg Trp Gln Gln
                260                 265                 270

Gly Asp Thr Phe Thr Cys Ala Val Met His Glu Ala Leu His Asn His
                275                 280                 285

Tyr Thr Asp Leu Ser Leu Ser His Ser Pro Gly Lys Gly Gly Gly Gly
                290                 295                 300

Ser Gly Gly Gly Gly His Ala Glu Gly Thr Phe Thr Ser Asp Val Ser
305                 310                 315                 320

Ser Tyr Leu Glu Gly Gln Ala Ala Lys Glu Phe Ile Ala Trp Leu Val
                325                 330                 335

Lys Gly Gly Gly
            340

<210> SEQ ID NO 42
<211> LENGTH: 340
<212> TYPE: PRT
<213> ORGANISM: Artificial Sequence
<220> FEATURE:
<223> OTHER INFORMATION: Synthetic: ssGLP1-G8/GLP1-2G_III_ VARcaIgGD

<400> SEQUENCE: 42

Met Ala Val Leu Gly Leu Leu Phe Cys Leu Val Thr Phe Pro Ser Cys
1               5                   10                  15

Val Leu Ser His Gly Glu Gly Thr Phe Thr Ser Asp Val Ser Ser Tyr
                20                  25                  30

Leu Glu Gly Gln Ala Ala Lys Glu Phe Ile Ala Trp Leu Val Lys Gly
                35                  40                  45

Gly Gly Gly Ser Gly Gly Gly Gly Ser Gly Gly Gly Gly Ser Gly Gly
        50                  55                  60

Gly Gly Ser Pro Lys Glu Ser Thr Ser Lys Cys Ile Ser Pro Cys Pro
65                  70                  75                  80

Val Pro Glu Ser Leu Gly Gly Pro Ser Val Phe Ile Phe Pro Pro Lys
                85                  90                  95

Pro Lys Asp Thr Leu Leu Ile Ala Arg Thr Pro Glu Ile Thr Cys Val
                100                 105                 110

Val Leu Asp Leu Gly Arg Glu Asp Pro Glu Val Gln Ile Ser Trp Phe
            115                 120                 125

Val Asp Gly Lys Glu Val His Thr Ala Lys Thr Gln Pro Arg Glu Gln
        130                 135                 140

Gln Phe Asn Ser Thr Tyr Arg Val Val Ser Val Leu Pro Ile Gly His
145                 150                 155                 160

Gln Asp Trp Leu Thr Gly Lys Glu Phe Lys Cys Arg Val Asn His Ile
                165                 170                 175

Gly Leu Pro Ser Pro Ile Glu Arg Thr Ile Ser Lys Ala Arg Gly Gln
                180                 185                 190

Ala His Gln Pro Ser Val Tyr Val Leu Pro Pro Ser Pro Lys Glu Leu
            195                 200                 205

Ser Ser Ser Asp Thr Val Thr Leu Thr Cys Leu Ile Lys Asp Phe Phe
```

```
                210                 215                 220
Pro Pro Glu Ile Asp Val Glu Trp Gln Ser Asn Gly Gln Pro Glu Pro
225                 230                 235                 240

Glu Ser Lys Tyr His Thr Thr Ala Pro Gln Leu Asp Glu Asp Gly Ser
                245                 250                 255

Tyr Phe Leu Tyr Ser Lys Leu Ser Val Asp Lys Ser Arg Trp Gln Gln
            260                 265                 270

Gly Asp Thr Phe Thr Cys Ala Val Met His Glu Ala Leu His Asn His
        275                 280                 285

Tyr Thr Asp Leu Ser Leu Ser His Ser Pro Gly Lys Gly Gly Gly Gly
    290                 295                 300

Ser Gly Gly Gly Gly His Ala Glu Gly Thr Phe Thr Ser Asp Val Ser
305                 310                 315                 320

Ser Tyr Leu Glu Gly Gln Ala Ala Lys Glu Phe Ile Ala Trp Leu Val
                325                 330                 335

Lys Gly Gly Gly
            340
```

<210> SEQ ID NO 43
<211> LENGTH: 342
<212> TYPE: PRT
<213> ORGANISM: Artificial Sequence
<220> FEATURE:
<223> OTHER INFORMATION: Synthetic: ssGLP1-S8/GLP1-3G_III_ VARcaIgGD

<400> SEQUENCE: 43

```
Met Ala Val Leu Gly Leu Leu Phe Cys Leu Val Thr Phe Pro Ser Cys
1               5                   10                  15

Val Leu Ser His Ser Glu Gly Thr Phe Thr Ser Asp Val Ser Ser Tyr
                20                  25                  30

Leu Glu Gly Gln Ala Ala Lys Glu Phe Ile Ala Trp Leu Val Lys Gly
            35                  40                  45

Gly Ala Gly Gly Gly Gly Ser Gly Gly Gly Ser Gly Gly Gly Ser
    50                  55                  60

Gly Gly Gly Ser Pro Lys Glu Ser Thr Ser Lys Cys Ile Ser Pro Cys
65                  70                  75                  80

Pro Val Pro Glu Ser Leu Gly Gly Pro Ser Val Phe Ile Phe Pro Pro
                85                  90                  95

Lys Pro Lys Asp Thr Leu Leu Ile Ala Arg Thr Pro Glu Ile Thr Cys
            100                 105                 110

Val Val Leu Asp Leu Gly Arg Glu Asp Pro Glu Val Gln Ile Ser Trp
        115                 120                 125

Phe Val Asp Gly Lys Glu Val His Thr Ala Lys Thr Gln Pro Arg Glu
    130                 135                 140

Gln Gln Phe Asn Ser Thr Tyr Arg Val Val Ser Val Leu Pro Ile Gly
145                 150                 155                 160

His Gln Asp Trp Leu Thr Gly Lys Glu Phe Lys Cys Arg Val Asn His
                165                 170                 175

Ile Gly Leu Pro Ser Pro Ile Glu Arg Thr Ile Ser Lys Ala Arg Gly
            180                 185                 190

Gln Ala His Gln Pro Ser Val Tyr Val Leu Pro Pro Ser Pro Lys Glu
        195                 200                 205

Leu Ser Ser Ser Asp Thr Val Thr Leu Thr Cys Leu Ile Lys Asp Phe
    210                 215                 220

Phe Pro Pro Glu Ile Asp Val Glu Trp Gln Ser Asn Gly Gln Pro Glu
```

```
            225                 230                 235                 240

Pro Glu Ser Lys Tyr His Thr Thr Ala Pro Gln Leu Asp Glu Asp Gly
                245                 250                 255

Ser Tyr Phe Leu Tyr Ser Lys Leu Ser Val Asp Lys Ser Arg Trp Gln
                260                 265                 270

Gln Gly Asp Thr Phe Thr Cys Ala Val Met His Glu Ala Leu His Asn
                275                 280                 285

His Tyr Thr Asp Leu Ser Leu Ser His Ser Pro Gly Lys Gly Gly Gly
                290                 295                 300

Gly Ser Gly Gly Gly Gly His Ala Glu Gly Thr Phe Thr Ser Asp Val
305                 310                 315                 320

Ser Ser Tyr Leu Glu Gly Gln Ala Ala Lys Glu Phe Ile Ala Trp Leu
                325                 330                 335

Val Lys Gly Gly Gly Gly
                340

<210> SEQ ID NO 44
<211> LENGTH: 337
<212> TYPE: PRT
<213> ORGANISM: Artificial Sequence
<220> FEATURE:
<223> OTHER INFORMATION: Synthetic: ssGLP1-G8/GLP1-3G_III_ VAReqIgG2

<400> SEQUENCE: 44

Met Ala Val Leu Gly Leu Leu Phe Cys Leu Val Thr Phe Pro Ser Cys
1               5                   10                  15

Val Leu Ser His Gly Glu Gly Thr Phe Thr Ser Asp Val Ser Ser Tyr
                20                  25                  30

Leu Glu Gly Gln Ala Ala Lys Glu Phe Ile Ala Trp Leu Val Lys Gly
            35                  40                  45

Gly Ala Gly Gly Gly Gly Ser Gly Gly Ser Gly Gly Gly Ser
        50                  55                  60

Gly Gly Gly Ser Asp Met Ser Lys Cys Pro Lys Cys Pro Ala Pro Glu
65                  70                  75                  80

Leu Leu Gly Gly Pro Ser Val Phe Ile Phe Pro Pro Asn Pro Lys Asp
                85                  90                  95

Thr Leu Met Ile Ser Arg Thr Pro Val Val Thr Cys Val Val Val Asn
                100                 105                 110

Leu Ser Asp Gln Tyr Pro Asp Val Gln Phe Ser Trp Tyr Val Asp Asn
            115                 120                 125

Thr Glu Val His Ser Ala Ile Thr Lys Gln Arg Glu Ala Gln Phe Asn
        130                 135                 140

Ser Thr Tyr Arg Val Val Ser Val Leu Pro Ile Gln His Gln Asp Trp
145                 150                 155                 160

Leu Ser Gly Lys Glu Phe Lys Cys Ser Val Thr Asn Val Gly Val Pro
                165                 170                 175

Gln Pro Ile Ser Arg Ala Ile Ser Arg Gly Lys Gly Pro Ser Arg Val
                180                 185                 190

Pro Gln Val Tyr Val Leu Pro Pro His Pro Asp Glu Leu Ala Lys Ser
            195                 200                 205

Lys Val Ser Val Thr Cys Leu Val Lys Asp Phe Tyr Pro Pro Asp Ile
        210                 215                 220

Ser Val Glu Trp Gln Ser Asn Arg Trp Pro Glu Leu Glu Gly Lys Tyr
225                 230                 235                 240

Ser Thr Thr Pro Ala Gln Leu Asp Gly Asp Gly Ser Tyr Phe Leu Tyr
```

```
                245                 250                 255
Ser Lys Leu Ser Leu Glu Thr Ser Arg Trp Gln Gln Val Glu Ser Phe
            260                 265                 270

Thr Cys Ala Val Met His Glu Ala Leu His Asn His Tyr Thr Lys Thr
        275                 280                 285

Asp Ile Ser Glu Ser Leu Gly Lys Gly Gly Gly Ser Gly Gly Gly
    290                 295                 300

Gly His Ala Glu Gly Thr Phe Thr Ser Asp Val Ser Ser Tyr Leu Glu
305                 310                 315                 320

Gly Gln Ala Ala Lys Glu Phe Ile Ala Trp Leu Val Lys Gly Gly Gly
            325                 330                 335

Gly

<210> SEQ ID NO 45
<211> LENGTH: 298
<212> TYPE: PRT
<213> ORGANISM: Artificial Sequence
<220> FEATURE:
<223> OTHER INFORMATION: Synthetic: ssGLP1-G8_I_VAReqIgG2

<400> SEQUENCE: 45

Met Ala Val Leu Gly Leu Leu Phe Cys Leu Val Thr Phe Pro Ser Cys
1               5                   10                  15

Val Leu Ser His Gly Glu Gly Thr Phe Thr Ser Asp Val Ser Ser Tyr
            20                  25                  30

Leu Glu Gly Gln Ala Ala Lys Glu Phe Ile Ala Trp Leu Val Lys Gly
        35                  40                  45

Gly Ala Gly Gly Gly Gly Ser Gly Gly Ser Gly Gly Gly Ser
    50                  55                  60

Gly Gly Gly Ser Ser Val Pro Lys Pro Gln Cys Pro Pro Tyr Thr His
65                  70                  75                  80

Ser Lys Phe Leu Gly Gly Pro Ser Val Phe Ile Phe Pro Pro Asn Pro
                85                  90                  95

Lys Asp Thr Leu Met Ile Ser Arg Thr Pro Val Val Thr Cys Val Val
            100                 105                 110

Val Asn Leu Ser Asp Gln Tyr Pro Asp Val Gln Phe Ser Trp Tyr Val
        115                 120                 125

Asp Asn Thr Glu Val His Ser Ala Ile Thr Lys Gln Arg Glu Ala Gln
145                 150                 155                 160
                130                 135                 140

Phe Asn Ser Thr Tyr Arg Val Val Ser Val Leu Pro Ile Gln His Gln
145                 150                 155                 160

Asp Trp Leu Ser Gly Lys Glu Phe Lys Cys Ser Val Thr Asn Val Gly
                165                 170                 175

Val Pro Gln Pro Ile Ser Arg Ala Ile Ser Arg Gly Lys Gly Pro Ser
            180                 185                 190

Arg Val Pro Gln Val Tyr Val Leu Pro Pro His Pro Asp Glu Leu Ala
        195                 200                 205

Lys Ser Lys Val Ser Val Thr Cys Leu Val Lys Asp Phe Tyr Pro Pro
    210                 215                 220

Asp Ile Ser Val Glu Trp Gln Ser Asn Arg Trp Pro Glu Leu Glu Gly
225                 230                 235                 240

Lys Tyr Ser Thr Thr Pro Ala Gln Leu Asp Gly Asp Gly Ser Tyr Phe
                245                 250                 255

Leu Tyr Ser Lys Leu Ser Leu Glu Thr Ser Arg Trp Gln Gln Val Glu
            260                 265                 270
```

Ser Phe Thr Cys Ala Val Met His Glu Ala Leu His Asn His Tyr Thr
            275                 280                 285

Lys Thr Asp Ile Ser Glu Ser Leu Gly Lys
    290                 295

<210> SEQ ID NO 46
<211> LENGTH: 337
<212> TYPE: PRT
<213> ORGANISM: Artificial Sequence
<220> FEATURE:
<223> OTHER INFORMATION: Synthetic: ssGLP1-S8/GLP1-3G_III_ VAReqIgG2

<400> SEQUENCE: 46

Met Ala Val Leu Gly Leu Leu Phe Cys Leu Val Thr Phe Pro Ser Cys
1               5                   10                  15

Val Leu Ser His Ser Glu Gly Thr Phe Thr Ser Asp Val Ser Ser Tyr
            20                  25                  30

Leu Glu Gly Gln Ala Ala Lys Glu Phe Ile Ala Trp Leu Val Lys Gly
        35                  40                  45

Gly Ala Gly Gly Gly Gly Ser Gly Gly Gly Ser Gly Gly Gly Ser
    50                  55                  60

Gly Gly Gly Ser Asp Met Ser Lys Cys Pro Lys Cys Pro Ala Pro Glu
65                  70                  75                  80

Leu Leu Gly Gly Pro Ser Val Phe Ile Phe Pro Pro Asn Pro Lys Asp
                85                  90                  95

Thr Leu Met Ile Ser Arg Thr Pro Val Val Thr Cys Val Val Val Asn
            100                 105                 110

Leu Ser Asp Gln Tyr Pro Asp Val Gln Phe Ser Trp Tyr Val Asp Asn
        115                 120                 125

Thr Glu Val His Ser Ala Ile Thr Lys Gln Arg Glu Ala Gln Phe Asn
    130                 135                 140

Ser Thr Tyr Arg Val Val Ser Val Leu Pro Ile Gln His Gln Asp Trp
145                 150                 155                 160

Leu Ser Gly Lys Glu Phe Lys Cys Ser Val Thr Asn Val Gly Val Pro
                165                 170                 175

Gln Pro Ile Ser Arg Ala Ile Ser Arg Gly Lys Gly Pro Ser Arg Val
            180                 185                 190

Pro Gln Val Tyr Val Leu Pro Pro His Pro Asp Glu Leu Ala Lys Ser
        195                 200                 205

Lys Val Ser Val Thr Cys Leu Val Lys Asp Phe Tyr Pro Pro Asp Ile
    210                 215                 220

Ser Val Glu Trp Gln Ser Asn Arg Trp Pro Glu Leu Glu Gly Lys Tyr
225                 230                 235                 240

Ser Thr Thr Pro Ala Gln Leu Asp Gly Asp Gly Ser Tyr Phe Leu Tyr
                245                 250                 255

Ser Lys Leu Ser Leu Glu Thr Ser Arg Trp Gln Gln Val Glu Ser Phe
            260                 265                 270

Thr Cys Ala Val Met His Glu Ala Leu His Asn His Tyr Thr Lys Thr
        275                 280                 285

Asp Ile Ser Glu Ser Leu Gly Lys Gly Gly Gly Ser Gly Gly Gly
    290                 295                 300

Gly His Ala Glu Gly Thr Phe Thr Ser Asp Val Ser Ser Tyr Leu Glu
305                 310                 315                 320

Gly Gln Ala Ala Lys Glu Phe Ile Ala Trp Leu Val Lys Gly Gly Gly
                325                 330                 335

Gly

<210> SEQ ID NO 47
<211> LENGTH: 298
<212> TYPE: PRT
<213> ORGANISM: Artificial Sequence
<220> FEATURE:
<223> OTHER INFORMATION: Synthetic: ssGLP1-S8_I_VAReqIgG2

<400> SEQUENCE: 47

```
Met Ala Val Leu Gly Leu Leu Phe Cys Leu Val Thr Phe Pro Ser Cys
1               5                   10                  15

Val Leu Ser His Ser Glu Gly Thr Phe Thr Ser Asp Val Ser Ser Tyr
            20                  25                  30

Leu Glu Gly Gln Ala Ala Lys Glu Phe Ile Ala Trp Leu Val Lys Gly
        35                  40                  45

Gly Ala Gly Gly Gly Gly Ser Gly Gly Ser Gly Gly Gly Ser
    50                  55                  60

Gly Gly Gly Ser Ser Val Pro Lys Pro Gln Cys Pro Pro Tyr Thr His
65                  70                  75                  80

Ser Lys Phe Leu Gly Gly Pro Ser Val Phe Ile Phe Pro Pro Asn Pro
                85                  90                  95

Lys Asp Thr Leu Met Ile Ser Arg Thr Pro Val Val Thr Cys Val Val
            100                 105                 110

Val Asn Leu Ser Asp Gln Tyr Pro Asp Val Gln Phe Ser Trp Tyr Val
        115                 120                 125

Asp Asn Thr Glu Val His Ser Ala Ile Thr Lys Gln Arg Glu Ala Gln
130                 135                 140

Phe Asn Ser Thr Tyr Arg Val Val Ser Val Leu Pro Ile Gln His Gln
145                 150                 155                 160

Asp Trp Leu Ser Gly Lys Glu Phe Lys Cys Ser Val Thr Asn Val Gly
                165                 170                 175

Val Pro Gln Pro Ile Ser Arg Ala Ile Ser Arg Gly Lys Gly Pro Ser
            180                 185                 190

Arg Val Pro Gln Val Tyr Val Leu Pro Pro His Pro Asp Glu Leu Ala
        195                 200                 205

Lys Ser Lys Val Ser Val Thr Cys Leu Val Lys Asp Phe Tyr Pro Pro
210                 215                 220

Asp Ile Ser Val Glu Trp Gln Ser Asn Arg Trp Pro Glu Leu Glu Gly
225                 230                 235                 240

Lys Tyr Ser Thr Thr Pro Ala Gln Leu Asp Gly Asp Ser Tyr Phe
                245                 250                 255

Leu Tyr Ser Lys Leu Ser Leu Glu Thr Ser Arg Trp Gln Gln Val Glu
            260                 265                 270

Ser Phe Thr Cys Ala Val Met His Glu Ala Leu His Asn His Tyr Thr
        275                 280                 285

Lys Thr Asp Ile Ser Glu Ser Leu Gly Lys
    290                 295
```

<210> SEQ ID NO 48
<211> LENGTH: 757
<212> TYPE: PRT
<213> ORGANISM: Artificial Sequence
<220> FEATURE:
<223> OTHER INFORMATION: Synthetic: Feline glucagon-like peptide 1
      receptor (GLP1R)

```
<400> SEQUENCE: 48

Met Gly Leu Val Ala Pro Val Val Leu Leu His Gln Asp Asp Glu Glu
1               5                   10                  15

His Gly Gln Asp Glu Gly Pro Glu Asp Gly Ser Gly Tyr Leu Leu Gly
                20                  25                  30

Thr Leu Thr Arg Phe Ser Ser Asp Phe Asp Ser Ala Pro Glu Val Ile
            35                  40                  45

Leu Ala Pro Asp Asp Gln Leu Gln Leu Pro His Pro Ser Ser Arg Glu
    50                  55                  60

Asn Phe Trp Ala Arg Thr Gly Leu Cys Ala Glu Ser Phe Leu Leu Arg
65                  70                  75                  80

Pro Val Gly Pro Val Gly Pro Val Met Gly Trp Ser Glu Gly Phe His
                85                  90                  95

Lys Arg Asn Ser Arg Gln Glu Phe Leu Arg Arg Leu Phe Ala Gly
                100                 105                 110

Gly Leu Cys Ala Ala Ser Thr Gln Glu Ser Arg Asn Arg Cys Ser Ser
            115                 120                 125

Arg Gly Cys Lys Ser Ser Pro Ala Asp Cys Pro Glu Leu Asp Arg Thr
    130                 135                 140

Gln His Leu Gly Asn Ser Val Gly Pro Ile Gln Ala Ala His Gln Glu
145                 150                 155                 160

Leu Ala Leu Gly Ala Gly Gly Pro Gly Asp Glu Cys Gln Cys Cys Ser
                165                 170                 175

Val Ser Asn Ser Leu Phe Ile Pro Glu Pro Gln Ser Thr Cys Pro Tyr
            180                 185                 190

Asn Gly Tyr Thr Ser Trp Pro Leu Glu Gly Asn Leu Arg Val Ala Cys
    195                 200                 205

Ala Pro Pro Pro Pro Pro Ala Arg Thr Leu Phe Gly Gly Ser Arg
210                 215                 220

Arg Gly Ala Val Asp Lys Lys Ala Gly Gly Asn Arg Ser Pro Gly
225                 230                 235                 240

Gly Gly Ala Gly Thr Gly Glu Phe Gly Ala Pro Gly Ala Gly Gly
                245                 250                 255

Leu Gly Arg Arg Pro Glu Val Gly Ala Trp Thr Ala Ala Glu Gly Thr
            260                 265                 270

Asn Pro Ala Asp Leu Ala Ser Ser Pro Pro Pro Ser Thr Arg Pro
            275                 280                 285

Pro Ala Ala Pro Arg Pro Pro Cys Ala Asp Phe Cys Ala Ala Ser Pro
    290                 295                 300

Gln Thr Thr Phe Pro Thr Pro Ser Pro Arg Arg Pro Leu Pro Ala Ser
305                 310                 315                 320

Gly Gly Ala Thr Val Ser Leu Ser Glu Thr Val Gln Lys Trp Arg Glu
                325                 330                 335

Tyr Arg His Gln Cys Gln Arg Phe Leu Thr Glu Ala Pro Pro Ala
                340                 345                 350

Thr Gly Leu Phe Cys Asn Arg Thr Phe Asp Glu Tyr Ala Cys Trp Pro
            355                 360                 365

Asp Gly Leu Pro Gly Ser Phe Val Asn Val Ser Cys Pro Trp Tyr Leu
    370                 375                 380

Pro Trp Ala Ser Ser Val Leu Gln Gly His Val Tyr Arg Phe Cys Thr
385                 390                 395                 400

Ala Glu Gly Leu Trp Leu Arg Gln Asp Asn Ser Ser Leu Pro Trp Arg
                405                 410                 415
```

-continued

Asn Leu Ser Glu Cys Glu Ser Lys Arg Gly Glu Arg Ser Ser Pro
            420                 425                 430

Glu Glu Gln Leu Leu Ser Phe Ser Ile Ile Tyr Thr Val Gly Tyr Thr
            435                 440                 445

Leu Ser Phe Ser Ala Leu Val Ile Ala Ser Ala Ile Leu Leu Ser Phe
450                 455                 460

Arg His Leu His Cys Thr Arg Asn Tyr Ile His Leu Asn Leu Phe Ala
465                 470                 475                 480

Ser Phe Ile Leu Arg Ala Leu Ser Val Phe Ile Arg Asp Ala Val Leu
                485                 490                 495

Lys Trp Met Tyr Ser Thr Ala Pro Gln Gln His Gln Trp Asp Gly Leu
                500                 505                 510

Leu Ser Tyr Gln Asp Ser Leu Gly Cys Arg Leu Val Phe Leu Leu Met
                515                 520                 525

Gln Tyr Cys Val Ala Ala Asn Tyr Tyr Trp Leu Leu Val Glu Gly Val
            530                 535                 540

Tyr Leu Tyr Thr Leu Leu Ala Phe Ser Val Phe Ser Glu Gln Arg Ile
545                 550                 555                 560

Phe Arg Leu Tyr Leu Ser Ile Gly Trp Gly Val Pro Leu Leu Phe Val
                565                 570                 575

Ile Trp Gly Ile Val Lys Tyr Leu Tyr Glu Asp Glu Gly Cys Trp Thr
                580                 585                 590

Arg Asn Ser Asn Met Asn Tyr Trp Leu Ile Ile Arg Leu Pro Ile Leu
            595                 600                 605

Phe Ala Ile Gly Val Asn Phe Leu Ile Phe Val Arg Val Ile Cys Ile
610                 615                 620

Val Val Ser Lys Leu Lys Ala Asn Leu Met Cys Lys Thr Asp Ile Lys
625                 630                 635                 640

Cys Arg Leu Ala Lys Ser Thr Leu Thr Leu Ile Pro Leu Leu Gly Thr
                645                 650                 655

His Glu Val Val Phe Ala Phe Val Met Asp Glu His Ala Arg Gly Thr
                660                 665                 670

Leu Arg Phe Ile Lys Leu Phe Thr Glu Leu Ser Phe Thr Ser Phe Gln
                675                 680                 685

Gly Leu Met Val Ala Ile Leu Tyr Cys Phe Val Asn Asn Glu Val Gln
            690                 695                 700

Met Glu Phe Arg Arg Ser Trp Glu Arg Trp Arg Leu Lys His Leu His
705                 710                 715                 720

Ile Gln Arg Asp Ser Ser Met Lys Pro Leu Lys Cys Pro Thr Ser Ser
                725                 730                 735

Leu Thr Ser Gly Gly Thr Val Gly Ser Ser Val Tyr Ala Ala Ser Cys
                740                 745                 750

Gln Ala Ser Cys Ser
        755

<210> SEQ ID NO 49
<211> LENGTH: 126
<212> TYPE: PRT
<213> ORGANISM: Artificial Sequence
<220> FEATURE:
<223> OTHER INFORMATION: Synthetic: Mature feline glucagon-like peptide
      1 receptor-N-terminal domain (GLP1R-N)

<400> SEQUENCE: 49

Arg Pro Leu Pro Ala Ser Gly Gly Ala Thr Val Ser Leu Ser Glu Thr

```
1               5                   10                  15
Val Gln Lys Trp Arg Glu Tyr Arg His Gln Cys Gln Arg Phe Leu Thr
                20                  25                  30
Glu Ala Pro Pro Ala Thr Gly Leu Phe Cys Asn Arg Thr Phe Asp
                35                  40                  45
Glu Tyr Ala Cys Trp Pro Asp Gly Leu Pro Gly Ser Phe Val Asn Val
                50                  55                  60
Ser Cys Pro Trp Tyr Leu Pro Trp Ala Ser Ser Val Leu Gln Gly His
65                  70                  75                  80
Val Tyr Arg Phe Cys Thr Ala Glu Gly Leu Trp Leu Arg Gln Asp Asn
                85                  90                  95
Ser Ser Leu Pro Trp Arg Asn Leu Ser Glu Cys Glu Glu Ser Lys Arg
                100                 105                 110
Gly Glu Arg Ser Ser Pro Glu Glu Gln Leu Leu Ser Phe Ser
                115                 120                 125
```

<210> SEQ ID NO 50
<211> LENGTH: 392
<212> TYPE: PRT
<213> ORGANISM: Artificial Sequence
<220> FEATURE:
<223> OTHER INFORMATION: Synthetic: ssFeGLP1R-N_huFc_ PolyHis

<400> SEQUENCE: 50

```
Met Glu Thr Asp Thr Leu Leu Leu Trp Val Leu Leu Leu Trp Val Pro
1               5                   10                  15
Gly Ser Thr Gly Arg Pro Leu Pro Ala Ser Gly Gly Ala Thr Val Ser
                20                  25                  30
Leu Ser Glu Thr Val Gln Lys Trp Arg Glu Tyr Arg His Gln Cys Gln
                35                  40                  45
Arg Phe Leu Thr Glu Ala Pro Pro Ala Thr Gly Leu Phe Cys Asn
        50                  55                  60
Arg Thr Phe Asp Glu Tyr Ala Cys Trp Pro Asp Gly Leu Pro Gly Ser
65                  70                  75                  80
Phe Val Asn Val Ser Cys Pro Trp Tyr Leu Pro Trp Ala Ser Ser Val
                85                  90                  95
Leu Gln Gly His Val Tyr Arg Phe Cys Thr Ala Glu Gly Leu Trp Leu
                100                 105                 110
Arg Gln Asp Asn Ser Ser Leu Pro Trp Arg Asn Leu Ser Glu Cys Glu
                115                 120                 125
Glu Ser Lys Arg Gly Glu Arg Ser Ser Pro Glu Glu Gln Leu Leu Ser
        130                 135                 140
Phe Ser Gly Ser Glu Asn Leu Tyr Phe Gln Gly Pro Lys Ser Cys Asp
145                 150                 155                 160
Lys Thr His Thr Cys Pro Pro Cys Pro Ala Pro Glu Leu Leu Gly Gly
                165                 170                 175
Pro Ser Val Phe Leu Phe Pro Pro Lys Pro Lys Asp Thr Leu Met Ile
                180                 185                 190
Ser Arg Thr Pro Glu Val Thr Cys Val Val Val Asp Val Ser His Glu
                195                 200                 205
Asp Pro Glu Val Lys Phe Asn Trp Tyr Val Asp Gly Val Glu Val His
                210                 215                 220
Asn Ala Lys Thr Lys Pro Arg Glu Glu Gln Tyr Asn Ser Thr Tyr Arg
225                 230                 235                 240
Val Val Ser Val Leu Thr Val Leu His Gln Asp Trp Leu Asn Gly Lys
```

-continued

```
                245                 250                 255
Glu Tyr Lys Cys Lys Val Ser Asn Lys Ala Leu Pro Ala Pro Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Arg Asp Glu Leu Thr Lys Asn Gln Val Ser Leu
    290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
        355                 360                 365

Glu Ala Leu His Asn His Tyr Thr Gln Lys Ser Leu Ser Leu Ser Pro
    370                 375                 380

Gly Lys His His His His His His
385                 390

<210> SEQ ID NO 51
<211> LENGTH: 156
<212> TYPE: PRT
<213> ORGANISM: Artificial Sequence
<220> FEATURE:
<223> OTHER INFORMATION: Synthetic: ssFeGLP1R-N_PolyHis

<400> SEQUENCE: 51

Met Glu Thr Asp Thr Leu Leu Leu Trp Val Leu Leu Leu Trp Val Pro
1               5                   10                  15

Gly Ser Thr Gly Arg Pro Leu Pro Ala Ser Gly Gly Ala Thr Val Ser
            20                  25                  30

Leu Ser Glu Thr Val Gln Lys Trp Arg Glu Tyr Arg His Gln Cys Gln
        35                  40                  45

Arg Phe Leu Thr Glu Ala Pro Pro Pro Ala Thr Gly Leu Phe Cys Asn
    50                  55                  60

Arg Thr Phe Asp Glu Tyr Ala Cys Trp Pro Asp Gly Leu Pro Gly Ser
65                  70                  75                  80

Phe Val Asn Val Ser Cys Pro Trp Tyr Leu Pro Trp Ala Ser Ser Val
                85                  90                  95

Leu Gln Gly His Val Tyr Arg Phe Cys Thr Ala Glu Gly Leu Trp Leu
            100                 105                 110

Arg Gln Asp Asn Ser Ser Leu Pro Trp Arg Asn Leu Ser Glu Cys Glu
        115                 120                 125

Glu Ser Lys Arg Gly Glu Arg Ser Ser Pro Glu Glu Gln Leu Leu Ser
    130                 135                 140

Phe Ser Gly Gly Gly Ser His His His His His His
145                 150                 155

<210> SEQ ID NO 52
<211> LENGTH: 326
<212> TYPE: PRT
<213> ORGANISM: Artificial Sequence
<220> FEATURE:
<223> OTHER INFORMATION: Synthetic: GLP1-G8/Gluc-3G_IV_ WTfeIgG2

<400> SEQUENCE: 52
```

-continued

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Ser Gly Gly Gly Gly Ser
        35                  40                  45

Pro Lys Thr Ala Ser Thr Ile Glu Ser Lys Thr Gly Glu Gly Pro Lys
    50                  55                  60

Cys Pro Val Pro Glu Ile Pro Gly Ala Pro Ser Val Phe Ile Phe Pro
65                  70                  75                  80

Pro Lys Pro Lys Asp Thr Leu Ser Ile Ser Arg Thr Pro Glu Val Thr
                85                  90                  95

Cys Leu Val Val Asp Leu Gly Pro Asp Asp Ser Asn Val Gln Ile Thr
                100                 105                 110

Trp Phe Val Asp Asn Thr Glu Met His Thr Ala Lys Thr Arg Pro Arg
            115                 120                 125

Glu Glu Gln Phe Asn Ser Thr Tyr Arg Val Val Ser Val Leu Pro Ile
    130                 135                 140

Leu His Gln Asp Trp Leu Lys Gly Lys Glu Phe Lys Cys Lys Val Asn
145                 150                 155                 160

Ser Lys Ser Leu Pro Ser Ala Met Glu Arg Thr Ile Ser Lys Ala Lys
                165                 170                 175

Gly Gln Pro His Glu Pro Gln Val Tyr Val Leu Pro Pro Thr Gln Glu
            180                 185                 190

Glu Leu Ser Glu Asn Lys Val Ser Val Thr Cys Leu Ile Lys Gly Phe
    195                 200                 205

His Pro Pro Asp Ile Ala Val Glu Trp Glu Ile Thr Gly Gln Pro Glu
210                 215                 220

Pro Glu Asn Asn Tyr Gln Thr Thr Pro Pro Gln Leu Asp Ser Asp Gly
225                 230                 235                 240

Thr Tyr Phe Leu Tyr Ser Arg Leu Ser Val Asp Arg Ser His Trp Gln
                245                 250                 255

Arg Gly Asn Thr Tyr Thr Cys Ser Val Ser His Glu Ala Leu His Ser
            260                 265                 270

His His Thr Gln Lys Ser Leu Thr Gln Ser Pro Gly Lys Gly Gly Gly
    275                 280                 285

Gly Ser Gly Gly Gly His Ser Gln Gly Thr Phe Thr Ser Asp Tyr
    290                 295                 300

Ser Lys Tyr Leu Asp Ser Arg Arg Ala Gln Asp Phe Val Gln Trp Leu
305                 310                 315                 320

Met Asn Thr Gly Gly Gly
                325
```

<210> SEQ ID NO 53
<211> LENGTH: 326
<212> TYPE: PRT
<213> ORGANISM: Artificial Sequence
<220> FEATURE:
<223> OTHER INFORMATION: Synthetic: Gluc/GLP1-2G_V_ WTfeIgG2

<400> SEQUENCE: 53

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Gly Gly
            20                  25                  30
```

```
Gly Ser Gly Gly Gly Ser Gly Gly Gly Ser Gly Gly Gly
         35                  40                  45

Ser Pro Lys Thr Ala Ser Thr Ile Glu Ser Lys Thr Gly Glu Gly Pro
 50                  55                  60

Lys Cys Pro Val Pro Glu Ile Pro Gly Ala Pro Ser Val Phe Ile Phe
 65                  70                  75                  80

Pro Pro Lys Pro Lys Asp Thr Leu Ser Ile Ser Arg Thr Pro Glu Val
                 85                  90                  95

Thr Cys Leu Val Val Asp Leu Gly Pro Asp Asp Ser Asn Val Gln Ile
                100                 105                 110

Thr Trp Phe Val Asp Asn Thr Glu Met His Thr Ala Lys Thr Arg Pro
            115                 120                 125

Arg Glu Glu Gln Phe Asn Ser Thr Tyr Arg Val Val Ser Val Leu Pro
130                 135                 140

Ile Leu His Gln Asp Trp Leu Lys Gly Lys Glu Phe Lys Cys Lys Val
145                 150                 155                 160

Asn Ser Lys Ser Leu Pro Ser Ala Met Glu Arg Thr Ile Ser Lys Ala
                165                 170                 175

Lys Gly Gln Pro His Glu Pro Gln Val Tyr Val Leu Pro Pro Thr Gln
            180                 185                 190

Glu Glu Leu Ser Glu Asn Lys Val Ser Val Thr Cys Leu Ile Lys Gly
        195                 200                 205

Phe His Pro Pro Asp Ile Ala Val Glu Trp Glu Ile Thr Gly Gln Pro
210                 215                 220

Glu Pro Glu Asn Asn Tyr Gln Thr Thr Pro Pro Gln Leu Asp Ser Asp
225                 230                 235                 240

Gly Thr Tyr Phe Leu Tyr Ser Arg Leu Ser Val Asp Arg Ser His Trp
                245                 250                 255

Gln Arg Gly Asn Thr Tyr Thr Cys Ser Val Ser His Glu Ala Leu His
            260                 265                 270

Ser His His Thr Gln Lys Ser Leu Thr Gln Ser Pro Gly Lys Gly Gly
        275                 280                 285

Gly Gly Ser Gly Gly Gly Gly His Ala Glu Gly Thr Phe Thr Ser Asp
290                 295                 300

Val Ser Ser Tyr Leu Glu Gly Gln Ala Ala Lys Glu Phe Ile Ala Trp
305                 310                 315                 320

Leu Val Lys Gly Gly Gly
                325

<210> SEQ ID NO 54
<211> LENGTH: 324
<212> TYPE: PRT
<213> ORGANISM: Artificial Sequence
<220> FEATURE:
<223> OTHER INFORMATION: Synthetic: GLP1-G8/Glu-4G_IV_ VARcaIgGD

<400> SEQUENCE: 54

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly Ala Gly
                20                  25                  30

Gly Gly Gly Gly Ser Gly Gly Gly Ser Gly Gly Gly Ser Gly Gly Gly
            35                  40                  45

Ser Pro Lys Glu Ser Thr Ser Lys Cys Ile Ser Pro Cys Pro Val Pro
 50                  55                  60
```

```
Glu Ser Leu Gly Gly Pro Ser Val Phe Ile Phe Pro Pro Lys Pro Lys
 65                  70                  75                  80

Asp Thr Leu Leu Ile Ala Arg Thr Pro Glu Ile Thr Cys Val Val Leu
                 85                  90                  95

Asp Leu Gly Arg Glu Asp Pro Glu Val Gln Ile Ser Trp Phe Val Asp
             100                 105                 110

Gly Lys Glu Val His Thr Ala Lys Thr Gln Pro Arg Glu Gln Gln Phe
         115                 120                 125

Asn Ser Thr Tyr Arg Val Val Ser Val Leu Pro Ile Gly His Gln Asp
     130                 135                 140

Trp Leu Thr Gly Lys Glu Phe Lys Cys Arg Val Asn His Ile Gly Leu
145                 150                 155                 160

Pro Ser Pro Ile Glu Arg Thr Ile Ser Lys Ala Arg Gly Gln Ala His
                 165                 170                 175

Gln Pro Ser Val Tyr Val Leu Pro Pro Ser Pro Lys Glu Leu Ser Ser
            180                 185                 190

Ser Asp Thr Val Thr Leu Thr Cys Leu Ile Lys Asp Phe Phe Pro Pro
        195                 200                 205

Glu Ile Asp Val Glu Trp Gln Ser Asn Gly Gln Pro Glu Pro Glu Ser
    210                 215                 220

Lys Tyr His Thr Thr Ala Pro Gln Leu Asp Glu Asp Gly Ser Tyr Phe
225                 230                 235                 240

Leu Tyr Ser Lys Leu Ser Val Asp Lys Ser Arg Trp Gln Gln Gly Asp
                245                 250                 255

Thr Phe Thr Cys Ala Val Met His Glu Ala Leu His Asn His Tyr Thr
                260                 265                 270

Asp Leu Ser Leu Ser His Ser Pro Gly Lys Gly Gly Gly Ser Gly
            275                 280                 285

Gly Gly Gly His Ser Gln Gly Thr Phe Thr Ser Asp Tyr Ser Lys Tyr
        290                 295                 300

Leu Asp Ser Arg Arg Ala Gln Asp Phe Val Gln Trp Leu Met Asn Thr
305                 310                 315                 320

Gly Gly Gly Gly

<210> SEQ ID NO 55
<211> LENGTH: 323
<212> TYPE: PRT
<213> ORGANISM: Artificial Sequence
<220> FEATURE:
<223> OTHER INFORMATION: Synthetic: Gluc/GLP1-3G_V_ VARcaIgGD

<400> SEQUENCE: 55

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Ala Gly
             20                  25                  30

Gly Gly Gly Gly Ser Gly Gly Gly Ser Gly Gly Gly Gly
         35                  40                  45

Ser Pro Lys Glu Ser Thr Ser Lys Cys Ile Ser Pro Cys Pro Val Pro
    50                  55                  60

Glu Ser Leu Gly Gly Pro Ser Val Phe Ile Phe Pro Pro Lys Pro Lys
 65                 70                  75                  80

Asp Thr Leu Leu Ile Ala Arg Thr Pro Glu Ile Thr Cys Val Val Leu
                 85                  90                  95

Asp Leu Gly Arg Glu Asp Pro Glu Val Gln Ile Ser Trp Phe Val Asp
```

-continued

Gly Lys Glu Val His Thr Ala Lys Thr Gln Pro Arg Glu Gln Gln Phe
100                     105                     110               115

Asn Ser Thr Tyr Arg Val Val Ser Val Leu Pro Ile Gly His Gln Asp
            120                     125                     130   140...

Trp Leu Thr Gly Lys Glu Phe Lys Cys Arg Val Asn His Ile Gly Leu
145                     150                     155                 160

Pro Ser Pro Ile Glu Arg Thr Ile Ser Lys Ala Arg Gly Gln Ala His
                165                     170                     175

Gln Pro Ser Val Tyr Val Leu Pro Pro Ser Pro Lys Glu Leu Ser Ser
                180                     185                     190

Ser Asp Thr Val Thr Leu Thr Cys Leu Ile Lys Asp Phe Phe Pro Pro
                195                     200                     205

Glu Ile Asp Val Glu Trp Gln Ser Asn Gly Gln Pro Glu Pro Glu Ser
210                     215                     220

Lys Tyr His Thr Thr Ala Pro Gln Leu Asp Glu Asp Gly Ser Tyr Phe
225                     230                     235                 240

Leu Tyr Ser Lys Leu Ser Val Asp Lys Ser Arg Trp Gln Gln Gly Asp
                245                     250                     255

Thr Phe Thr Cys Ala Val Met His Glu Ala Leu His Asn His Tyr Thr
                260                     265                     270

Asp Leu Ser Leu Ser His Ser Pro Gly Lys Gly Gly Gly Ser Gly
                275                     280                     285

Gly Gly Gly His Ala Glu Gly Thr Phe Thr Ser Asp Val Ser Ser Tyr
290                     295                     300

Leu Glu Gly Gln Ala Ala Lys Glu Phe Ile Ala Trp Leu Val Lys Gly
305                     310                     315                 320

Gly Gly Gly

<210> SEQ ID NO 56
<211> LENGTH: 319
<212> TYPE: PRT
<213> ORGANISM: Artificial Sequence
<220> FEATURE:
<223> OTHER INFORMATION: Synthetic: GLP1-G8/Gluc-4G_IV_ VAReqIgGD

<400> SEQUENCE: 56

His Gly Glu Gly Thr Phe Thr Ser Asp Val Ser Ser Tyr Leu Glu Gly
1               5                   10                      15

Gln Ala Ala Lys Glu Phe Ile Ala Trp Leu Val Lys Gly Gly Ala Gly
                20                      25                      30

Gly Gly Gly Gly Ser Gly Gly Gly Ser Gly Gly Gly Ser Gly Gly Gly
            35                      40                      45

Ser Asp Met Ser Lys Cys Pro Lys Cys Pro Ala Pro Glu Leu Leu Gly
        50                      55                      60

Gly Pro Ser Val Phe Ile Phe Pro Pro Asn Pro Lys Asp Thr Leu Met
65                      70                      75                  80

Ile Ser Arg Thr Pro Val Val Thr Cys Val Val Val Asn Leu Ser Asp
                85                      90                      95

Gln Tyr Pro Asp Val Gln Phe Ser Trp Tyr Val Asp Asn Thr Glu Val
                100                     105                     110

His Ser Ala Ile Thr Lys Gln Arg Glu Ala Gln Phe Asn Ser Thr Tyr
            115                     120                     125

Arg Val Val Ser Val Leu Pro Ile Gln His Gln Asp Trp Leu Ser Gly
130                     135                     140

```
Lys Glu Phe Lys Cys Ser Val Thr Asn Val Gly Val Pro Gln Pro Ile
145                 150                 155                 160

Ser Arg Ala Ile Ser Arg Gly Lys Gly Pro Ser Arg Val Pro Gln Val
                165                 170                 175

Tyr Val Leu Pro Pro His Pro Asp Glu Leu Ala Lys Ser Lys Val Ser
            180                 185                 190

Val Thr Cys Leu Val Lys Asp Phe Tyr Pro Asp Ile Ser Val Glu
        195                 200                 205

Trp Gln Ser Asn Arg Trp Pro Glu Leu Glu Gly Lys Tyr Ser Thr Thr
    210                 215                 220

Pro Ala Gln Leu Asp Gly Asp Gly Ser Tyr Phe Leu Tyr Ser Lys Leu
225                 230                 235                 240

Ser Leu Glu Thr Ser Arg Trp Gln Gln Val Glu Ser Phe Thr Cys Ala
                245                 250                 255

Val Met His Glu Ala Leu His Asn His Tyr Thr Lys Thr Asp Ile Ser
            260                 265                 270

Glu Ser Leu Gly Lys Gly Gly Gly Ser Gly Gly Gly Gly His Ser
        275                 280                 285

Gln Gly Thr Phe Thr Ser Asp Tyr Ser Lys Tyr Leu Asp Ser Arg Arg
    290                 295                 300

Ala Gln Asp Phe Val Gln Trp Leu Met Asn Thr Gly Gly Gly Gly
305                 310                 315

<210> SEQ ID NO 57
<211> LENGTH: 318
<212> TYPE: PRT
<213> ORGANISM: Artificial Sequence
<220> FEATURE:
<223> OTHER INFORMATION: Synthetic: Gluc/GLP1-3G_V_ VAReqIgG2

<400> SEQUENCE: 57

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Ala Gly
                20                  25                  30

Gly Gly Gly Gly Ser Gly Gly Gly Ser Gly Gly Gly Ser Gly Gly Gly
            35                  40                  45

Ser Asp Met Ser Lys Cys Pro Lys Cys Pro Ala Pro Glu Leu Leu Gly
        50                  55                  60

Gly Pro Ser Val Phe Ile Phe Pro Pro Asn Pro Lys Asp Thr Leu Met
65                  70                  75                  80

Ile Ser Arg Thr Pro Val Val Thr Cys Val Val Val Asn Leu Ser Asp
                85                  90                  95

Gln Tyr Pro Asp Val Gln Phe Ser Trp Tyr Val Asp Asn Thr Glu Val
            100                 105                 110

His Ser Ala Ile Thr Lys Gln Arg Glu Ala Gln Phe Asn Ser Thr Tyr
        115                 120                 125

Arg Val Val Ser Val Leu Pro Ile Gln His Gln Asp Trp Leu Ser Gly
    130                 135                 140

Lys Glu Phe Lys Cys Ser Val Thr Asn Val Gly Val Pro Gln Pro Ile
145                 150                 155                 160

Ser Arg Ala Ile Ser Arg Gly Lys Gly Pro Ser Arg Val Pro Gln Val
                165                 170                 175

Tyr Val Leu Pro Pro His Pro Asp Glu Leu Ala Lys Ser Lys Val Ser
            180                 185                 190
```

-continued

```
Val Thr Cys Leu Val Lys Asp Phe Tyr Pro Asp Ile Ser Val Glu
            195                 200                 205

Trp Gln Ser Asn Arg Trp Pro Glu Leu Glu Gly Lys Tyr Ser Thr Thr
210                 215                 220

Pro Ala Gln Leu Asp Gly Asp Gly Ser Tyr Phe Leu Tyr Ser Lys Leu
225                 230                 235                 240

Ser Leu Glu Thr Ser Arg Trp Gln Gln Val Glu Ser Phe Thr Cys Ala
            245                 250                 255

Val Met His Glu Ala Leu His Asn His Tyr Thr Lys Thr Asp Ile Ser
            260                 265                 270

Glu Ser Leu Gly Lys Gly Gly Gly Ser Gly Gly Gly Gly His Ala
            275                 280                 285

Glu Gly Thr Phe Thr Ser Asp Val Ser Ser Tyr Leu Glu Gly Gln Ala
            290                 295                 300

Ala Lys Glu Phe Ile Ala Trp Leu Val Lys Gly Gly Gly
305                 310                 315

<210> SEQ ID NO 58
<211> LENGTH: 321
<212> TYPE: PRT
<213> ORGANISM: Artificial Sequence
<220> FEATURE:
<223> OTHER INFORMATION: Synthetic: GLP1-G8/Glu-4G_IV_ huIgG4

<400> SEQUENCE: 58

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
            20                  25                  30

Gly Gly Gly Gly Ser Gly Gly Gly Ser Gly Gly Gly Ser Gly Gly Gly
            35                  40                  45

Ser Ser Glu Ser Lys Tyr Gly Pro Pro Cys Pro Pro Cys Pro Ala Pro
50                  55                  60

Glu Phe Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
            85                  90                  95

Asp Val Ser Gln Glu Asp Pro Glu Val Gln Phe Asn Trp Tyr Val Asp
            100                 105                 110

Gly Val Glu Val His Asn Ala Lys Thr Lys Pro Arg Glu Glu Gln Phe
            115                 120                 125

Asn Ser Thr Tyr Arg Val Val Ser Val Leu Thr Val Leu His Gln Asp
130                 135                 140

Trp Leu Asn Gly Lys Glu Tyr Lys Cys Lys Val Ser Asn Lys Gly Leu
145                 150                 155                 160

Pro Ser Ser Ile Glu Lys Thr Ile Ser Lys Ala Lys Gly Gln Pro Arg
            165                 170                 175

Glu Pro Gln Val Tyr Thr Leu Pro Pro Ser Gln Glu Glu Met Thr Lys
            180                 185                 190

Asn Gln Val Ser Leu Thr Cys Leu Val Lys Gly Phe Tyr Pro Ser Asp
            195                 200                 205

Ile Ala Val Glu Trp Glu Ser Asn Gly Gln Pro Glu Asn Asn Tyr Lys
            210                 215                 220

Thr Thr Pro Pro Val Leu Asp Ser Asp Gly Ser Phe Phe Leu Tyr Ser
225                 230                 235                 240
```

Arg Leu Thr Val Asp Lys Ser Arg Trp Gln Glu Gly Asn Val Phe Ser
            245                 250                 255

Cys Ser Val Met His Glu Ala Leu His Asn His Tyr Thr Gln Lys Ser
            260                 265                 270

Leu Ser Leu Ser Leu Gly Lys Gly Gly Gly Ser Gly Gly Gly Gly
            275                 280                 285

His Ser Gln Gly Thr Phe Thr Ser Asp Tyr Ser Lys Tyr Leu Asp Ser
            290                 295                 300

Arg Arg Ala Gln Asp Phe Val Gln Trp Leu Met Asn Thr Gly Gly Gly
305                 310                 315                 320

Gly

<210> SEQ ID NO 59
<211> LENGTH: 321
<212> TYPE: PRT
<213> ORGANISM: Artificial Sequence
<220> FEATURE:
<223> OTHER INFORMATION: Synthetic: Gluc/GLP1-3G_V_huIgG4

<400> SEQUENCE: 59

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Gly Gly
            20                  25                  30

Gly Gly Ser Gly Gly Gly Ser Gly Gly Gly Gly Ser Ser
            35                  40                  45

Glu Ser Lys Tyr Gly Pro Pro Cys Pro Pro Cys Pro Ala Pro Glu Phe
50                  55                  60

Leu Gly Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
            85                  90                  95

Ser Gln Glu Asp Pro Glu Val Gln Phe Asn Trp Tyr Val Asp Gly Val
            100                 105                 110

Glu Val His Asn Ala Lys Thr Lys Pro Arg Glu Glu Gln Phe Asn Ser
            115                 120                 125

Thr Tyr Arg Val Val Ser Val Leu Thr Val Leu His Gln Asp Trp Leu
            130                 135                 140

Asn Gly Lys Glu Tyr Lys Cys Lys Val Ser Asn Lys Gly Leu Pro Ser
145                 150                 155                 160

Ser Ile Glu Lys Thr Ile Ser Lys Ala Lys Gly Gln Pro Arg Glu Pro
            165                 170                 175

Gln Val Tyr Thr Leu Pro Pro Ser Gln Glu Glu Met Thr Lys Asn Gln
            180                 185                 190

Val Ser Leu Thr Cys Leu Val Lys Gly Phe Tyr Pro Ser Asp Ile Ala
            195                 200                 205

Val Glu Trp Glu Ser Asn Gly Gln Pro Glu Asn Asn Tyr Lys Thr Thr
            210                 215                 220

Pro Pro Val Leu Asp Ser Asp Gly Ser Phe Phe Leu Tyr Ser Arg Leu
225                 230                 235                 240

Thr Val Asp Lys Ser Arg Trp Gln Glu Gly Asn Val Phe Ser Cys Ser
            245                 250                 255

Val Met His Glu Ala Leu His Asn His Tyr Thr Gln Lys Ser Leu Ser
            260                 265                 270

```
Leu Ser Leu Gly Lys Gly Gly Ser Gly Gly Gly His Ala
        275             280             285
Glu Gly Thr Phe Thr Ser Asp Val Ser Ser Tyr Leu Glu Gly Gln Ala
    290                 295                 300
Ala Lys Glu Phe Ile Ala Trp Leu Val Lys Gly Gly Ala Gly Gly Gly
305                 310                 315                 320
Gly

<210> SEQ ID NO 60
<211> LENGTH: 221
<212> TYPE: PRT
<213> ORGANISM: Artificial Sequence
<220> FEATURE:
<223> OTHER INFORMATION: Synthetic: Variant canine IgG-A Fc , C1q -,
      Protein A +, I(21)T, Q(207)H

<400> SEQUENCE: 60

Pro Val Pro Glu Pro Leu Gly Gly Pro Ser Val Leu Ile Phe Pro Pro
1               5                   10                  15
Lys Pro Lys Asp Thr Leu Arg Ile Thr Arg Thr Pro Glu Val Thr Cys
            20                  25                  30
Val Val Leu Asp Leu Gly Arg Glu Asp Pro Glu Val Gln Ile Ser Trp
        35                  40                  45
Phe Val Asp Gly Lys Glu Val His Thr Ala Lys Thr Gln Ser Arg Glu
    50                  55                  60
Gln Gln Phe Asn Gly Thr Tyr Arg Val Val Ser Val Leu Pro Ile Glu
65                  70                  75                  80
His Gln Asp Trp Leu Thr Gly Lys Glu Phe Lys Cys Arg Val Asn His
                85                  90                  95
Ile Asp Leu Pro Ser Pro Ile Glu Arg Thr Ile Ser Lys Ala Arg Gly
            100                 105                 110
Arg Ala His Lys Pro Ser Val Tyr Val Leu Pro Pro Ser Pro Lys Glu
        115                 120                 125
Leu Ser Ser Ser Asp Thr Val Ser Ile Thr Cys Leu Ile Lys Asp Phe
    130                 135                 140
Tyr Pro Pro Asp Ile Asp Val Glu Trp Gln Ser Asn Gly Gln Gln Glu
145                 150                 155                 160
Pro Glu Arg Lys His Arg Met Thr Pro Pro Gln Leu Asp Glu Asp Gly
                165                 170                 175
Ser Tyr Phe Leu Tyr Ser Lys Leu Ser Val Asp Lys Ser Arg Trp Gln
            180                 185                 190
Gln Gly Asp Pro Phe Thr Cys Ala Val Met His Glu Thr Leu His Asn
        195                 200                 205
His Tyr Thr Asp Leu Ser Leu Ser His Ser Pro Gly Lys
    210                 215                 220

<210> SEQ ID NO 61
<211> LENGTH: 220
<212> TYPE: PRT
<213> ORGANISM: Artificial Sequence
<220> FEATURE:
<223> OTHER INFORMATION: Synthetic: Variant canine IgG-C Fc , C1q +,
      Protein A +, I(21)T

<400> SEQUENCE: 61

Pro Gly Cys Gly Leu Leu Gly Gly Pro Ser Val Phe Ile Phe Pro Pro
1               5                   10                  15
Lys Pro Lys Asp Thr Leu Val Thr Ala Arg Thr Pro Thr Val Thr Cys
```

```
            20                  25                  30
Val Val Val Asp Leu Asp Pro Glu Asn Pro Glu Val Gln Ile Ser Trp
         35                  40                  45

Phe Val Asp Ser Lys Gln Val Gln Thr Ala Asn Thr Gln Pro Arg Glu
 50                  55                  60

Glu Gln Ser Asn Gly Thr Tyr Arg Val Val Ser Val Leu Pro Ile Gly
 65                  70                  75                  80

His Gln Asp Trp Leu Ser Gly Lys Gln Phe Lys Cys Lys Val Asn Asn
                 85                  90                  95

Lys Ala Leu Pro Ser Pro Ile Glu Ile Ile Ser Lys Thr Pro Gly
             100                 105                 110

Gln Ala His Gln Pro Asn Val Tyr Val Leu Pro Pro Ser Arg Asp Glu
             115                 120                 125

Met Ser Lys Asn Thr Val Thr Leu Thr Cys Leu Val Lys Asp Phe Phe
130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                 165                 170                 175

Tyr Phe Leu Tyr Ser Lys Leu Ser Val Asp Lys Ser Arg Trp Gln Arg
                 180                 185                 190

Gly Asp Thr Phe Ile Cys Ala Val Met His Glu Ala Leu His Asn His
                 195                 200                 205

Tyr Thr Gln Ile Ser Leu Ser His Ser Pro Gly Lys
         210                 215                 220

<210> SEQ ID NO 62
<211> LENGTH: 221
<212> TYPE: PRT
<213> ORGANISM: Artificial Sequence
<220> FEATURE:
<223> OTHER INFORMATION: Synthetic: Variant canine IgG-D Fc , C1q -,
      Protein A +, I(21)T, Q(207)H

<400> SEQUENCE: 62

Pro Val Pro Glu Ser Leu Gly Gly Pro Ser Val Phe Ile Phe Pro Pro
 1               5                  10                  15

Lys Pro Lys Asp Thr Leu Arg Ile Thr Arg Thr Pro Glu Ile Thr Cys
             20                  25                  30

Val Val Leu Asp Leu Gly Arg Glu Asp Pro Glu Val Gln Ile Ser Trp
         35                  40                  45

Phe Val Asp Gly Lys Glu Val His Thr Ala Lys Thr Gln Pro Arg Glu
 50                  55                  60

Gln Gln Phe Asn Ser Thr Tyr Arg Val Val Ser Val Leu Pro Ile Glu
 65                  70                  75                  80

His Gln Asp Trp Leu Thr Gly Lys Glu Phe Lys Cys Arg Val Asn His
                 85                  90                  95

Ile Gly Leu Pro Ser Pro Ile Glu Arg Thr Ile Ser Lys Ala Arg Gly
             100                 105                 110

Gln Ala His Gln Pro Ser Val Tyr Val Leu Pro Pro Ser Pro Lys Glu
             115                 120                 125

Leu Ser Ser Ser Asp Thr Val Thr Leu Thr Cys Leu Ile Lys Asp Phe
130                 135                 140

Phe Pro Pro Glu Ile Asp Val Glu Trp Gln Ser Asn Gly Gln Pro Glu
145                 150                 155                 160
```

```
Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Thr Phe Thr Cys Ala Val Met His Glu Ala Leu His Asn
        195                 200                 205

His Tyr Thr Asp Leu Ser Leu Ser His Ser Pro Gly Lys
    210                 215                 220

<210> SEQ ID NO 63
<211> LENGTH: 214
<212> TYPE: PRT
<213> ORGANISM: Unknown
<220> FEATURE:
<223> OTHER INFORMATION: Wild-type equine IgG1 Fc , Protein A +, C1q +

<400> SEQUENCE: 63

Gly Gly Pro Ser Val Phe Leu Phe Pro Pro Asn Pro Lys Asp Thr Leu
1               5                   10                  15

Met Ile Thr Arg Thr Pro Glu Val Thr Cys Val Val Val Asp Val Ser
            20                  25                  30

Gln Glu Asn Pro Asp Val Lys Phe Asn Trp Tyr Met Asp Gly Val Glu
        35                  40                  45

Val Arg Thr Ala Thr Thr Arg Pro Lys Glu Glu Gln Phe Asn Ser Thr
    50                  55                  60

Tyr Arg Val Val Ser Val Leu Arg Ile Gln His Gln Asp Trp Leu Ser
65                  70                  75                  80

Gly Lys Glu Phe Lys Cys Lys Val Asn Asn Gln Ala Leu Pro Gln Pro
                85                  90                  95

Ile Glu Arg Thr Ile Thr Lys Thr Lys Gly Arg Ser Gln Glu Pro Gln
            100                 105                 110

Val Tyr Val Leu Ala Pro His Pro Asp Glu Ser Lys Lys Ser Lys Val
        115                 120                 125

Ser Val Thr Cys Leu Val Lys Asp Phe Tyr Pro Pro Glu Ile Asn Ile
    130                 135                 140

Glu Trp Gln Ser Asn Gly Gln Pro Glu Leu Glu Thr Lys Tyr Ser Thr
145                 150                 155                 160

Thr Gln Ala Gln Gln Asp Ser Asp Gly Ser Tyr Phe Leu Tyr Ser Lys
                165                 170                 175

Leu Ser Val Asp Arg Asn Arg Trp Gln Gln Gly Thr Thr Phe Thr Cys
            180                 185                 190

Gly Val Met His Glu Ala Leu His Asn His Tyr Thr Gln Lys Asn Val
        195                 200                 205

Ser Lys Asn Pro Gly Lys
    210

<210> SEQ ID NO 64
<211> LENGTH: 214
<212> TYPE: PRT
<213> ORGANISM: Unknown
<220> FEATURE:
<223> OTHER INFORMATION: Wild-type equine IgG2 Fc, Protein A -, C1q -

<400> SEQUENCE: 64

Gly Gly Pro Ser Val Phe Ile Phe Pro Pro Asn Pro Lys Asp Ala Leu
1               5                   10                  15

Met Ile Ser Arg Thr Pro Val Val Thr Cys Val Val Val Asn Leu Ser
            20                  25                  30
```

```
Asp Gln Tyr Pro Asp Val Gln Phe Ser Trp Tyr Val Asp Asn Thr Glu
            35                  40                  45

Val His Ser Ala Ile Thr Lys Gln Arg Glu Ala Gln Phe Asn Ser Thr
 50                  55                  60

Tyr Arg Val Val Ser Val Leu Pro Ile Gln His Gln Asp Trp Leu Ser
 65                  70                  75                  80

Gly Lys Glu Phe Lys Cys Ser Val Thr Asn Val Gly Val Pro Gln Pro
                 85                  90                  95

Ile Ser Arg Ala Ile Ser Arg Gly Lys Gly Pro Ser Arg Val Pro Gln
            100                 105                 110

Val Tyr Val Leu Pro Pro His Pro Asp Glu Leu Ala Lys Ser Lys Val
            115                 120                 125

Ser Val Thr Cys Leu Val Lys Asp Phe Tyr Pro Pro Asp Ile Ser Val
        130                 135                 140

Glu Trp Gln Ser Asn Arg Trp Pro Glu Leu Glu Gly Lys Tyr Ser Thr
145                 150                 155                 160

Thr Pro Ala Gln Leu Asp Gly Asp Gly Ser Tyr Phe Leu Tyr Ser Lys
                165                 170                 175

Leu Ser Leu Glu Thr Ser Arg Trp Gln Gln Val Glu Ser Phe Thr Cys
            180                 185                 190

Ala Val Met His Glu Ala Leu His Asn His Phe Thr Lys Thr Asp Ile
            195                 200                 205

Ser Glu Ser Leu Gly Lys
            210

<210> SEQ ID NO 65
<211> LENGTH: 214
<212> TYPE: PRT
<213> ORGANISM: Unknown
<220> FEATURE:
<223> OTHER INFORMATION: Wild-type equine IgG3 Fc, Protein A +, C1q+

<400> SEQUENCE: 65

Gly Gly Pro Ser Val Phe Ile Phe Pro Pro Lys Pro Lys Asp Val Leu
1               5                  10                  15

Met Ile Thr Arg Met Pro Glu Val Thr Cys Leu Val Val Asp Val Ser
            20                  25                  30

His Asp Ser Ser Asp Val Leu Phe Thr Trp Tyr Val Asp Gly Thr Glu
            35                  40                  45

Val Lys Thr Ala Lys Thr Met Pro Asn Glu Glu Gln Asn Asn Ser Thr
 50                  55                  60

Tyr Arg Val Val Ser Val Leu Arg Ile Gln His Gln Asp Trp Leu Asn
 65                  70                  75                  80

Gly Lys Lys Phe Lys Cys Lys Val Asn Asn Gln Ala Leu Pro Ala Pro
                 85                  90                  95

Val Glu Arg Thr Ile Ser Lys Ala Thr Gly Gln Thr Arg Val Pro Gln
            100                 105                 110

Val Tyr Val Leu Ala Pro His Pro Asp Glu Leu Ser Lys Asn Lys Val
            115                 120                 125

Ser Val Thr Cys Leu Val Lys Asp Phe Tyr Pro Asp Ile Thr Val
        130                 135                 140

Glu Trp Gln Ser Asn Glu His Pro Glu Pro Gly Lys Tyr Arg Thr
145                 150                 155                 160

Thr Glu Ala Gln Lys Asp Ser Asp Gly Ser Tyr Phe Leu Tyr Ser Lys
                165                 170                 175
```

```
Leu Thr Val Glu Lys Asp Arg Trp Gln Gln Gly Thr Thr Phe Thr Cys
            180                 185                 190

Val Val Met His Glu Ala Leu His Asn His Val Met Gln Lys Asn Ile
            195                 200                 205

Ser Lys Asn Pro Gly Lys
            210

<210> SEQ ID NO 66
<211> LENGTH: 214
<212> TYPE: PRT
<213> ORGANISM: Unknown
<220> FEATURE:
<223> OTHER INFORMATION: Wild-type equine IgG4 Fc, Protein A +, C1q +

<400> SEQUENCE: 66

Val Gly Pro Ser Val Phe Ile Phe Pro Pro Lys Pro Lys Asp Val Leu
1               5                   10                  15

Met Ile Ser Arg Thr Pro Thr Val Thr Cys Val Val Val Asp Val Gly
            20                  25                  30

His Asp Phe Pro Asp Val Gln Phe Asn Trp Tyr Val Asp Gly Val Glu
            35                  40                  45

Thr His Thr Ala Thr Thr Glu Pro Lys Gln Glu Gln Phe Asn Ser Thr
    50                  55                  60

Tyr Arg Val Val Ser Val Leu Pro Ile Gln His Lys Asp Trp Leu Ser
65                  70                  75                  80

Gly Lys Glu Phe Lys Cys Lys Val Asn Asn Lys Ala Leu Pro Ala Pro
                85                  90                  95

Val Glu Arg Thr Ile Ser Ala Pro Thr Gly Gln Pro Arg Glu Pro Gln
            100                 105                 110

Val Tyr Val Leu Ala Pro His Arg Asp Glu Leu Ser Lys Asn Lys Val
            115                 120                 125

Ser Val Thr Cys Leu Val Lys Asp Phe Tyr Pro Pro Asp Ile Asp Ile
        130                 135                 140

Glu Trp Lys Ser Asn Gly Gln Pro Glu Pro Glu Thr Lys Tyr Ser Thr
145                 150                 155                 160

Thr Pro Ala Gln Leu Asp Ser Asp Gly Ser Tyr Phe Leu Tyr Ser Lys
                165                 170                 175

Leu Thr Val Glu Thr Asn Arg Trp Gln Gln Gly Thr Thr Phe Thr Cys
            180                 185                 190

Ala Val Met His Glu Ala Leu His Asn His Tyr Thr Glu Lys Ser Val
            195                 200                 205

Ser Lys Ser Pro Gly Lys
            210

<210> SEQ ID NO 67
<211> LENGTH: 214
<212> TYPE: PRT
<213> ORGANISM: Unknown
<220> FEATURE:
<223> OTHER INFORMATION: Wild-type equine IgG5 Fc, Protein A -, C1q -

<400> SEQUENCE: 67

Gly Gly Pro Ser Val Phe Ile Phe Pro Pro Lys Pro Lys Asp Val Leu
1               5                   10                  15

Met Ile Ser Arg Lys Pro Glu Val Thr Cys Val Val Val Asp Leu Gly
            20                  25                  30

His Asp Asp Pro Asp Val Gln Phe Thr Trp Phe Val Asp Gly Val Glu
```

```
                 35                  40                  45
Thr His Thr Ala Thr Thr Glu Pro Lys Glu Glu Gln Phe Asn Ser Thr
 50                  55                  60

Tyr Arg Val Val Ser Val Leu Pro Ile Gln His Gln Asp Trp Leu Ser
 65                  70                  75                  80

Gly Lys Glu Phe Lys Cys Ser Val Thr Ser Lys Ala Leu Pro Ala Pro
                 85                  90                  95

Val Glu Arg Thr Ile Ser Lys Ala Lys Gly Gln Leu Arg Val Pro Gln
                100                 105                 110

Val Tyr Val Leu Ala Pro His Pro Asp Glu Leu Ala Lys Asn Thr Val
                115                 120                 125

Ser Val Thr Cys Leu Val Lys Asp Phe Tyr Pro Pro Glu Ile Asp Val
            130                 135                 140

Glu Trp Gln Ser Asn Glu His Pro Glu Pro Gly Lys Tyr Ser Thr
145                 150                 155                 160

Thr Pro Ala Gln Leu Asn Ser Asp Gly Ser Tyr Phe Leu Tyr Ser Lys
                165                 170                 175

Leu Ser Val Glu Thr Ser Arg Trp Lys Gln Gly Glu Ser Phe Thr Cys
                180                 185                 190

Gly Val Met His Glu Ala Val Glu Asn His Tyr Thr Gln Lys Asn Val
                195                 200                 205

Ser His Ser Pro Gly Lys
                210

<210> SEQ ID NO 68
<211> LENGTH: 214
<212> TYPE: PRT
<213> ORGANISM: Unknown
<220> FEATURE:
<223> OTHER INFORMATION: Wild-type equine IgG6 Fc, Protein A -, C1q -

<400> SEQUENCE: 68

Gly Arg Pro Ser Val Phe Ile Phe Pro Pro Asn Pro Lys Asp Thr Leu
  1               5                  10                  15

Met Ile Ser Arg Thr Pro Glu Val Thr Cys Val Val Val Asp Val Ser
                 20                  25                  30

Gln Glu Asn Pro Asp Val Lys Phe Asn Trp Tyr Val Asp Gly Val Glu
                 35                  40                  45

Ala His Thr Ala Thr Thr Lys Ala Lys Glu Lys Gln Asp Asn Ser Thr
 50                  55                  60

Tyr Arg Val Val Ser Val Leu Pro Ile Gln His Gln Asp Trp Arg Arg
 65                  70                  75                  80

Gly Lys Glu Phe Lys Cys Lys Val Asn Asn Arg Ala Leu Pro Ala Pro
                 85                  90                  95

Val Glu Arg Thr Ile Thr Lys Ala Lys Gly Glu Leu Gln Asp Pro Gln
                100                 105                 110

Val Tyr Ile Leu Ala Pro His Pro Asp Glu Val Thr Lys Asn Thr Val
                115                 120                 125

Ser Val Thr Cys Leu Val Lys Asp Phe Tyr Pro Pro Asp Ile Asn Val
            130                 135                 140

Glu Trp Gln Ser Asn Glu Pro Glu Pro Val Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asp Arg Trp Glu Gln Gly Glu Ser Phe Thr Cys
```

```
                180                 185                 190
Val Val Met His Glu Ala Ile Arg His Thr Tyr Arg Gln Lys Ser Ile
            195                 200                 205

Thr Asn Phe Pro Gly Lys
        210

<210> SEQ ID NO 69
<211> LENGTH: 214
<212> TYPE: PRT
<213> ORGANISM: Unknown
<220> FEATURE:
<223> OTHER INFORMATION: Wild-type equine IgG7 Fc, Protein A +, C1q +

<400> SEQUENCE: 69

Val Gly Pro Ser Val Phe Ile Phe Pro Pro Lys Pro Lys Asp Val Leu
1               5                   10                  15

Met Ile Ser Arg Thr Pro Thr Val Thr Cys Val Val Val Asp Val Gly
            20                  25                  30

His Asp Phe Pro Asp Val Gln Phe Asn Trp Tyr Val Asp Gly Val Glu
        35                  40                  45

Thr His Thr Ala Thr Thr Glu Pro Lys Gln Glu Gln Asn Asn Ser Thr
    50                  55                  60

Tyr Arg Val Val Ser Ile Leu Ala Ile Gln His Lys Asp Trp Leu Ser
65                  70                  75                  80

Gly Lys Glu Phe Lys Cys Lys Val Asn Asn Gln Ala Leu Pro Ala Pro
                85                  90                  95

Val Gln Lys Thr Ile Ser Lys Pro Thr Gly Gln Pro Arg Glu Pro Gln
            100                 105                 110

Val Tyr Val Leu Ala Pro His Pro Asp Glu Leu Ser Lys Asn Lys Val
        115                 120                 125

Ser Val Thr Cys Leu Val Lys Asp Phe Tyr Pro Pro Asp Ile Asp Ile
    130                 135                 140

Glu Trp Lys Ser Asn Gly Gln Pro Glu Pro Glu Thr Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asn Arg Trp Gln Gln Gly Thr Thr Phe Thr Cys
            180                 185                 190

Ala Val Met His Glu Ala Leu His Asn His Tyr Thr Glu Lys Ser Val
        195                 200                 205

Ser Lys Ser Pro Gly Lys
    210

<210> SEQ ID NO 70
<211> LENGTH: 214
<212> TYPE: PRT
<213> ORGANISM: Artificial Sequence
<220> FEATURE:
<223> OTHER INFORMATION: Synthetic: Variant equine IgG1 Fc , Protein
      A +, C1q - , K(87)S

<400> SEQUENCE: 70

Gly Gly Pro Ser Val Phe Leu Phe Pro Pro Asn Pro Lys Asp Thr Leu
1               5                   10                  15

Met Ile Thr Arg Thr Pro Glu Val Thr Cys Val Val Val Asp Val Ser
            20                  25                  30

Gln Glu Asn Pro Asp Val Lys Phe Asn Trp Tyr Met Asp Gly Val Glu
        35                  40                  45
```

```
Val Arg Thr Ala Thr Thr Arg Pro Lys Glu Glu Gln Phe Asn Ser Thr
    50                  55                  60

Tyr Arg Val Val Ser Val Leu Arg Ile Gln His Gln Asp Trp Leu Ser
65                  70                  75                  80

Gly Lys Glu Phe Lys Cys Ser Val Asn Asn Gln Ala Leu Pro Gln Pro
                85                  90                  95

Ile Glu Arg Thr Ile Thr Lys Thr Lys Gly Arg Ser Gln Glu Pro Gln
                100                 105                 110

Val Tyr Val Leu Ala Pro His Pro Asp Glu Ser Lys Lys Ser Lys Val
                115                 120                 125

Ser Val Thr Cys Leu Val Lys Asp Phe Tyr Pro Pro Glu Ile Asn Ile
            130                 135                 140

Glu Trp Gln Ser Asn Gly Gln Pro Glu Leu Glu Thr Lys Tyr Ser Thr
145                 150                 155                 160

Thr Gln Ala Gln Gln Asp Ser Asp Gly Ser Tyr Phe Leu Tyr Ser Lys
                165                 170                 175

Leu Ser Val Asp Arg Asn Arg Trp Gln Gln Gly Thr Thr Phe Thr Cys
                180                 185                 190

Gly Val Met His Glu Ala Leu His Asn His Tyr Thr Gln Lys Asn Val
                195                 200                 205

Ser Lys Asn Pro Gly Lys
                210

<210> SEQ ID NO 71
<211> LENGTH: 214
<212> TYPE: PRT
<213> ORGANISM: Artificial Sequence
<220> FEATURE:
<223> OTHER INFORMATION: Synthetic: Variant equine IgG2 Fc, C1q -,
      Protein A +, F(203)Y

<400> SEQUENCE: 71

Gly Gly Pro Ser Val Phe Ile Phe Pro Pro Asn Pro Lys Asp Ala Leu
1               5                   10                  15

Met Ile Ser Arg Thr Pro Val Val Thr Cys Val Val Val Asn Leu Ser
                20                  25                  30

Asp Gln Tyr Pro Asp Val Gln Phe Ser Trp Tyr Val Asp Asn Thr Glu
            35                  40                  45

Val His Ser Ala Ile Thr Lys Gln Arg Glu Ala Gln Phe Asn Ser Thr
    50                  55                  60

Tyr Arg Val Val Ser Val Leu Pro Ile Gln His Gln Asp Trp Leu Ser
65                  70                  75                  80

Gly Lys Glu Phe Lys Cys Ser Val Thr Asn Val Gly Val Pro Gln Pro
                85                  90                  95

Ile Ser Arg Ala Ile Ser Arg Gly Lys Gly Pro Ser Arg Val Pro Gln
                100                 105                 110

Val Tyr Val Leu Pro Pro His Pro Asp Glu Leu Ala Lys Ser Lys Val
                115                 120                 125

Ser Val Thr Cys Leu Val Lys Asp Phe Tyr Pro Pro Asp Ile Ser Val
            130                 135                 140

Glu Trp Gln Ser Asn Arg Trp Pro Glu Leu Gly Lys Tyr Ser Thr
145                 150                 155                 160

Thr Pro Ala Gln Leu Asp Gly Asp Gly Ser Tyr Phe Leu Tyr Ser Lys
                165                 170                 175

Leu Ser Leu Glu Thr Ser Arg Trp Gln Gln Gly Glu Ser Phe Thr Cys
```

180                 185                 190
Ala Val Met His Glu Ala Leu His Asn His Tyr Thr Lys Thr Asp Ile
            195                 200                 205

Ser Glu Ser Leu Gly Lys
        210

<210> SEQ ID NO 72
<211> LENGTH: 214
<212> TYPE: PRT
<213> ORGANISM: Artificial Sequence
<220> FEATURE:
<223> OTHER INFORMATION: Synthetic: Variant equine IgG2 Fc, C1q -,
      Protein A +, A(15)T, F(203)Y

<400> SEQUENCE: 72

Gly Gly Pro Ser Val Phe Ile Phe Pro Pro Asn Pro Lys Asp Thr Leu
1               5                   10                  15

Met Ile Ser Arg Thr Pro Val Val Thr Cys Val Val Val Asn Leu Ser
            20                  25                  30

Asp Gln Tyr Pro Asp Val Gln Phe Ser Trp Tyr Val Asp Asn Thr Glu
        35                  40                  45

Val His Ser Ala Ile Thr Lys Gln Arg Glu Ala Gln Phe Asn Ser Thr
    50                  55                  60

Tyr Arg Val Val Ser Val Leu Pro Ile Gln His Gln Asp Trp Leu Ser
65                  70                  75                  80

Gly Lys Glu Phe Lys Cys Ser Val Thr Asn Val Gly Val Pro Gln Pro
                85                  90                  95

Ile Ser Arg Ala Ile Ser Arg Gly Lys Gly Pro Ser Arg Val Pro Gln
            100                 105                 110

Val Tyr Val Leu Pro Pro His Pro Asp Glu Leu Ala Lys Ser Lys Val
        115                 120                 125

Ser Val Thr Cys Leu Val Lys Asp Phe Tyr Pro Pro Asp Ile Ser Val
    130                 135                 140

Glu Trp Gln Ser Asn Arg Trp Pro Glu Leu Glu Gly Lys Tyr Ser Thr
145                 150                 155                 160

Thr Pro Ala Gln Leu Asp Gly Asp Gly Ser Tyr Phe Leu Tyr Ser Lys
                165                 170                 175

Leu Ser Leu Glu Thr Ser Arg Trp Gln Gln Val Glu Ser Phe Thr Cys
            180                 185                 190

Ala Val Met His Glu Ala Leu His Asn His Tyr Thr Lys Thr Asp Ile
        195                 200                 205

Ser Glu Ser Leu Gly Lys
        210

<210> SEQ ID NO 73
<211> LENGTH: 214
<212> TYPE: PRT
<213> ORGANISM: Artificial Sequence
<220> FEATURE:
<223> OTHER INFORMATION: Synthetic: Variant equine IgG3 Fc, Protein A +,
      C1q - , K(87)S

<400> SEQUENCE: 73

Gly Gly Pro Ser Val Phe Ile Phe Pro Pro Lys Pro Lys Asp Val Leu
1               5                   10                  15

Met Ile Thr Arg Met Pro Glu Val Thr Cys Leu Val Val Asp Val Ser
            20                  25                  30

His Asp Ser Ser Asp Val Leu Phe Thr Trp Tyr Val Asp Gly Thr Glu

```
            35                  40                  45
Val Lys Thr Ala Lys Thr Met Pro Asn Glu Glu Gln Asn Asn Ser Thr
 50                  55                  60

Tyr Arg Val Val Ser Val Leu Arg Ile Gln His Gln Asp Trp Leu Asn
 65                  70                  75                  80

Gly Lys Lys Phe Lys Cys Ser Val Asn Asn Gln Ala Leu Pro Ala Pro
                 85                  90                  95

Val Glu Arg Thr Ile Ser Lys Ala Thr Gly Gln Thr Arg Val Pro Gln
            100                 105                 110

Val Tyr Val Leu Ala Pro His Pro Asp Glu Leu Ser Lys Asn Lys Val
            115                 120                 125

Ser Val Thr Cys Leu Val Lys Asp Phe Tyr Pro Pro Asp Ile Thr Val
 130                 135                 140

Glu Trp Gln Ser Asn Glu His Pro Glu Pro Gly Lys Tyr Arg Thr
145                 150                 155                 160

Thr Glu Ala Gln Lys Asp Ser Asp Gly Ser Tyr Phe Leu Tyr Ser Lys
                165                 170                 175

Leu Thr Val Glu Lys Asp Arg Trp Gln Gln Gly Thr Thr Phe Thr Cys
            180                 185                 190

Val Val Met His Glu Ala Leu His Asn His Val Met Gln Lys Asn Ile
            195                 200                 205

Ser Lys Asn Pro Gly Lys
            210

<210> SEQ ID NO 74
<211> LENGTH: 214
<212> TYPE: PRT
<213> ORGANISM: Artificial Sequence
<220> FEATURE:
<223> OTHER INFORMATION: Synthetic: Variant equine IgG4 Fc, Protein A +,
      C1q - , K(87)S

<400> SEQUENCE: 74

Val Gly Pro Ser Val Phe Ile Phe Pro Pro Lys Pro Lys Asp Val Leu
1               5                   10                  15

Met Ile Ser Arg Thr Pro Thr Val Thr Cys Val Val Val Asp Val Gly
            20                  25                  30

His Asp Phe Pro Asp Val Gln Phe Asn Trp Tyr Val Asp Gly Val Glu
            35                  40                  45

Thr His Thr Ala Thr Thr Glu Pro Lys Gln Glu Gln Phe Asn Ser Thr
 50                  55                  60

Tyr Arg Val Val Ser Val Leu Pro Ile Gln His Lys Asp Trp Leu Ser
 65                  70                  75                  80

Gly Lys Glu Phe Lys Cys Ser Val Asn Asn Lys Ala Leu Pro Ala Pro
                 85                  90                  95

Val Glu Arg Thr Ile Ser Ala Pro Thr Gly Gln Pro Arg Glu Pro Gln
            100                 105                 110

Val Tyr Val Leu Ala Pro His Arg Asp Glu Leu Ser Lys Asn Lys Val
            115                 120                 125

Ser Val Thr Cys Leu Val Lys Asp Phe Tyr Pro Pro Asp Ile Asp Ile
 130                 135                 140

Glu Trp Lys Ser Asn Gly Gln Pro Glu Pro Glu Thr Lys Tyr Ser Thr
145                 150                 155                 160

Thr Pro Ala Gln Leu Asp Ser Asp Gly Ser Tyr Phe Leu Tyr Ser Lys
                165                 170                 175
```

```
Leu Thr Val Glu Thr Asn Arg Trp Gln Gly Thr Phe Thr Cys
                180                 185                 190

Ala Val Met His Glu Ala Leu His Asn His Tyr Thr Glu Lys Ser Val
                195                 200                 205

Ser Lys Ser Pro Gly Lys
            210

<210> SEQ ID NO 75
<211> LENGTH: 214
<212> TYPE: PRT
<213> ORGANISM: Artificial Sequence
<220> FEATURE:
<223> OTHER INFORMATION: Synthetic: Variant equine IgG5 Fc, C1q -,
      Protein A +, V(199)L, E(200)H

<400> SEQUENCE: 75

Gly Gly Pro Ser Val Phe Ile Phe Pro Pro Lys Pro Lys Asp Val Leu
1               5                   10                  15

Met Ile Ser Arg Lys Pro Glu Val Thr Cys Val Val Val Asp Leu Gly
                20                  25                  30

His Asp Asp Pro Asp Val Gln Phe Thr Trp Phe Val Asp Gly Val Glu
            35                  40                  45

Thr His Thr Ala Thr Thr Glu Pro Lys Glu Glu Gln Phe Asn Ser Thr
        50                  55                  60

Tyr Arg Val Val Ser Val Leu Pro Ile Gln His Gln Asp Trp Leu Ser
65                  70                  75                  80

Gly Lys Glu Phe Lys Cys Ser Val Thr Ser Lys Ala Leu Pro Ala Pro
                85                  90                  95

Val Glu Arg Thr Ile Ser Lys Ala Lys Gly Gln Leu Arg Val Pro Gln
                100                 105                 110

Val Tyr Val Leu Ala Pro His Pro Asp Glu Leu Ala Lys Asn Thr Val
            115                 120                 125

Ser Val Thr Cys Leu Val Lys Asp Phe Tyr Pro Pro Glu Ile Asp Val
        130                 135                 140

Glu Trp Gln Ser Asn Glu His Pro Glu Pro Glu Gly Lys Tyr Ser Thr
145                 150                 155                 160

Thr Pro Ala Gln Leu Asn Ser Asp Gly Ser Tyr Phe Leu Tyr Ser Lys
                165                 170                 175

Leu Ser Val Glu Thr Ser Arg Trp Lys Gln Gly Glu Ser Phe Thr Cys
                180                 185                 190

Gly Val Met His Glu Ala Leu His Asn His Tyr Thr Gln Lys Asn Val
                195                 200                 205

Ser His Ser Pro Gly Lys
            210

<210> SEQ ID NO 76
<211> LENGTH: 214
<212> TYPE: PRT
<213> ORGANISM: Artificial Sequence
<220> FEATURE:
<223> OTHER INFORMATION: Synthetic: Variant equine IgG6 Fc, C1q -,
      Protein A +, I(199)L , R(200)H, H(201)N, T(202)H

<400> SEQUENCE: 76

Gly Arg Pro Ser Val Phe Ile Phe Pro Pro Asn Pro Lys Asp Thr Leu
1               5                   10                  15

Met Ile Ser Arg Thr Pro Glu Val Thr Cys Val Val Val Asp Val Ser
                20                  25                  30
```

```
Gln Glu Asn Pro Asp Val Lys Phe Asn Trp Tyr Val Asp Gly Val Glu
         35                  40                  45

Ala His Thr Ala Thr Thr Lys Ala Lys Glu Lys Gln Asp Asn Ser Thr
 50                  55                  60

Tyr Arg Val Val Ser Val Leu Pro Ile Gln His Gln Asp Trp Arg Arg
 65                  70                  75                  80

Gly Lys Glu Phe Lys Cys Lys Val Asn Asn Arg Ala Leu Pro Ala Pro
                 85                  90                  95

Val Glu Arg Thr Ile Thr Lys Ala Lys Gly Glu Leu Gln Asp Pro Gln
                100                 105                 110

Val Tyr Ile Leu Ala Pro His Pro Asp Glu Val Thr Lys Asn Thr Val
            115                 120                 125

Ser Val Thr Cys Leu Val Lys Asp Phe Tyr Pro Pro Asp Ile Asn Val
130                 135                 140

Glu Trp Gln Ser Asn Glu Glu Pro Glu Pro Glu Val Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asp Arg Trp Glu Gln Gly Glu Ser Phe Thr Cys
            180                 185                 190

Val Val Met His Glu Ala Leu His Asn His Tyr Arg Gln Lys Ser Ile
        195                 200                 205

Thr Asn Phe Pro Gly Lys
        210

<210> SEQ ID NO 77
<211> LENGTH: 214
<212> TYPE: PRT
<213> ORGANISM: Artificial Sequence
<220> FEATURE:
<223> OTHER INFORMATION: Synthetic: Variant equine IgG7 Fc, Protein A +,
      C1q - , K(87)S

<400> SEQUENCE: 77

Val Gly Pro Ser Val Phe Ile Phe Pro Pro Lys Pro Lys Asp Val Leu
1               5                  10                  15

Met Ile Ser Arg Thr Pro Thr Val Thr Cys Val Val Val Asp Val Gly
            20                  25                  30

His Asp Phe Pro Asp Val Gln Phe Asn Trp Tyr Val Asp Gly Val Glu
         35                  40                  45

Thr His Thr Ala Thr Thr Glu Pro Lys Gln Glu Gln Asn Asn Ser Thr
 50                  55                  60

Tyr Arg Val Val Ser Ile Leu Ala Ile Gln His Lys Asp Trp Leu Ser
 65                  70                  75                  80

Gly Lys Glu Phe Lys Cys Ser Val Asn Asn Gln Ala Leu Pro Ala Pro
                 85                  90                  95

Val Gln Lys Thr Ile Ser Lys Pro Thr Gly Gln Pro Arg Glu Pro Gln
                100                 105                 110

Val Tyr Val Leu Ala Pro His Pro Asp Glu Leu Ser Lys Asn Lys Val
            115                 120                 125

Ser Val Thr Cys Leu Val Lys Asp Phe Tyr Pro Pro Asp Ile Asp Ile
130                 135                 140

Glu Trp Lys Ser Asn Gly Gln Pro Glu Pro Glu Thr Lys Tyr Ser Thr
145                 150                 155                 160

Thr Pro Ala Gln Leu Asp Gly Asp Gly Ser Tyr Phe Leu Tyr Ser Lys
                165                 170                 175
```

-continued

Leu Thr Val Glu Thr Asn Arg Trp Gln Gln Gly Thr Thr Phe Thr Cys
                180                 185                 190

Ala Val Met His Glu Ala Leu His Asn His Tyr Thr Glu Lys Ser Val
            195                 200                 205

Ser Lys Ser Pro Gly Lys
        210

<210> SEQ ID NO 78
<211> LENGTH: 220
<212> TYPE: PRT
<213> ORGANISM: Artificial Sequence
<220> FEATURE:
<223> OTHER INFORMATION: Synthetic: Variant canine IgG-B Fc, Protein
      A +, C1q - , K(93)R

<400> SEQUENCE: 78

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Arg Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 79
<211> LENGTH: 220
<212> TYPE: PRT
<213> ORGANISM: Artificial Sequence
<220> FEATURE:
<223> OTHER INFORMATION: Synthetic: Variant canine IgG-C Fc, Protein
      A -, C1q - , K(93)R

<400> SEQUENCE: 79

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

```
Val Val Val Asp Leu Asp Pro Glu Asn Pro Glu Val Gln Ile Ser Trp
            35                  40                  45

Phe Val Asp Ser Lys Gln Val Gln Thr Ala Asn Thr Gln Pro Arg Glu
 50                  55                  60

Glu Gln Ser Asn Gly Thr Tyr Arg Val Val Ser Val Leu Pro Ile Gly
 65                  70                  75                  80

His Gln Asp Trp Leu Ser Gly Lys Gln Phe Lys Cys Arg Val Asn Asn
                 85                  90                  95

Lys Ala Leu Pro Ser Pro Ile Glu Glu Ile Ser Lys Thr Pro Gly
                100                 105                 110

Gln Ala His Gln Pro Asn Val Tyr Val Leu Pro Pro Ser Arg Asp Glu
                115                 120                 125

Met Ser Lys Asn Thr Val Thr Leu Thr Cys Leu Val Lys Asp Phe Phe
130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
                195                 200                 205

Tyr Thr Gln Ile Ser Leu Ser His Ser Pro Gly Lys
                210                 215                 220

<210> SEQ ID NO 80
<211> LENGTH: 237
<212> TYPE: PRT
<213> ORGANISM: Unknown
<220> FEATURE:
<223> OTHER INFORMATION: Alternative wild-type feline IgG1a Fc, Protein
      A +, C1q +

<400> SEQUENCE: 80

Arg Lys Thr Asp His Pro Pro Gly Pro Lys Thr Gly Glu Gly Pro Lys
 1               5                  10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
                35                  40                  45

Cys Leu Val Val Asp Leu Gly Pro Asp Asp Ser Asp Val Gln Ile Thr
 50                  55                  60

Trp Phe Val Asp Asn Thr Gln Val Tyr Thr Ala Lys Thr Ser Pro Arg
 65                  70                  75                  80

Glu Glu Gln Phe Asn Ser Thr Tyr Arg Val Val Ser Val Leu Pro Ile
                 85                  90                  95

Leu His Gln Asp Trp Leu Lys Gly Lys Glu Phe Lys Cys Lys Val Asn
                100                 105                 110

Ser Lys Ser Leu Pro Ser Pro Ile Glu Arg Thr Ile Ser Lys Ala Lys
                115                 120                 125

Gly Gln Pro His Glu Pro Gln Val Tyr Val Leu Pro Pro Ala Gln Glu
                130                 135                 140

Glu Leu Ser Glu Asn Lys Val Ser Val Thr Cys Leu Ile Lys Ser Phe
145                 150                 155                 160

His Pro Pro Asp Ile Ala Val Glu Trp Glu Ile Thr Gly Gln Pro Glu
```

```
                    165                 170                 175
Pro Glu Asn Asn Tyr Arg Thr Thr Pro Pro Gln Leu Asp Ser Asp Gly
                180                 185                 190

Thr Tyr Phe Val Tyr Ser Lys Leu Ser Val Asp Arg Ser His Trp Gln
            195                 200                 205

Arg Gly Asn Thr Tyr Thr Cys Ser Val Ser His Glu Ala Leu His Ser
        210                 215                 220

His His Thr Gln Lys Ser Leu Thr Gln Ser Pro Gly Lys
225                 230                 235

<210> SEQ ID NO 81
<211> LENGTH: 237
<212> TYPE: PRT
<213> ORGANISM: Unknown
<220> FEATURE:
<223> OTHER INFORMATION: Alternative wild-type feline IgG1b Fc, Protein
      A +, C1q +

<400> SEQUENCE: 81

Arg Lys Thr Asp His Pro Pro Gly Pro Lys Thr Gly Glu Gly Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
        50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 82
<211> LENGTH: 237
<212> TYPE: PRT
<213> ORGANISM: Artificial Sequence
<220> FEATURE:
<223> OTHER INFORMATION: Synthetic: Variant feline IgG1a Fc, Protein
      A +, C1q -, P(198)A
```

```
<400> SEQUENCE: 82

Arg Lys Thr Asp His Pro Pro Gly Pro Lys Thr Gly Glu Gly Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Ser Asp Val Gln Ile Thr
        50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Tyr Ser Lys Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 83
<211> LENGTH: 237
<212> TYPE: PRT
<213> ORGANISM: Artificial Sequence
<220> FEATURE:
<223> OTHER INFORMATION: Synthetic: Variant feline IgG1b Fc, Protein
      A +, C1q -, P(198)A

<400> SEQUENCE: 83

Arg Lys Thr Asp His Pro Pro Gly Pro Lys Thr Gly Glu Gly Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Ser Asp Val Gln Ile Thr
        50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110
```

```
Ser Lys Ser Leu Pro Ser Pro Ile Glu Arg Thr Ile Ser Lys Asp Lys
            115                 120                 125

Gly Gln Pro His Glu Pro Gln Val Tyr Val Leu Pro Pro Ala Gln Glu
130                 135                 140

Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235
```

<210> SEQ ID NO 84
<211> LENGTH: 220
<212> TYPE: PRT
<213> ORGANISM: Artificial Sequence
<220> FEATURE:
<223> OTHER INFORMATION: Synthetic: Variant canine IgG-C Fc , C1q - ,
      K(93)R , Protein A +, I(21)T, V(23)L, T(24)I

<400> SEQUENCE: 84

```
Pro Gly Cys Gly Leu Leu Gly Gly Pro Ser Val Phe Ile Phe Pro Pro
1               5                   10                  15

Lys Pro Lys Asp Thr Leu Leu Ile Ala Arg Thr Pro Thr Val Thr Cys
            20                  25                  30

Val Val Val Asp Leu Asp Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Arg Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
        115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Ile Ser Leu Ser His Ser Pro Gly Lys
    210                 215                 220
```

<210> SEQ ID NO 85

```
<211> LENGTH: 31
<212> TYPE: PRT
<213> ORGANISM: Unknown
<220> FEATURE:
<223> OTHER INFORMATION: Wild-type GLP1 (7-37)

<400> SEQUENCE: 85

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Ala Gly
            20                  25                  30

<210> SEQ ID NO 86
<211> LENGTH: 29
<212> TYPE: PRT
<213> ORGANISM: Artificial Sequence
<220> FEATURE:
<223> OTHER INFORMATION: Synthetic: GLP1-S8 (7-35)

<400> SEQUENCE: 86

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 87
<211> LENGTH: 29
<212> TYPE: PRT
<213> ORGANISM: Artificial Sequence
<220> FEATURE:
<223> OTHER INFORMATION: Synthetic: GLP1-G8 (7-35)

<400> SEQUENCE: 87

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 88
<211> LENGTH: 1
<212> TYPE: PRT
<213> ORGANISM: Artificial Sequence
<220> FEATURE:
<223> OTHER INFORMATION: Synthetic: 1G extension

<400> SEQUENCE: 88

Gly
1

<210> SEQ ID NO 89
<211> LENGTH: 2
<212> TYPE: PRT
<213> ORGANISM: Artificial Sequence
<220> FEATURE:
<223> OTHER INFORMATION: Synthetic: 2G extension

<400> SEQUENCE: 89

Gly Gly
1

<210> SEQ ID NO 90
<211> LENGTH: 3
<212> TYPE: PRT
<213> ORGANISM: Artificial Sequence
<220> FEATURE:
<223> OTHER INFORMATION: Synthetic: 3G extension
```

```
<400> SEQUENCE: 90

Gly Gly Gly
1

<210> SEQ ID NO 91
<211> LENGTH: 4
<212> TYPE: PRT
<213> ORGANISM: Artificial Sequence
<220> FEATURE:
<223> OTHER INFORMATION: Synthetic: 4G extension

<400> SEQUENCE: 91

Gly Gly Gly Gly
1

<210> SEQ ID NO 92
<211> LENGTH: 5
<212> TYPE: PRT
<213> ORGANISM: Artificial Sequence
<220> FEATURE:
<223> OTHER INFORMATION: Synthetic: 5G extension

<400> SEQUENCE: 92

Gly Gly Gly Gly Gly
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic: 6G extension

<400> SEQUENCE: 93

Gly Gly Gly Gly Gly Gly
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic: 7G extension

<400> SEQUENCE: 94

Gly Gly Gly Gly Gly Gly Gly
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic: 8G extension

<400> SEQUENCE: 95

Gly Gly Gly Gly Gly Gly Gly Gly
1               5

<210> SEQ ID NO 96
<211> LENGTH: 305
<212> TYPE: PRT
<213> ORGANISM: Artificial Sequence
<220> FEATURE:
<223> OTHER INFORMATION: Synthetic: ssGLP1-G8_I_WTfeIgG2
```

<400> SEQUENCE: 96

```
Met Ala Val Leu Gly Leu Leu Phe Cys Leu Val Thr Phe Pro Ser Cys
1               5                   10                  15

Val Leu Ser His Gly Glu Gly Thr Phe Thr Ser Asp Val Ser Ser Tyr
            20                  25                  30

Leu Glu Gly Gln Ala Ala Lys Glu Phe Ile Ala Trp Leu Val Lys Gly
        35                  40                  45

Gly Ala Gly Gly Gly Gly Ser Gly Gly Ser Gly Gly Gly Ser
    50                  55                  60

Gly Gly Gly Ser Pro Lys Thr Ala Ser Thr Ile Glu Ser Lys Thr Gly
65                  70                  75                  80

Glu Gly Pro Lys Cys Pro Val Pro Glu Ile Pro Gly Ala Pro Ser Val
                85                  90                  95

Phe Ile Phe Pro Pro Lys Pro Lys Asp Thr Leu Ser Ile Ser Arg Thr
                100                 105                 110

Pro Glu Val Thr Cys Leu Val Val Asp Leu Gly Pro Asp Asp Ser Asn
            115                 120                 125

Val Gln Ile Thr Trp Phe Val Asp Asn Thr Glu Met His Thr Ala Lys
    130                 135                 140

Thr Arg Pro Arg Glu Glu Gln Phe Asn Ser Thr Tyr Arg Val Val Ser
145                 150                 155                 160

Val Leu Pro Ile Leu His Gln Asp Trp Leu Lys Gly Lys Glu Phe Lys
                165                 170                 175

Cys Lys Val Asn Ser Lys Ser Leu Pro Ser Ala Met Glu Arg Thr Ile
            180                 185                 190

Ser Lys Ala Lys Gly Gln Pro His Glu Pro Gln Val Tyr Val Leu Pro
    195                 200                 205

Pro Thr Gln Glu Glu Leu Ser Glu Asn Lys Val Ser Val Thr Cys Leu
210                 215                 220

Ile Lys Gly Phe His Pro Pro Asp Ile Ala Val Glu Trp Glu Ile Thr
225                 230                 235                 240

Gly Gln Pro Glu Pro Glu Asn Asn Tyr Gln Thr Thr Pro Pro Gln Leu
                245                 250                 255

Asp Ser Asp Gly Thr Tyr Phe Leu Tyr Ser Arg Leu Ser Val Asp Arg
            260                 265                 270

Ser His Trp Gln Arg Gly Asn Thr Tyr Thr Cys Ser Val Ser His Glu
    275                 280                 285

Ala Leu His Ser His His Thr Gln Lys Ser Leu Thr Gln Ser Pro Gly
    290                 295                 300

Lys
305
```

<210> SEQ ID NO 97
<211> LENGTH: 346
<212> TYPE: PRT
<213> ORGANISM: Artificial Sequence
<220> FEATURE:
<223> OTHER INFORMATION: Synthetic: ssGLP1-G8/GLP1-3G_III_ WTfeIgG2

<400> SEQUENCE: 97

```
Met Ala Val Leu Gly Leu Leu Phe Cys Leu Val Thr Phe Pro Ser Cys
1               5                   10                  15

Val Leu Ser His Gly Glu Gly Thr Phe Thr Ser Asp Val Ser Ser Tyr
            20                  25                  30

Leu Glu Gly Gln Ala Ala Lys Glu Phe Ile Ala Trp Leu Val Lys Gly
```

```
            35                  40                  45
Gly Ala Gly Gly Gly Gly Ser Gly Gly Ser Gly Gly Ser
 50                  55                  60
Gly Gly Gly Ser Pro Lys Thr Ala Ser Thr Ile Glu Ser Lys Thr Gly
 65                  70                  75                  80
Glu Gly Pro Lys Cys Pro Val Pro Glu Ile Pro Gly Ala Pro Ser Val
                 85                  90                  95
Phe Ile Phe Pro Pro Lys Pro Lys Asp Thr Leu Ser Ile Ser Arg Thr
            100                 105                 110
Pro Glu Val Thr Cys Leu Val Val Asp Leu Gly Pro Asp Asp Ser Asn
        115                 120                 125
Val Gln Ile Thr Trp Phe Val Asp Asn Thr Glu Met His Thr Ala Lys
    130                 135                 140
Thr Arg Pro Arg Glu Glu Gln Phe Asn Ser Thr Tyr Arg Val Val Ser
145                 150                 155                 160
Val Leu Pro Ile Leu His Gln Asp Trp Leu Lys Gly Lys Glu Phe Lys
                165                 170                 175
Cys Lys Val Asn Ser Lys Ser Leu Pro Ser Ala Met Glu Arg Thr Ile
            180                 185                 190
Ser Lys Ala Lys Gly Gln Pro His Glu Pro Gln Val Tyr Val Leu Pro
        195                 200                 205
Pro Thr Gln Glu Glu Leu Ser Glu Asn Lys Val Ser Val Thr Cys Leu
    210                 215                 220
Ile Lys Gly Phe His Pro Pro Asp Ile Ala Val Glu Trp Glu Ile Thr
225                 230                 235                 240
Gly Gln Pro Glu Pro Glu Asn Asn Tyr Gln Thr Thr Pro Pro Gln Leu
                245                 250                 255
Asp Ser Asp Gly Thr Tyr Phe Leu Tyr Ser Arg Leu Ser Val Asp Arg
            260                 265                 270
Ser His Trp Gln Arg Gly Asn Thr Tyr Thr Cys Ser Val Ser His Glu
        275                 280                 285
Ala Leu His Ser His His Thr Gln Lys Ser Leu Thr Gln Ser Pro Gly
    290                 295                 300
Lys Gly Gly Gly Gly Ser Gly Gly Gly Gly His Ala Glu Gly Thr Phe
305                 310                 315                 320
Thr Ser Asp Val Ser Ser Tyr Leu Glu Gly Gln Ala Ala Lys Glu Phe
                325                 330                 335
Ile Ala Trp Leu Val Lys Gly Gly Gly
            340                 345

<210> SEQ ID NO 98
<211> LENGTH: 30
<212> TYPE: PRT
<213> ORGANISM: Artificial Sequence
<220> FEATURE:
<223> OTHER INFORMATION: Synthetic: Variant GLP1 (7-36)

<400> SEQUENCE: 98

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Ala
            20                  25                  30

<210> SEQ ID NO 99
<211> LENGTH: 29
<212> TYPE: PRT
```

<213> ORGANISM: Artificial Sequence
<220> FEATURE:
<223> OTHER INFORMATION: Synthetic: Variant GLP1 (7-35)

<400> SEQUENCE: 99

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 100
<211> LENGTH: 229
<212> TYPE: PRT
<213> ORGANISM: Unknown
<220> FEATURE:
<223> OTHER INFORMATION: Wild-type equine Fc IgG2 (including equine IgG2 hinge), Protein A - , C1q -

<400> SEQUENCE: 100

Val Pro Lys Pro Gln Cys Pro Pro Tyr Thr His Ser Lys Phe Leu Gly
1               5                   10                  15

Gly Pro Ser Val Phe Ile Phe Pro Pro Asn Pro Lys Asp Ala Leu Met
            20                  25                  30

Ile Ser Arg Thr Pro Val Val Thr Cys Val Val Val Asn Leu Ser Asp
        35                  40                  45

Gln Tyr Pro Asp Val Gln Phe Ser Trp Tyr Val Asp Asn Thr Glu Val
    50                  55                  60

His Ser Ala Ile Thr Lys Gln Arg Glu Ala Gln Phe Asn Ser Thr Tyr
65                  70                  75                  80

Arg Val Val Ser Val Leu Pro Ile Gln His Gln Asp Trp Leu Ser Gly
                85                  90                  95

Lys Glu Phe Lys Cys Ser Val Thr Asn Val Gly Val Pro Gln Pro Ile
            100                 105                 110

Ser Arg Ala Ile Ser Arg Gly Lys Gly Pro Ser Arg Val Pro Gln Val
        115                 120                 125

Tyr Val Leu Pro Pro His Pro Asp Glu Leu Ala Lys Ser Lys Val Ser
    130                 135                 140

Val Thr Cys Leu Val Lys Asp Phe Tyr Pro Pro Asp Ile Ser Val Glu
145                 150                 155                 160

Trp Gln Ser Asn Arg Trp Pro Glu Leu Glu Gly Lys Tyr Ser Thr Thr
                165                 170                 175

Pro Ala Gln Leu Asp Gly Asp Gly Ser Tyr Phe Leu Tyr Ser Lys Leu
            180                 185                 190

Ser Leu Glu Thr Ser Arg Trp Gln Gln Val Glu Ser Phe Thr Cys Ala
        195                 200                 205

Val Met His Glu Ala Leu His Asn His Phe Thr Lys Thr Asp Ile Ser
    210                 215                 220

Glu Ser Leu Gly Lys
225

<210> SEQ ID NO 101
<211> LENGTH: 14
<212> TYPE: PRT
<213> ORGANISM: Unknown
<220> FEATURE:
<223> OTHER INFORMATION: Wild-type equine IgG1 hinge

<400> SEQUENCE: 101

Asp Met Ser Lys Cys Pro Lys Cys Pro Ala Pro Glu Leu Leu

```
<210> SEQ ID NO 102
<211> LENGTH: 15
<212> TYPE: PRT
<213> ORGANISM: Unknown
<220> FEATURE:
<223> OTHER INFORMATION: Wild-type equine IgG2 hinge

<400> SEQUENCE: 102

Val Pro Lys Pro Gln Cys Pro Pro Tyr Thr His Ser Lys Phe Leu
1               5                   10                  15

<210> SEQ ID NO 103
<211> LENGTH: 318
<212> TYPE: PRT
<213> ORGANISM: Artificial Sequence
<220> FEATURE:
<223> OTHER INFORMATION: Synthetic: GLP1-G8/GLP1-3G_III_ VAReqIgG2

<400> SEQUENCE: 103

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
                20                  25                  30

Gly Gly Gly Gly Ser Gly Gly Gly Ser Gly Gly Gly Ser Gly Gly Gly
        35                  40                  45

Ser Asp Met Ser Lys Cys Pro Lys Cys Pro Ala Pro Glu Leu Leu Gly
    50                  55                  60

Gly Pro Ser Val Phe Ile Phe Pro Pro Asn Pro Lys Asp Thr Leu Met
65                  70                  75                  80

Ile Ser Arg Thr Pro Val Val Thr Cys Val Val Val Asn Leu Ser Asp
                85                  90                  95

Gln Tyr Pro Asp Val Gln Phe Ser Trp Tyr Val Asp Asn Thr Glu Val
                100                 105                 110

His Ser Ala Ile Thr Lys Gln Arg Glu Ala Gln Phe Asn Ser Thr Tyr
            115                 120                 125

Arg Val Val Ser Val Leu Pro Ile Gln His Gln Asp Trp Leu Ser Gly
        130                 135                 140

Lys Glu Phe Lys Cys Ser Val Thr Asn Val Gly Val Pro Gln Pro Ile
145                 150                 155                 160

Ser Arg Ala Ile Ser Arg Gly Lys Gly Pro Ser Arg Val Pro Gln Val
                165                 170                 175

Tyr Val Leu Pro Pro His Pro Asp Glu Leu Ala Lys Ser Lys Val Ser
                180                 185                 190

Val Thr Cys Leu Val Lys Asp Phe Tyr Pro Pro Asp Ile Ser Val Glu
            195                 200                 205

Trp Gln Ser Asn Arg Trp Pro Glu Leu Glu Gly Lys Tyr Ser Thr Thr
        210                 215                 220

Pro Ala Gln Leu Asp Gly Asp Gly Ser Tyr Phe Leu Tyr Ser Lys Leu
225                 230                 235                 240

Ser Leu Glu Thr Ser Arg Trp Gln Gln Val Glu Ser Phe Thr Cys Ala
                245                 250                 255

Val Met His Glu Ala Leu His Asn His Tyr Thr Lys Thr Asp Ile Ser
                260                 265                 270

Glu Ser Leu Gly Lys Gly Gly Gly Ser Gly Gly Gly Gly His Ala
            275                 280                 285
```

Glu Gly Thr Phe Thr Ser Asp Val Ser Ser Tyr Leu Glu Gly Gln Ala
        290                 295                 300

Ala Lys Glu Phe Ile Ala Trp Leu Val Lys Gly Gly Gly
305                 310                 315

<210> SEQ ID NO 104
<211> LENGTH: 279
<212> TYPE: PRT
<213> ORGANISM: Artificial Sequence
<220> FEATURE:
<223> OTHER INFORMATION: Synthetic: GLP1-G8_I_VAReqIgG2

<400> SEQUENCE: 104

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Ala Gly
            20                  25                  30

Gly Gly Gly Gly Ser Gly Gly Ser Gly Gly Gly Ser Gly Gly Gly
        35                  40                  45

Ser Ser Val Pro Lys Pro Gln Cys Pro Pro Tyr Thr His Ser Lys Phe
    50                  55                  60

Leu Gly Gly Pro Ser Val Phe Ile Phe Pro Pro Asn Pro Lys Asp Thr
65                  70                  75                  80

Leu Met Ile Ser Arg Thr Pro Val Val Thr Cys Val Val Asn Leu
                85                  90                  95

Ser Asp Gln Tyr Pro Asp Val Gln Phe Ser Trp Tyr Val Asp Asn Thr
            100                 105                 110

Glu Val His Ser Ala Ile Thr Lys Gln Arg Glu Ala Gln Phe Asn Ser
        115                 120                 125

Thr Tyr Arg Val Val Ser Val Leu Pro Ile Gln His Gln Asp Trp Leu
    130                 135                 140

Ser Gly Lys Glu Phe Lys Cys Ser Val Thr Asn Val Gly Val Pro Gln
145                 150                 155                 160

Pro Ile Ser Arg Ala Ile Ser Arg Gly Lys Gly Pro Ser Arg Val Pro
                165                 170                 175

Gln Val Tyr Val Leu Pro Pro His Pro Asp Glu Leu Ala Lys Ser Lys
            180                 185                 190

Val Ser Val Thr Cys Leu Val Lys Asp Phe Tyr Pro Pro Asp Ile Ser
        195                 200                 205

Val Glu Trp Gln Ser Asn Arg Trp Pro Glu Leu Glu Gly Lys Tyr Ser
    210                 215                 220

Thr Thr Pro Ala Gln Leu Asp Gly Asp Gly Ser Tyr Phe Leu Tyr Ser
225                 230                 235                 240

Lys Leu Ser Leu Glu Thr Ser Arg Trp Gln Gln Val Glu Ser Phe Thr
                245                 250                 255

Cys Ala Val Met His Glu Ala Leu His Asn His Tyr Thr Lys Thr Asp
            260                 265                 270

Ile Ser Glu Ser Leu Gly Lys
        275

<210> SEQ ID NO 105
<211> LENGTH: 321
<212> TYPE: PRT
<213> ORGANISM: Artificial Sequence
<220> FEATURE:
<223> OTHER INFORMATION: Synthetic: GLP1-G8/GLP1-2G_III_ VARcaIgGD

<400> SEQUENCE: 105

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Ser Gly Gly Gly Ser
        35                  40                  45

Pro Lys Glu Ser Thr Cys Lys Cys Ile Ser Pro Cys Pro Val Pro Glu
50                  55                  60

Ser Leu Gly Gly Pro Ser Val Phe Ile Phe Pro Pro Lys Pro Lys Asp
65                  70                  75                  80

Thr Leu Leu Ile Ala Arg Thr Pro Glu Ile Thr Cys Val Val Leu Asp
                85                  90                  95

Leu Gly Arg Glu Asp Pro Glu Val Gln Ile Ser Trp Phe Val Asp Gly
            100                 105                 110

Lys Glu Val His Thr Ala Lys Thr Gln Pro Arg Glu Gln Gln Phe Asn
            115                 120                 125

Ser Thr Tyr Arg Val Val Ser Val Leu Pro Ile Gly His Gln Asp Trp
130                 135                 140

Leu Thr Gly Lys Glu Phe Lys Cys Arg Val Asn His Ile Gly Leu Pro
145                 150                 155                 160

Ser Pro Ile Glu Arg Thr Ile Ser Lys Ala Arg Gly Gln Ala His Gln
                165                 170                 175

Pro Ser Val Tyr Val Leu Pro Pro Ser Pro Lys Glu Leu Ser Ser Ser
            180                 185                 190

Asp Thr Val Thr Leu Thr Cys Leu Ile Lys Asp Phe Phe Pro Pro Glu
            195                 200                 205

Ile Asp Val Glu Trp Gln Ser Asn Gly Gln Pro Glu Pro Glu Ser Lys
210                 215                 220

Tyr His Thr Thr Ala Pro Gln Leu Asp Glu Asp Gly Ser Tyr Phe Leu
225                 230                 235                 240

Tyr Ser Lys Leu Ser Val Asp Lys Ser Arg Trp Gln Gln Gly Asp Thr
                245                 250                 255

Phe Thr Cys Ala Val Met His Glu Ala Leu His Asn His Tyr Thr Asp
            260                 265                 270

Leu Ser Leu Ser His Ser Pro Gly Lys Gly Gly Gly Ser Gly Gly
            275                 280                 285

Gly Gly His Ala Glu Gly Thr Phe Thr Ser Asp Val Ser Ser Tyr Leu
        290                 295                 300

Glu Gly Gln Ala Ala Lys Glu Phe Ile Ala Trp Leu Val Lys Gly Gly
305                 310                 315                 320

Gly

<210> SEQ ID NO 106
<211> LENGTH: 321
<212> TYPE: PRT
<213> ORGANISM: Artificial Sequence
<220> FEATURE:
<223> OTHER INFORMATION: Synthetic: GLP1-G8/GLP1-2G_III_ VARcaIgGD

<400> SEQUENCE: 106

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

```
Ser Gly Gly Gly Gly Ser Gly Gly Gly Ser Gly Gly Gly Ser
         35                  40                  45

Pro Lys Glu Ser Thr Ser Lys Cys Ile Ser Pro Cys Pro Val Pro Glu
 50                  55                  60

Ser Leu Gly Gly Pro Ser Val Phe Ile Phe Pro Pro Lys Pro Lys Asp
 65                  70                  75                  80

Thr Leu Leu Ile Ala Arg Thr Pro Glu Ile Thr Cys Val Val Leu Asp
                 85                  90                  95

Leu Gly Arg Glu Asp Pro Glu Val Gln Ile Ser Trp Phe Val Asp Gly
                100                 105                 110

Lys Glu Val His Thr Ala Lys Thr Gln Pro Arg Glu Gln Gln Phe Asn
                115                 120                 125

Ser Thr Tyr Arg Val Val Ser Val Leu Pro Ile Gly His Gln Asp Trp
130                 135                 140

Leu Thr Gly Lys Glu Phe Lys Cys Arg Val Asn His Ile Gly Leu Pro
145                 150                 155                 160

Ser Pro Ile Glu Arg Thr Ile Ser Lys Ala Arg Gly Gln Ala His Gln
                165                 170                 175

Pro Ser Val Tyr Val Leu Pro Pro Ser Pro Lys Glu Leu Ser Ser Ser
                180                 185                 190

Asp Thr Val Thr Leu Thr Cys Leu Ile Lys Asp Phe Phe Pro Pro Glu
                195                 200                 205

Ile Asp Val Glu Trp Gln Ser Asn Gly Gln Pro Glu Pro Glu Ser Lys
                210                 215                 220

Tyr His Thr Thr Ala Pro Gln Leu Asp Glu Asp Gly Ser Tyr Phe Leu
225                 230                 235                 240

Tyr Ser Lys Leu Ser Val Asp Lys Ser Arg Trp Gln Gln Gly Asp Thr
                245                 250                 255

Phe Thr Cys Ala Val Met His Glu Ala Leu His Asn His Tyr Thr Asp
                260                 265                 270

Leu Ser Leu Ser His Ser Pro Gly Lys Gly Gly Gly Ser Gly Gly
                275                 280                 285

Gly Gly His Ala Glu Gly Thr Phe Thr Ser Asp Val Ser Ser Tyr Leu
        290                 295                 300

Glu Gly Gln Ala Ala Lys Glu Phe Ile Ala Trp Leu Val Lys Gly Gly
305                 310                 315                 320

Gly

<210> SEQ ID NO 107
<211> LENGTH: 237
<212> TYPE: PRT
<213> ORGANISM: Unknown
<220> FEATURE:
<223> OTHER INFORMATION: Wild-type canine IgG-B Fc with hinge, Protein
      A +, C1q +, CD16 +

<400> SEQUENCE: 107

Pro Lys Arg Glu Asn Gly Arg Val Pro Arg Pro Asp Cys Pro Lys
 1               5                  10                  15

Cys Pro Ala Pro Glu Met Leu Gly Gly Pro Ser Val Phe Ile Phe Pro
                 20                  25                  30

Pro Lys Pro Lys Asp Thr Leu Leu Ile Ala Arg Thr Pro Glu Val Thr
                 35                  40                  45

Cys Val Val Val Asp Leu Asp Pro Glu Asp Pro Glu Val Gln Ile Ser
 50                  55                  60
```

```
Trp Phe Val Asp Gly Lys Gln Met Gln Thr Ala Lys Thr Gln Pro Arg
 65                  70                  75                  80

Glu Glu Gln Phe Asn Gly Thr Tyr Arg Val Val Ser Val Leu Pro Ile
                 85                  90                  95

Gly His Gln Asp Trp Leu Lys Gly Lys Gln Phe Thr Cys Lys Val Asn
                100                 105                 110

Asn Lys Ala Leu Pro Ser Pro Ile Glu Arg Thr Ile Ser Lys Ala Arg
            115                 120                 125

Gly Gln Ala His Gln Pro Ser Val Tyr Val Leu Pro Pro Ser Arg Glu
        130                 135                 140

Glu Leu Ser Lys Asn Thr Val Ser Leu Thr Cys Leu Ile Lys Asp Phe
145                 150                 155                 160

Phe Pro Pro Asp Ile Asp Val Glu Trp Gln Ser Asn Gly Gln Gln Glu
                165                 170                 175

Pro Glu Ser Lys Tyr Arg Thr Thr Pro Pro Gln Leu Asp Glu Asp Gly
                180                 185                 190

Ser Tyr Phe Leu Tyr Ser Lys Leu Ser Val Asp Lys Ser Arg Trp Gln
            195                 200                 205

Arg Gly Asp Thr Phe Ile Cys Ala Val Met His Glu Ala Leu His Asn
210                 215                 220

His Tyr Thr Gln Glu Ser Leu Ser His Ser Pro Gly Lys
                225                 230                 235

<210> SEQ ID NO 108
<211> LENGTH: 235
<212> TYPE: PRT
<213> ORGANISM: Unknown
<220> FEATURE:
<223> OTHER INFORMATION: Wild-type canine IgG-C Fc with hinge, Protein
      A , C1q +, CD16 +

<400> SEQUENCE: 108

Ala Lys Glu Cys Glu Cys Lys Cys Asn Cys Asn Asn Cys Pro Cys Pro
 1               5                  10                  15

Gly Cys Gly Leu Leu Gly Gly Pro Ser Val Phe Ile Phe Pro Pro Lys
                20                  25                  30

Pro Lys Asp Ile Leu Val Thr Ala Arg Thr Pro Thr Val Thr Cys Val
            35                  40                  45

Val Val Asp Leu Asp Pro Glu Asn Pro Glu Val Gln Ile Ser Trp Phe
 50                  55                  60

Val Asp Ser Lys Gln Val Gln Thr Ala Asn Thr Gln Pro Arg Glu Glu
 65                  70                  75                  80

Gln Ser Asn Gly Thr Tyr Arg Val Val Ser Val Leu Pro Ile Gly His
                 85                  90                  95

Gln Asp Trp Leu Ser Gly Lys Gln Phe Lys Cys Lys Val Asn Asn Lys
                100                 105                 110

Ala Leu Pro Ser Pro Ile Glu Glu Ile Ile Ser Lys Thr Pro Gly Gln
            115                 120                 125

Ala His Gln Pro Asn Val Tyr Val Leu Pro Pro Ser Arg Asp Glu Met
        130                 135                 140

Ser Lys Asn Thr Val Thr Leu Thr Cys Leu Val Lys Asp Phe Phe Pro
145                 150                 155                 160

Pro Glu Ile Asp Val Glu Trp Gln Ser Asn Gly Gln Gln Glu Pro Glu
                165                 170                 175

Ser Lys Tyr Arg Met Thr Pro Pro Gln Leu Asp Glu Asp Gly Ser Tyr
            180                 185                 190
```

Phe Leu Tyr Ser Lys Leu Ser Val Asp Lys Ser Arg Trp Gln Arg Gly
        195                 200                 205

Asp Thr Phe Ile Cys Ala Val Met His Glu Ala Leu His Asn His Tyr
        210                 215                 220

Thr Gln Ile Ser Leu Ser His Ser Pro Gly Lys
225                 230                 235

<210> SEQ ID NO 109
<211> LENGTH: 221
<212> TYPE: PRT
<213> ORGANISM: Artificial Sequence
<220> FEATURE:
<223> OTHER INFORMATION: Variant canine IgG-A Fc, Heterodimer chain 3,
      T(138)W

<400> SEQUENCE: 109

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Ser Arg Glu
    50                  55                  60

Gln Gln Phe Asn Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
            100                 105                 110

Arg Ala His Lys Pro Ser Val Tyr Val Leu Pro Pro Ser Pro Lys Glu
        115                 120                 125

Leu Ser Ser Ser Asp Thr Val Ser Ile Trp Cys Leu Ile Lys Asp Phe
    130                 135                 140

Tyr Pro Pro Asp Ile Asp Val Glu Trp Gln Ser Asn Gly Gln Gln Glu
145                 150                 155                 160

Pro Glu Arg Lys His Arg Met Thr Pro Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Pro Phe Thr Cys Ala Val Met His Glu Thr Leu Gln Asn
        195                 200                 205

His Tyr Thr Asp Leu Ser Leu Ser His Ser Pro Gly Lys
    210                 215                 220

<210> SEQ ID NO 110
<211> LENGTH: 221
<212> TYPE: PRT
<213> ORGANISM: Artificial Sequence
<220> FEATURE:
<223> OTHER INFORMATION: Variant canine IgG-A Fc, Heterodimer chain 4,
      T(138)S, L(140)A, Y(181)T

<400> SEQUENCE: 110

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
            20                  25                  30

```
Val Val Leu Asp Leu Gly Arg Glu Asp Pro Glu Val Gln Ile Ser Trp
            35                  40                  45

Phe Val Asp Gly Lys Glu Val His Thr Ala Lys Thr Gln Ser Arg Glu
    50                  55                  60

Gln Gln Phe Asn Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
            100                 105                 110

Arg Ala His Lys Pro Ser Val Tyr Val Leu Pro Pro Ser Pro Lys Glu
            115                 120                 125

Leu Ser Ser Ser Asp Thr Val Ser Ile Ser Cys Ala Ile Lys Asp Phe
            130                 135                 140

Tyr Pro Pro Asp Ile Asp Val Glu Trp Gln Ser Asn Gly Gln Gln Glu
145                 150                 155                 160

Pro Glu Arg Lys His Arg Met Thr Pro Pro Gln Leu Asp Glu Asp Gly
            165                 170                 175

Ser Tyr Phe Leu Thr Ser Lys Leu Ser Val Asp Lys Ser Arg Trp Gln
            180                 185                 190

Gln Gly Asp Pro Phe Thr Cys Ala Val Met His Glu Thr Leu Gln Asn
            195                 200                 205

His Tyr Thr Asp Leu Ser Leu Ser His Ser Pro Gly Lys
            210                 215                 220

<210> SEQ ID NO 111
<211> LENGTH: 220
<212> TYPE: PRT
<213> ORGANISM: Artificial Sequence
<220> FEATURE:
<223> OTHER INFORMATION: Variant canine IgG-B Fc, Heterodimer chain 3,
      T(137)W

<400> SEQUENCE: 111

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
            35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
            115                 120                 125

Leu Ser Lys Asn Thr Val Ser Leu Trp Cys Leu Ile Lys Asp Phe Phe
            130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
```

165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Glu Ser Leu Ser His Ser Pro Gly Lys
            210                 215                 220

<210> SEQ ID NO 112
<211> LENGTH: 220
<212> TYPE: PRT
<213> ORGANISM: Artificial Sequence
<220> FEATURE:
<223> OTHER INFORMATION: Variant canine IgG-B Fc, Heterodimer chain 4,
      T(137)S, L(139)A, Y(180)T

<400> SEQUENCE: 112

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Ser Cys Ala Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Thr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Glu Ser Leu Ser His Ser Pro Gly Lys
            210                 215                 220

<210> SEQ ID NO 113
<211> LENGTH: 220
<212> TYPE: PRT
<213> ORGANISM: Artificial Sequence
<220> FEATURE:
<223> OTHER INFORMATION: Variant canine IgG-C Fc, Heterodimer chain 3,
      T(137)W

<400> SEQUENCE: 113

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys

```
                20                  25                  30
Val Val Val Asp Leu Asp Pro Glu Asn Pro Glu Val Gln Ile Ser Trp
            35                  40                  45
Phe Val Asp Ser Lys Gln Val Gln Thr Ala Asn Thr Gln Pro Arg Glu
        50                  55                  60
Glu Gln Ser Asn Gly Thr Tyr Arg Val Val Ser Val Leu Pro Ile Gly
65                  70                  75                  80
His Gln Asp Trp Leu Ser Gly Lys Gln Phe Lys Cys Lys Val Asn Asn
                85                  90                  95
Lys Ala Leu Pro Ser Pro Ile Glu Glu Ile Ile Ser Lys Thr Pro Gly
            100                 105                 110
Gln Ala His Gln Pro Asn Val Tyr Val Leu Pro Pro Ser Arg Asp Glu
        115                 120                 125
Met Ser Lys Asn Thr Val Thr Leu Trp Cys Leu Val Lys Asp Phe Phe
    130                 135                 140
Pro Pro Glu Ile Asp Val Glu Trp Gln Ser Asn Gly Gln Gln Glu Pro
145                 150                 155                 160
Glu Ser Lys Tyr Arg Met Thr Pro Pro Gln Leu Asp Glu Asp Gly Ser
                165                 170                 175
Tyr Phe Leu Tyr Ser Lys Leu Ser Val Asp Lys Ser Arg Trp Gln Arg
            180                 185                 190
Gly Asp Thr Phe Ile Cys Ala Val Met His Glu Ala Leu His Asn His
        195                 200                 205
Tyr Thr Gln Ile Ser Leu Ser His Ser Pro Gly Lys
    210                 215                 220

<210> SEQ ID NO 114
<211> LENGTH: 220
<212> TYPE: PRT
<213> ORGANISM: Artificial Sequence
<220> FEATURE:
<223> OTHER INFORMATION: Variant canine IgG-C Fc, Heterodimer chain 4,
      T(137)S, L(139)A, Y(180)T

<400> SEQUENCE: 114

Pro Gly Cys Gly Leu Leu Gly Gly Pro Ser Val Phe Ile Phe Pro Pro
1               5                   10                  15
Lys Pro Lys Asp Ile Leu Val Thr Ala Arg Thr Pro Thr Val Thr Cys
            20                  25                  30
Val Val Val Asp Leu Asp Pro Glu Asn Pro Glu Val Gln Ile Ser Trp
        35                  40                  45
Phe Val Asp Ser Lys Gln Val Gln Thr Ala Asn Thr Gln Pro Arg Glu
    50                  55                  60
Glu Gln Ser Asn Gly Thr Tyr Arg Val Val Ser Val Leu Pro Ile Gly
65                  70                  75                  80
His Gln Asp Trp Leu Ser Gly Lys Gln Phe Lys Cys Lys Val Asn Asn
                85                  90                  95
Lys Ala Leu Pro Ser Pro Ile Glu Glu Ile Ile Ser Lys Thr Pro Gly
            100                 105                 110
Gln Ala His Gln Pro Asn Val Tyr Val Leu Pro Pro Ser Arg Asp Glu
        115                 120                 125
Met Ser Lys Asn Thr Val Thr Leu Ser Cys Ala Val Lys Asp Phe Phe
    130                 135                 140
Pro Pro Glu Ile Asp Val Glu Trp Gln Ser Asn Gly Gln Gln Glu Pro
145                 150                 155                 160
```

```
Glu Ser Lys Tyr Arg Met Thr Pro Pro Gln Leu Asp Glu Asp Gly Ser
                165                 170                 175

Tyr Phe Leu Thr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Ile Ser Leu Ser His Ser Pro Gly Lys
    210                 215                 220

<210> SEQ ID NO 115
<211> LENGTH: 221
<212> TYPE: PRT
<213> ORGANISM: Artificial Sequence
<220> FEATURE:
<223> OTHER INFORMATION: Variant canine IgG-D Fc, Heterodimer chain 3,
      T(138)W

<400> SEQUENCE: 115

Pro Val Pro Glu Ser Leu Gly Gly Pro Ser Val Phe Ile Phe Pro Pro
1               5                   10                  15

Lys Pro Lys Asp Ile Leu Arg Ile Thr Arg Thr Pro Glu Ile Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Pro Arg Glu
    50                  55                  60

Gln Gln Phe Asn Ser Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Trp Cys Leu Ile Lys Asp Phe
    130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Thr Phe Thr Cys Ala Val Met His Glu Ala Leu Gln Asn
        195                 200                 205

His Tyr Thr Asp Leu Ser Leu Ser His Ser Pro Gly Lys
    210                 215                 220

<210> SEQ ID NO 116
<211> LENGTH: 221
<212> TYPE: PRT
<213> ORGANISM: Artificial Sequence
<220> FEATURE:
<223> OTHER INFORMATION: Variant canine IgG-D Fc, Heterodimer chain 4,
      T(138)S, L(140)A, Y(181)T

<400> SEQUENCE: 116

Pro Val Pro Glu Ser Leu Gly Gly Pro Ser Val Phe Ile Phe Pro Pro
1               5                   10                  15
```

```
Lys Pro Lys Asp Ile Leu Arg Ile Thr Arg Thr Pro Glu Ile Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Pro Arg Glu
    50                  55                  60

Gln Gln Phe Asn Ser Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Ser Cys Ala Ile Lys Asp Phe
    130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Thr Ser Lys Leu Ser Val Asp Lys Ser Arg Trp Gln
            180                 185                 190

Gln Gly Asp Thr Phe Thr Cys Ala Val Met His Glu Ala Leu Gln Asn
        195                 200                 205

His Tyr Thr Asp Leu Ser Leu Ser His Ser Pro Gly Lys
    210                 215                 220

<210> SEQ ID NO 117
<211> LENGTH: 237
<212> TYPE: PRT
<213> ORGANISM: Unknown
<220> FEATURE:
<223> OTHER INFORMATION: Wild-type feline IgG1a Fc, Protein A +, C1q +

<400> SEQUENCE: 117

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Lys Ser Phe
145                 150                 155                 160
```

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Tyr Ser Lys Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 118
<211> LENGTH: 237
<212> TYPE: PRT
<213> ORGANISM: Unknown
<220> FEATURE:
<223> OTHER INFORMATION: Wild-type feline IgG1b Fc, Protein A +, C1q +

<400> SEQUENCE: 118

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 119
<211> LENGTH: 237
<212> TYPE: PRT
<213> ORGANISM: Artificial Sequence
<220> FEATURE:
<223> OTHER INFORMATION: Variant feline IgG2 Fc, Heterodimer chain 1,
      T(154)W

<400> SEQUENCE: 119

```
Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asn Val Gln Ile Thr
    50                  55                  60

Trp Phe Val Asp Asn Thr Glu Met His Thr Ala Lys Thr Arg Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
    130                 135                 140

Glu Leu Ser Glu Asn Lys Val Ser Val Trp Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235
```

<210> SEQ ID NO 120
<211> LENGTH: 237
<212> TYPE: PRT
<213> ORGANISM: Artificial Sequence
<220> FEATURE:
<223> OTHER INFORMATION: Variant feline IgG2 Fc, Heterodimer chain 2,
    T(154)S, L(156)A, Y(197)T

<400> SEQUENCE: 120

```
Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asn Val Gln Ile Thr
    50                  55                  60

Trp Phe Val Asp Asn Thr Glu Met His Thr Ala Lys Thr Arg Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110
```

```
Ser Lys Ser Leu Pro Ser Ala Met Glu Arg Thr Ile Ser Lys Ala Lys
            115                 120                 125

Gly Gln Pro His Glu Pro Gln Val Tyr Val Leu Pro Pro Thr Gln Glu
    130                 135                 140

Glu Leu Ser Glu Asn Lys Val Ser Val Ser Cys Ala Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Gln Leu Asp Ser Asp Gly
                180                 185                 190

Thr Tyr Phe Leu Thr Ser Arg Leu Ser Val Asp Arg Ser His Trp Gln
                195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235
```

<210> SEQ ID NO 121
<211> LENGTH: 237
<212> TYPE: PRT
<213> ORGANISM: Artificial Sequence
<220> FEATURE:
<223> OTHER INFORMATION: Variant feline IgG1a Fc, Heterodimer chain 1, T(154)W

<400> SEQUENCE: 121

```
Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
            115                 120                 125

Gly Gln Pro His Glu Pro Gln Val Tyr Val Leu Pro Pro Ala Gln Glu
    130                 135                 140

Glu Leu Ser Glu Asn Lys Val Ser Val Trp Cys Leu Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Gln Leu Asp Ser Asp Gly
                180                 185                 190

Thr Tyr Phe Val Tyr Ser Lys Leu Ser Val Asp Arg Ser His Trp Gln
                195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235
```

<210> SEQ ID NO 122
<211> LENGTH: 237
<212> TYPE: PRT
<213> ORGANISM: Artificial Sequence
<220> FEATURE:
<223> OTHER INFORMATION: Variant feline IgG1a Fc, Heterodimer chain 2,
      T(154)S, L(156)A, Y(197)T

<400> SEQUENCE: 122

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65              70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Ser Cys Ala Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Thr Ser Lys Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 123
<211> LENGTH: 237
<212> TYPE: PRT
<213> ORGANISM: Artificial Sequence
<220> FEATURE:
<223> OTHER INFORMATION: Variant feline IgG1b Fc, Heterodimer chain 1,
      T(154)W

<400> SEQUENCE: 123

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asp Val Gln Ile Thr
    50                  55                  60

```
Trp Phe Val Asp Asn Thr Gln Val Tyr Thr Ala Lys Thr Ser Pro Arg
 65                  70                  75                  80

Glu Glu Gln Phe Asn Ser Thr Tyr Arg Val Val Ser Val Leu Pro Ile
             85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Trp Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 124
<211> LENGTH: 237
<212> TYPE: PRT
<213> ORGANISM: Artificial Sequence
<220> FEATURE:
<223> OTHER INFORMATION: Variant feline IgG1b Fc, Heterodimer chain 2,
      T(154)S, L(156)A, Y(197)T

<400> SEQUENCE: 124

Arg Lys Thr Asp His Pro Pro Gly Pro Lys Pro Cys Asp Cys Pro Lys
 1               5                  10                  15

Cys Pro Pro Pro Glu Met Leu Gly Gly Pro Ser Ile Phe Ile Phe Pro
             20                  25                  30

Pro Lys Pro Lys Asp Thr Leu Ser Ile Ser Arg Thr Pro Glu Val Thr
         35                  40                  45

Cys Leu Val Val Asp Leu Gly Pro Asp Asp Ser Asp Val Gln Ile Thr
     50                  55                  60

Trp Phe Val Asp Asn Thr Gln Val Tyr Thr Ala Lys Thr Ser Pro Arg
 65                  70                  75                  80

Glu Glu Gln Phe Asn Ser Thr Tyr Arg Val Val Ser Val Leu Pro Ile
             85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Ser Cys Ala Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
```

```
                    180                 185                 190
Thr Tyr Phe Leu Thr Ser Arg Leu Ser Val Asp Arg Ser Arg Trp Gln
            195                 200                 205
Arg Gly Asn Thr Tyr Thr Cys Ser Val Ser His Glu Ala Leu His Ser
            210                 215                 220
His His Thr Gln Lys Ser Leu Thr Gln Ser Pro Gly Lys
225                 230                 235

<210> SEQ ID NO 125
<211> LENGTH: 237
<212> TYPE: PRT
<213> ORGANISM: Artificial Sequence
<220> FEATURE:
<223> OTHER INFORMATION: Variant feline IgG2 Fc, with feline IgG1 hinge

<400> SEQUENCE: 125

Arg Lys Thr Asp His Pro Pro Gly Pro Lys Pro Cys Asp Cys Pro Lys
1               5                   10                  15
Cys Pro Pro Pro Glu Met Leu Gly Gly Pro Ser Val Phe Ile Phe Pro
            20                  25                  30
Pro Lys Pro Lys Asp Thr Leu Ser Ile Ser Arg Thr Pro Glu Val Thr
        35                  40                  45
Cys Leu Val Val Asp Leu Gly Pro Asp Asp Ser Asn Val Gln Ile Thr
    50                  55                  60
Trp Phe Val Asp Asn Thr Glu Met His Thr Ala Lys Thr Arg Pro Arg
65                  70                  75                  80
Glu Glu Gln Phe Asn Ser Thr Tyr Arg Val Val Ser Val Leu Pro Ile
                85                  90                  95
Leu His Gln Asp Trp Leu Lys Gly Lys Glu Phe Lys Cys Lys Val Asn
            100                 105                 110
Ser Lys Ser Leu Pro Ser Ala Met Glu Arg Thr Ile Ser Lys Ala Lys
        115                 120                 125
Gly Gln Pro His Glu Pro Gln Val Tyr Val Leu Pro Pro Thr Gln Glu
    130                 135                 140
Glu Leu Ser Glu Asn Lys Val Ser Val Thr Cys Leu Ile Lys Gly Phe
145                 150                 155                 160
His Pro Pro Asp Ile Ala Val Glu Trp Glu Ile Thr Gly Gln Pro Glu
                165                 170                 175
Pro Glu Asn Asn Tyr Gln Thr Thr Pro Pro Gln Leu Asp Ser Asp Gly
            180                 185                 190
Thr Tyr Phe Leu Tyr Ser Arg Leu Ser Val Asp Arg Ser His Trp Gln
        195                 200                 205
Arg Gly Asn Thr Tyr Thr Cys Ser Val Ser His Glu Ala Leu His Ser
    210                 215                 220
His His Thr Gln Lys Ser Leu Thr Gln Ser Pro Gly Lys
225                 230                 235

<210> SEQ ID NO 126
<211> LENGTH: 237
<212> TYPE: PRT
<213> ORGANISM: Artificial Sequence
<220> FEATURE:
<223> OTHER INFORMATION: Variant feline IgG2 Fc with modified hinge,
      K(16)P

<400> SEQUENCE: 126

Pro Lys Thr Ala Ser Thr Ile Glu Ser Lys Thr Gly Glu Gly Pro Pro
1               5                   10                  15
```

Cys Pro Val Pro Glu Ile Pro Gly Ala Pro Ser Val Phe Ile Phe Pro
            20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Ser Asn Val Gln Ile Thr
 50                  55                  60

Trp Phe Val Asp Asn Thr Glu Met His Thr Ala Lys Thr Arg Pro Arg
 65                  70                  75                  80

Glu Glu Gln Phe Asn Ser Thr Tyr Arg Val Val Ser Val Leu Pro Ile
                 85                  90                  95

Leu His Gln Asp Trp Leu Lys Gly Lys Glu Phe Lys Cys Lys Val Asn
             100                 105                 110

Ser Lys Ser Leu Pro Ser Ala Met Glu Arg Thr Ile Ser Lys Ala Lys
             115                 120                 125

Gly Gln Pro His Glu Pro Gln Val Tyr Val Leu Pro Pro Thr Gln Glu
130                 135                 140

Glu Leu Ser Glu Asn Lys Val Ser Val Thr Cys Leu Ile Lys Gly Phe
145                 150                 155                 160

His Pro Pro Asp Ile Ala Val Glu Trp Glu Ile Thr Gly Gln Pro Glu
                 165                 170                 175

Pro Glu Asn Asn Tyr Gln Thr Thr Pro Pro Gln Leu Asp Ser Asp Gly
             180                 185                 190

Thr Tyr Phe Leu Tyr Ser Arg Leu Ser Val Asp Arg Ser His Trp Gln
             195                 200                 205

Arg Gly Asn Thr Tyr Thr Cys Ser Val Ser His Glu Ala Leu His Ser
        210                 215                 220

His His Thr Gln Lys Ser Leu Thr Gln Ser Pro Gly Lys
225                 230                 235

<210> SEQ ID NO 127
<211> LENGTH: 237
<212> TYPE: PRT
<213> ORGANISM: Artificial Sequence
<220> FEATURE:
<223> OTHER INFORMATION: Variant feline IgG1a Fc with modified hinge,
      K(16)P

<400> SEQUENCE: 127

Arg Lys Thr Asp His Pro Pro Gly Pro Lys Pro Cys Asp Cys Pro Pro
1               5                   10                  15

Cys Pro Pro Pro Glu Met Leu Gly Gly Pro Ser Ile Phe Ile Phe Pro
            20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Ser Asp Val Gln Ile Thr
 50                  55                  60

Trp Phe Val Asp Asn Thr Gln Val Tyr Thr Ala Lys Thr Ser Pro Arg
 65                  70                  75                  80

Glu Glu Gln Phe Asn Ser Thr Tyr Arg Val Val Ser Val Leu Pro Ile
                 85                  90                  95

Leu His Gln Asp Trp Leu Lys Gly Lys Glu Phe Lys Cys Lys Val Asn
             100                 105                 110

Ser Lys Ser Leu Pro Ser Pro Ile Glu Arg Thr Ile Ser Lys Ala Lys
             115                 120                 125

Gly Gln Pro His Glu Pro Gln Val Tyr Val Leu Pro Pro Ala Gln Glu

```
              130                 135                 140
Glu Leu Ser Glu Asn Lys Val Ser Val Thr Cys Leu Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Tyr Ser Lys Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 128
<211> LENGTH: 237
<212> TYPE: PRT
<213> ORGANISM: Artificial Sequence
<220> FEATURE:
<223> OTHER INFORMATION: Variant feline IgG1b Fc with modified hinge,
      K(16)P

<400> SEQUENCE: 128

Arg Lys Thr Asp His Pro Pro Gly Pro Lys Pro Cys Asp Cys Pro Pro
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
        50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 129
<211> LENGTH: 244
```

```
<212> TYPE: PRT
<213> ORGANISM: Unknown
<220> FEATURE:
<223> OTHER INFORMATION: Wild-type equine IgG2 Fc with hinge, Protein
      A , C1q

<400> SEQUENCE: 129

Pro Pro Cys Val Leu Ser Ala Glu Gly Val Ile Pro Ile Pro Ser Val
1               5                   10                  15

Pro Lys Pro Gln Cys Pro Pro Tyr Thr His Ser Lys Phe Leu Gly Gly
            20                  25                  30

Pro Ser Val Phe Ile Phe Pro Pro Asn Pro Lys Asp Ala Leu Met Ile
        35                  40                  45

Ser Arg Thr Pro Val Val Thr Cys Val Val Val Asn Leu Ser Asp Gln
50                  55                  60

Tyr Pro Asp Val Gln Phe Ser Trp Tyr Val Asp Asn Thr Glu Val His
65                  70                  75                  80

Ser Ala Ile Thr Lys Gln Arg Glu Ala Gln Phe Asn Ser Thr Tyr Arg
                85                  90                  95

Val Val Ser Val Leu Pro Ile Gln His Gln Asp Trp Leu Ser Gly Lys
            100                 105                 110

Glu Phe Lys Cys Ser Val Thr Asn Val Gly Val Pro Gln Pro Ile Ser
        115                 120                 125

Arg Ala Ile Ser Arg Gly Lys Gly Pro Ser Arg Val Pro Gln Val Tyr
    130                 135                 140

Val Leu Pro Pro His Pro Asp Glu Leu Ala Lys Ser Lys Val Ser Val
145                 150                 155                 160

Thr Cys Leu Val Lys Asp Phe Tyr Pro Pro Asp Ile Ser Val Glu Trp
                165                 170                 175

Gln Ser Asn Arg Trp Pro Glu Leu Glu Gly Lys Tyr Ser Thr Thr Pro
            180                 185                 190

Ala Gln Leu Asp Gly Asp Gly Ser Tyr Phe Leu Tyr Ser Lys Leu Ser
        195                 200                 205

Leu Glu Thr Ser Arg Trp Gln Gln Val Glu Ser Phe Thr Cys Ala Val
    210                 215                 220

Met His Glu Ala Leu His Asn His Phe Thr Lys Thr Asp Ile Ser Glu
225                 230                 235                 240

Ser Leu Gly Lys

<210> SEQ ID NO 130
<211> LENGTH: 244
<212> TYPE: PRT
<213> ORGANISM: Artificial Sequence
<220> FEATURE:
<223> OTHER INFORMATION: Variant equine IgG2 Fc with modified hinge,
      Protein A , C1q , Q(20)P

<400> SEQUENCE: 130

Pro Pro Cys Val Leu Ser Ala Glu Gly Val Ile Pro Ile Pro Ser Val
1               5                   10                  15

Pro Lys Pro Pro Cys Pro Pro Tyr Thr His Ser Lys Phe Leu Gly Gly
            20                  25                  30

Pro Ser Val Phe Ile Phe Pro Pro Asn Pro Lys Asp Ala Leu Met Ile
        35                  40                  45

Ser Arg Thr Pro Val Val Thr Cys Val Val Val Asn Leu Ser Asp Gln
50                  55                  60

Tyr Pro Asp Val Gln Phe Ser Trp Tyr Val Asp Asn Thr Glu Val His
```

| | | 65 | | | 70 | | | 75 | | | 80 |

Ser Ala Ile Thr Lys Gln Arg Glu Ala Gln Phe Asn Ser Thr Tyr Arg
                85                 90                 95

Val Val Ser Val Leu Pro Ile Gln His Gln Asp Trp Leu Ser Gly Lys
              100               105               110

Glu Phe Lys Cys Ser Val Thr Asn Val Gly Val Pro Gln Pro Ile Ser
              115               120               125

Arg Ala Ile Ser Arg Gly Lys Gly Pro Ser Arg Val Pro Gln Val Tyr
    130                 135               140

Val Leu Pro Pro His Pro Asp Glu Leu Ala Lys Ser Lys Val Ser Val
145                 150               155              160

Thr Cys Leu Val Lys Asp Phe Tyr Pro Pro Asp Ile Ser Val Glu Trp
              165               170               175

Gln Ser Asn Arg Trp Pro Glu Leu Glu Gly Lys Tyr Ser Thr Thr Pro
            180               185               190

Ala Gln Leu Asp Gly Asp Gly Ser Tyr Phe Leu Tyr Ser Lys Leu Ser
              195               200               205

Leu Glu Thr Ser Arg Trp Gln Gln Val Glu Ser Phe Thr Cys Ala Val
    210                 215               220

Met His Glu Ala Leu His Asn His Phe Thr Lys Thr Asp Ile Ser Glu
225                 230               235              240

Ser Leu Gly Lys

<210> SEQ ID NO 131
<211> LENGTH: 244
<212> TYPE: PRT
<213> ORGANISM: Artificial Sequence
<220> FEATURE:
<223> OTHER INFORMATION: Variant equine IgG2 Fc with modified hinge,
      Protein A , C1q , C(3)S

<400> SEQUENCE: 131

Pro Pro Ser Val Leu Ser Ala Glu Gly Val Ile Pro Ile Pro Ser Val
1                5                 10                15

Pro Lys Pro Gln Cys Pro Pro Tyr Thr His Ser Lys Phe Leu Gly Gly
            20               25               30

Pro Ser Val Phe Ile Phe Pro Pro Asn Pro Lys Asp Ala Leu Met Ile
              35               40               45

Ser Arg Thr Pro Val Val Thr Cys Val Val Val Asn Leu Ser Asp Gln
    50                 55               60

Tyr Pro Asp Val Gln Phe Ser Trp Tyr Val Asp Asn Thr Glu Val His
65                 70               75              80

Ser Ala Ile Thr Lys Gln Arg Glu Ala Gln Phe Asn Ser Thr Tyr Arg
              85               90               95

Val Val Ser Val Leu Pro Ile Gln His Gln Asp Trp Leu Ser Gly Lys
            100               105               110

Glu Phe Lys Cys Ser Val Thr Asn Val Gly Val Pro Gln Pro Ile Ser
            115               120               125

Arg Ala Ile Ser Arg Gly Lys Gly Pro Ser Arg Val Pro Gln Val Tyr
    130                 135               140

Val Leu Pro Pro His Pro Asp Glu Leu Ala Lys Ser Lys Val Ser Val
145                 150               155              160

Thr Cys Leu Val Lys Asp Phe Tyr Pro Pro Asp Ile Ser Val Glu Trp
              165               170               175

Gln Ser Asn Arg Trp Pro Glu Leu Glu Gly Lys Tyr Ser Thr Thr Pro 180                 185                 190
Ala Gln Leu Asp Gly Asp Gly Ser Tyr Phe Leu Tyr Ser Lys Leu Ser
                195                 200                 205

Leu Glu Thr Ser Arg Trp Gln Gln Val Glu Ser Phe Thr Cys Ala Val
        210                 215                 220

Met His Glu Ala Leu His Asn His Phe Thr Lys Thr Asp Ile Ser Glu
225                 230                 235                 240

Ser Leu Gly Lys

<210> SEQ ID NO 132
<211> LENGTH: 244
<212> TYPE: PRT
<213> ORGANISM: Artificial Sequence
<220> FEATURE:
<223> OTHER INFORMATION: Variant equine IgG2 Fc with modified hinge,
      Protein A , C1q , C(3)S, Q(20)P

<400> SEQUENCE: 132

Pro Pro Ser Val Leu Ser Ala Glu Gly Val Ile Pro Ile Pro Ser Val
1               5                   10                  15

Pro Lys Pro Pro Cys Pro Pro Tyr Thr His Ser Lys Phe Leu Gly Gly
            20                  25                  30

Pro Ser Val Phe Ile Phe Pro Pro Asn Pro Lys Asp Ala Leu Met Ile
        35                  40                  45

Ser Arg Thr Pro Val Val Thr Cys Val Val Val Asn Leu Ser Asp Gln
    50                  55                  60

Tyr Pro Asp Val Gln Phe Ser Trp Tyr Val Asp Asn Thr Glu Val His
65                  70                  75                  80

Ser Ala Ile Thr Lys Gln Arg Glu Ala Gln Phe Asn Ser Thr Tyr Arg
                85                  90                  95

Val Val Ser Val Leu Pro Ile Gln His Gln Asp Trp Leu Ser Gly Lys
            100                 105                 110

Glu Phe Lys Cys Ser Val Thr Asn Val Gly Val Pro Gln Pro Ile Ser
        115                 120                 125

Arg Ala Ile Ser Arg Gly Lys Gly Pro Ser Arg Val Pro Gln Val Tyr
    130                 135                 140

Val Leu Pro Pro His Pro Asp Glu Leu Ala Lys Ser Lys Val Ser Val
145                 150                 155                 160

Thr Cys Leu Val Lys Asp Phe Tyr Pro Pro Asp Ile Ser Val Glu Trp
                165                 170                 175

Gln Ser Asn Arg Trp Pro Glu Leu Glu Gly Lys Tyr Ser Thr Thr Pro
            180                 185                 190

Ala Gln Leu Asp Gly Asp Gly Ser Tyr Phe Leu Tyr Ser Lys Leu Ser
        195                 200                 205

Leu Glu Thr Ser Arg Trp Gln Gln Val Glu Ser Phe Thr Cys Ala Val
    210                 215                 220

Met His Glu Ala Leu His Asn His Phe Thr Lys Thr Asp Ile Ser Glu
225                 230                 235                 240

Ser Leu Gly Lys

<210> SEQ ID NO 133
<211> LENGTH: 244
<212> TYPE: PRT
<213> ORGANISM: Artificial Sequence
<220> FEATURE:
<223> OTHER INFORMATION: Variant equine IgG2 Fc with hinge, Protein A +,
      C1q , A(45)T, F(233)Y

<400> SEQUENCE: 133

Pro Pro Cys Val Leu Ser Ala Glu Gly Val Ile Pro Ile Pro Ser Val
1               5                   10                  15

Pro Lys Pro Gln Cys Pro Pro Tyr Thr His Ser Lys Phe Leu Gly Gly
            20                  25                  30

Pro Ser Val Phe Ile Phe Pro Pro Asn Pro Lys Asp Thr Leu Met Ile
        35                  40                  45

Ser Arg Thr Pro Val Val Thr Cys Val Val Asn Leu Ser Asp Gln
    50                  55                  60

Tyr Pro Asp Val Gln Phe Ser Trp Tyr Val Asp Asn Thr Glu Val His
65                  70                  75                  80

Ser Ala Ile Thr Lys Gln Arg Glu Ala Gln Phe Asn Ser Thr Tyr Arg
                85                  90                  95

Val Val Ser Val Leu Pro Ile Gln His Gln Asp Trp Leu Ser Gly Lys
            100                 105                 110

Glu Phe Lys Cys Ser Val Thr Asn Val Gly Val Pro Gln Pro Ile Ser
        115                 120                 125

Arg Ala Ile Ser Arg Gly Lys Gly Pro Ser Arg Val Pro Gln Val Tyr
    130                 135                 140

Val Leu Pro Pro His Pro Asp Glu Leu Ala Lys Ser Lys Val Ser Val
145                 150                 155                 160

Thr Cys Leu Val Lys Asp Phe Tyr Pro Pro Asp Ile Ser Val Glu Trp
                165                 170                 175

Gln Ser Asn Arg Trp Pro Glu Leu Glu Gly Lys Tyr Ser Thr Thr Pro
            180                 185                 190

Ala Gln Leu Asp Gly Asp Gly Ser Tyr Phe Leu Tyr Ser Lys Leu Ser
        195                 200                 205

Leu Glu Thr Ser Arg Trp Gln Gln Val Glu Ser Phe Thr Cys Ala Val
    210                 215                 220

Met His Glu Ala Leu His Asn His Tyr Thr Lys Thr Asp Ile Ser Glu
225                 230                 235                 240

Ser Leu Gly Lys

<210> SEQ ID NO 134
<211> LENGTH: 244
<212> TYPE: PRT
<213> ORGANISM: Artificial Sequence
<220> FEATURE:
<223> OTHER INFORMATION: Variant equine IgG2 Fc with modified hinge,
      Protein A +, C1q , Q(20)P, A(45)T, F(233)Y

<400> SEQUENCE: 134

Pro Pro Cys Val Leu Ser Ala Glu Gly Val Ile Pro Ile Pro Ser Val
1               5                   10                  15

Pro Lys Pro Pro Cys Pro Pro Tyr Thr His Ser Lys Phe Leu Gly Gly
            20                  25                  30

Pro Ser Val Phe Ile Phe Pro Pro Asn Pro Lys Asp Thr Leu Met Ile
        35                  40                  45

Ser Arg Thr Pro Val Val Thr Cys Val Val Asn Leu Ser Asp Gln
    50                  55                  60

Tyr Pro Asp Val Gln Phe Ser Trp Tyr Val Asp Asn Thr Glu Val His
65                  70                  75                  80

Ser Ala Ile Thr Lys Gln Arg Glu Ala Gln Phe Asn Ser Thr Tyr Arg
                85                  90                  95

Val Val Ser Val Leu Pro Ile Gln His Gln Asp Trp Leu Ser Gly Lys
            100                 105                 110

Glu Phe Lys Cys Ser Val Thr Asn Val Gly Val Pro Gln Pro Ile Ser
            115                 120                 125

Arg Ala Ile Ser Arg Gly Lys Gly Pro Ser Arg Val Pro Gln Val Tyr
        130                 135                 140

Val Leu Pro Pro His Pro Asp Glu Leu Ala Lys Ser Lys Val Ser Val
145                 150                 155                 160

Thr Cys Leu Val Lys Asp Phe Tyr Pro Pro Asp Ile Ser Val Glu Trp
                165                 170                 175

Gln Ser Asn Arg Trp Pro Glu Leu Glu Gly Lys Tyr Ser Thr Thr Pro
            180                 185                 190

Ala Gln Leu Asp Gly Asp Gly Ser Tyr Phe Leu Tyr Ser Lys Leu Ser
        195                 200                 205

Leu Glu Thr Ser Arg Trp Gln Gln Val Glu Ser Phe Thr Cys Ala Val
210                 215                 220

Met His Glu Ala Leu His Asn His Tyr Thr Lys Thr Asp Ile Ser Glu
225                 230                 235                 240

Ser Leu Gly Lys

<210> SEQ ID NO 135
<211> LENGTH: 244
<212> TYPE: PRT
<213> ORGANISM: Artificial Sequence
<220> FEATURE:
<223> OTHER INFORMATION: Variant equine IgG2 Fc with modified hinge,
      Protein A +, C1q , C(3)S, Q(20)P, A(45)T, F(233)Y

<400> SEQUENCE: 135

Pro Pro Ser Val Leu Ser Ala Glu Gly Val Ile Pro Ile Pro Ser Val
1               5                   10                  15

Pro Lys Pro Pro Cys Pro Pro Tyr Thr His Ser Lys Phe Leu Gly Gly
            20                  25                  30

Pro Ser Val Phe Ile Phe Pro Pro Asn Pro Lys Asp Thr Leu Met Ile
        35                  40                  45

Ser Arg Thr Pro Val Val Thr Cys Val Val Val Asn Leu Ser Asp Gln
    50                  55                  60

Tyr Pro Asp Val Gln Phe Ser Trp Tyr Val Asp Asn Thr Glu Val His
65                  70                  75                  80

Ser Ala Ile Thr Lys Gln Arg Glu Ala Gln Phe Asn Ser Thr Tyr Arg
                85                  90                  95

Val Val Ser Val Leu Pro Ile Gln His Gln Asp Trp Leu Ser Gly Lys
            100                 105                 110

Glu Phe Lys Cys Ser Val Thr Asn Val Gly Val Pro Gln Pro Ile Ser
            115                 120                 125

Arg Ala Ile Ser Arg Gly Lys Gly Pro Ser Arg Val Pro Gln Val Tyr
        130                 135                 140

Val Leu Pro Pro His Pro Asp Glu Leu Ala Lys Ser Lys Val Ser Val
145                 150                 155                 160

Thr Cys Leu Val Lys Asp Phe Tyr Pro Pro Asp Ile Ser Val Glu Trp
                165                 170                 175

Gln Ser Asn Arg Trp Pro Glu Leu Glu Gly Lys Tyr Ser Thr Thr Pro
            180                 185                 190

Ala Gln Leu Asp Gly Asp Gly Ser Tyr Phe Leu Tyr Ser Lys Leu Ser
        195                 200                 205

-continued

Leu Glu Thr Ser Arg Trp Gln Gln Val Glu Ser Phe Thr Cys Ala Val
210                 215                 220

Met His Glu Ala Leu His Asn His Tyr Thr Lys Thr Asp Ile Ser Glu
225                 230                 235                 240

Ser Leu Gly Lys

<210> SEQ ID NO 136
<211> LENGTH: 237
<212> TYPE: PRT
<213> ORGANISM: Artificial Sequence
<220> FEATURE:
<223> OTHER INFORMATION: Variant feline IgG1a Fc, Protein A +, C1q ,
      P(198)A

<400> SEQUENCE: 136

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Val Tyr Ser Lys Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 137
<211> LENGTH: 237
<212> TYPE: PRT
<213> ORGANISM: Artificial Sequence
<220> FEATURE:
<223> OTHER INFORMATION: Variant feline IgG1b Fc, Protein A +, C1q ,
      P(198)A

<400> SEQUENCE: 137

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro

-continued

```
                20                  25                  30
Pro Lys Pro Lys Asp Thr Leu Ser Ile Ser Arg Thr Pro Glu Val Thr
             35                  40                  45
Cys Leu Val Val Asp Leu Gly Pro Asp Ser Asp Val Gln Ile Thr
 50                  55                  60
Trp Phe Val Asp Asn Thr Gln Val Tyr Thr Ala Lys Thr Ser Pro Arg
 65                  70                  75                  80
Glu Glu Gln Phe Asn Ser Thr Tyr Arg Val Ser Val Leu Pro Ile
                 85                  90                  95
Leu His Gln Asp Trp Leu Lys Gly Lys Glu Phe Lys Cys Lys Val Asn
                100                 105                 110
Ser Lys Ser Leu Pro Ser Pro Ile Glu Arg Thr Ile Ser Lys Asp Lys
             115                 120                 125
Gly Gln Pro His Glu Pro Gln Val Tyr Val Leu Pro Pro Ala Gln Glu
130                 135                 140
Glu Leu Ser Glu Asn Lys Val Ser Val Thr Cys Leu Ile Glu Gly Phe
145                 150                 155                 160
Tyr Pro Ser Asp Ile Ala Val Glu Trp Glu Ile Thr Gly Gln Pro Glu
                165                 170                 175
Pro Glu Asn Asn Tyr Arg Thr Thr Pro Pro Gln Leu Asp Ser Asp Gly
                180                 185                 190
Thr Tyr Phe Leu Tyr Ser Arg Leu Ser Val Asp Arg Ser Arg Trp Gln
                195                 200                 205
Arg Gly Asn Thr Tyr Thr Cys Ser Val Ser His Glu Ala Leu His Ser
210                 215                 220
His His Thr Gln Lys Ser Leu Thr Gln Ser Pro Gly Lys
225                 230                 235

<210> SEQ ID NO 138
<211> LENGTH: 30
<212> TYPE: PRT
<213> ORGANISM: Unknown
<220> FEATURE:
<223> OTHER INFORMATION: Wild-type equine IgG2 hinge

<400> SEQUENCE: 138

Pro Pro Cys Val Leu Ser Ala Glu Gly Val Ile Pro Ile Pro Ser Val
 1               5                   10                  15
Pro Lys Pro Gln Cys Pro Pro Tyr Thr His Ser Lys Phe Leu
                20                  25                  30

<210> SEQ ID NO 139
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q +,
      CD16 , M(5)P

<400> SEQUENCE: 139

Pro Ala Pro Glu Pro Leu Gly Gly Pro Ser Val Phe Ile Phe Pro Pro
 1               5                   10                  15
Lys Pro Lys Asp Thr Leu Leu Ile Ala Arg Thr Pro Glu Val Thr Cys
                20                  25                  30
Val Val Val Asp Leu Asp Pro Glu Asp Pro Glu Val Gln Ile Ser Trp
             35                  40                  45
Phe Val Asp Gly Lys Gln Met Gln Thr Ala Lys Thr Gln Pro Arg Glu
 50                  55                  60
```

```
Glu Gln Phe Asn Gly Thr Tyr Arg Val Val Ser Val Leu Pro Ile Gly
 65                  70                  75                  80

His Gln Asp Trp Leu Lys Gly Lys Gln Phe Thr Cys Lys Val Asn Asn
                 85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 140
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q +,
      CD16 , P(39)R

<400> SEQUENCE: 140

Pro Ala Pro Glu Met Leu Gly Gly Pro Ser Val Phe Ile Phe Pro Pro
  1               5                  10                  15

Lys Pro Lys Asp Thr Leu Leu Ile Ala Arg Thr Pro Glu Val Thr Cys
             20                  25                  30

Val Val Val Asp Leu Asp Arg Glu Asp Pro Glu Val Gln Ile Ser Trp
         35                  40                  45

Phe Val Asp Gly Lys Gln Met Gln Thr Ala Lys Thr Gln Pro Arg Glu
     50                  55                  60

Glu Gln Phe Asn Gly Thr Tyr Arg Val Val Ser Val Leu Pro Ile Gly
 65                  70                  75                  80

His Gln Asp Trp Leu Lys Gly Lys Gln Phe Thr Cys Lys Val Asn Asn
                 85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
```

Tyr Thr Gln Glu Ser Leu Ser His Ser Pro Gly Lys
    210                 215                 220

<210> SEQ ID NO 141
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q +,
      CD16 , D(38)G

<400> SEQUENCE: 141

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Gly Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 142
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q +,
      CD16 , K(97)I

<400> SEQUENCE: 142

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu

```
            50                  55                  60
Glu Gln Phe Asn Gly Thr Tyr Arg Val Ser Val Leu Pro Ile Gly
 65                  70                  75                  80

His Gln Asp Trp Leu Lys Gly Lys Gln Phe Thr Cys Lys Val Asn Asn
                 85                  90                  95

Ile Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
            115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Glu Ser Leu Ser His Ser Pro Gly Lys
            210                 215                 220
```

<210> SEQ ID NO 143
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q +,
      CD16 , A(98)G

<400> SEQUENCE: 143

```
Pro Ala Pro Glu Met Leu Gly Gly Pro Ser Val Phe Ile Phe Pro Pro
 1               5                  10                  15

Lys Pro Lys Asp Thr Leu Leu Ile Ala Arg Thr Pro Glu Val Thr Cys
             20                  25                  30

Val Val Val Asp Leu Asp Pro Glu Asp Pro Glu Val Gln Ile Ser Trp
         35                  40                  45

Phe Val Asp Gly Lys Gln Met Gln Thr Ala Lys Thr Gln Pro Arg Glu
 50                  55                  60

Glu Gln Phe Asn Gly Thr Tyr Arg Val Ser Val Leu Pro Ile Gly
 65                  70                  75                  80

His Gln Asp Trp Leu Lys Gly Lys Gln Phe Thr Cys Lys Val Asn Asn
                 85                  90                  95

Lys Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
            115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190
```

```
Gly Asp Thr Phe Ile Cys Ala Val Met His Glu Ala Leu His Asn His
        195                 200                 205

Tyr Thr Gln Glu Ser Leu Ser His Ser Pro Gly Lys
        210                 215                 220

<210> SEQ ID NO 144
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q +,
      CD16 , D(38)G, K(97)I, A(98)G

<400> SEQUENCE: 144

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Gly Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
        210                 215                 220

<210> SEQ ID NO 145
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q ,
      CD16 , D(38)G, K(93)R, K(97)I, A(98)G

<400> SEQUENCE: 145

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Gly Pro Glu Asp Pro Glu Val Gln Ile Ser Trp
        35                  40                  45
```

```
Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
 65              70                  75                  80

His Gln Asp Trp Leu Lys Gly Lys Gln Phe Thr Cys Arg Val Asn Asn
                 85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
            115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
            165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Glu Ser Leu Ser His Ser Pro Gly Lys
            210                 215                 220

<210> SEQ ID NO 146
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q +,
      CD16 , M(5)P, P(39)R

<400> SEQUENCE: 146

Pro Ala Pro Glu Pro Leu Gly Gly Pro Ser Val Phe Ile Phe Pro Pro
  1               5                  10                  15

Lys Pro Lys Asp Thr Leu Leu Ile Ala Arg Thr Pro Glu Val Thr Cys
             20                  25                  30

Val Val Val Asp Leu Asp Arg Glu Asp Pro Glu Val Gln Ile Ser Trp
         35                  40                  45

Phe Val Asp Gly Lys Gln Met Gln Thr Ala Lys Thr Gln Pro Arg Glu
    50                  55                  60

Glu Gln Phe Asn Gly Thr Tyr Arg Val Val Ser Val Leu Pro Ile Gly
 65              70                  75                  80

His Gln Asp Trp Leu Lys Gly Lys Gln Phe Thr Cys Lys Val Asn Asn
                 85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
            115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
            165                 170                 175

Tyr Phe Leu Tyr Ser Lys Leu Ser Val Asp Lys Ser Arg Trp Gln Arg
            180                 185                 190
```

Gly Asp Thr Phe Ile Cys Ala Val Met His Glu Ala Leu His Asn His
         195                 200                 205

Tyr Thr Gln Glu Ser Leu Ser His Ser Pro Gly Lys
    210                 215                 220

<210> SEQ ID NO 147
<211> LENGTH: 220
<212> TYPE: PRT
<213> ORGANISM: Artificial Sequence
<220> FEATURE:
<223> OTHER INFORMATION: Variant canine IgG-B Fc, Protein A +, C1q ,
      CD16 , M(5)P, P(39)R, K(93)R

<400> SEQUENCE: 147

Pro Ala Pro Glu Pro Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Arg Glu Asp Pro Glu Val Gln Ile Ser Trp
        35                  40                  45

Phe Val Asp Gly Lys Gln Met Gln Thr Ala Lys Thr Gln Pro Arg Glu
50                  55                  60

Glu Gln Phe Asn Gly Thr Tyr Arg Val Val Ser Val Leu Pro Ile Gly
65                  70                  75                  80

His Gln Asp Trp Leu Lys Gly Lys Gln Phe Thr Cys Arg Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 148
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q +,
      CD16 , L(5)P

<400> SEQUENCE: 148

Pro Gly Cys Gly Pro Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

Val Val Val Asp Leu Asp Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
            115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
    210                 215                 220

<210> SEQ ID NO 149
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q +,
      CD16 , P(39)R

<400> SEQUENCE: 149

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

Val Val Val Asp Leu Asp Arg Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
            115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg

```
            180                 185                 190
Gly Asp Thr Phe Ile Cys Ala Val Met His Glu Ala Leu His Asn His
            195                 200                 205

Tyr Thr Gln Ile Ser Leu Ser His Ser Pro Gly Lys
            210                 215                 220

<210> SEQ ID NO 150
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q +,
      CD16 , D(38)G

<400> SEQUENCE: 150

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

Val Val Val Asp Leu Gly Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ser Lys Thr Pro Gly
            100                 105                 110

Gln Ala His Gln Pro Asn Val Tyr Val Leu Pro Pro Ser Arg Asp Glu
        115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
            210                 215                 220

<210> SEQ ID NO 151
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q +,
      CD16 , K(97)I

<400> SEQUENCE: 151

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

Val Val Val Asp Leu Asp Pro Glu Asn Pro Glu Val Gln Ile Ser Trp
```

```
            35                  40                  45
Phe Val Asp Ser Lys Gln Val Gln Thr Ala Asn Thr Gln Pro Arg Glu
 50                  55                  60
Glu Gln Ser Asn Gly Thr Tyr Arg Val Val Ser Val Leu Pro Ile Gly
 65                  70                  75                  80
His Gln Asp Trp Leu Ser Gly Lys Gln Phe Lys Cys Lys Val Asn Asn
                 85                  90                  95
Ile Ala Leu Pro Ser Pro Ile Glu Glu Ile Ile Ser Lys Thr Pro Gly
                100                 105                 110
Gln Ala His Gln Pro Asn Val Tyr Val Leu Pro Pro Ser Arg Asp Glu
                115                 120                 125
Met Ser Lys Asn Thr Val Thr Leu Thr Cys Leu Val Lys Asp Phe Phe
                130                 135                 140
Pro Pro Glu Ile Asp Val Glu Trp Gln Ser Asn Gly Gln Gln Glu Pro
145                 150                 155                 160
Glu Ser Lys Tyr Arg Met Thr Pro Pro Gln Leu Asp Glu Asp Gly Ser
                165                 170                 175
Tyr Phe Leu Tyr Ser Lys Leu Ser Val Asp Lys Ser Arg Trp Gln Arg
                180                 185                 190
Gly Asp Thr Phe Ile Cys Ala Val Met His Glu Ala Leu His Asn His
                195                 200                 205
Tyr Thr Gln Ile Ser Leu Ser His Ser Pro Gly Lys
                210                 215                 220

<210> SEQ ID NO 152
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q +,
      CD16 , A(98)G

<400> SEQUENCE: 152

Pro Gly Cys Gly Leu Leu Gly Gly Pro Ser Val Phe Ile Phe Pro Pro
 1                   5                  10                  15
Lys Pro Lys Asp Ile Leu Val Thr Ala Arg Thr Pro Thr Val Thr Cys
                 20                  25                  30
Val Val Val Asp Leu Asp Pro Glu Asn Pro Glu Val Gln Ile Ser Trp
                 35                  40                  45
Phe Val Asp Ser Lys Gln Val Gln Thr Ala Asn Thr Gln Pro Arg Glu
 50                  55                  60
Glu Gln Ser Asn Gly Thr Tyr Arg Val Val Ser Val Leu Pro Ile Gly
 65                  70                  75                  80
His Gln Asp Trp Leu Ser Gly Lys Gln Phe Lys Cys Lys Val Asn Asn
                 85                  90                  95
Lys Gly Leu Pro Ser Pro Ile Glu Glu Ile Ile Ser Lys Thr Pro Gly
                100                 105                 110
Gln Ala His Gln Pro Asn Val Tyr Val Leu Pro Pro Ser Arg Asp Glu
                115                 120                 125
Met Ser Lys Asn Thr Val Thr Leu Thr Cys Leu Val Lys Asp Phe Phe
                130                 135                 140
Pro Pro Glu Ile Asp Val Glu Trp Gln Ser Asn Gly Gln Gln Glu Pro
145                 150                 155                 160
Glu Ser Lys Tyr Arg Met Thr Pro Pro Gln Leu Asp Glu Asp Gly Ser
                165                 170                 175
```

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
    210                 215                 220

<210> SEQ ID NO 153
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q ,
      CD16 +, K(93)R

<400> SEQUENCE: 153

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

Val Val Val Asp Leu Asp Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Arg Val Asn Asn
                85                  90                  95

Lys Ala Leu Pro Ser Pro Ile Glu Glu Ile Ser Lys Thr Pro Gly
            100                 105                 110

Gln Ala His Gln Pro Asn Val Tyr Val Leu Pro Pro Ser Arg Asp Glu
        115                 120                 125

Met Ser Lys Asn Thr Val Thr Leu Thr Cys Leu Val Lys Asp Phe Phe
130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
    210                 215                 220

<210> SEQ ID NO 154
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q +,
      CD16 , D(38)G, K(97)I, A(98)G

<400> SEQUENCE: 154

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

```
Val Val Val Asp Leu Gly Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Ile Gly Leu Pro Ser Pro Ile Glu Glu Ile Ile Ser Lys Thr Pro Gly
                100                 105                 110

Gln Ala His Gln Pro Asn Val Tyr Val Leu Pro Pro Ser Arg Asp Glu
                115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
        210                 215                 220

<210> SEQ ID NO 155
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q ,
      CD16 , D(38)G, K(93)R, K(97)I, A(98)G

<400> SEQUENCE: 155

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
                20                  25                  30

Val Val Val Asp Leu Gly Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Arg Val Asn Asn
                85                  90                  95

Ile Gly Leu Pro Ser Pro Ile Glu Glu Ile Ile Ser Lys Thr Pro Gly
                100                 105                 110

Gln Ala His Gln Pro Asn Val Tyr Val Leu Pro Pro Ser Arg Asp Glu
                115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175
```

```
Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Ile Ser Leu Ser His Ser Pro Gly Lys
        210                 215             220

<210> SEQ ID NO 156
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q +,
      CD16 , L(5)P, P(39)R

<400> SEQUENCE: 156

Pro Gly Cys Gly Pro Leu Gly Gly Pro Ser Val Phe Ile Phe Pro Pro
1               5                   10                  15

Lys Pro Lys Asp Ile Leu Val Thr Ala Arg Thr Pro Val Thr Cys
            20                  25                  30

Val Val Val Asp Leu Asp Arg Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
        115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Ile Ser Leu Ser His Ser Pro Gly Lys
        210                 215             220

<210> SEQ ID NO 157
<211> LENGTH: 220
<212> TYPE: PRT
<213> ORGANISM: Artificial Sequence
<220> FEATURE:
<223> OTHER INFORMATION: Variant canine IgG-C Fc, Protein A +, C1q .
      CD16 , M(5)P, P(39)R, K(93)R

<400> SEQUENCE: 157

Pro Gly Cys Gly Pro Leu Gly Gly Pro Ser Val Phe Ile Phe Pro Pro
1               5                   10                  15

Lys Pro Lys Asp Ile Leu Val Thr Ala Arg Thr Pro Val Thr Cys
            20                  25                  30
```

```
Val Val Val Asp Leu Asp Arg Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Thr Tyr Arg Val Val Ser Val Leu Pro Ile Gly
65                  70                  75                  80

His Gln Asp Trp Leu Ser Gly Lys Gln Phe Lys Cys Arg Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
            115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
            210                 215                 220

<210> SEQ ID NO 158
<211> LENGTH: 221
<212> TYPE: PRT
<213> ORGANISM: Artificial Sequence
<220> FEATURE:
<223> OTHER INFORMATION: Aglycosyl variant canine IgG A Fc, N(68)X
<220> FEATURE:
<221> NAME/KEY: MISC_FEATURE
<222> LOCATION: (68)..(68)
<223> OTHER INFORMATION: X = any amino acid except N

<400> SEQUENCE: 158

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Ser Arg Glu
    50                  55                  60

Gln Gln Phe Xaa Gly Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
            100                 105                 110

Arg Ala His Lys Pro Ser Val Tyr Val Leu Pro Pro Ser Pro Lys Glu
            115                 120                 125

Leu Ser Ser Ser Asp Thr Val Ser Ile Thr Cys Leu Ile Lys Asp Phe
            130                 135                 140

Tyr Pro Pro Asp Ile Asp Val Glu Trp Gln Ser Asn Gly Gln Gln Glu
```

```
145                 150                 155                 160

Pro Glu Arg Lys His Arg Met Thr Pro Pro Gln Leu Asp Glu Asp Gly
                165                 170                 175

Ser Tyr Phe Leu Tyr Ser Lys Leu Ser Val Asp Lys Ser Arg Trp Gln
                180                 185                 190

Gln Gly Asp Pro Phe Thr Cys Ala Val Met His Glu Thr Leu Gln Asn
                195                 200                 205

His Tyr Thr Asp Leu Ser Leu Ser His Ser Pro Gly Lys
                210                 215                 220

<210> SEQ ID NO 159
<211> LENGTH: 221
<212> TYPE: PRT
<213> ORGANISM: Artificial Sequence
<220> FEATURE:
<223> OTHER INFORMATION: Aglycosyl variant canine IgG A Fc, G(69)P

<400> SEQUENCE: 159

Pro Val Pro Glu Pro Leu Gly Gly Pro Ser Val Leu Ile Phe Pro Pro
1               5                   10                  15

Lys Pro Lys Asp Ile Leu Arg Ile Thr Arg Thr Pro Glu Val Thr Cys
                20                  25                  30

Val Val Leu Asp Leu Gly Arg Glu Asp Pro Glu Val Gln Ile Ser Trp
            35                  40                  45

Phe Val Asp Gly Lys Glu Val His Thr Ala Lys Thr Gln Ser Arg Glu
    50                  55                  60

Gln Gln Phe Asn Pro Thr Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
                100                 105                 110

Arg Ala His Lys Pro Ser Val Tyr Val Leu Pro Pro Ser Pro Lys Glu
            115                 120                 125

Leu Ser Ser Ser Asp Thr Val Ser Ile Thr Cys Leu Ile Lys Asp Phe
    130                 135                 140

Tyr Pro Pro Asp Ile Asp Val Glu Trp Gln Ser Asn Gly Gln Gln Glu
145                 150                 155                 160

Pro Glu Arg Lys His Arg Met Thr Pro Pro Gln Leu Asp Glu Asp Gly
                165                 170                 175

Ser Tyr Phe Leu Tyr Ser Lys Leu Ser Val Asp Lys Ser Arg Trp Gln
                180                 185                 190

Gln Gly Asp Pro Phe Thr Cys Ala Val Met His Glu Thr Leu Gln Asn
                195                 200                 205

His Tyr Thr Asp Leu Ser Leu Ser His Ser Pro Gly Lys
                210                 215                 220

<210> SEQ ID NO 160
<211> LENGTH: 221
<212> TYPE: PRT
<213> ORGANISM: Artificial Sequence
<220> FEATURE:
<223> OTHER INFORMATION: Aglycosyl variant canine IgG A Fc, T(70)X
<220> FEATURE:
<221> NAME/KEY: MISC_FEATURE
<222> LOCATION: (70)..(70)
<223> OTHER INFORMATION: X = any amino acid except T or S

<400> SEQUENCE: 160
```

```
Pro Val Pro Glu Pro Leu Gly Gly Pro Ser Val Ile Phe Pro Pro
1               5                   10                  15

Lys Pro Lys Asp Ile Leu Arg Ile Thr Arg Thr Pro Glu Val Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Ser Arg Glu
    50                  55                  60

Gln Gln Phe Asn Gly Xaa Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Asp Leu Pro Ser Pro Ile Glu Arg Thr Ile Ser Lys Ala Arg Gly
                100                 105                 110

Arg Ala His Lys Pro Ser Val Tyr Val Leu Pro Pro Ser Pro Lys Glu
            115                 120                 125

Leu Ser Ser Ser Asp Thr Val Ser Ile Thr Cys Leu Ile Lys Asp Phe
    130                 135                 140

Tyr Pro Pro Asp Ile Asp Val Glu Trp Gln Ser Asn Gly Gln Gln Glu
145                 150                 155                 160

Pro Glu Arg Lys His Arg Met Thr Pro Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Pro Phe Thr Cys Ala Val Met His Glu Thr Leu Gln Asn
        195                 200                 205

His Tyr Thr Asp Leu Ser Leu Ser His Ser Pro Gly Lys
    210                 215                 220

<210> SEQ ID NO 161
<211> LENGTH: 220
<212> TYPE: PRT
<213> ORGANISM: Artificial Sequence
<220> FEATURE:
<223> OTHER INFORMATION: Aglycosyl variant canine IgG B Fc, N(68)X
<220> FEATURE:
<221> NAME/KEY: MISC_FEATURE
<222> LOCATION: (68)..(68)
<223> OTHER INFORMATION: X = any amino acid except N

<400> SEQUENCE: 161

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Xaa Gly Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
```

```
            115                 120                 125
Leu Ser Lys Asn Thr Val Ser Leu Thr Cys Leu Ile Lys Asp Phe Phe
        130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 162
<211> LENGTH: 220
<212> TYPE: PRT
<213> ORGANISM: Artificial Sequence
<220> FEATURE:
<223> OTHER INFORMATION: Aglycosyl variant canine IgG B Fc, G(69)P

<400> SEQUENCE: 162

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
        35                  40                  45

Phe Val Asp Gly Lys Gln Met Gln Thr Ala Lys Thr Gln Pro Arg Glu
    50                  55                  60

Glu Gln Phe Asn Pro Thr Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
    130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

<210> SEQ ID NO 163
<211> LENGTH: 220
<212> TYPE: PRT
<213> ORGANISM: Artificial Sequence
<220> FEATURE:
<223> OTHER INFORMATION: Aglycosyl variant canine IgG B Fc, T(70)X
```

```
<220> FEATURE:
<221> NAME/KEY: MISC_FEATURE
<222> LOCATION: (70)..(70)
<223> OTHER INFORMATION: X = any amino acid except T or S

<400> SEQUENCE: 163
```

Pro Ala Pro Glu Met Leu Gly Gly Pro Ser Val Phe Ile Phe Pro Pro
1               5                   10                  15

Lys Pro Lys Asp Thr Leu Leu Ile Ala Arg Thr Pro Glu Val Thr Cys
            20                  25                  30

Val Val Val Asp Leu Asp Pro Glu Asp Pro Glu Val Gln Ile Ser Trp
                35                  40                  45

Phe Val Asp Gly Lys Gln Met Gln Thr Ala Lys Thr Gln Pro Arg Glu
        50                  55                  60

Glu Gln Phe Asn Gly Xaa Tyr Arg Val Val Ser Val Leu Pro Ile Gly
65                  70                  75                  80

His Gln Asp Trp Leu Lys Gly Lys Gln Phe Thr Cys Lys Val Asn Asn
                85                  90                  95

Lys Ala Leu Pro Ser Pro Ile Glu Arg Thr Ile Ser Lys Ala Arg Gly
            100                 105                 110

Gln Ala His Gln Pro Ser Val Tyr Val Leu Pro Pro Ser Arg Glu Glu
        115                 120                 125

Leu Ser Lys Asn Thr Val Ser Leu Thr Cys Leu Ile Lys Asp Phe Phe
130                 135                 140

Pro Pro Asp Ile Asp Val Glu Trp Gln Ser Asn Gly Gln Gln Glu Pro
145                 150                 155                 160

Glu Ser Lys Tyr Arg Thr Thr Pro Pro Gln Leu Asp Glu Asp Gly Ser
                165                 170                 175

Tyr Phe Leu Tyr Ser Lys Leu Ser Val Asp Lys Ser Arg Trp Gln Arg
            180                 185                 190

Gly Asp Thr Phe Ile Cys Ala Val Met His Glu Ala Leu His Asn His
        195                 200                 205

Tyr Thr Gln Glu Ser Leu Ser His Ser Pro Gly Lys
    210                 215                 220

```
<210> SEQ ID NO 164
<211> LENGTH: 220
<212> TYPE: PRT
<213> ORGANISM: Artificial Sequence
<220> FEATURE:
<223> OTHER INFORMATION: Aglycosyl variant canine IgG C Fc, N(68)X
<220> FEATURE:
<221> NAME/KEY: MISC_FEATURE
<222> LOCATION: (68)..(68)
<223> OTHER INFORMATION: X = any amino acid except N

<400> SEQUENCE: 164
```

Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Val Thr Cys
            20                  25                  30

Val Val Val Asp Leu Asp Pro Glu Asn Pro Glu Val Gln Ile Ser Trp
                35                  40                  45

Phe Val Asp Ser Lys Gln Val Gln Thr Ala Asn Thr Gln Pro Arg Glu
        50                  55                  60

Glu Gln Ser Xaa Gly Thr Tyr Arg Val Val Ser Val Leu Pro Ile Gly
65                  70                  75                  80

His Gln Asp Trp Leu Ser Gly Lys Gln Phe Lys Cys Lys Val Asn Asn

```
                    85                  90                  95
Lys Ala Leu Pro Ser Pro Ile Glu Glu Ile Ile Ser Lys Thr Pro Gly
                100                 105                 110
Gln Ala His Gln Pro Asn Val Tyr Val Leu Pro Pro Ser Arg Asp Glu
                115                 120                 125
Met Ser Lys Asn Thr Val Thr Leu Thr Cys Leu Val Lys Asp Phe Phe
            130                 135                 140
Pro Pro Glu Ile Asp Val Glu Trp Gln Ser Asn Gly Gln Gln Glu Pro
145                 150                 155                 160
Glu Ser Lys Tyr Arg Met Thr Pro Pro Gln Leu Asp Glu Asp Gly Ser
                165                 170                 175
Tyr Phe Leu Tyr Ser Lys Leu Ser Val Asp Lys Ser Arg Trp Gln Arg
            180                 185                 190
Gly Asp Thr Phe Ile Cys Ala Val Met His Glu Ala Leu His Asn His
                195                 200                 205
Tyr Thr Gln Ile Ser Leu Ser His Ser Pro Gly Lys
            210                 215                 220

<210> SEQ ID NO 165
<211> LENGTH: 220
<212> TYPE: PRT
<213> ORGANISM: Artificial Sequence
<220> FEATURE:
<223> OTHER INFORMATION: Aglycosyl variant canine IgG C Fc, G(69)P

<400> SEQUENCE: 165

Pro Gly Cys Gly Leu Leu Gly Gly Pro Ser Val Phe Ile Phe Pro Pro
1               5                   10                  15
Lys Pro Lys Asp Ile Leu Val Thr Ala Arg Thr Pro Thr Val Thr Cys
                20                  25                  30
Val Val Val Asp Leu Asp Pro Glu Asn Pro Glu Val Gln Ile Ser Trp
            35                  40                  45
Phe Val Asp Ser Lys Gln Val Gln Thr Ala Asn Thr Gln Pro Arg Glu
    50                  55                  60
Glu Gln Ser Asn Pro Thr Tyr Arg Val Val Ser Val Leu Pro Ile Gly
65                  70                  75                  80
His Gln Asp Trp Leu Ser Gly Lys Gln Phe Lys Cys Lys Val Asn Asn
                85                  90                  95
Lys Ala Leu Pro Ser Pro Ile Glu Glu Ile Ile Ser Lys Thr Pro Gly
                100                 105                 110
Gln Ala His Gln Pro Asn Val Tyr Val Leu Pro Pro Ser Arg Asp Glu
                115                 120                 125
Met Ser Lys Asn Thr Val Thr Leu Thr Cys Leu Val Lys Asp Phe Phe
            130                 135                 140
Pro Pro Glu Ile Asp Val Glu Trp Gln Ser Asn Gly Gln Gln Glu Pro
145                 150                 155                 160
Glu Ser Lys Tyr Arg Met Thr Pro Pro Gln Leu Asp Glu Asp Gly Ser
                165                 170                 175
Tyr Phe Leu Tyr Ser Lys Leu Ser Val Asp Lys Ser Arg Trp Gln Arg
            180                 185                 190
Gly Asp Thr Phe Ile Cys Ala Val Met His Glu Ala Leu His Asn His
                195                 200                 205
Tyr Thr Gln Ile Ser Leu Ser His Ser Pro Gly Lys
            210                 215                 220
```

<210> SEQ ID NO 166
<211> LENGTH: 220
<212> TYPE: PRT
<213> ORGANISM: Artificial Sequence
<220> FEATURE:
<223> OTHER INFORMATION: Aglycosyl variant canine IgG C Fc, T(70)X
<220> FEATURE:
<221> NAME/KEY: MISC_FEATURE
<222> LOCATION: (70)..(70)
<223> OTHER INFORMATION: X = any amino acid except T or S

<400> SEQUENCE: 166

```
Pro Gly Cys Gly Leu Leu Gly Gly Pro Ser Val Phe Ile Phe Pro Pro
1               5                   10                  15

Lys Pro Lys Asp Ile Leu Val Thr Ala Arg Thr Pro Thr Val Thr Cys
            20                  25                  30

Val Val Val Asp Leu Asp Pro Glu Asn Pro Glu Val Gln Ile Ser Trp
        35                  40                  45

Phe Val Asp Ser Lys Gln Val Gln Thr Ala Asn Thr Gln Pro Arg Glu
    50                  55                  60

Glu Gln Ser Asn Gly Xaa Tyr Arg Val Val Ser Val Leu Pro Ile Gly
65                  70                  75                  80

His Gln Asp Trp Leu Ser Gly Lys Gln Phe Lys Cys Lys Val Asn Asn
                85                  90                  95

Lys Ala Leu Pro Ser Pro Ile Glu Glu Ile Ile Ser Lys Thr Pro Gly
            100                 105                 110

Gln Ala His Gln Pro Asn Val Tyr Val Leu Pro Pro Ser Arg Asp Glu
        115                 120                 125

Met Ser Lys Asn Thr Val Thr Leu Thr Cys Leu Val Lys Asp Phe Phe
    130                 135                 140

Pro Pro Glu Ile Asp Val Glu Trp Gln Ser Asn Gly Gln Gln Glu Pro
145                 150                 155                 160

Glu Ser Lys Tyr Arg Met Thr Pro Gln Leu Asp Glu Asp Gly Ser
                165                 170                 175

Tyr Phe Leu Tyr Ser Lys Leu Ser Val Asp Lys Ser Arg Trp Gln Arg
                180                 185                 190

Gly Asp Thr Phe Ile Cys Ala Val Met His Glu Ala Leu His Asn His
            195                 200                 205

Tyr Thr Gln Ile Ser Leu Ser His Ser Pro Gly Lys
    210                 215                 220
```

<210> SEQ ID NO 167
<211> LENGTH: 221
<212> TYPE: PRT
<213> ORGANISM: Artificial Sequence
<220> FEATURE:
<223> OTHER INFORMATION: Aglycosyl variant canine IgG D Fc, N(68)X
<220> FEATURE:
<221> NAME/KEY: MISC_FEATURE
<222> LOCATION: (68)..(68)
<223> OTHER INFORMATION: X = any amino acid except N

<400> SEQUENCE: 167

```
Pro Val Pro Glu Ser Leu Gly Gly Pro Ser Val Phe Ile Phe Pro Pro
1               5                   10                  15

Lys Pro Lys Asp Ile Leu Arg Ile Thr Arg Thr Pro Glu Ile Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Pro Arg Glu
```

```
                    50                  55                  60
Gln Gln Phe Xaa Ser Thr Tyr Arg Val Val Ser Val Leu Pro Ile Glu
 65                  70                  75                  80

His Gln Asp Trp Leu Thr Gly Lys Glu Phe Lys Cys Arg Val Asn His
                 85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Thr Cys Leu Ile Lys Asp Phe
    130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Thr Phe Thr Cys Ala Val Met His Glu Ala Leu Gln Asn
        195                 200                 205

His Tyr Thr Asp Leu Ser Leu Ser His Ser Pro Gly Lys
    210                 215                 220

<210> SEQ ID NO 168
<211> LENGTH: 221
<212> TYPE: PRT
<213> ORGANISM: Artificial Sequence
<220> FEATURE:
<223> OTHER INFORMATION: Aglycosyl variant canine IgG D Fc, S(69)P

<400> SEQUENCE: 168

Pro Val Pro Glu Ser Leu Gly Gly Pro Ser Val Phe Ile Phe Pro Pro
  1               5                  10                  15

Lys Pro Lys Asp Ile Leu Arg Ile Thr Arg Thr Pro Glu Ile Thr Cys
             20                  25                  30

Val Val Leu Asp Leu Gly Arg Glu Asp Pro Glu Val Gln Ile Ser Trp
         35                  40                  45

Phe Val Asp Gly Lys Glu Val His Thr Ala Lys Thr Gln Pro Arg Glu
 50                  55                  60

Gln Gln Phe Asn Pro Thr Tyr Arg Val Val Ser Val Leu Pro Ile Glu
 65                  70                  75                  80

His Gln Asp Trp Leu Thr Gly Lys Glu Phe Lys Cys Arg Val Asn His
                 85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Thr Cys Leu Ile Lys Asp Phe
    130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Thr Phe Thr Cys Ala Val Met His Glu Ala Leu Gln Asn
```

```
                195                 200                 205
His Tyr Thr Asp Leu Ser Leu Ser His Ser Pro Gly Lys
    210                 215                 220

<210> SEQ ID NO 169
<211> LENGTH: 221
<212> TYPE: PRT
<213> ORGANISM: Artificial Sequence
<220> FEATURE:
<223> OTHER INFORMATION: Aglycosyl variant canine IgG D Fc, T(70)X
<220> FEATURE:
<221> NAME/KEY: MISC_FEATURE
<222> LOCATION: (70)..(70)
<223> OTHER INFORMATION: X = any amino acid except T or S

<400> SEQUENCE: 169

Pro Val Pro Glu Ser Leu Gly Gly Pro Ser Val Phe Ile Phe Pro Pro
1               5                   10                  15

Lys Pro Lys Asp Ile Leu Arg Ile Thr Arg Thr Pro Glu Ile Thr Cys
            20                  25                  30

Val Val Leu Asp Leu Gly Arg Glu Asp Pro Glu Val Gln Ile Ser Trp
        35                  40                  45

Phe Val Asp Gly Lys Glu Val His Thr Ala Lys Thr Gln Pro Arg Glu
    50                  55                  60

Gln Gln Phe Asn Ser Xaa Tyr Arg Val Val Ser Val Leu Pro Ile Glu
65                  70                  75                  80

His Gln Asp Trp Leu Thr Gly Lys Glu Phe Lys Cys Arg Val Asn His
                85                  90                  95

Ile Gly Leu Pro Ser Pro Ile Glu Arg Thr Ile Ser Lys Ala Arg Gly
            100                 105                 110

Gln Ala His Gln Pro Ser Val Tyr Val Leu Pro Pro Ser Pro Lys Glu
        115                 120                 125

Leu Ser Ser Ser Asp Thr Val Thr Leu Thr Cys Leu Ile Lys Asp Phe
    130                 135                 140

Phe Pro Pro Glu Ile Asp Val Glu Trp Gln Ser Asn Gly Gln Pro Glu
145                 150                 155                 160

Pro Glu Ser Lys Tyr His Thr Thr Ala Pro Gln Leu Asp Glu Asp Gly
                165                 170                 175

Ser Tyr Phe Leu Tyr Ser Lys Leu Ser Val Asp Lys Ser Arg Trp Gln
            180                 185                 190

Gln Gly Asp Thr Phe Thr Cys Ala Val Met His Glu Ala Leu Gln Asn
        195                 200                 205

His Tyr Thr Asp Leu Ser Leu Ser His Ser Pro Gly Lys
    210                 215                 220

<210> SEQ ID NO 170
<211> LENGTH: 237
<212> TYPE: PRT
<213> ORGANISM: Artificial Sequence
<220> FEATURE:
<223> OTHER INFORMATION: Aglycosyl variant feline IgG1a Fc, N(85)X
<220> FEATURE:
<221> NAME/KEY: MISC_FEATURE
<222> LOCATION: (85)..(85)
<223> OTHER INFORMATION: X = any amino acid except N

<400> SEQUENCE: 170

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
```

-continued

```
                20                  25                  30
Pro Lys Pro Lys Asp Thr Leu Ser Ile Ser Arg Thr Pro Glu Val Thr
            35                  40                  45
Cys Leu Val Val Asp Leu Gly Pro Asp Ser Asp Val Gln Ile Thr
        50                  55                  60
Trp Phe Val Asp Asn Thr Gln Val Tyr Thr Ala Lys Thr Ser Pro Arg
65                  70                  75                  80
Glu Glu Gln Phe Xaa Ser Thr Tyr Arg Val Val Ser Val Leu Pro Ile
                85                  90                  95
Leu His Gln Asp Trp Leu Lys Gly Lys Glu Phe Lys Cys Lys Val Asn
                100                 105                 110
Ser Lys Ser Leu Pro Ser Pro Ile Glu Arg Thr Ile Ser Lys Ala Lys
            115                 120                 125
Gly Gln Pro His Glu Pro Gln Val Tyr Val Leu Pro Pro Ala Gln Glu
            130                 135                 140
Glu Leu Ser Glu Asn Lys Val Ser Val Thr Cys Leu Ile Lys Ser Phe
145                 150                 155                 160
His Pro Pro Asp Ile Ala Val Glu Trp Glu Ile Thr Gly Gln Pro Glu
                165                 170                 175
Pro Glu Asn Asn Tyr Arg Thr Thr Pro Pro Gln Leu Asp Ser Asp Gly
                180                 185                 190
Thr Tyr Phe Val Tyr Ser Lys Leu Ser Val Asp Arg Ser His Trp Gln
            195                 200                 205
Arg Gly Asn Thr Tyr Thr Cys Ser Val Ser His Glu Ala Leu His Ser
        210                 215                 220
His His Thr Gln Lys Ser Leu Thr Gln Ser Pro Gly Lys
225                 230                 235

<210> SEQ ID NO 171
<211> LENGTH: 237
<212> TYPE: PRT
<213> ORGANISM: Artificial Sequence
<220> FEATURE:
<223> OTHER INFORMATION: Aglycosyl variant feline IgG1a Fc, S(86)P

<400> SEQUENCE: 171

Arg Lys Thr Asp His Pro Pro Gly Pro Lys Pro Cys Asp Cys Pro Lys
1               5                   10                  15
Cys Pro Pro Pro Glu Met Leu Gly Gly Pro Ser Ile Phe Ile Phe Pro
                20                  25                  30
Pro Lys Pro Lys Asp Thr Leu Ser Ile Ser Arg Thr Pro Glu Val Thr
            35                  40                  45
Cys Leu Val Val Asp Leu Gly Pro Asp Ser Asp Val Gln Ile Thr
        50                  55                  60
Trp Phe Val Asp Asn Thr Gln Val Tyr Thr Ala Lys Thr Ser Pro Arg
65                  70                  75                  80
Glu Glu Gln Phe Asn Pro Thr Tyr Arg Val Val Ser Val Leu Pro Ile
                85                  90                  95
Leu His Gln Asp Trp Leu Lys Gly Lys Glu Phe Lys Cys Lys Val Asn
                100                 105                 110
Ser Lys Ser Leu Pro Ser Pro Ile Glu Arg Thr Ile Ser Lys Ala Lys
            115                 120                 125
Gly Gln Pro His Glu Pro Gln Val Tyr Val Leu Pro Pro Ala Gln Glu
            130                 135                 140
Glu Leu Ser Glu Asn Lys Val Ser Val Thr Cys Leu Ile Lys Ser Phe
```

-continued

```
                145                 150                 155                 160
His Pro Pro Asp Ile Ala Val Glu Trp Glu Ile Thr Gly Gln Pro Glu
                    165                 170                 175

Pro Glu Asn Asn Tyr Arg Thr Thr Pro Pro Gln Leu Asp Ser Asp Gly
                180                 185                 190

Thr Tyr Phe Val Tyr Ser Lys Leu Ser Val Asp Arg Ser His Trp Gln
            195                 200                 205

Arg Gly Asn Thr Tyr Thr Cys Ser Val Ser His Glu Ala Leu His Ser
        210                 215                 220

His His Thr Gln Lys Ser Leu Thr Gln Ser Pro Gly Lys
225                 230                 235

<210> SEQ ID NO 172
<211> LENGTH: 237
<212> TYPE: PRT
<213> ORGANISM: Artificial Sequence
<220> FEATURE:
<223> OTHER INFORMATION: Aglycosyl  variant feline IgG1a Fc, T(87)X
<220> FEATURE:
<221> NAME/KEY: MISC_FEATURE
<222> LOCATION: (87)..(87)
<223> OTHER INFORMATION: X = any amino acid except T or S

<400> SEQUENCE: 172

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
        50                  55                  60

Trp Phe Val Asp Asn Thr Gln Val Tyr Thr Ala Lys Thr Ser Pro Arg
65                  70                  75                  80

Glu Glu Gln Phe Asn Ser Xaa Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125

Gly Gln Pro His Glu Pro Gln Val Tyr Val Leu Pro Pro Ala Gln Glu
130                 135                 140

Glu Leu Ser Glu Asn Lys Val Ser Val Thr Cys Leu Ile Lys Ser Phe
145                 150                 155                 160

His Pro Pro Asp Ile Ala Val Glu Trp Glu Ile Thr Gly Gln Pro Glu
                    165                 170                 175

Pro Glu Asn Asn Tyr Arg Thr Thr Pro Pro Gln Leu Asp Ser Asp Gly
                180                 185                 190

Thr Tyr Phe Val Tyr Ser Lys Leu Ser Val Asp Arg Ser His Trp Gln
            195                 200                 205

Arg Gly Asn Thr Tyr Thr Cys Ser Val Ser His Glu Ala Leu His Ser
        210                 215                 220

His His Thr Gln Lys Ser Leu Thr Gln Ser Pro Gly Lys
225                 230                 235

<210> SEQ ID NO 173
<211> LENGTH: 237
```

```
<212> TYPE: PRT
<213> ORGANISM: Artificial Sequence
<220> FEATURE:
<223> OTHER INFORMATION: Aglycosyl variant feline IgG1b Fc, N(85)X
<220> FEATURE:
<221> NAME/KEY: MISC_FEATURE
<222> LOCATION: (85)..(85)
<223> OTHER INFORMATION: X = any amino acid except N

<400> SEQUENCE: 173
```

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg
65                  70                  75                  80

Glu Glu Gln Phe Xaa Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

```
<210> SEQ ID NO 174
<211> LENGTH: 237
<212> TYPE: PRT
<213> ORGANISM: Artificial Sequence
<220> FEATURE:
<223> OTHER INFORMATION: Aglycosyl variant feline IgG1b Fc, S(86)P

<400> SEQUENCE: 174
```

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
    50                  55                  60

Trp Phe Val Asp Asn Thr Gln Val Tyr Thr Ala Lys Thr Ser Pro Arg

```
                65                  70                  75                  80
Glu Glu Gln Phe Asn Pro Thr Tyr Arg Val Val Ser Val Leu Pro Ile
                    85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 175
<211> LENGTH: 237
<212> TYPE: PRT
<213> ORGANISM: Artificial Sequence
<220> FEATURE:
<223> OTHER INFORMATION: Aglycosyl  variant feline IgG1b Fc, T(87)X
<220> FEATURE:
<221> NAME/KEY: MISC_FEATURE
<222> LOCATION: (87)..(87)
<223> OTHER INFORMATION: X = any amino acid except T or S

<400> SEQUENCE: 175

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asp Val Gln Ile Thr
        50                  55                  60

Trp Phe Val Asp Asn Thr Gln Val Tyr Thr Ala Lys Thr Ser Pro Arg
65                  70                  75                  80

Glu Glu Gln Phe Asn Ser Xaa Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
    130                 135                 140

Glu Leu Ser Glu Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175
```

Pro Glu Asn Asn Tyr Arg Thr Thr Pro Pro Gln Leu Asp Ser Asp Gly
            180                 185                 190

Thr Tyr Phe Leu Tyr Ser Arg Leu Ser Val Asp Arg Ser Arg Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 176
<211> LENGTH: 237
<212> TYPE: PRT
<213> ORGANISM: Artificial Sequence
<220> FEATURE:
<223> OTHER INFORMATION: Aglycosyl variant feline IgG2 Fc, N(85)X
<220> FEATURE:
<221> NAME/KEY: MISC_FEATURE
<222> LOCATION: (85)..(85)
<223> OTHER INFORMATION: X= any amino acid except N

<400> SEQUENCE: 176

Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asn Val Gln Ile Thr
    50                  55                  60

Trp Phe Val Asp Asn Thr Glu Met His Thr Ala Lys Thr Arg Pro Arg
65                  70                  75                  80

Glu Glu Gln Phe Xaa Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
    130                 135                 140

Glu Leu Ser Glu Asn Lys Val Ser Val Thr Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 177
<211> LENGTH: 237
<212> TYPE: PRT
<213> ORGANISM: Artificial Sequence
<220> FEATURE:
<223> OTHER INFORMATION: Aglycosyl variant feline IgG2 Fc, S(86)P

<400> SEQUENCE: 177

Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asn Val Gln Ile Thr
    50                  55                  60

Trp Phe Val Asp Asn Thr Glu Met His Thr Ala Lys Thr Arg Pro Arg
65                  70                  75                  80

Glu Glu Gln Phe Asn Pro Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
130                 135                 140

Glu Leu Ser Glu Asn Lys Val Ser Val Thr Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 178
<211> LENGTH: 237
<212> TYPE: PRT
<213> ORGANISM: Artificial Sequence
<220> FEATURE:
<223> OTHER INFORMATION: Aglycosyl variant feline IgG2 Fc, T(87)X
<220> FEATURE:
<221> NAME/KEY: MISC_FEATURE
<222> LOCATION: (87)..(87)
<223> OTHER INFORMATION: X = any amino acid except T or S

<400> SEQUENCE: 178

Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Asp Ser Asn Val Gln Ile Thr
    50                  55                  60

Trp Phe Val Asp Asn Thr Glu Met His Thr Ala Lys Thr Arg Pro Arg
65                  70                  75                  80

Glu Glu Gln Phe Asn Ser Xaa Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
    130                 135                 140

Glu Leu Ser Glu Asn Lys Val Ser Val Thr Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 179
<211> LENGTH: 214
<212> TYPE: PRT
<213> ORGANISM: Artificial Sequence
<220> FEATURE:
<223> OTHER INFORMATION: Aglycosyl variant equine IgG1 Fc, N(62)X
<220> FEATURE:
<221> NAME/KEY: MISC_FEATURE
<222> LOCATION: (62)..(62)
<223> OTHER INFORMATION: X = any amino acid except N

<400> SEQUENCE: 179

Gly Gly Pro Ser Val Phe Leu Phe Pro Pro Asn Pro Lys Asp Thr Leu
1               5                   10                  15

Met Ile Thr Arg Thr Pro Glu Val Thr Cys Val Val Asp Val Ser
            20                  25                  30

Gln Glu Asn Pro Asp Val Lys Phe Asn Trp Tyr Met Asp Gly Val Glu
        35                  40                  45

Val Arg Thr Ala Thr Thr Arg Pro Lys Glu Glu Gln Phe Xaa Ser Thr
50                  55                  60

Tyr Arg Val Val Ser Val Leu Arg Ile Gln His Gln Asp Trp Leu Ser
65                  70                  75                  80

Gly Lys Glu Phe Lys Cys Lys Val Asn Asn Gln Ala Leu Pro Gln Pro
                85                  90                  95

Ile Glu Arg Thr Ile Thr Lys Thr Lys Gly Arg Ser Gln Glu Pro Gln
            100                 105                 110

Val Tyr Val Leu Ala Pro His Pro Asp Glu Ser Lys Lys Ser Lys Val
        115                 120                 125

Ser Val Thr Cys Leu Val Lys Asp Phe Tyr Pro Pro Glu Ile Asn Ile
    130                 135                 140

Glu Trp Gln Ser Asn Gly Gln Pro Glu Leu Glu Thr Lys Tyr Ser Thr
145                 150                 155                 160

Thr Gln Ala Gln Gln Asp Ser Asp Gly Ser Tyr Phe Leu Tyr Ser Lys
                165                 170                 175

Leu Ser Val Asp Arg Asn Arg Trp Gln Gln Gly Thr Thr Phe Thr Cys
            180                 185                 190

Gly Val Met His Glu Ala Leu His Asn His Tyr Thr Gln Lys Asn Val
        195                 200                 205

Ser Lys Asn Pro Gly Lys
    210

<210> SEQ ID NO 180
<211> LENGTH: 214
<212> TYPE: PRT
<213> ORGANISM: Artificial Sequence
<220> FEATURE:
<223> OTHER INFORMATION: Aglycosyl variant equine IgG1 Fc, S(63)P

<400> SEQUENCE: 180

Gly Gly Pro Ser Val Phe Leu Phe Pro Pro Asn Pro Lys Asp Thr Leu
1               5                   10                  15

Met Ile Thr Arg Thr Pro Glu Val Thr Cys Val Val Val Asp Val Ser
            20                  25                  30

Gln Glu Asn Pro Asp Val Lys Phe Asn Trp Tyr Met Asp Gly Val Glu
        35                  40                  45

Val Arg Thr Ala Thr Thr Arg Pro Lys Glu Glu Gln Phe Asn Pro Thr
    50                  55                  60

Tyr Arg Val Val Ser Val Leu Arg Ile Gln His Gln Asp Trp Leu Ser
65                  70                  75                  80

Gly Lys Glu Phe Lys Cys Lys Val Asn Asn Gln Ala Leu Pro Gln Pro
                85                  90                  95

Ile Glu Arg Thr Ile Thr Lys Thr Lys Gly Arg Ser Gln Glu Pro Gln
            100                 105                 110

Val Tyr Val Leu Ala Pro His Pro Asp Glu Ser Lys Lys Ser Lys Val
        115                 120                 125

Ser Val Thr Cys Leu Val Lys Asp Phe Tyr Pro Pro Glu Ile Asn Ile
    130                 135                 140

Glu Trp Gln Ser Asn Gly Gln Pro Glu Leu Glu Thr Lys Tyr Ser Thr
145                 150                 155                 160

Thr Gln Ala Gln Gln Asp Ser Asp Gly Ser Tyr Phe Leu Tyr Ser Lys
                165                 170                 175

Leu Ser Val Asp Arg Asn Arg Trp Gln Gln Gly Thr Thr Phe Thr Cys
            180                 185                 190

Gly Val Met His Glu Ala Leu His Asn His Tyr Thr Gln Lys Asn Val
        195                 200                 205

Ser Lys Asn Pro Gly Lys
    210

<210> SEQ ID NO 181
<211> LENGTH: 214
<212> TYPE: PRT
<213> ORGANISM: Artificial Sequence
<220> FEATURE:
<223> OTHER INFORMATION: Aglycosyl variant equine IgG1 Fc, T(64)X
<220> FEATURE:
<221> NAME/KEY: MISC_FEATURE
<222> LOCATION: (64)..(64)
<223> OTHER INFORMATION: X = any amino acid except T or S

<400> SEQUENCE: 181

Gly Gly Pro Ser Val Phe Leu Phe Pro Pro Asn Pro Lys Asp Thr Leu
1               5                   10                  15

Met Ile Thr Arg Thr Pro Glu Val Thr Cys Val Val Val Asp Val Ser
            20                  25                  30

Gln Glu Asn Pro Asp Val Lys Phe Asn Trp Tyr Met Asp Gly Val Glu
        35                  40                  45

Val Arg Thr Ala Thr Thr Arg Pro Lys Glu Glu Gln Phe Asn Ser Xaa
 50                  55                  60

Tyr Arg Val Val Ser Val Leu Arg Ile Gln His Gln Asp Trp Leu Ser
 65                  70                  75                  80

Gly Lys Glu Phe Lys Cys Lys Val Asn Asn Gln Ala Leu Pro Gln Pro
                 85                  90                  95

Ile Glu Arg Thr Ile Thr Lys Thr Lys Gly Arg Ser Gln Glu Pro Gln
            100                 105                 110

Val Tyr Val Leu Ala Pro His Pro Asp Glu Ser Lys Lys Ser Lys Val
        115                 120                 125

Ser Val Thr Cys Leu Val Lys Asp Phe Tyr Pro Pro Glu Ile Asn Ile
130                 135                 140

Glu Trp Gln Ser Asn Gly Gln Pro Glu Leu Glu Thr Lys Tyr Ser Thr
145                 150                 155                 160

Thr Gln Ala Gln Gln Asp Ser Asp Gly Ser Tyr Phe Leu Tyr Ser Lys
                165                 170                 175

Leu Ser Val Asp Arg Asn Arg Trp Gln Gln Gly Thr Thr Phe Thr Cys
            180                 185                 190

Gly Val Met His Glu Ala Leu His Asn His Tyr Thr Gln Lys Asn Val
        195                 200                 205

Ser Lys Asn Pro Gly Lys
        210

<210> SEQ ID NO 182
<211> LENGTH: 214
<212> TYPE: PRT
<213> ORGANISM: Artificial Sequence
<220> FEATURE:
<223> OTHER INFORMATION: Aglycosyl variant equine IgG2 Fc, N(62)X
<220> FEATURE:
<221> NAME/KEY: MISC_FEATURE
<222> LOCATION: (62)..(62)
<223> OTHER INFORMATION: X = any amino acid except N

<400> SEQUENCE: 182

Gly Gly Pro Ser Val Phe Ile Phe Pro Pro Asn Pro Lys Asp Ala Leu
1               5                   10                  15

Met Ile Ser Arg Thr Pro Val Val Thr Cys Val Val Val Asn Leu Ser
            20                  25                  30

Asp Gln Tyr Pro Asp Val Gln Phe Ser Trp Tyr Val Asp Asn Thr Glu
        35                  40                  45

Val His Ser Ala Ile Thr Lys Gln Arg Glu Ala Gln Phe Xaa Ser Thr
 50                  55                  60

Tyr Arg Val Val Ser Val Leu Pro Ile Gln His Gln Asp Trp Leu Ser
 65                  70                  75                  80

Gly Lys Glu Phe Lys Cys Ser Val Thr Asn Val Gly Val Pro Gln Pro
                 85                  90                  95

Ile Ser Arg Ala Ile Ser Arg Gly Lys Gly Pro Ser Arg Val Pro Gln
            100                 105                 110

Val Tyr Val Leu Pro Pro His Pro Asp Glu Leu Ala Lys Ser Lys Val
        115                 120                 125

Ser Val Thr Cys Leu Val Lys Asp Phe Tyr Pro Asp Ile Ser Val
130                 135                 140

Glu Trp Gln Ser Asn Arg Trp Pro Glu Leu Glu Gly Lys Tyr Ser Thr
145                 150                 155                 160

Thr Pro Ala Gln Leu Asp Gly Asp Gly Ser Tyr Phe Leu Tyr Ser Lys
                165                 170                 175

```
Leu Ser Leu Glu Thr Ser Arg Trp Gln Gln Val Glu Ser Phe Thr Cys
            180                 185                 190

Ala Val Met His Glu Ala Leu His Asn His Phe Thr Lys Thr Asp Ile
        195                 200                 205

Ser Glu Ser Leu Gly Lys
        210

<210> SEQ ID NO 183
<211> LENGTH: 214
<212> TYPE: PRT
<213> ORGANISM: Artificial Sequence
<220> FEATURE:
<223> OTHER INFORMATION: Aglycosyl variant equine IgG2 Fc, S(63)P

<400> SEQUENCE: 183

Gly Gly Pro Ser Val Phe Ile Phe Pro Pro Asn Pro Lys Asp Ala Leu
1               5                   10                  15

Met Ile Ser Arg Thr Pro Val Val Thr Cys Val Val Val Asn Leu Ser
            20                  25                  30

Asp Gln Tyr Pro Asp Val Gln Phe Ser Trp Tyr Val Asp Asn Thr Glu
        35                  40                  45

Val His Ser Ala Ile Thr Lys Gln Arg Glu Ala Gln Phe Asn Pro Thr
    50                  55                  60

Tyr Arg Val Val Ser Val Leu Pro Ile Gln His Gln Asp Trp Leu Ser
65                  70                  75                  80

Gly Lys Glu Phe Lys Cys Ser Val Thr Asn Val Gly Val Pro Gln Pro
                85                  90                  95

Ile Ser Arg Ala Ile Ser Arg Gly Lys Gly Pro Ser Arg Val Pro Gln
            100                 105                 110

Val Tyr Val Leu Pro Pro His Pro Asp Glu Leu Ala Lys Ser Lys Val
        115                 120                 125

Ser Val Thr Cys Leu Val Lys Asp Phe Tyr Pro Pro Asp Ile Ser Val
    130                 135                 140

Glu Trp Gln Ser Asn Arg Trp Pro Glu Leu Glu Gly Lys Tyr Ser Thr
145                 150                 155                 160

Thr Pro Ala Gln Leu Asp Gly Asp Gly Ser Tyr Phe Leu Tyr Ser Lys
                165                 170                 175

Leu Ser Leu Glu Thr Ser Arg Trp Gln Gln Val Glu Ser Phe Thr Cys
            180                 185                 190

Ala Val Met His Glu Ala Leu His Asn His Phe Thr Lys Thr Asp Ile
        195                 200                 205

Ser Glu Ser Leu Gly Lys
        210

<210> SEQ ID NO 184
<211> LENGTH: 214
<212> TYPE: PRT
<213> ORGANISM: Artificial Sequence
<220> FEATURE:
<223> OTHER INFORMATION: Aglycosyl variant equine IgG2 Fc, T(64)X
<220> FEATURE:
<221> NAME/KEY: MISC_FEATURE
<222> LOCATION: (64)..(64)
<223> OTHER INFORMATION: X = any amino acid except T or S

<400> SEQUENCE: 184

Gly Gly Pro Ser Val Phe Ile Phe Pro Pro Asn Pro Lys Asp Ala Leu
1               5                   10                  15
```

```
Met Ile Ser Arg Thr Pro Val Val Thr Cys Val Val Asn Leu Ser
            20                  25                  30

Asp Gln Tyr Pro Asp Val Gln Phe Ser Trp Tyr Val Asn Thr Glu
        35                  40                  45

Val His Ser Ala Ile Thr Lys Gln Arg Glu Ala Gln Phe Asn Ser Xaa
50                  55                  60

Tyr Arg Val Val Ser Val Leu Pro Ile Gln His Gln Asp Trp Leu Ser
65                  70                  75                  80

Gly Lys Glu Phe Lys Cys Ser Val Thr Asn Val Gly Val Pro Gln Pro
                85                  90                  95

Ile Ser Arg Ala Ile Ser Arg Gly Lys Gly Pro Ser Arg Val Pro Gln
                100                 105                 110

Val Tyr Val Leu Pro Pro His Pro Asp Glu Leu Ala Lys Ser Lys Val
            115                 120                 125

Ser Val Thr Cys Leu Val Lys Asp Phe Tyr Pro Pro Asp Ile Ser Val
        130                 135                 140

Glu Trp Gln Ser Asn Arg Trp Pro Glu Leu Gly Leu Tyr Ser Thr
145                 150                 155                 160

Thr Pro Ala Gln Leu Asp Gly Asp Gly Ser Tyr Phe Leu Tyr Ser Lys
                165                 170                 175

Leu Ser Leu Glu Thr Ser Arg Trp Gln Gln Val Glu Ser Phe Thr Cys
                180                 185                 190

Ala Val Met His Glu Ala Leu His Asn His Phe Thr Lys Thr Asp Ile
            195                 200                 205

Ser Glu Ser Leu Gly Lys
        210

<210> SEQ ID NO 185
<211> LENGTH: 214
<212> TYPE: PRT
<213> ORGANISM: Artificial Sequence
<220> FEATURE:
<223> OTHER INFORMATION: Aglycosyl variant equine IgG3 Fc, N(62)X
<220> FEATURE:
<221> NAME/KEY: MISC_FEATURE
<222> LOCATION: (62)..(62)
<223> OTHER INFORMATION: X = any amino acid except N

<400> SEQUENCE: 185

Gly Gly Pro Ser Val Phe Ile Phe Pro Pro Lys Pro Lys Asp Val Leu
1               5                   10                  15

Met Ile Thr Arg Met Pro Glu Val Thr Cys Leu Val Val Asp Val Ser
            20                  25                  30

His Asp Ser Ser Asp Val Leu Phe Thr Trp Tyr Val Asp Gly Thr Glu
        35                  40                  45

Val Lys Thr Ala Lys Thr Met Pro Asn Glu Glu Gln Asn Xaa Ser Thr
    50                  55                  60

Tyr Arg Val Val Ser Val Leu Arg Ile Gln His Gln Asp Trp Leu Asn
65                  70                  75                  80

Gly Lys Lys Phe Lys Cys Lys Val Asn Asn Gln Ala Leu Pro Ala Pro
                85                  90                  95

Val Glu Arg Thr Ile Ser Lys Ala Thr Gly Gln Thr Arg Val Pro Gln
                100                 105                 110

Val Tyr Val Leu Ala Pro His Pro Asp Glu Leu Ser Lys Asn Lys Val
            115                 120                 125

Ser Val Thr Cys Leu Val Lys Asp Phe Tyr Pro Pro Asp Ile Thr Val
        130                 135                 140
```

Glu Trp Gln Ser Asn Glu His Pro Glu Pro Glu Gly Lys Tyr Arg Thr
145                 150                 155                 160

Thr Glu Ala Gln Lys Asp Ser Asp Gly Ser Tyr Phe Leu Tyr Ser Lys
                165                 170                 175

Leu Thr Val Glu Lys Asp Arg Trp Gln Gln Gly Thr Thr Phe Thr Cys
            180                 185                 190

Val Val Met His Glu Ala Leu His Asn His Val Met Gln Lys Asn Ile
        195                 200                 205

Ser Lys Asn Pro Gly Lys
    210

<210> SEQ ID NO 186
<211> LENGTH: 214
<212> TYPE: PRT
<213> ORGANISM: Artificial Sequence
<220> FEATURE:
<223> OTHER INFORMATION: Aglycosyl variant equine IgG3 Fc, S(63)P

<400> SEQUENCE: 186

Gly Gly Pro Ser Val Phe Ile Phe Pro Pro Lys Pro Lys Asp Val Leu
1               5                   10                  15

Met Ile Thr Arg Met Pro Glu Val Thr Cys Leu Val Val Asp Val Ser
            20                  25                  30

His Asp Ser Ser Asp Val Leu Phe Thr Trp Tyr Val Asp Gly Thr Glu
        35                  40                  45

Val Lys Thr Ala Lys Thr Met Pro Asn Glu Glu Gln Asn Asn Pro Thr
    50                  55                  60

Tyr Arg Val Val Ser Val Leu Arg Ile Gln His Gln Asp Trp Leu Asn
65                  70                  75                  80

Gly Lys Lys Phe Lys Cys Lys Val Asn Asn Gln Ala Leu Pro Ala Pro
                85                  90                  95

Val Glu Arg Thr Ile Ser Lys Ala Thr Gly Gln Thr Arg Val Pro Gln
            100                 105                 110

Val Tyr Val Leu Ala Pro His Pro Asp Glu Leu Ser Lys Asn Lys Val
        115                 120                 125

Ser Val Thr Cys Leu Val Lys Asp Phe Tyr Pro Pro Asp Ile Thr Val
    130                 135                 140

Glu Trp Gln Ser Asn Glu His Pro Glu Pro Glu Gly Lys Tyr Arg Thr
145                 150                 155                 160

Thr Glu Ala Gln Lys Asp Ser Asp Gly Ser Tyr Phe Leu Tyr Ser Lys
                165                 170                 175

Leu Thr Val Glu Lys Asp Arg Trp Gln Gln Gly Thr Thr Phe Thr Cys
            180                 185                 190

Val Val Met His Glu Ala Leu His Asn His Val Met Gln Lys Asn Ile
        195                 200                 205

Ser Lys Asn Pro Gly Lys
    210

<210> SEQ ID NO 187
<211> LENGTH: 214
<212> TYPE: PRT
<213> ORGANISM: Artificial Sequence
<220> FEATURE:
<223> OTHER INFORMATION: Aglycosyl variant equine IgG3 Fc, T(64)X
<220> FEATURE:
<221> NAME/KEY: MISC_FEATURE
<222> LOCATION: (64)..(64)
<223> OTHER INFORMATION: X = any amino acid except T or S

<400> SEQUENCE: 187

Gly Gly Pro Ser Val Phe Ile Phe Pro Pro Lys Pro Lys Asp Val Leu
1               5                   10                  15

Met Ile Thr Arg Met Pro Glu Val Thr Cys Leu Val Val Asp Val Ser
            20                  25                  30

His Asp Ser Ser Asp Val Leu Phe Thr Trp Tyr Val Asp Gly Thr Glu
        35                  40                  45

Val Lys Thr Ala Lys Thr Met Pro Asn Glu Glu Gln Asn Asn Ser Xaa
    50                  55                  60

Tyr Arg Val Val Ser Val Leu Arg Ile Gln His Gln Asp Trp Leu Asn
65                  70                  75                  80

Gly Lys Lys Phe Lys Cys Lys Val Asn Asn Gln Ala Leu Pro Ala Pro
                85                  90                  95

Val Glu Arg Thr Ile Ser Lys Ala Thr Gly Gln Thr Arg Val Pro Gln
            100                 105                 110

Val Tyr Val Leu Ala Pro His Pro Asp Glu Leu Ser Lys Asn Lys Val
        115                 120                 125

Ser Val Thr Cys Leu Val Lys Asp Phe Tyr Pro Pro Asp Ile Thr Val
    130                 135                 140

Glu Trp Gln Ser Asn Glu His Pro Glu Pro Glu Gly Lys Tyr Arg Thr
145                 150                 155                 160

Thr Glu Ala Gln Lys Asp Ser Asp Gly Ser Tyr Phe Leu Tyr Ser Lys
                165                 170                 175

Leu Thr Val Glu Lys Asp Arg Trp Gln Gln Gly Thr Thr Phe Thr Cys
            180                 185                 190

Val Val Met His Glu Ala Leu His Asn His Val Met Gln Lys Asn Ile
        195                 200                 205

Ser Lys Asn Pro Gly Lys
    210

<210> SEQ ID NO 188
<211> LENGTH: 214
<212> TYPE: PRT
<213> ORGANISM: Artificial Sequence
<220> FEATURE:
<223> OTHER INFORMATION: Aglycosyl variant equine IgG4 Fc, N(62)X
<220> FEATURE:
<221> NAME/KEY: MISC_FEATURE
<222> LOCATION: (62)..(62)
<223> OTHER INFORMATION: X = any amino acid except N

<400> SEQUENCE: 188

Val Gly Pro Ser Val Phe Ile Phe Pro Pro Lys Pro Lys Asp Val Leu
1               5                   10                  15

Met Ile Ser Arg Thr Pro Thr Val Thr Cys Val Val Asp Val Gly
            20                  25                  30

His Asp Phe Pro Asp Val Gln Phe Asn Trp Tyr Val Asp Gly Val Glu
        35                  40                  45

Thr His Thr Ala Thr Thr Glu Pro Lys Gln Glu Gln Phe Xaa Ser Thr
    50                  55                  60

Tyr Arg Val Val Ser Val Leu Pro Ile Gln His Lys Asp Trp Leu Ser
65                  70                  75                  80

Gly Lys Glu Phe Lys Cys Lys Val Asn Asn Lys Ala Leu Pro Ala Pro
                85                  90                  95

Val Glu Arg Thr Ile Ser Ala Pro Thr Gly Gln Pro Arg Glu Pro Gln
            100                 105                 110

```
Val Tyr Val Leu Ala Pro His Arg Asp Glu Leu Ser Lys Asn Lys Val
        115                 120                 125

Ser Val Thr Cys Leu Val Lys Asp Phe Tyr Pro Pro Asp Ile Asp Ile
    130                 135                 140

Glu Trp Lys Ser Asn Gly Gln Pro Glu Pro Glu Thr Lys Tyr Ser Thr
145                 150                 155                 160

Thr Pro Ala Gln Leu Asp Ser Asp Gly Ser Tyr Phe Leu Tyr Ser Lys
            165                 170                 175

Leu Thr Val Glu Thr Asn Arg Trp Gln Gln Gly Thr Thr Phe Thr Cys
                180                 185                 190

Ala Val Met His Glu Ala Leu His Asn His Tyr Thr Glu Lys Ser Val
        195                 200                 205

Ser Lys Ser Pro Gly Lys
    210

<210> SEQ ID NO 189
<211> LENGTH: 214
<212> TYPE: PRT
<213> ORGANISM: Artificial Sequence
<220> FEATURE:
<223> OTHER INFORMATION: Aglycosyl variant equine IgG4 Fc, S(63)P

<400> SEQUENCE: 189

Val Gly Pro Ser Val Phe Ile Phe Pro Pro Lys Pro Lys Asp Val Leu
1               5                   10                  15

Met Ile Ser Arg Thr Pro Thr Val Thr Cys Val Val Val Asp Val Gly
            20                  25                  30

His Asp Phe Pro Asp Val Gln Phe Asn Trp Tyr Val Asp Gly Val Glu
        35                  40                  45

Thr His Thr Ala Thr Thr Glu Pro Lys Gln Glu Gln Phe Asn Pro Thr
    50                  55                  60

Tyr Arg Val Val Ser Val Leu Pro Ile Gln His Lys Asp Trp Leu Ser
65                  70                  75                  80

Gly Lys Glu Phe Lys Cys Lys Val Asn Asn Lys Ala Leu Pro Ala Pro
                85                  90                  95

Val Glu Arg Thr Ile Ser Ala Pro Thr Gly Gln Pro Arg Glu Pro Gln
            100                 105                 110

Val Tyr Val Leu Ala Pro His Arg Asp Glu Leu Ser Lys Asn Lys Val
        115                 120                 125

Ser Val Thr Cys Leu Val Lys Asp Phe Tyr Pro Pro Asp Ile Asp Ile
    130                 135                 140

Glu Trp Lys Ser Asn Gly Gln Pro Glu Pro Glu Thr Lys Tyr Ser Thr
145                 150                 155                 160

Thr Pro Ala Gln Leu Asp Ser Asp Gly Ser Tyr Phe Leu Tyr Ser Lys
            165                 170                 175

Leu Thr Val Glu Thr Asn Arg Trp Gln Gln Gly Thr Thr Phe Thr Cys
                180                 185                 190

Ala Val Met His Glu Ala Leu His Asn His Tyr Thr Glu Lys Ser Val
        195                 200                 205

Ser Lys Ser Pro Gly Lys
    210

<210> SEQ ID NO 190
<211> LENGTH: 214
<212> TYPE: PRT
<213> ORGANISM: Artificial Sequence
```

```
<220> FEATURE:
<223> OTHER INFORMATION: Aglycosyl variant equine IgG4 Fc, T(64)X
<220> FEATURE:
<221> NAME/KEY: MISC_FEATURE
<222> LOCATION: (64)..(64)
<223> OTHER INFORMATION: X = any amino acid except T or S

<400> SEQUENCE: 190

Val Gly Pro Ser Val Phe Ile Phe Pro Pro Lys Pro Lys Asp Val Leu
1               5                   10                  15

Met Ile Ser Arg Thr Pro Thr Val Thr Cys Val Val Val Asp Val Gly
            20                  25                  30

His Asp Phe Pro Asp Val Gln Phe Asn Trp Tyr Val Asp Gly Val Glu
        35                  40                  45

Thr His Thr Ala Thr Thr Glu Pro Lys Gln Glu Gln Phe Asn Ser Xaa
    50                  55                  60

Tyr Arg Val Val Ser Val Leu Pro Ile Gln His Lys Asp Trp Leu Ser
65                  70                  75                  80

Gly Lys Glu Phe Lys Cys Lys Val Asn Asn Lys Ala Leu Pro Ala Pro
                85                  90                  95

Val Glu Arg Thr Ile Ser Ala Pro Thr Gly Gln Pro Arg Glu Pro Gln
            100                 105                 110

Val Tyr Val Leu Ala Pro His Arg Asp Glu Leu Ser Lys Asn Lys Val
        115                 120                 125

Ser Val Thr Cys Leu Val Lys Asp Phe Tyr Pro Pro Asp Ile Asp Ile
    130                 135                 140

Glu Trp Lys Ser Asn Gly Gln Pro Glu Pro Gly Thr Lys Tyr Ser Thr
145                 150                 155                 160

Thr Pro Ala Gln Leu Asp Ser Asp Gly Ser Tyr Phe Leu Tyr Ser Lys
                165                 170                 175

Leu Thr Val Glu Thr Asn Arg Trp Gln Gln Gly Thr Thr Phe Thr Cys
            180                 185                 190

Ala Val Met His Glu Ala Leu His Asn His Tyr Thr Glu Lys Ser Val
        195                 200                 205

Ser Lys Ser Pro Gly Lys
    210

<210> SEQ ID NO 191
<211> LENGTH: 214
<212> TYPE: PRT
<213> ORGANISM: Artificial Sequence
<220> FEATURE:
<223> OTHER INFORMATION: Aglycosyl variant equine IgG5 Fc, N(62)X
<220> FEATURE:
<221> NAME/KEY: MISC_FEATURE
<222> LOCATION: (62)..(62)
<223> OTHER INFORMATION: X = any amino acid except N

<400> SEQUENCE: 191

Gly Gly Pro Ser Val Phe Ile Phe Pro Pro Lys Pro Lys Asp Val Leu
1               5                   10                  15

Met Ile Ser Arg Lys Pro Glu Val Thr Cys Val Val Val Asp Leu Gly
            20                  25                  30

His Asp Asp Pro Asp Val Gln Phe Thr Trp Phe Val Asp Gly Val Glu
        35                  40                  45

Thr His Thr Ala Thr Thr Glu Pro Lys Glu Glu Gln Phe Xaa Pro Thr
    50                  55                  60

Tyr Arg Val Val Ser Val Leu Pro Ile Gln His Gln Asp Trp Leu Ser
65                  70                  75                  80
```

Gly Lys Glu Phe Lys Cys Ser Val Thr Ser Lys Ala Leu Pro Ala Pro
                85                  90                  95

Val Glu Arg Thr Ile Ser Lys Ala Lys Gly Gln Leu Arg Val Pro Gln
            100                 105                 110

Val Tyr Val Leu Ala Pro His Pro Asp Glu Leu Ala Lys Asn Thr Val
        115                 120                 125

Ser Val Thr Cys Leu Val Lys Asp Phe Tyr Pro Pro Glu Ile Asp Val
    130                 135                 140

Glu Trp Gln Ser Asn Glu His Pro Glu Pro Glu Gly Lys Tyr Ser Thr
145                 150                 155                 160

Thr Pro Ala Gln Leu Asn Ser Asp Gly Ser Tyr Phe Leu Tyr Ser Lys
                165                 170                 175

Leu Ser Val Glu Thr Ser Arg Trp Lys Gln Gly Glu Ser Phe Thr Cys
            180                 185                 190

Gly Val Met His Glu Ala Val Glu Asn His Tyr Thr Gln Lys Asn Val
        195                 200                 205

Ser His Ser Pro Gly Lys
    210

<210> SEQ ID NO 192
<211> LENGTH: 214
<212> TYPE: PRT
<213> ORGANISM: Artificial Sequence
<220> FEATURE:
<223> OTHER INFORMATION: Aglycosyl variant equine IgG5 Fc, S(63)P

<400> SEQUENCE: 192

Gly Gly Pro Ser Val Phe Ile Phe Pro Pro Lys Pro Lys Asp Val Leu
1               5                   10                  15

Met Ile Ser Arg Lys Pro Glu Val Thr Cys Val Val Val Asp Leu Gly
            20                  25                  30

His Asp Asp Pro Asp Val Gln Phe Thr Trp Phe Val Asp Gly Val Glu
        35                  40                  45

Thr His Thr Ala Thr Thr Glu Pro Lys Glu Glu Gln Phe Asn Pro Thr
    50                  55                  60

Tyr Arg Val Val Ser Val Leu Pro Ile Gln His Gln Asp Trp Leu Ser
65                  70                  75                  80

Gly Lys Glu Phe Lys Cys Ser Val Thr Ser Lys Ala Leu Pro Ala Pro
                85                  90                  95

Val Glu Arg Thr Ile Ser Lys Ala Lys Gly Gln Leu Arg Val Pro Gln
            100                 105                 110

Val Tyr Val Leu Ala Pro His Pro Asp Glu Leu Ala Lys Asn Thr Val
        115                 120                 125

Ser Val Thr Cys Leu Val Lys Asp Phe Tyr Pro Pro Glu Ile Asp Val
    130                 135                 140

Glu Trp Gln Ser Asn Glu His Pro Glu Pro Glu Gly Lys Tyr Ser Thr
145                 150                 155                 160

Thr Pro Ala Gln Leu Asn Ser Asp Gly Ser Tyr Phe Leu Tyr Ser Lys
                165                 170                 175

Leu Ser Val Glu Thr Ser Arg Trp Lys Gln Gly Glu Ser Phe Thr Cys
            180                 185                 190

Gly Val Met His Glu Ala Val Glu Asn His Tyr Thr Gln Lys Asn Val
        195                 200                 205

Ser His Ser Pro Gly Lys
    210

<210> SEQ ID NO 193
<211> LENGTH: 214
<212> TYPE: PRT
<213> ORGANISM: Artificial Sequence
<220> FEATURE:
<223> OTHER INFORMATION: Aglycosyl variant equine IgG5 Fc, T(64)X
<220> FEATURE:
<221> NAME/KEY: MISC_FEATURE
<222> LOCATION: (64)..(64)
<223> OTHER INFORMATION: X = any amino acid except T or S

<400> SEQUENCE: 193

```
Gly Gly Pro Ser Val Phe Ile Phe Pro Pro Lys Pro Lys Asp Val Leu
1               5                   10                  15

Met Ile Ser Arg Lys Pro Glu Val Thr Cys Val Val Val Asp Leu Gly
            20                  25                  30

His Asp Asp Pro Asp Val Gln Phe Thr Trp Phe Val Asp Gly Val Glu
        35                  40                  45

Thr His Thr Ala Thr Thr Glu Pro Lys Glu Glu Gln Phe Asn Ser Xaa
    50                  55                  60

Tyr Arg Val Val Ser Val Leu Pro Ile Gln His Gln Asp Trp Leu Ser
65                  70                  75                  80

Gly Lys Glu Phe Lys Cys Ser Val Thr Ser Lys Ala Leu Pro Ala Pro
                85                  90                  95

Val Glu Arg Thr Ile Ser Lys Ala Lys Gly Gln Leu Arg Val Pro Gln
            100                 105                 110

Val Tyr Val Leu Ala Pro His Pro Asp Glu Leu Ala Lys Asn Thr Val
        115                 120                 125

Ser Val Thr Cys Leu Val Lys Asp Phe Tyr Pro Pro Glu Ile Asp Val
    130                 135                 140

Glu Trp Gln Ser Asn Glu His Pro Glu Pro Glu Gly Lys Tyr Ser Thr
145                 150                 155                 160

Thr Pro Ala Gln Leu Asn Ser Asp Gly Ser Tyr Phe Leu Tyr Ser Lys
                165                 170                 175

Leu Ser Val Glu Thr Ser Arg Trp Lys Gln Gly Glu Ser Phe Thr Cys
            180                 185                 190

Gly Val Met His Glu Ala Val Glu Asn His Tyr Thr Gln Lys Asn Val
        195                 200                 205

Ser His Ser Pro Gly Lys
    210
```

<210> SEQ ID NO 194
<211> LENGTH: 214
<212> TYPE: PRT
<213> ORGANISM: Artificial Sequence
<220> FEATURE:
<223> OTHER INFORMATION: Aglycosyl variant equine IgG6 Fc, N(62)X
<220> FEATURE:
<221> NAME/KEY: MISC_FEATURE
<222> LOCATION: (62)..(62)
<223> OTHER INFORMATION: X = any amino acid except N

<400> SEQUENCE: 194

```
Gly Arg Pro Ser Val Phe Ile Phe Pro Pro Asn Pro Lys Asp Thr Leu
1               5                   10                  15

Met Ile Ser Arg Thr Pro Glu Val Thr Cys Val Val Val Asp Val Ser
            20                  25                  30

Gln Glu Asn Pro Asp Val Lys Phe Asn Trp Tyr Val Asp Gly Val Glu
        35                  40                  45
```

Ala His Thr Ala Thr Thr Lys Ala Lys Glu Lys Gln Asp Xaa Ser Thr
        50                  55                  60

Tyr Arg Val Val Ser Val Leu Pro Ile Gln His Gln Asp Trp Arg Arg
 65                  70                  75                  80

Gly Lys Glu Phe Lys Cys Lys Val Asn Asn Arg Ala Leu Pro Ala Pro
                85                  90                  95

Val Glu Arg Thr Ile Thr Lys Ala Lys Gly Glu Leu Gln Asp Pro Gln
                100                 105                 110

Val Tyr Ile Leu Ala Pro His Pro Asp Glu Val Thr Lys Asn Thr Val
            115                 120                 125

Ser Val Thr Cys Leu Val Lys Asp Phe Tyr Pro Pro Asp Ile Asn Val
130                 135                 140

Glu Trp Gln Ser Asn Glu Glu Pro Glu Pro Glu Val Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asp Arg Trp Glu Gln Gly Glu Ser Phe Thr Cys
                180                 185                 190

Val Val Met His Glu Ala Ile Arg His Thr Tyr Arg Gly Lys Ser Ile
                195                 200                 205

Thr Asn Phe Pro Gly Lys
            210

<210> SEQ ID NO 195
<211> LENGTH: 214
<212> TYPE: PRT
<213> ORGANISM: Artificial Sequence
<220> FEATURE:
<223> OTHER INFORMATION: Aglycosyl variant equine IgG6 Fc, S(63)P

<400> SEQUENCE: 195

Gly Arg Pro Ser Val Phe Ile Phe Pro Pro Asn Pro Lys Asp Thr Leu
 1               5                  10                  15

Met Ile Ser Arg Thr Pro Glu Val Thr Cys Val Val Val Asp Val Ser
                20                  25                  30

Gln Glu Asn Pro Asp Val Lys Phe Asn Trp Tyr Val Asp Gly Val Glu
            35                  40                  45

Ala His Thr Ala Thr Thr Lys Ala Lys Glu Lys Gln Asp Asn Pro Thr
        50                  55                  60

Tyr Arg Val Val Ser Val Leu Pro Ile Gln His Gln Asp Trp Arg Arg
 65                  70                  75                  80

Gly Lys Glu Phe Lys Cys Lys Val Asn Asn Arg Ala Leu Pro Ala Pro
                85                  90                  95

Val Glu Arg Thr Ile Thr Lys Ala Lys Gly Glu Leu Gln Asp Pro Gln
                100                 105                 110

Val Tyr Ile Leu Ala Pro His Pro Asp Glu Val Thr Lys Asn Thr Val
            115                 120                 125

Ser Val Thr Cys Leu Val Lys Asp Phe Tyr Pro Pro Asp Ile Asn Val
130                 135                 140

Glu Trp Gln Ser Asn Glu Glu Pro Glu Pro Glu Val Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asp Arg Trp Glu Gln Gly Glu Ser Phe Thr Cys
                180                 185                 190

```
Val Val Met His Glu Ala Ile Arg His Thr Tyr Arg Gln Lys Ser Ile
        195                 200                 205

Thr Asn Phe Pro Gly Lys
    210

<210> SEQ ID NO 196
<211> LENGTH: 214
<212> TYPE: PRT
<213> ORGANISM: Artificial Sequence
<220> FEATURE:
<223> OTHER INFORMATION: Aglycosyl variant equine IgG6 Fc, T(64)X
<220> FEATURE:
<221> NAME/KEY: MISC_FEATURE
<222> LOCATION: (64)..(64)
<223> OTHER INFORMATION: X = any amino acid except T or S

<400> SEQUENCE: 196

Gly Arg Pro Ser Val Phe Ile Phe Pro Pro Asn Pro Lys Asp Thr Leu
1               5                   10                  15

Met Ile Ser Arg Thr Pro Glu Val Thr Cys Val Val Val Asp Val Ser
            20                  25                  30

Gln Glu Asn Pro Asp Val Lys Phe Asn Trp Tyr Val Asp Gly Val Glu
        35                  40                  45

Ala His Thr Ala Thr Thr Lys Ala Lys Glu Lys Gln Asp Asn Ser Xaa
    50                  55                  60

Tyr Arg Val Val Ser Val Leu Pro Ile Gln His Gln Asp Trp Arg Arg
65                  70                  75                  80

Gly Lys Glu Phe Lys Cys Lys Val Asn Asn Arg Ala Leu Pro Ala Pro
                85                  90                  95

Val Glu Arg Thr Ile Thr Lys Ala Lys Gly Glu Leu Gln Asp Pro Gln
            100                 105                 110

Val Tyr Ile Leu Ala Pro His Pro Asp Glu Val Thr Lys Asn Thr Val
        115                 120                 125

Ser Val Thr Cys Leu Val Lys Asp Phe Tyr Pro Pro Asp Ile Asn Val
    130                 135                 140

Glu Trp Gln Ser Asn Glu Glu Pro Glu Pro Glu Val Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asp Arg Trp Glu Gln Gly Glu Ser Phe Thr Cys
            180                 185                 190

Val Val Met His Glu Ala Ile Arg His Thr Tyr Arg Gln Lys Ser Ile
        195                 200                 205

Thr Asn Phe Pro Gly Lys
    210

<210> SEQ ID NO 197
<211> LENGTH: 214
<212> TYPE: PRT
<213> ORGANISM: Artificial Sequence
<220> FEATURE:
<223> OTHER INFORMATION: Aglycosyl variant equine IgG7 Fc, N(62)X
<220> FEATURE:
<221> NAME/KEY: MISC_FEATURE
<222> LOCATION: (62)..(62)
<223> OTHER INFORMATION: X = any amino acid except N

<400> SEQUENCE: 197

Val Gly Pro Ser Val Phe Ile Phe Pro Pro Lys Pro Lys Asp Val Leu
1               5                   10                  15
```

```
Met Ile Ser Arg Thr Pro Thr Val Thr Cys Val Val Asp Val Gly
            20                  25                  30

His Asp Phe Pro Asp Val Gln Phe Asn Trp Tyr Val Asp Gly Val Glu
            35                  40                  45

Thr His Thr Ala Thr Thr Glu Pro Lys Gln Glu Gln Asn Xaa Ser Thr
 50                  55                  60

Tyr Arg Val Val Ser Ile Leu Ala Ile Gln His Lys Asp Trp Leu Ser
 65                  70                  75                  80

Gly Lys Glu Phe Lys Cys Lys Val Asn Asn Gln Ala Leu Pro Ala Pro
                 85                  90                  95

Val Gln Lys Thr Ile Ser Lys Pro Thr Gly Gln Pro Arg Glu Pro Gln
            100                 105                 110

Val Tyr Val Leu Ala Pro His Pro Asp Glu Leu Ser Lys Asn Lys Val
            115                 120                 125

Ser Val Thr Cys Leu Val Lys Asp Phe Tyr Pro Pro Asp Ile Asp Ile
130                 135                 140

Glu Trp Lys Ser Asn Gly Gln Pro Glu Pro Glu Thr Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asn Arg Trp Gln Gln Gly Thr Thr Phe Thr Cys
            180                 185                 190

Ala Val Met His Glu Ala Leu His Asn His Tyr Thr Glu Lys Ser Val
                195                 200                 205

Ser Lys Ser Pro Gly Lys
            210

<210> SEQ ID NO 198
<211> LENGTH: 214
<212> TYPE: PRT
<213> ORGANISM: Artificial Sequence
<220> FEATURE:
<223> OTHER INFORMATION: Aglycosyl variant equine IgG7 Fc, S(63)P

<400> SEQUENCE: 198

Val Gly Pro Ser Val Phe Ile Phe Pro Pro Lys Pro Lys Asp Val Leu
1               5                   10                  15

Met Ile Ser Arg Thr Pro Thr Val Thr Cys Val Val Asp Val Gly
            20                  25                  30

His Asp Phe Pro Asp Val Gln Phe Asn Trp Tyr Val Asp Gly Val Glu
            35                  40                  45

Thr His Thr Ala Thr Thr Glu Pro Lys Gln Glu Gln Asn Asn Pro Thr
 50                  55                  60

Tyr Arg Val Val Ser Ile Leu Ala Ile Gln His Lys Asp Trp Leu Ser
 65                  70                  75                  80

Gly Lys Glu Phe Lys Cys Lys Val Asn Asn Gln Ala Leu Pro Ala Pro
                 85                  90                  95

Val Gln Lys Thr Ile Ser Lys Pro Thr Gly Gln Pro Arg Glu Pro Gln
            100                 105                 110

Val Tyr Val Leu Ala Pro His Pro Asp Glu Leu Ser Lys Asn Lys Val
            115                 120                 125

Ser Val Thr Cys Leu Val Lys Asp Phe Tyr Pro Pro Asp Ile Asp Ile
130                 135                 140

Glu Trp Lys Ser Asn Gly Gln Pro Glu Pro Glu Thr Lys Tyr Ser Thr
145                 150                 155                 160
```

```
Thr Pro Ala Gln Leu Asp Gly Asp Gly Ser Tyr Phe Leu Tyr Ser Lys
                165                 170                 175

Leu Thr Val Glu Thr Asn Arg Trp Gln Gln Gly Thr Thr Phe Thr Cys
            180                 185                 190

Ala Val Met His Glu Ala Leu His Asn His Tyr Thr Glu Lys Ser Val
        195                 200                 205

Ser Lys Ser Pro Gly Lys
    210

<210> SEQ ID NO 199
<211> LENGTH: 214
<212> TYPE: PRT
<213> ORGANISM: Artificial Sequence
<220> FEATURE:
<223> OTHER INFORMATION: Aglycosyl variant equine IgG7 Fc, T(64)X
<220> FEATURE:
<221> NAME/KEY: MISC_FEATURE
<222> LOCATION: (64)..(64)
<223> OTHER INFORMATION: X = any amino acid except T or S

<400> SEQUENCE: 199

Val Gly Pro Ser Val Phe Ile Phe Pro Pro Lys Pro Lys Asp Val Leu
1               5                   10                  15

Met Ile Ser Arg Thr Pro Thr Val Thr Cys Val Val Val Asp Val Gly
            20                  25                  30

His Asp Phe Pro Asp Val Gln Phe Asn Trp Tyr Val Asp Gly Val Glu
        35                  40                  45

Thr His Thr Ala Thr Thr Glu Pro Lys Gln Glu Gln Asn Asn Ser Xaa
    50                  55                  60

Tyr Arg Val Val Ser Ile Leu Ala Ile Gln His Lys Asp Trp Leu Ser
65                  70                  75                  80

Gly Lys Glu Phe Lys Cys Lys Val Asn Asn Gln Ala Leu Pro Ala Pro
                85                  90                  95

Val Gln Lys Thr Ile Ser Lys Pro Thr Gly Gln Pro Arg Glu Pro Gln
            100                 105                 110

Val Tyr Val Leu Ala Pro His Pro Asp Glu Leu Ser Lys Asn Lys Val
        115                 120                 125

Ser Val Thr Cys Leu Val Lys Asp Phe Tyr Pro Pro Asp Ile Asp Ile
    130                 135                 140

Glu Trp Lys Ser Asn Gly Gln Pro Glu Pro Glu Thr Lys Tyr Ser Thr
145                 150                 155                 160

Thr Pro Ala Gln Leu Asp Gly Asp Gly Ser Tyr Phe Leu Tyr Ser Lys
                165                 170                 175

Leu Thr Val Glu Thr Asn Arg Trp Gln Gln Gly Thr Thr Phe Thr Cys
            180                 185                 190

Ala Val Met His Glu Ala Leu His Asn His Tyr Thr Glu Lys Ser Val
        195                 200                 205

Ser Lys Ser Pro Gly Lys
    210
```

IgG Fc VARIANTS FOR VETERINARY USE

CROSS-REFERENCE TO RELATED APPLICATIONS

This application is a national stage entry of International Patent Application No. PCT/IB2018/056142, filed Aug. 15, 2018, which claims the benefit of priority of U.S. Provisional Application No. 62/545,858, filed Aug. 15, 2017, which is incorporated by reference herein in its entirety for any purpose.

FIELD

The present disclosure relates to variant IgG Fc polypeptides of companion animals with enhanced features, including increased Protein A binding (e.g., for ease of purification), decreased C1q binding (e.g., for reduced complement-mediated immune responses), decreased CD16 binding (e.g., for reduced antibody-dependent cellular cytotoxicity (ADCC) induction, increased stability, and/or the ability to form heterodimeric proteins. The variant IgG Fc polypeptides of the present disclosure may have broad applicability in companion animal therapeutics. For example, variant IgG Fc polypeptides may be used in the design and production of long-acting GLP1 polypeptides for treating, for example, diabetes, obesity, or related indications, in companion animals, such as canines, felines, and equines. In addition, variant IgG Fc polypeptides may be used in the design and production of antibodies or fusion proteins for treating various disorders in companion animals.

BACKGROUND

IgG Fc plays an important role in Fc-mediated functions though interactions with FcRn, Fc receptor, and C1q. In companion animals, various IgG subtypes possess differences in these functions, which are often considered when choosing a particular IgG antibody or IgG Fc fusion protein for therapeutic or diagnostic applications. For example, the ability of an IgG subtype to have weak or no measurable binding affinity to C1q or CD16 may be advantageous. In addition, IgG Fc's ability to bind Protein A may be useful for purification using a Protein A affinity purification platform.

However, most IgG Fc subtypes of canine, feline, and equine do not possess Protein A binding properties, weak or no measurable binding affinity to CD16, and weak or no measurable binding affinity to C1q. For example, of the four canine IgG Fc subtypes (IgG-A, IgG-B, IgG-C, and IgG-D), only canine IgG-B Fc has appreciable affinity to Protein A. Meanwhile only canine IgG-A Fc and IgG-D Fc have no or weak C1q binding or CD16 binding. Antibodies and Fc fusion proteins comprising variant IgG Fc polypeptides that have reduced binding to C1q and/or CD16, and/or that able to bind Protein A are desirable.

Glucagon-like peptide-1 (GLP1) is a potent antihyperglycemic hormone, which plays an important role in regulating blood glucose level. Native GLP1 has an in vivo half-life of approximately 2 minutes. Long-acting GLP1 polypeptides can be used to treat diabetes and obesity, prevent diabetes, control hyperglycemic conditions, lower lipids, treat conditions that would benefit from lowered blood glucose levels, suppress gastric or intestinal movement, slow gastric emptying, and/or decrease food intake. There remains a need for long-acting GLP1 polypeptides for treating high blood glucose or uncontrollable blood glucose-induced conditions in companion animals, such as canines, felines, and equines.

SUMMARY OF THE INVENTION

Embodiment 1

A polypeptide comprising a variant IgG Fc polypeptide comprising at least one amino acid modification relative to a wild-type IgG Fc polypeptide of a companion animal species, wherein the variant IgG Fc polypeptide has increased binding affinity to Protein A relative to the wild-type IgG Fc polypeptide.

Embodiment 2

A polypeptide comprising a variant IgG Fc polypeptide comprising at least one amino acid modification relative to a wild-type IgG Fc polypeptide of a companion animal species, wherein the variant IgG Fc polypeptide has reduced binding affinity to C1q and/or CD16 relative to the wild-type IgG Fc polypeptide.

Embodiment 3

The polypeptide of embodiment 1 or embodiment 2, wherein the variant IgG Fc polypeptide binds to C1q and/or CD16 with a dissociation constant ($K_d$) of greater than $5 \times 10^{-6}$ M, greater than $1 \times 10^{-5}$ M, greater than $5 \times 10^{-5}$ M, greater than $1 \times 10^{-4}$ M, greater than $5 \times 10^{-4}$ M, or greater than $1 \times 10^{-3}$ M, as measured by biolayer interferometry.

Embodiment 4

The polypeptide of any one of the preceding embodiments, wherein the variant IgG Fc polypeptide has increased binding affinity to Protein A relative to the wild-type IgG Fc polypeptide.

Embodiment 5

The polypeptide of any one of the preceding embodiments, wherein the variant IgG Fc polypeptide binds to Protein A with a dissociation constant ($K_d$) of less than $5 \times 10^{-6}$ M, less than $1 \times 10^{-6}$ M, less than $5 \times 10^{-7}$ M, less than $1 \times 10^{-7}$ M, less than $5 \times 10^{-8}$ M, less than $1 \times 10^{-8}$ M, less than $5 \times 10^{-9}$ M, less than $1 \times 10^{-9}$ M, less than $5 \times 10^{-10}$ M, less than $1 \times 10^{-10}$ M, less than $5 \times 10^{-11}$ M, less than $1 \times 10^{-11}$ M, less than $5 \times 10^{-12}$ M, or less than $1 \times 10^{-12}$ M, as measured by biolayer interferometry.

Embodiment 6

The polypeptide of any one of the preceding embodiments, wherein the companion animal species is canine, feline, or equine.

Embodiment 7

The polypeptide of any one of the preceding embodiments, wherein the wild-type IgG Fc polypeptide is
a) a canine IgG-A Fc, IgG-B Fc, IgG-C Fc, or IgG-D Fc;
b) an equine IgG1 Fc, IgG2 Fc, IgG3 Fc, IgG4 Fc, IgG5 Fc, IgG6 Fc, or IgG7 Fc; or
c) a feline IgG1a Fc, IgG1b Fc, or IgG2 Fc.

Embodiment 8

A polypeptide comprising a variant IgG Fc polypeptide comprising at least one amino acid modification to a hinge region relative to a wild-type feline or equine IgG Fc polypeptide, wherein the variant IgG Fc polypeptide has increased recombinant production and/or increased hinge disulfide formation relative to the wild-type IgG Fc polypeptide, as determined by SDS-PAGE analysis under reducing and/or nonreducing conditions.

Embodiment 9

The polypeptide of any one the preceding embodiments, wherein the variant IgG Fc polypeptide comprises:
a) at least one amino acid substitution relative to a wild-type feline IgG Fc polypeptide, wherein the variant IgG Fc polypeptide comprises an amino acid substitution at a position corresponding to position 16 of SEQ ID NO: 16, SEQ ID NO: 80, SEQ ID NO: 81, SEQ ID NO: 117, or SEQ ID NO: 118;
b) at least one amino acid substitution relative to a wild-type equine IgG Fc polypeptide, wherein the variant IgG Fc polypeptide comprises an amino acid substitution at a position corresponding to position 3 of SEQ ID NO: 129; and/or
c) at least one amino acid substitution relative to a wild-type equine IgG Fc polypeptide, wherein the variant IgG Fc polypeptide comprises an amino acid substitution at a position corresponding to position 20 of SEQ ID NO: 129.

Embodiment 10

The polypeptide of any one the preceding embodiments, wherein the variant IgG Fc polypeptide comprises:
a) at least one amino acid substitution relative to a wild-type feline IgG Fc polypeptide, wherein the variant IgG Fc polypeptide comprises an amino acid substitution at position 16 of SEQ ID NO: 16, SEQ ID NO: 80, SEQ ID NO: 81, SEQ ID NO: 117, or SEQ ID NO: 118;
b) at least one amino acid substitution relative to a wild-type equine IgG Fc polypeptide, wherein the variant IgG Fc polypeptide comprises an amino acid substitution at position 3 of SEQ ID NO: 129; and/or
c) at least one amino acid substitution relative to a wild-type equine IgG Fc polypeptide, wherein the variant IgG Fc polypeptide comprises an amino acid substitution at position 20 of SEQ ID NO: 129.

Embodiment 11

The polypeptide of any one the preceding embodiments, wherein the variant IgG Fc polypeptide comprises:
a) at least one amino acid substitution relative to a wild-type feline IgG Fc polypeptide, wherein the variant IgG Fc polypeptide comprises a proline at a position corresponding to position 16 or at position 16 of SEQ ID NO: 16, SEQ ID NO: 80, SEQ ID NO: 81, SEQ ID NO: 117, or SEQ ID NO: 118;
b) at least one amino acid substitution relative to a wild-type equine IgG Fc polypeptide, wherein the variant IgG Fc polypeptide comprises a serine at a position corresponding to position 3 or at position 3 of SEQ ID NO: 129; and/or
c) at least one amino acid substitution relative to a wild-type equine IgG Fc polypeptide, wherein the variant IgG Fc polypeptide comprises a proline at a position corresponding to position 20 or at position 20 of SEQ ID NO: 129.

Embodiment 12

The polypeptide of any one the preceding embodiments, wherein the variant IgG Fc polypeptide comprises a hinge region or a portion of a hinge region from an IgG Fc polypeptide of a different isotype.

Embodiment 13

The polypeptide of any one of the preceding embodiments, wherein the variant IgG Fc polypeptide comprises a hinge region or a portion of a hinge region from a wild-type feline IgG-1a Fc polypeptide, from a wild-type feline IgG-1b Fc polypeptide, or from a wild-type equine IgG1 Fc polypeptide.

Embodiment 14

The polypeptide of any one of the preceding embodiments, wherein the variant IgG Fc polypeptide comprises SEQ ID NO: 19, SEQ ID NO: 125 or SEQ ID NO: 126, SEQ ID NO: 127, SEQ ID NO: 128, SEQ ID NO: SEQ ID NO: 129, SEQ ID NO: 130, SEQ ID NO: 131, SEQ ID NO: 132, SEQ ID NO: 133, SEQ ID N: 134, SEQ ID NO: 135.

Embodiment 15

A polypeptide comprising an amino acid sequence of SEQ ID NO: 19, SEQ ID NO: 125 or SEQ ID NO: 126, SEQ ID NO: 127, SEQ ID NO: 128, SEQ ID NO: SEQ ID NO: 129, SEQ ID NO: 130, SEQ ID NO: 131, SEQ ID NO: 132, SEQ ID NO: 133, SEQ ID N: 134, SEQ ID NO: 135.

Embodiment 16

A polypeptide comprising a variant IgG2 Fc polypeptide comprising at least one amino acid substitution relative to a wild-type feline IgG2 Fc polypeptide, wherein the at least one amino acid substitution is a cysteine, and wherein the variant IgG2 Fc polypeptide is capable of forming at least one additional inter-chain disulfide linkage relative to the wild-type feline IgG2 Fc polypeptide.

Embodiment 17

The polypeptide of any one of the preceding embodiments, wherein the variant IgG Fc polypeptide comprises at least one amino acid substitution relative to a wild-type feline IgG Fc polypeptide, wherein the at least one amino acid substitution is a cysteine, and wherein the variant IgG Fc polypeptide is capable of forming at least one additional inter-chain disulfide linkage relative to the wild-type feline IgG Fc polypeptide.

Embodiment 18

The polypeptide of any one of the preceding embodiments, wherein the variant IgG Fc polypeptide comprises a cysteine at a position corresponding to position 8, position 9, position 10, position 11, position 12, position 13, position 14, position 15, or position 16 of SEQ ID NO: 16.

Embodiment 19

The polypeptide of any one of the preceding embodiments, wherein the variant IgG Fc polypeptide comprises a cysteine at a position corresponding to position 14 of SEQ ID NO: 16.

Embodiment 20

The polypeptide of any one of the preceding embodiments, wherein the variant IgG Fc polypeptide comprises a cysteine at position 14 of SEQ ID NO: 16.

Embodiment 21

The polypeptide of any one of the preceding embodiments, wherein the variant IgG Fc polypeptide is at least 90% identical, at least 95% identical, at least 97% identical, or at least 99% identical to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 100, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO:122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, or SEQ ID NO: 157.

Embodiment 22

The polypeptide of any one of the preceding embodiments, wherein the variant IgG Fc polypeptide comprises SEQ ID NO: 17.

Embodiment 23

A polypeptide comprising an amino acid sequence of SEQ ID NO: 17.

Embodiment 24

The polypeptide of any one of the preceding embodiments, wherein the variant IgG Fc polypeptide comprises:
a) an amino acid substitution at a position corresponding to position 21 of SEQ ID NO: 1, an amino acid substitution at a position corresponding to position 23 of SEQ ID NO: 1, an amino acid substitution at a position corresponding to position 25 of SEQ ID NO: 1, an amino acid substitution at a position corresponding to position 80 of SEQ ID NO: 1, an amino acid substitution at a position corresponding to position 205 of SEQ ID NO: 1, and/or an amino acid substitution at a position corresponding to position 207 of SEQ ID NO: 1;
b) an amino acid substitution at a position corresponding to position 21 of SEQ ID NO: 3, an amino acid substitution at a position corresponding to position 23 of SEQ ID NO: 3, and/or an amino acid substitution at a position corresponding to position 24 of SEQ ID NO: 3;
c) an amino acid substitution at a position corresponding to position 21 of SEQ ID NO: 4, an amino acid substitution at a position corresponding to position 23 of SEQ ID NO: 4, an amino acid substitution at a position corresponding to position 25 of SEQ ID NO: 4, an amino acid substitution at a position corresponding to position 80 of SEQ ID NO: 4, and/or an amino acid substitution at a position corresponding to position 207 of SEQ ID NO: 4;
d) an amino acid substitution at a position corresponding to position 15 of SEQ ID NO: 64, and/or an amino acid substitution at a position corresponding to position 203 of SEQ ID NO: 64;
e) an amino acid substitution at a position corresponding to position 199 of SEQ ID NO: 67, and/or an amino acid substitution at a position corresponding to position 200 of SEQ ID NO: 67; and/or
f) an amino acid substitution at a position corresponding to position 199 of SEQ ID NO: 68, an amino acid substitution at a position corresponding to position 200 of SEQ ID NO: 68, an amino acid substitution at a position corresponding to position 201 of SEQ ID NO: 68, and/or an amino acid substitution at a position corresponding to position 202 of SEQ ID NO: 68.

Embodiment 25

The polypeptide of any one of the preceding embodiments, wherein the variant IgG Fc polypeptide comprises:
a) an amino acid substitution at position 21 of SEQ ID NO: 1, an amino acid substitution at position 23 of SEQ ID NO: 1, an amino acid substitution at position 25 of SEQ ID NO: 1, an amino acid substitution at position 80 of SEQ ID NO: 1, an amino acid substitution at position 205 of SEQ ID NO: 1, and/or an amino acid substitution at position 207 of SEQ ID NO: 1;
b) an amino acid substitution at position 21 of SEQ ID NO: 3, an amino acid substitution at position 23 of SEQ ID NO: 3, and/or an amino acid substitution at position 24 of SEQ ID NO: 3;
c) an amino acid substitution at position 21 of SEQ ID NO: 4, an amino acid substitution at position 23 of SEQ ID NO: 4, an amino acid substitution at position 25 of SEQ ID NO: 4, an amino acid substitution at position 80 of SEQ ID NO: 4, and/or an amino acid substitution at position 207 of SEQ ID NO: 4;
d) an amino acid substitution at position 15 of SEQ ID NO: 64, and/or an amino acid substitution at position 203 of SEQ ID NO: 64;
e) an amino acid substitution at position 199 of SEQ ID NO: 67, and/or an amino acid substitution at position 200 of SEQ ID NO: 67; and/or
f) an amino acid substitution at position 199 of SEQ ID NO: 68, an amino acid substitution at position 200 of SEQ ID NO: 68, an amino acid substitution at position 201 of SEQ ID NO: 68, and/or an amino acid substitution at position 202 of SEQ ID NO: 68.

Embodiment 26

The polypeptide of any one of the preceding embodiments, wherein the variant IgG Fc polypeptide comprises:
a) a threonine at a position corresponding to position 21 of SEQ ID NO: 1, a leucine at a position corresponding to position 23 of SEQ ID NO: 1, an alanine at a position corresponding to position 25 of SEQ ID NO: 1, a glycine at a position corresponding to position 80 of SEQ ID NO: 1, an alanine at a position corresponding to position 205 of SEQ ID NO: 1, and/or a histidine at a position corresponding to position 207 of SEQ ID NO: 1;
b) a threonine at a position corresponding to position 21 of SEQ ID NO: 3, a leucine at a position corresponding to position 23 of SEQ ID NO: 3, and/or an isoleucine at a position corresponding to position 24 of SEQ ID NO: 3;
c) a threonine at a position corresponding to position 21 of SEQ ID NO: 4, a leucine at a position corresponding to position 23 of SEQ ID NO: 4, an alanine at a position corresponding to position 25 of SEQ ID NO: 4, a glycine at a position corresponding to position 80 of SEQ ID NO: 4, and/or a histidine at a position corresponding to position 207 of SEQ ID NO: 4;
d) a threonine or a valine at a position corresponding to position 15 of SEQ ID NO: 64, and/or a tyrosine or a valine at a position corresponding to position 203 of SEQ ID NO: 64;
e) a leucine at a position corresponding to position 199 of SEQ ID NO: 67, and/or a histidine at a position corresponding to position 200 of SEQ ID NO: 67; and/or
f) a leucine at a position corresponding to position 199 of SEQ ID NO: 68, a histidine at a position corresponding to position 200 of SEQ ID NO: 68, an asparagine at a position corresponding to position 201 of SEQ ID NO: 68, and/or a histidine at a position corresponding to position 202 of SEQ ID NO: 68.

Embodiment 27

The polypeptide of any one of the preceding embodiments, wherein the variant IgG Fc polypeptide comprises:
a) a threonine at position 21 of SEQ ID NO: 1, a leucine at position 23 of SEQ ID NO: 1, an alanine at position 25 of SEQ ID NO: 1, a glycine at position 80 of SEQ ID NO: 1, an alanine at position 205 of SEQ ID NO: 1, and/or a histidine at position 207 of SEQ ID NO: 1;
b) a threonine at position 21 of SEQ ID NO: 3, a leucine at position 23 of SEQ ID NO: 3, and/or an isoleucine at position 24 of SEQ ID NO: 3;
c) a threonine at a position 21 of SEQ ID NO: 4, a leucine at position 23 of SEQ ID NO: 4, an alanine at position 25 of SEQ ID NO: 4, a glycine at position 80 of SEQ ID NO: 4, and/or a histidine at position 207 of SEQ ID NO: 4;
d) a threonine or a valine at position 15 of SEQ ID NO: 64, and/or a tyrosine or a valine at position 203 of SEQ ID NO: 64;
e) a leucine at position 199 of SEQ ID NO: 67, and/or a histidine at position 200 of SEQ ID NO: 67; and/or
f) a leucine at position 199 of SEQ ID NO: 68, a histidine at position 200 of SEQ ID NO: 68, an asparagine at position 201 of SEQ ID NO: 68, and/or a histidine at position 202 of SEQ ID NO: 68.

Embodiment 28

The polypeptide of any one of the preceding embodiments, wherein the variant IgG Fc polypeptide comprises an amino acid sequence of:
a) SEQ ID NO: 5, SEQ ID NO: 6, SEQ ID NO: 7, SEQ ID NO: 60, SEQ ID NO: 61, SEQ ID NO: 62, or SEQ ID NO: 84; or
b) SEQ ID NO: 19, SEQ ID NO: 71, SEQ ID NO: 72, SEQ ID NO: 75, or SEQ ID NO: 76.

Embodiment 29

A polypeptide comprising an amino sequence of SEQ ID NO: 5, SEQ ID NO: 6, SEQ ID NO: 7, SEQ ID NO: 60, SEQ ID NO: 61, SEQ ID NO: 62, SEQ ID NO: 84, SEQ ID NO: 19, SEQ ID NO: 71, SEQ ID NO: 72, SEQ ID NO: 75, or SEQ ID NO: 76.

Embodiment 30

The polypeptide of any one of the preceding embodiments, wherein the variant IgG Fc polypeptide comprises:
a) an amino acid substitution at a position corresponding to position 93 of SEQ ID NO: 2, or an amino acid substitution at a position corresponding to position 93 of SEQ ID NO: 3;
b) an amino acid substitution at a position corresponding to position 87 of SEQ ID NO: 63, an amino acid substitution at a position corresponding to position 87 of SEQ ID NO: 65, an amino acid substitution at a position corresponding to position 87 of SEQ ID NO: 66, or an amino acid substitution at a position corresponding to position 87 of SEQ ID NO: 69; or
c) an amino acid substitution at a position corresponding to position 198 of SEQ ID NO: 80, or an amino acid substitution at a position corresponding to position 198 of SEQ ID NO: 81.

Embodiment 31

The polypeptide of any one of the preceding embodiments, wherein the variant IgG Fc polypeptide comprises:
a) an amino acid substitution at position 93 of SEQ ID NO: 2, or an amino acid substitution at position 93 of SEQ ID NO: 3;
b) an amino acid substitution at position 87 of SEQ ID NO: 63, an amino acid substitution at position 87 of SEQ ID NO: 65, an amino acid substitution at position 87 of SEQ ID NO: 66, or an amino acid substitution at position 87 of SEQ ID NO: 69; or
c) an amino acid substitution at position 198 of SEQ ID NO: 80, or an amino acid substitution at position 198 of SEQ ID NO: 81.

Embodiment 32

The polypeptide of any one of the preceding embodiments, wherein the variant IgG Fc polypeptide comprises:
a) an arginine at a position corresponding to position 93 of SEQ ID NO: 2, or an arginine at a position corresponding to position 93 of SEQ ID NO: 3;
b) a serine at a position corresponding to position 87 of SEQ ID NO: 63, a serine substitution at a position corresponding to position 87 of SEQ ID NO: 65, a serine at a position corresponding to position 87 of SEQ ID NO: 66, or a serine at a position corresponding to position 87 of SEQ ID NO: 69; or
c) an alanine at a position corresponding to position 198 of SEQ ID NO: 80, or an alanine at a position corresponding to position 198 of SEQ ID NO: 81.

Embodiment 33

The polypeptide of any one of the preceding embodiments, wherein the variant IgG Fc polypeptide comprises:
a) an arginine at position 93 of SEQ ID NO: 2, or an arginine at position 93 of SEQ ID NO: 3;
b) a serine at position 87 of SEQ ID NO: 63, a serine at position 87 of SEQ ID NO: 65, a serine at position 87 of SEQ ID NO: 66, or a serine at position 87 of SEQ ID NO: 69; or
c) an alanine at position 198 of SEQ ID NO: 80, or alanine at position 198 of SEQ ID NO: 81.

Embodiment 34

The polypeptide of any one of the preceding embodiments, wherein the variant IgG Fc polypeptide comprises the amino acid sequence of:
a) SEQ ID NO: 78, SEQ ID NO: 79, or SEQ ID NO: 84; or
b) SEQ ID NO: 70, SEQ ID NO: 73, SEQ ID NO: 74, or SEQ ID NO: 77; or
c) SEQ ID NO: 82 or SEQ ID NO: 83.

Embodiment 35

A polypeptide comprising an amino sequence of SEQ ID NO: 78, SEQ ID NO: 79, SEQ ID NO: 84, SEQ ID NO: 70, SEQ ID NO: 73, SEQ ID NO: 74, SEQ ID NO: 77, SEQ ID NO: 82, or SEQ ID NO: 83.

Embodiment 36

The polypeptide of any one of the preceding embodiments, wherein the variant IgG Fc polypeptide comprises:
a) an amino acid substitution at a position corresponding to position 5 of SEQ ID NO: 2, an amino acid substitution at a position corresponding to position 38 of SEQ ID NO: 2, an amino acid substitution at a position corresponding to position 39 of SEQ ID NO: 2, an amino acid substitution at a position corresponding to position 97 of SEQ ID NO: 2, and/or an amino acid substitution at a position corresponding to position 98 of SEQ ID NO: 2; or
b) an amino acid substitution at a position corresponding to position 5 of SEQ ID NO: 3, an amino acid substitution at a position corresponding to position 38 of SEQ ID NO: 3, an amino acid substitution at a position corresponding to position 39 of SEQ ID NO: 3, an amino acid substitution at a position corresponding to position 97 of SEQ ID NO: 3, and/or an amino acid substitution at a position corresponding to position 98 of SEQ ID NO: 3.

Embodiment 37

The polypeptide of any one of the preceding embodiments, wherein the variant IgG Fc polypeptide comprises:
a) an amino acid substitution at position 5 of SEQ ID NO: 2, an amino acid substitution at position 38 of SEQ ID NO: 2, an amino acid substitution at position 39 of SEQ ID NO: 2, an amino acid substitution at position 97 of SEQ ID NO: 2, and/or an amino acid substitution at position 98 of SEQ ID NO: 2; or
b) an amino acid substitution at position 5 of SEQ ID NO: 3, an amino acid substitution at position 38 of SEQ ID NO: 3, an amino acid substitution at position 39 of SEQ ID NO: 3, an amino acid substitution at position 97 of SEQ ID NO: 3, and/or an amino acid substitution at position 98 of SEQ ID NO: 3.

Embodiment 38

The polypeptide of any one of the preceding embodiments, wherein the variant IgG Fc polypeptide comprises:
a) a proline at a position corresponding to position 5 of SEQ ID NO: 2, a glycine at a position corresponding to position 38 of SEQ ID NO: 2, an arginine at a position corresponding to position 39 of SEQ ID NO: 2, an isoleucine at a position corresponding to position 97 of SEQ ID NO: 2, and/or a glycine at a position corresponding to position 98 of SEQ ID NO: 2; or
b) a proline at a position corresponding to position 5 of SEQ ID NO: 3, a glycine at a position corresponding to position 38 of SEQ ID NO: 3, an arginine at a position corresponding to position 39 of SEQ ID NO: 3, an isoleucine at a position corresponding to position 97 of SEQ ID NO: 3, and/or a glycine at a position corresponding to position 98 of SEQ ID NO: 3.

Embodiment 39

The polypeptide of any one of the preceding embodiments, wherein the variant IgG Fc polypeptide comprises:
a) a proline at position 5 of SEQ ID NO: 2, a glycine at position 38 of SEQ ID NO: 2, an arginine at position 39 of SEQ ID NO: 2, an isoleucine at position 97 of SEQ ID NO: 2, and/or a glycine at position 98 of SEQ ID NO: 2; or
b) a proline at position 5 of SEQ ID NO: 3, a glycine at position 38 of SEQ ID NO: 3, an arginine at position 39 of SEQ ID NO: 3, an isoleucine at position 97 of SEQ ID NO: 3, and/or a glycine at position 98 of SEQ ID NO: 3.

Embodiment 40

The polypeptide of any one of the preceding embodiments, wherein the variant IgG Fc polypeptide comprises an amino acid sequence of:
a) SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, or SEQ ID NO: 147; or
b) SEQ ID NO: 148, SEQ ID NO: 149, SEQ ID NO: 150, SEQ ID NO: 151, SEQ ID NO: 152, SEQ ID NO: 154, SEQ ID NO: 155, SEQ ID NO: 156, or SEQ ID NO: 157.

Embodiment 41

A polypeptide comprising an amino sequence of SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 154, SEQ ID NO: 155, SEQ ID NO: 156, or SEQ ID NO: 157.

Embodiment 42

A polypeptide comprising a variant IgG Fc polypeptide comprising:
  a) a tyrosine or a tryptophan at a position corresponding to position 138 of SEQ ID NO: 1, a tyrosine or a tryptophan at a position corresponding to position 137 of SEQ ID NO: 2, a tyrosine or a tryptophan at a position corresponding to position 137 of SEQ ID NO: 3, or a tyrosine or a tryptophan at a position corresponding to position 138 of SEQ ID NO: 4; or
  b) a tyrosine or a tryptophan at a position corresponding to position 154 of SEQ ID NO: 16, a tyrosine or a tryptophan at a position corresponding to position 154 of SEQ ID NO: 80 or SEQ ID NO: 117, or a tyrosine or a tryptophan at a position corresponding to position 154 of SEQ ID NO: 81 or SEQ ID NO: 118.

Embodiment 43

The polypeptide of any one of the preceding embodiments, wherein the variant IgG Fc polypeptide comprises:
  a) a tyrosine or a tryptophan at position 138 of SEQ ID NO: 1, a tyrosine or a tryptophan at position 137 of SEQ ID NO: 2, a tyrosine or a tryptophan at position 137 of SEQ ID NO: 3, or a tyrosine or a tryptophan at position 138 of SEQ ID NO: 4; or
  b) a tyrosine or a tryptophan at position 154 of SEQ ID NO: 16, a tyrosine or a tryptophan at position 154 of SEQ ID NO: 80 or SEQ ID NO: 117, or a tyrosine or a tryptophan at a position corresponding to position 154 of SEQ ID NO: 81 or SEQ ID NO: 118.

Embodiment 44

The polypeptide of any one of the preceding embodiments, wherein the variant IgG Fc polypeptide comprises an amino acid sequence of SEQ ID NO: 8, SEQ ID NO: 10, SEQ ID NO: 12, SEQ ID NO: 14, SEQ ID NO: 109, SEQ ID NO: 111, SEQ ID NO: 113, SEQ ID NO: 115, SEQ ID NO: 119, SEQ ID NO: 121, or SEQ ID NO: 123.

Embodiment 45

A polypeptide comprising an amino acid sequence of SEQ ID NO: 8, SEQ ID NO: 10, SEQ ID NO: 12, SEQ ID NO: 14, SEQ ID NO: 109, SEQ ID NO: 111, SEQ ID NO: 113, SEQ ID NO: 115, SEQ ID NO: 119, SEQ ID NO: 121, or SEQ ID NO: 123.

Embodiment 46

A contiguous polypeptide comprising the polypeptide of any one of the preceding embodiments and a glucagon-like peptide-1 (GLP1) polypeptide.

Embodiment 47

A contiguous polypeptide comprising the polypeptide of any one of the preceding embodiments and a glucagon polypeptide.

Embodiment 48

A polypeptide comprising a variant IgG Fc polypeptide comprising:
  a) a serine at a position corresponding to position 138 of SEQ ID NO: 1, a serine at a position corresponding to position 137 of SEQ ID NO: 2, a serine at a position corresponding to position 137 of SEQ ID NO: 3, a serine at a position corresponding to position 138 of SEQ ID NO: 4, a serine at a position corresponding to position 154 of SEQ ID NO: 16, a serine at a position corresponding to position 154 of SEQ ID NO: 80 or SEQ ID NO: 117, or a serine at a position corresponding to position 154 of SEQ ID NO: 81 or SEQ ID NO: 118;
  b) an alanine at a position corresponding to position 140 of SEQ ID NO: 1, an alanine at a position corresponding to position 139 of SEQ ID NO: 2, an alanine at a position corresponding to position 139 of SEQ ID NO: 3, an alanine at a position corresponding to position 140 of SEQ ID NO: 4, an alanine at a position corresponding to position 156 of SEQ ID NO: 16, an alanine at a position corresponding to position 156 of SEQ ID NO: 80 or SEQ ID NO: 117, or an alanine at a position corresponding to position 156 of SEQ ID NO: 81 or SEQ ID NO: 118; and/or
  c) a threonine at a position corresponding to position 181 of SEQ ID NO: 1, a threonine at a position corresponding to position 180 of SEQ ID NO: 2, a threonine at a position corresponding to position 180 of SEQ ID NO: 3, a threonine at a position corresponding to position 181 of SEQ ID NO: 4, a threonine at a position corresponding to position 197 of SEQ ID NO: 16, a threonine at a position corresponding to position 197 of SEQ ID NO: 80 or SEQ ID NO: 117, or a threonine at a position corresponding to position 197 of SEQ ID NO: 81 or SEQ ID NO: 118.

Embodiment 49

The polypeptide of any one of the preceding embodiments, wherein the variant IgG Fc polypeptide comprises:
  a) a serine at position 138 of SEQ ID NO: 1, a serine at position 137 of SEQ ID NO: 2, a serine at position 137 of SEQ ID NO: 3, a serine at position 138 of SEQ ID NO: 4, a serine at position 154 of SEQ ID NO: 16, a serine at position 154 of SEQ ID NO: 80 or SEQ ID NO: 117, or a serine at position 154 of SEQ ID NO: 81 or SEQ ID NO: 118;
  b) an alanine at position 140 of SEQ ID NO: 1, an alanine at position 139 of SEQ ID NO: 2, an alanine at position 139 of SEQ ID NO: 3, an alanine at position 140 of SEQ ID NO: 4, an alanine at position 156 of SEQ ID NO: 16, an alanine at position 156 of SEQ ID NO: 80 or SEQ ID NO: 117, or an alanine at position 156 of SEQ ID NO: 81 or SEQ ID NO: 118; and/or;
  c) a threonine at position 181 of SEQ ID NO: 1, a threonine at position 181 of SEQ ID NO: 2, a threonine at position 181 of SEQ ID NO: 3, a threonine at position 181 of SEQ ID NO: 4, a threonine at position 197 of SEQ ID NO: 16, a threonine at position 197 of SEQ ID NO: 80 or SEQ ID NO: 117, or a threonine at position 197 of SEQ ID NO: 81 or SEQ ID NO: 118.

Embodiment 50

The polypeptide of any one of the preceding embodiments, wherein the variant IgG Fc polypeptide comprises an amino acid sequence of SEQ ID NO: 9, SEQ ID NO: 11, SEQ ID NO: 13, SEQ ID NO: 15, SEQ ID NO: 110, SEQ ID NO: 112, SEQ ID NO: 114, SEQ ID NO: 116, SEQ ID NO: 120, SEQ ID NO: 122, or SEQ ID NO: 124.

Embodiment 51

A polypeptide comprising an amino acid sequence of SEQ ID NO: 9, SEQ ID NO: 11, SEQ ID NO: 13, SEQ ID NO: 15, SEQ ID NO: 110, SEQ ID NO: 112, SEQ ID NO: 114, SEQ ID NO: 116, SEQ ID NO: 120, SEQ ID NO: 122, or SEQ ID NO: 124.

Embodiment 52

The polypeptide of any one of the preceding embodiments, wherein the polypeptide is glycoslylated.

Embodiment 53

The polypeptide of any one of embodiments 1 to 51, wherein the polypeptide is a glycosylated.

Embodiment 54

A contiguous polypeptide comprising the polypeptide of any one of embodiments 48 to 53 and a glucagon-like peptide-1 (GLP1) polypeptide.

Embodiment 55

A contiguous polypeptide comprising the polypeptide of any one of embodiments 48 to 53 and a glucagon polypeptide.

Embodiment 56

A heterodimeric protein comprising the contiguous polypeptide of embodiment 46 and the contiguous polypeptide of embodiment 54.

Embodiment 57

A heterodimeric protein comprising the contiguous polypeptide of embodiment 47 and the contiguous polypeptide of embodiment 55.

Embodiment 58

The contiguous polypeptide or heterodimeric protein of any one of embodiments 46, 47, or 54 to 57, wherein the GLP1 polypeptide is a wild-type GLP1 polypeptide, optionally comprising the amino acid sequence of SEQ ID NO: 85.

Embodiment 59

The contiguous polypeptide or heterodimeric protein of any one of embodiments 46, 47, or 54 to 58, wherein the GLP1 polypeptide is a variant GLP1 polypeptide.

Embodiment 60

The contiguous polypeptide or heterodimeric protein of any one of embodiments 46, 47, or 54 to 59, wherein the GLP1 polypeptide comprises the amino acid sequence of SEQ ID NO: 86, SEQ ID NO: 87, SEQ ID NO: 98, or SEQ ID NO: 99.

Embodiment 61

The contiguous polypeptide or heterodimeric protein of any one of embodiments 46, 47, or 54 to 60, wherein the glucagon polypeptide is a wild-type glucagon polypeptide, optionally comprising the amino acid sequence of SEQ ID NO: 21.

Embodiment 62

The contiguous polypeptide or heterodimeric protein of any one of embodiments 46, 47, or 54 to 61, wherein the glucagon polypeptide is a variant glucagon polypeptide.

Embodiment 63

A heterodimeric protein comprising:
i) a first variant canine IgG Fc polypeptide comprising at least one amino acid modification relative to a first wild-type canine IgG Fc polypeptide and a second variant canine IgG Fc polypeptide comprising at least one amino acid modification relative to a second wild-type canine IgG Fc polypeptide; or
ii) a first variant feline IgG Fc polypeptide comprising at least one amino acid modification relative to a first wild-type feline IgG Fc polypeptide and a second variant feline IgG Fc polypeptide comprising at least one amino acid modification relative to a second wild-type feline IgG Fc polypeptide, wherein:
  a) the first variant canine IgG Fc polypeptide comprises an amino acid substitution at a position corresponding to position 138 of SEQ ID NO: 1, position 137 of SEQ ID NO: 2, position 137 of SEQ ID NO: 3, or position 138 of SEQ ID NO: 4;
  b) the second variant canine IgG Fc polypeptide comprises an amino acid substitution at a position corresponding to position 138, position 140, and/or position 181 of SEQ ID NO: 1, position 137, position 139, and/or position 180 of SEQ ID NO: 2, position 137, position 139, and/or position 180 of SEQ ID NO: 3, or position 138, position 140, and/or position 181 of SEQ ID NO: 4;
  c) the first variant feline IgG Fc polypeptide comprises an amino acid substitution at a position corresponding to position 154 of SEQ ID NO: 6, of SEQ ID NO: 80, of SEQ ID NO: 81, of SEQ ID NO: 117, or of SEQ ID NO: 118; and/or
  d) the second variant feline IgG Fc polypeptide comprises an amino acid substitution at a position corresponding to position 154, position 156, and/or position 197 of SEQ ID NO: 6, of SEQ ID NO: 80, of SEQ ID NO: 81, of SEQ ID NO: 117, or of SEQ ID NO: 118.

Embodiment 64

The heterodimeric protein of embodiment 63, wherein the first wild-type canine IgG Fc polypeptide and the second wild-type canine IgG Fc polypeptide are from the same IgG subtype and/or the first wild-type feline IgG Fc polypeptide and the second wild-type feline IgG Fc polypeptide are from the same IgG subtype.

Embodiment 65

The heterodimeric protein of embodiment 63, wherein the first wild-type canine IgG Fc polypeptide and the second wild-type canine IgG Fc polypeptide are from a different IgG subtype and/or the first wild-type feline IgG Fc polypeptide and the second wild-type feline IgG Fc polypeptide are from the same IgG subtype.

Embodiment 66

The heterodimeric protein of any one of embodiments 63 to 65, wherein:
  a) the first variant canine IgG Fc polypeptide comprises a tyrosine or tryptophan at a position corresponding to position 138 of SEQ ID NO: 1, position 137 of SEQ ID NO: 2, position 137 of SEQ ID NO: 3, or position 138 of SEQ ID NO: 4; and/or
  b) the first variant feline IgG Fc polypeptide comprises a tryptophan at a position corresponding to position 154 of SEQ ID NO: 6, of SEQ ID NO: 80, of SEQ ID NO: 81, of SEQ ID NO: 117, or of SEQ ID NO: 118.

Embodiment 67

The heterodimeric protein of any one of embodiments 63 to 66, wherein:
  a) the second variant canine IgG Fc polypeptide comprises a serine at a position corresponding to position 138, an alanine at a position corresponding to position 140, and/or a threonine at a position corresponding to position 181 of SEQ ID NO: 1, a serine at a position corresponding to position 137, an alanine at a position corresponding to position 139, and/or a threonine at a position corresponding to position 180 of SEQ ID NO: 2, a serine at a position corresponding to position 137, an alanine at a position corresponding to position 139, and/or a threonine at a position corresponding to position 180 of SEQ ID NO: 3, and/or a serine at a position corresponding to position 138, an alanine at a position corresponding to position 140, and/or a threonine at a position corresponding to position 181 of SEQ ID NO: 4; and/or
  b) the second variant feline IgG Fc polypeptide comprises a serine at a position corresponding to position 154, an alanine at a position corresponding to position 156, and/or a threonine at a position corresponding to position 197 of SEQ ID NO: 6, of SEQ ID NO: 80, of SEQ ID NO: 81, of SEQ ID NO: 117, or of SEQ ID NO: 118.

Embodiment 68

The heterodimeric protein of any one of embodiments 63 to 67, wherein:
  a) the first variant canine IgG Fc polypeptide comprises an amino acid sequence of SEQ ID NO: 8, SEQ ID NO: 10, SEQ ID NO: 12, SEQ ID NO: 14, SEQ ID NO: 109, SEQ ID NO: 111, SEQ ID NO: 113, or SEQ ID NO: 115; and/or
  b) the first variant feline IgG Fc polypeptide comprises an amino acid sequence of SEQ ID NO: 119, SEQ ID NO: 121, or SEQ ID NO: 123.

Embodiment 69

The heterodimeric protein of any one of embodiments 63 to 68, wherein:
  a) the second variant canine IgG Fc polypeptide comprises an amino acid sequence of SEQ ID NO: 9, SEQ ID NO: 11, SEQ ID NO: 13, SEQ ID NO: 15, SEQ ID NO: 110, SEQ ID NO: 112, SEQ ID NO: 114, or SEQ ID NO: 116; and/or
  b) the second variant feline IgG Fc polypeptide comprises an amino acid sequence of SEQ ID NO: 120, SEQ ID NO: 122, or SEQ ID NO: 123.

Embodiment 70

The polypeptide, the contiguous polypeptide, or the heterodimeric protein of any one of embodiments 42 to 69, wherein the variant IgG Fc polypeptide, the first variant IgG Fc polypeptide, and/or the second variant IgG Fc polypeptide comprises at least one additional amino acid modification relative to a wild-type IgG Fc polypeptide and has increased binding affinity to Protein A relative to the wild-type IgG Fc polypeptide.

Embodiment 71

The polypeptide, the contiguous polypeptide, or the heterodimeric protein of any one of embodiments 42 to 70, wherein the variant IgG Fc polypeptide, the first variant IgG Fc polypeptide, and/or the second variant IgG Fc polypeptide comprises:
  a) an amino acid substitution at a position corresponding to position 21 of SEQ ID NO: 1, an amino acid substitution at a position corresponding to position 23 of SEQ ID NO: 1, an amino acid substitution at a position corresponding to position 25 of SEQ ID NO: 1, an amino acid substitution at a position corresponding to position 80 of SEQ ID NO: 1, an amino acid substitution at a position corresponding to position 205 of SEQ ID NO: 1, and/or an amino acid substitution at a position corresponding to position 207 of SEQ ID NO: 1;
  b) an amino acid substitution at a position corresponding to position 21 of SEQ ID NO: 3, an amino acid substitution at a position corresponding to position 23 of SEQ ID NO: 3, and/or an amino acid substitution at a position corresponding to position 24 of SEQ ID NO: 3; or
  c) an amino acid substitution at a position corresponding to position 21 of SEQ ID NO: 4, an amino acid substitution at a position corresponding to position 23 of SEQ ID NO: 4, an amino acid substitution at a position corresponding to position 25 of SEQ ID NO: 4, an amino acid substitution at a position corresponding to position 80 of SEQ ID NO: 4, and/or an amino acid substitution at a position corresponding to position 207 of SEQ ID NO: 4.

Embodiment 72

The polypeptide, the contiguous polypeptide, or the heterodimeric protein of any one of embodiments 42 to 71, wherein the variant IgG Fc polypeptide, the first variant IgG Fc polypeptide, and/or the second variant IgG Fc polypeptide comprises:
  a) an amino acid substitution at position 21 of SEQ ID NO: 1, an amino acid substitution at position 23 of SEQ ID NO: 1, an amino acid substitution at position 25 of SEQ ID NO: 1, an amino acid substitution at position 80 of SEQ ID NO: 1, an amino acid substitution at position 205 of SEQ ID NO: 1, and/or an amino acid substitution at position 207 of SEQ ID NO: 1;
  b) an amino acid substitution at position 21 of SEQ ID NO: 3, an amino acid substitution at position 23 of SEQ ID NO: 3, and/or an amino acid substitution at position 24 of SEQ ID NO: 3; or c) an amino acid substitution at position 21 of SEQ ID NO: 4, an amino acid substitution at position 23 of SEQ ID NO: 4, an amino acid substitution at position 25 of SEQ ID NO: 4, an amino acid substitution at position 80 of SEQ ID NO: 4, and/or an amino acid substitution at position 207 of SEQ ID NO: 4.

Embodiment 73

The polypeptide, the contiguous polypeptide, or the heterodimeric protein of any one of embodiments 42 to 72, wherein the variant IgG Fc polypeptide, the first variant IgG Fc polypeptide, and/or the second variant IgG Fc polypeptide comprises:
- a) a threonine at a position corresponding to position 21 of SEQ ID NO: 1, a leucine at a position corresponding to position 23 of SEQ ID NO: 1, an alanine at a position corresponding to position 25 of SEQ ID NO: 1, a glycine at a position corresponding to position 80 of SEQ ID NO: 1, an alanine at a position corresponding to position 205 of SEQ ID NO: 1, and/or a histidine at a position corresponding to position 207 of SEQ ID NO: 1;
- b) a threonine at a position corresponding to position 21 of SEQ ID NO: 3, a leucine at a position corresponding to position 23 of SEQ ID NO: 3, and/or an isoleucine at a position corresponding to position 24 of SEQ ID NO: 3; or
- c) a threonine at a position corresponding to position 21 of SEQ ID NO: 4, a leucine at a position corresponding to position 23 of SEQ ID NO: 4, an alanine at a position corresponding to position 25 of SEQ ID NO: 4, a glycine at a position corresponding to position 80 of SEQ ID NO: 4, and/or a histidine at a position corresponding to position 207 of SEQ ID NO: 4.

Embodiment 74

The polypeptide, the contiguous polypeptide, or the heterodimeric protein of any one of embodiments 42 to 73, wherein the variant IgG Fc polypeptide, the first variant IgG Fc polypeptide, and/or the second variant IgG Fc polypeptide comprises:
- a) a threonine at position 21 of SEQ ID NO: 1, a leucine at position 23 of SEQ ID NO: 1, an alanine at position 25 of SEQ ID NO: 1, a glycine at position 80 of SEQ ID NO: 1, an alanine at position 205 of SEQ ID NO: 1, and/or a histidine at position 207 of SEQ ID NO: 1;
- b) a threonine at position 21 of SEQ ID NO: 3, a leucine at position 23 of SEQ ID NO: 3, and/or an isoleucine at position 24 of SEQ ID NO: 3; or
- c) a threonine at position 21 of SEQ ID NO: 4, a leucine at position 23 of SEQ ID NO: 4, an alanine at position 25 of SEQ ID NO: 4, a glycine at position 80 of SEQ ID NO: 4, and/or a histidine at position 207 of SEQ ID NO: 4.

Embodiment 75

The polypeptide, the contiguous polypeptide, or the heterodimeric protein of any one of embodiments 42 to 74, wherein the variant IgG Fc polypeptide, the first variant IgG Fc polypeptide, and/or the second variant IgG Fc polypeptide comprises at least one additional amino acid modification relative to a wild-type IgG Fc polypeptide and has decreased binding affinity to CD16 relative to the wild-type IgG Fc polypeptide.

Embodiment 76

The polypeptide, the contiguous polypeptide, or the heterodimeric protein of any one of embodiments 42 to 75, wherein the variant IgG Fc polypeptide, the first variant IgG Fc polypeptide, and/or the second variant IgG Fc polypeptide comprises:
- a) an amino acid substitution at a position corresponding to position 5 of SEQ ID NO: 2, an amino acid substitution at a position corresponding to position 38 of SEQ ID NO: 2, an amino acid substitution at a position corresponding to position 39 of SEQ ID NO: 2, an amino acid substitution at a position corresponding to position 97 of SEQ ID NO: 2, and/or an amino acid substitution at a position corresponding to position 98 of SEQ ID NO: 2; or
- b) an amino acid substitution at a position corresponding to position 5 of SEQ ID NO: 3, an amino acid substitution at a position corresponding to position 38 of SEQ ID NO: 3, an amino acid substitution at a position corresponding to position 39 of SEQ ID NO: 3, an amino acid substitution at a position corresponding to position 97 of SEQ ID NO: 3, and/or an amino acid substitution at a position corresponding to position 98 of SEQ ID NO: 3.

Embodiment 77

The polypeptide, the contiguous polypeptide, or the heterodimeric protein of any one of embodiments 42 to 76, wherein the variant IgG Fc polypeptide, the first variant IgG Fc polypeptide, and/or the second variant IgG Fc polypeptide comprises:
- a) an amino acid substitution at position 5 of SEQ ID NO: 2, an amino acid substitution at position 38 of SEQ ID NO: 2, an amino acid substitution at position 39 of SEQ ID NO: 2, an amino acid substitution at position 97 of SEQ ID NO: 2, and/or an amino acid substitution at position 98 of SEQ ID NO: 2; or
- b) an amino acid substitution at position 5 of SEQ ID NO: 3, an amino acid substitution at position 38 of SEQ ID NO: 3, an amino acid substitution at position 39 of SEQ ID NO: 3, an amino acid substitution at position 97 of SEQ ID NO: 3, and/or an amino acid substitution at position 98 of SEQ ID NO: 3.

Embodiment 78

The polypeptide, the contiguous polypeptide, or the heterodimeric protein of any one of embodiments 42 to 77, wherein the variant IgG Fc polypeptide, the first variant IgG Fc polypeptide, and/or the second variant IgG Fc polypeptide comprises:
- a) a proline at a position corresponding to position 5 of SEQ ID NO: 2, a glycine at a position corresponding to position 38 of SEQ ID NO: 2, an arginine at a position corresponding to position 39 of SEQ ID NO: 2, an isoleucine at a position corresponding to position 97 of SEQ ID NO: 2, and/or a glycine at a position corresponding to position 98 of SEQ ID NO: 2; or
- b) a proline at a position corresponding to position 5 of SEQ ID NO: 3, a glycine at a position corresponding to position 38 of SEQ ID NO: 3, an arginine at a position corresponding to position 39 of SEQ ID NO: 3, an isoleucine at a position corresponding to position 97 of SEQ ID NO: 3, and/or a glycine at a position corresponding to position 98 of SEQ ID NO: 3.

Embodiment 79

The polypeptide, the contiguous polypeptide, or the heterodimeric protein of any one of embodiments 42 to 78, wherein the variant IgG Fc polypeptide, the first variant IgG Fc polypeptide, and/or the second variant IgG Fc polypeptide comprises:
a) a proline at position 5 of SEQ ID NO: 2, a glycine at position 38 of SEQ ID NO: 2, an arginine at position 39 of SEQ ID NO: 2, an isoleucine at position 97 of SEQ ID NO: 2, and/or a glycine at position 98 of SEQ ID NO: 2; or
b) a proline at position 5 of SEQ ID NO: 3, a glycine at position 38 of SEQ ID NO: 3, an arginine at position 39 of SEQ ID NO: 3, an isoleucine at position 97 of SEQ ID NO: 3, and/or a glycine at position 98 of SEQ ID NO: 3.

Embodiment 80

The polypeptide, the contiguous polypeptide, or the heterodimeric protein of any one of embodiments 42 to 79, wherein the variant IgG Fc polypeptide, the first variant IgG Fc polypeptide, and/or the second variant IgG Fc polypeptide comprises at least one additional amino acid modification relative to a wild-type canine IgG Fc polypeptide and has decreased binding affinity to C1q relative to the wild-type canine IgG Fc polypeptide.

Embodiment 81

The polypeptide, the contiguous polypeptide, or the heterodimeric protein of any one of embodiments 42 to 80, wherein the variant IgG Fc polypeptide, the first variant IgG Fc polypeptide, and/or the second variant IgG Fc polypeptide comprises an amino acid substitution at a position corresponding to position 93 of SEQ ID NO: 2, or an amino acid substitution at a position corresponding to position 93 of SEQ ID NO: 3.

Embodiment 82

The polypeptide, the contiguous polypeptide, or the heterodimeric protein of any one of embodiments 42 to 81, wherein the variant IgG Fc polypeptide, the first variant IgG Fc polypeptide, and/or the second variant IgG Fc polypeptide comprises an amino acid substitution at position 93 of SEQ ID NO: 2, or an amino acid substitution at position 93 of SEQ ID NO: 3.

Embodiment 83

The polypeptide, the contiguous polypeptide, or the heterodimeric protein of any one of embodiments 42 to 82, wherein the variant IgG Fc polypeptide, the first variant IgG Fc polypeptide, and/or the second variant IgG Fc polypeptide comprises an arginine at a position corresponding to position 93 of SEQ ID NO: 2, or an arginine at a position corresponding to position 93 of SEQ ID NO: 3.

Embodiment 84

The polypeptide, the contiguous polypeptide, or the heterodimeric protein of any one of embodiments 42 to 83, wherein the variant IgG Fc polypeptide, the first variant IgG Fc polypeptide, and/or the second variant IgG Fc polypeptide comprises an arginine at position 93 of SEQ ID NO: 2, or an arginine at position 93 of SEQ ID NO: 3.

Embodiment 85

The polypeptide, the contiguous polypeptide, or the heterodimeric protein of any one of embodiments 1 to 84, wherein the polypeptide is an antibody, an antibody fusion, or a fusion polypeptide.

Embodiment 86

A contiguous polypeptide comprising:
a) a first glucagon-like peptide-1 (GLP1) polypeptide (GLP1A);
b) a first linker (L1);
c) an Fc polypeptide (Fc) of a companion animal species;
d) optionally, a second linker (L2); and
e) optionally, a second GLP1 polypeptide (GLP1B).

Embodiment 87

The contiguous polypeptide of embodiment 65 comprising:

GLP1A-L1-Fc; or    formula (I):

Fc-L1GLP1A.    formula (II):

Embodiment 88

The contiguous polypeptide of embodiment 65 comprising:

GLP1A-L1-Fc-L2-GLP1B.    formula (III):

Embodiment 89

The contiguous polypeptide of any one of embodiments 86 to 88, wherein GLP1B, if present, comprises the same amino acid sequence as GLP1A.

Embodiment 90

A contiguous polypeptide comprising:
a) a glucagon-like peptide-1 (GLP1) polypeptide;
b) a first linker (L1);
c) an Fc polypeptide (Fc);
d) a second linker (L2); and
e) a glucagon polypeptide (Gluc).

Embodiment 91

The contiguous polypeptide of embodiment 90 comprising:

GLP1-L1-Fc-L2-Gluc; or    Formula (IV):

Gluc-L1-Fc-L2-GLP1.    Formula (V):

Embodiment 92

The contiguous polypeptide of any one of embodiments 86 to 91, wherein GLP1A, GLP1, and/or GLP1B, if present, comprises a wild-type GLP1 polypeptide.

Embodiment 93

The contiguous polypeptide of any one of embodiments 86 to 92, wherein GLP1A, GLP1, and/or GLP1B, if present, comprises a variant GLP1 polypeptide.

Embodiment 94

The contiguous polypeptide of any one of embodiments 86 to 93, wherein GLP1A, GLP1, and/or GLP1B, if present, comprises an amino acid sequence of SEQ ID NO: 85, SEQ ID NO: 86, SEQ ID NO: 87, SEQ ID NO: 98, or SEQ ID NO: 99.

Embodiment 95

The contiguous polypeptide of any one of embodiments 86 to 94, wherein the glucagon polypeptide comprises a wild-type glucagon polypeptide, optionally comprising the amino acid sequence of SEQ ID NO: 21.

Embodiment 96

The contiguous polypeptide of any one of embodiments 86 to 95, wherein the glucagon polypeptide is a variant glucagon polypeptide.

Embodiment 97

The contiguous polypeptide of any one of embodiments 86 to 96, wherein the Fc polypeptide is a human IgG Fc.

Embodiment 98

The contiguous polypeptide of any one of embodiments 86 to 97, wherein the Fc polypeptide is a human IgG1 Fc, IgG2 Fc, IgG3 Fc, or IgG4 Fc.

Embodiment 99

The contiguous polypeptide of any one of embodiments 86 to 98, wherein the Fc polypeptide is an Fc of a companion animal species.

Embodiment 100

The contiguous polypeptide of any one of embodiments 86 to 97 or 99, wherein the Fc polypeptide comprises:
a) a canine IgG-A Fc, IgG-B Fc, IgG-C Fc, or IgG-D Fc;
b) an equine IgG1 Fc, IgG2 Fc, IgG3 Fc, IgG4 Fc, IgG5 Fc, IgG6 Fc, or IgG7 Fc; or
c) a feline IgG1a Fc, IgG1b Fc, or IgG2 Fc.

Embodiment 101

The contiguous polypeptide of any one of embodiments 86 to 100, wherein the Fc polypeptide is a wild-type IgG Fc polypeptide.

Embodiment 102

The contiguous polypeptide of any one of embodiments 86 to 100, wherein the Fc polypeptide is a variant IgG Fc polypeptide.

Embodiment 103

The contiguous polypeptide of any one of embodiments 86 to 102, wherein the Fc polypeptide comprises the polypeptide, the contiguous polypeptide, or the heterodimeric protein of any one of embodiments 1 to 84.

Embodiment 104

The contiguous polypeptide of any one of embodiments 85 to 102, wherein the contiguous polypeptide has a longer serum half-life than a wild-type GLP1 polypeptide.

Embodiment 105

The contiguous polypeptide of any one of embodiments 86 to 104, wherein L1 and L2, if present, each independently is a flexible linker.

Embodiment 106

The contiguous polypeptide of any one of embodiments 86 to 105, wherein the amino acid sequence of L1 and L2, if present, each independently comprises 100%, at least 95%, at least 90%, at least 85% serine and/or glycine amino acid residues.

Embodiment 107

The contiguous polypeptide of any one of embodiments 86 to 106, wherein the contiguous polypeptide comprises an extension at its C-terminus.

Embodiment 108

The contiguous polypeptide of any one of embodiments 86 to 107, wherein the contiguous polypeptide comprises a glycine residue, two glycine residues, three glycine residues, four glycine residues, five glycine residues, six glycine residues, seven glycine residues, eight glycine residues, or greater than eight glycine residues at its C-terminus.

Embodiment 109

The contiguous polypeptide of any one of embodiments 86 to 108, wherein the contiguous polypeptide comprises an amino acid sequence of SEQ ID NO: 88, SEQ ID NO: 89, SEQ ID NO: 90, SEQ ID NO: 91, SEQ ID NO: 92, SEQ ID NO: 93, SEQ ID NO: 94, or SEQ ID NO: 95 at its C-terminus.

Embodiment 110

The contiguous polypeptide of any one of embodiments 86 to 109, wherein the contiguous polypeptide comprises:
a) the amino acid sequence of SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47, SEQ ID NO: 96, SEQ ID NO: 97, SEQ ID NO: 103, SEQ ID NO: 104, SEQ ID NO: 105, or SEQ ID NO: 106; or
b) the amino acid sequence of SEQ ID NO: 52; SEQ ID NO: 53; SEQ ID NO: 54; SEQ ID NO: 55; SEQ ID NO: 56; SEQ ID NO: 57; SEQ ID NO: 58; or SEQ ID NO: 59.

Embodiment 111

A polypeptide comprising an amino acid sequence of SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47, SEQ ID NO: 96, SEQ ID NO: 97, SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 103; SEQ ID NO: 104, SEQ ID NO: 105, or SEQ ID NO: 106.

Embodiment 112

The polypeptide, the heterodimeric protein, or the contiguous polypeptide of any one of the preceding embodiments, wherein the at least one amino acid modification or substitution comprises an amino acid substitution with an amino acid derivative.

Embodiment 113

An isolated nucleic acid encoding the polypeptide, the heterodimeric protein, or the contiguous polypeptide of any one of the preceding embodiments.

Embodiment 114

A host cell comprising the nucleic acid of embodiment 113.

Embodiment 115

A method of producing a polypeptide comprising culturing the host cell of embodiment 114 and isolating the polypeptide.

Embodiment 116

A pharmaceutical composition comprising the polypeptide, the heterodimeric protein, or the contiguous polypeptide of any one of embodiments 1 to 112, and a pharmaceutically acceptable carrier.

Embodiment 117

A method of increasing production of cAMP in a cell, the method comprising exposing the cell to the polypeptide, the heterodimeric protein, the contiguous polypeptide, or the pharmaceutical composition of any one of embodiments 1 to 112 or 116 under conditions permissive for binding of the polypeptide, heterodimeric protein, or contiguous polypeptide to GLP1R.

Embodiment 118

The method of embodiment 117, wherein the cell is exposed to the polypeptide, heterodimeric protein, contiguous polypeptide, or the pharmaceutical composition ex vivo.

Embodiment 119

The method of embodiment 117, wherein the cell is exposed to the polypeptide, heterodimeric protein, contiguous polypeptide, or the pharmaceutical composition in vivo.

Embodiment 120

The method of any one of embodiments 118 to 119, wherein the cell is a human cell, a canine cell, a feline cell, or an equine cell.

Embodiment 121

A method of delivering a polypeptide to a subject comprising administering the polypeptide, the heterodimeric protein, the contiguous polypeptide, or the pharmaceutical composition of any one of embodiments 1 to 112 or 116 parenterally.

Embodiment 122

A method of delivering a polypeptide to a subject comprising administering the polypeptide, the heterodimeric protein, the contiguous polypeptide, or the pharmaceutical composition of any one of embodiments 1 to 112 or 116 by an intramuscular route, an intraperitoneal route, an intracerebrospinal route, a subcutaneous route, an intra-arterial route, an intrasynovial route, an intrathecal route, or an inhalation route.

Embodiment 123

A method of treating a subject having diabetes or obesity, the method comprising administering to the subject a therapeutically effective amount of the polypeptide, the heterodimeric protein, the contiguous polypeptide, or the pharmaceutical composition of any one of embodiments 1 to 112 or 116.

Embodiment 124

The method of embodiment 123, comprising administering insulin, a DPP4 inhibitor, a SGLT2 inhibitor, a biguanides sulfonylureas meglitinide derivative, an alpha-glucosidase inhibitor, a thiazolidinedion (TZD), an amylinomimetic, a bile acid sequestrant, a dopamine agonist.

Embodiment 125

The method of any one of embodiments 121 to 124, wherein the subject is a human subject.

Embodiment 126

The method of any one of embodiments 121 to 124, wherein the subject is a companion animal species.

Embodiment 127

The method of embodiment 126, wherein the companion animal species is canine, equine, or feline.

BRIEF DESCRIPTION OF THE DRAWINGS

FIG. 1 shows an alignment of canine IgG-A, B, C, and D Fc sequences. The boxes indicate the regions likely in contact with Protein A.

DESCRIPTION OF THE SEQUENCES

TABLE 1

Figure 2:
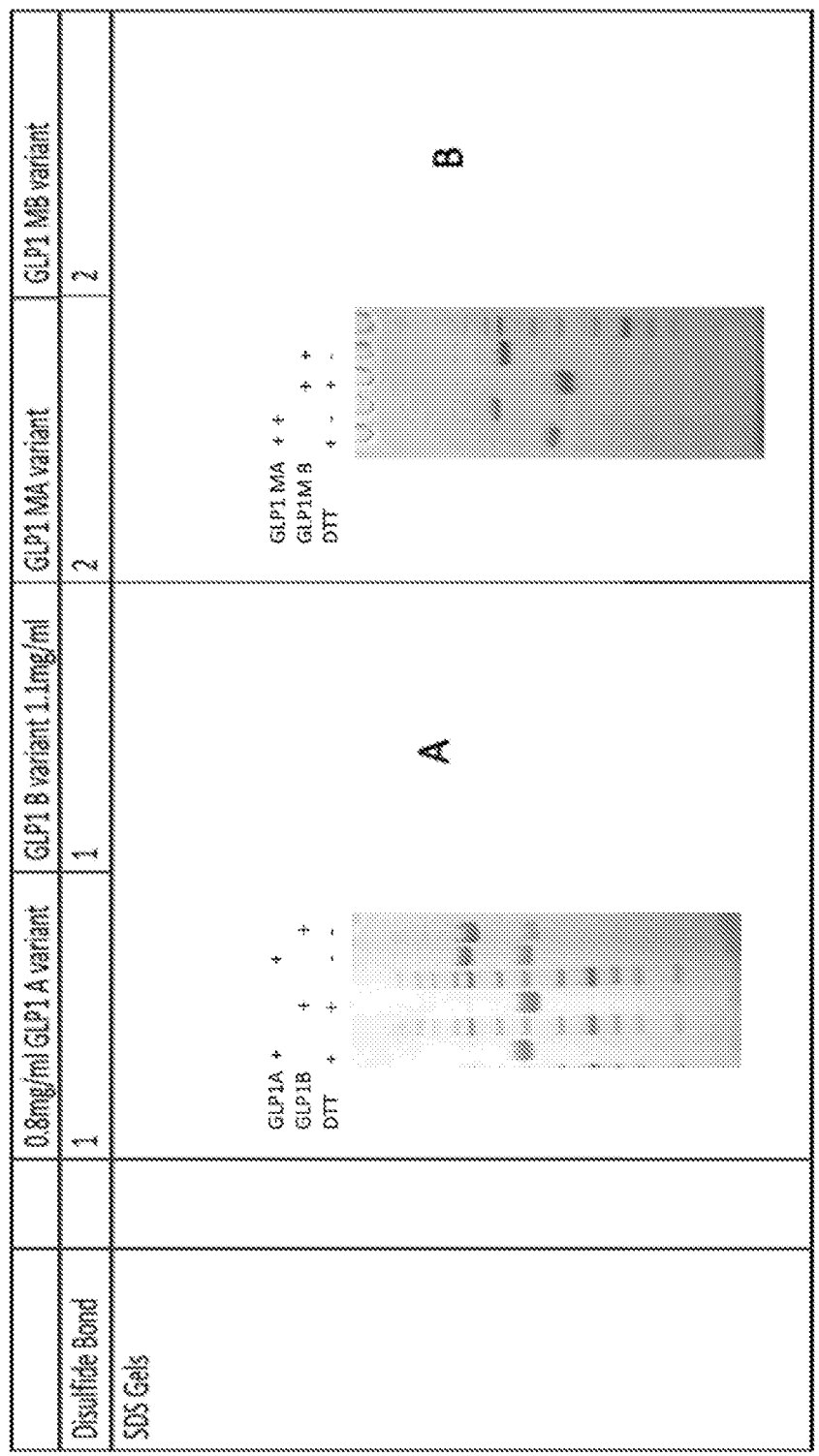
FIG. 2A shows an SDS-PAGE analysis of GLP1-G8/GLP-2G_III_WTfeIgG2 (SEQ ID NO: 23; "GLP1 A variant" in this figure) and GLP1-G8_I_WTfeIgG2 (SEQ ID NO: 24; "GLP1 B variant" in this figure) having wild-type feline IgG2 hinge with one disulfide bond in the absence and presence of reducing agent (DTT).
FIG. 2B shows an SDS-PAGE analysis of GLP1-G8/GLP-2G_III_VARfeIgG2 (SEQ ID NO: 25; "GLP1 MA variant" in this figure) of GLP1-G8_I_VARfeIgG2 (SEQ ID NO: 26; "GLP1 MB variant" in this figure) having variant feline IgG2 hinge with two disulfide bonds in the absence and presence of reducing agent (DTT).

Table 1 provides a listing of exemplary sequences referenced herein.
Description of the Sequences

| SEQ ID NO: | SEQUENCE | DESCRIPTION |
| --- | --- | --- |
| 1 | PVPEPLGGPSVLIFPPKPKDILRITRIPEVIC VVLDLGREDPEVQISWFVDGKEVHTAKTQSRE QQFNGTYRVVSVLPIEHQDWLTGKEFKCRVNH IDLPSPIERTISKARGRAHKPSVYVLPPSPKE LSSSDTVSITCLIKDFYPPDIDVEWQSNGQQE PERKHRMTPPQLDEDGSYFLYSKLSVDKSRWQ QGDPFTCAVMHETLQNHYTDLSLSHSPGK | Exemplary wild-type canine IgG-A Fc<br>Protein A-<br>C1q-<br>CD16- |
| 2 | PAPEMLGGPSVFIFPPKPKDILLIARTPEVIC VVVDLDPEDPEVQISWFVDGKQMQTAKTQPRE EQFNGTYRVVSVLPIGHQDWLKGKQFTCKVNN KALPSPIERTISKARGQAHQPSVYVLPPSREE LSKNTVSLTCLIKDFFPPDIDVEWQSNGQQEP ESKYRTTPPQLDEDGSYFLYSKLSVDKSRWQR GDTFICAVMHEALHNHYTQESLSHSPGK | Exemplary wild-type canine IgG-B Fc<br>Protein A+<br>C1q+<br>CD16+ |
| 107 | PKRENGRVPRPPDCPKCPAPEMLGGPSVFIFPP KPKDILLIARTPEVICVVVDLDPEDPEVQISW FVDGKQMQTAKTQPREEQFNGTYRVVSVLPIG HQDWLKGKQFTCKVNNKALPSPIERTISKARG QAHQPSVYVLPPSREELSKNIVSLICLIKDFF PPDIDVEWQSNGQQEPESKYRTTPPQLDEDGS YFLYSKLSVDKSRWQRGDTFICAVMHEALHNH YTQESLSHSPGK | Exemplary wild-type canine IgG-B Fc with hinge<br>Protein A+<br>C1q+<br>CD16+ |
| 3 | PGCGLLGGPSVFIFPPKPKDILVTARTPTVTC VVVDLDPENPEVQISWFVDSKQVQTANTQPRE EQSNGTYRVVSVLPIGHQDWLSGKQFKCKVNN KALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary wild-type canine IgG-C Fc<br>Protein A-<br>C1q+<br>CD16+ |
| 108 | AKECECKCNCNNCPCPGCGLLGGPSVFIFPPK PKDILVTARTPTVTCVVVDLDPENPEVQISWF VDSKQVQTANTQPREEQSNGTYRVVSVLPIGH QDWLSGKQFKCKVNNKALPSPIEEIISKTPGQ AHQPNVYVLPPSRDEMSKNIVTLICLVKDFFP PEIDVEWQSNGQQEPESKYRMTPPQLDEDGSY FLYSKLSVDKSRWQRGDTFICAVMHEALHNHY TQISLSHSPGK | Exemplary wild-type canine IgG-C Fc with hinge<br>Protein A-<br>C1q+<br>CD16+ |
| 4 | PVPESLGGPSVFIFPPKPKDILRITRIPEITC VVLDLGREDPEVQISWFVDGKEVHTAKTQPRE QQFNSTYRVVSVLPIEHQDWLIGKEFKCRVNH IGLPSPIERTISKARGQAHQPSVYVLPPSPKE LSSSDTVTLTCLIKDFFPPEIDVEWQSNGQPE | Exemplary wild-type canine IgG-D Fc<br>Protein A-<br>C1q-<br>CD16- |

TABLE 1-continued

Table 1 provides a listing of exemplary sequences referenced herein.
Description of the Sequences

| SEQ ID NO: | SEQUENCE | DESCRIPTION |
|---|---|---|
|  | PESKYHTTAPQLDEDGSYFLYSKLSVDKSRWQ<br>QGDTFTCAVMHEALQNHYTDLSLSHSPGK |  |
| 5 | PVPEPLGGPSVLIFPPKPKDTLLIARTPEVIC<br>VVLDLGREDPEVQISWFVDGKEVHIAKTQSRE<br>QQFNGTYRVVSVLPIGHQDWLIGKEFKCRVNH<br>IDLPSPIERTISKARGRAHKPSVYVLPPSPKE<br>LSSSDTVSITCLIKDFYPPDIDVEWQSNGQQE<br>PERKHRMTPPQLDEDGSYFLYSKLSVDKSRWQ<br>QGDPFTCAVMHEALHNHYTDLSLSHSPGK | Exemplary variant canine<br>IgG-A Fc<br>C1q-<br>Protein A+<br>I(21)T<br>R(23)L<br>T(25)A<br>E(80)G<br>T(205)A<br>Q(207)H |
| 6 | PGCGLLGGPSVFIFPPKPKDTLLIARTPTVTC<br>VVVDLDPENPEVQISWFVDSKQVQTANTQPRE<br>EQSNGTYRVVSVLPIGHQDWLSGKQFKCKVNN<br>KALPSPIEEIISKTPGQAHQPNVYVLPPSRDE<br>MSKNTVTLTCLVKDFFPPEIDVEWQSNGQQEP<br>ESKYRMTPPQLDEDGSYFLYSKLSVDKSRWQR<br>GDTFICAVMHEALHNHYTQISLSHSPGK | Exemplary variant canine<br>IgG-C Fc<br>C1q+<br>Protein A+<br>I(21)T<br>V(23)L<br>T(24)I |
| 7 | PVPESLGGPSVFIFPPKPKDTLLIARTPEITC<br>VVLDLGREDPEVQISWFVDGKEVHTAKTQPRE<br>QQFNSTYRVVSVLPIGHQDWLTGKEFKCRVNH<br>IGLPSPIERTISKARGQAHQPSVYVLPPSPKE<br>LSSSDTVTLTCLIKDFFPPEIDVEWQSNGQPE<br>PESKYHTTAPQLDEDGSYFLYSKLSVDKSRWQ<br>QGDTFTCAVMHEALHNHYTDLSLSHSPGK | Exemplary variant canine<br>IgG-D Fc<br>C1q-<br>Protein A+<br>I(21)T<br>R(23)L<br>T(25)A<br>E(80)G<br>Q(207)H |
| 8 | PVPEPLGGPSVLIFPPKPKDILRITRIPEVIC<br>VVLDLGREDPEVQISWFVDGKEVHTAKTQSRE<br>QQFNGTYRVVSVLPIEHQDWLTGKEFKCRVNH<br>IDLPSPIERTISKARGRAHKPSVYVLPPSPKE<br>LSSSDTVSIYCLIKDFYPPDIDVEWQSNGQQE<br>PERKHRMTPPQLDEDGSYFLYSKLSVDKSRWQ<br>QGDPFTCAVMHETLQNHYTDLSLSHSPGK | Exemplary variant canine<br>IgG-A Fc<br>Heterodimer chain 1 T(138)Y |
| 9 | PVPEPLGGPSVLIFPPKPKDILRITRIPEVIC<br>VVLDLGREDPEVQISWFVDGKEVHTAKTQSRE<br>QQFNGTYRVVSVLPIEHQDWLTGKEFKCRVNH<br>IDLPSPIERTISKARGRAHKPSVYVLPPSPKE<br>LSSSDTVSITCLIKDFYPPDIDVEWQSNGQQE<br>PERKHRMTPPQLDEDGSYFLTSKLSVDKSRWQ<br>QGDPFTCAVMHETLQNHYTDLSLSHSPGK | Exemplary variant canine<br>IgG-A Fc<br>Heterodimer chain 2<br>Y(181)T |
| 10 | PAPEMLGGPSVFIFPPKPKDILLIARTPEVIC<br>VVVDLDPEDPEVQISWFVDGKQMQTAKTQPRE<br>EQFNGTYRVVSVLPIGHQDWLKGKQFTCKVNN<br>KALPSPIERTISKARGQAHQPSVYVLPPSREE<br>LSKNTVSLYCLIKDFFPPDIDVEWQSNGQQEP<br>ESKYRTTPPQLDEDGSYFLYSKLSVDKSRWQR<br>GDTFICAVMHEALHNHYTQESLSHSPGK | Exemplary variant canine<br>IgG-B Fc<br>Heterodimer chain 1 T(137)Y |
| 11 | PAPEMLGGPSVFIFPPKPKDILLIARTPEVIC<br>VVVDLDPEDPEVQISWFVDGKQMQTAKTQPRE<br>EQFNGTYRVVSVLPIGHQDWLKGKQFTCKVNN<br>KALPSPIERTISKARGQAHQPSVYVLPPSREE<br>LSKNTVSLTCLIKDFFPPDIDVEWQSNGQQEP<br>ESKYRTTPPQLDEDGSYFLTSKLSVDKSRWQR<br>GDTFICAVMHEALHNHYTQESLSHSPGK | Exemplary variant canine<br>IgG-B Fc<br>Heterodimer chain 2<br>Y(180)T |
| 12 | PGCGLLGGPSVFIFPPKPKDILVTARTPTVTC<br>VVVDLDPENPEVQISWFVDSKQVQTANTQPRE<br>EQSNGTYRVVSVLPIGHQDWLSGKQFKCKVNN<br>KALPSPIEEIISKTPGQAHQPNVYVLPPSRDE<br>MSKNTVTLYCLVKDFFPPEIDVEWQSNGQQEP<br>ESKYRMTPPQLDEDGSYFLYSKLSVDKSRWQR<br>GDTFICAVMHEALHNHYTQISLSHSPGK | Exemplary variant canine<br>IgG-C Fc<br>Heterodimer chain 1 T(137)Y |
| 13 | PGCGLLGGPSVFIFPPKPKDILVTARTPTVTC<br>VVVDLDPENPEVQISWFVDSKQVQTANTQPRE | Exemplary variant canine<br>IgG-C Fc |

TABLE 1-continued

Table 1 provides a listing of exemplary sequences referenced herein.
Description of the Sequences

| SEQ ID NO: | SEQUENCE | DESCRIPTION |
|---|---|---|
|  | EQSNGTYRVVSVLPIGHQDWLSGKQFKCKVNN<br>KALPSPIEEIISKTPGQAHQPNVYVLPPSRDE<br>MSKNTVTLTCLVKDFFPPEIDVEWQSNGQQEP<br>ESKYRMTPPQLDEDGSYFLTSKLSVDKSRWQR<br>GDTFICAVMHEALHNHYTQISLSHSPGK | Heterodimer chain 2<br>Y(180)T |
| 14 | PVPESLGGPSVFIFPPKPKDILRITRITEITC<br>VVLDLGREDPEVQISWFVDGKEVHTAKTQPRE<br>QQFNSTYRVVSVLPIEHQDWLTGKEFKCRVNH<br>IGLPSPIERTISKARGQAHQPSVYVLPPSPKE<br>LSSSDTVTLYCLIKDFFPPEIDVEWQSNGQPE<br>PESKYHTTAPQLDEDGSYFLYSKLSVDKSRWQ<br>QGDTFTCAVMHEALQNHYTDLSLSHSPGK | Exemplary variant canine<br>IgG-D Fc<br>Heterodimer chain 1 T(138)Y |
| 15 | PVPESLGGPSVFIFPPKPKDILRITRITEITC<br>VVLDLGREDPEVQISWFVDGKEVHTAKTQPRE<br>QQFNSTYRVVSVLPIEHQDWLTGKEFKCRVNH<br>IGLPSPIERTISKARGQAHQPSVYVLPPSPKE<br>LSSSDTVTLTCLIKDFFPPEIDVEWQSNGQPE<br>PESKYHTTAPQLDEDGSYFLTSKLSVDKSRWQ<br>QGDTFTCAVMHEALQNHYTDLSLSHSPGK | Exemplary variant canine<br>IgG-D Fc<br>Heterodimer chain 2<br>Y(181)T |
| 109 | PVPEPLGGPSVLIFPPKPKDILRITRTPEVIC<br>VVLDLGREDPEVQISWFVDGKEVHTAKTQSRE<br>QQFNGTYRVVSVLPIEHQDWLTGKEFKCRVNH<br>IDLPSPIERTISKARGRAHKPSVYVLPPSPKE<br>LSSSDTVSIWCLIKDFYPPDIDVEWQSNGQQE<br>PERKHRMTPPQLDEDGSYFLYSKLSVDKSRWQ<br>QGDPFTCAVMHETLQNHYTDLSLSHSPGK | Exemplary variant canine<br>IgG-A Fc<br>Heterodimer chain 3<br>T(138)W |
| 110 | PVPEPLGGPSVLIFPPKPKDILRITRITEVIC<br>VVLDLGREDPEVQISWFVDGKEVHTAKTQSRE<br>QQFNGTYRVVSVLPIEHQDWLTGKEFKCRVNH<br>IDLPSPIERTISKARGRAHKPSVYVLPPSPKE<br>LSSSDTVSISCAIKDFYPPDIDVEWQSNGQQE<br>PERKHRMTPPQLDEDGSYFLTSKLSVDKSRWQ<br>QGDPFTCAVMHETLQNHYTDLSLSHSPGK | Exemplary variant canine<br>IgG-A Fc<br>Heterodimer chain 4<br>T(138)S<br>L(140)A<br>Y(181)T |
| 111 | PAPEMLGGPSVFIFPPKPKDILLIARTPEVIC<br>VVVDLDPEDPEVQISWFVDGKQMQTAKTQPRE<br>EQFNGTYRVVSVLPIGHQDWLKGKQFTCKVNN<br>KALPSPIERTISKARGQAHQPSVYVLPPSREE<br>LSKNTVSLWCLIKDFFPPDIDVEWQSNGQQEP<br>ESKYRTTPPQLDEDGSYFLYSKLSVDKSRWQR<br>GDTFICAVMHEALHNHYTQESLSHSPGK | Exemplary variant canine<br>IgG-B Fc<br>Heterodimer chain 3<br>T(137)W |
| 112 | PAPEMLGGPSVFIFPPKPKDTLLIARTPEVIC<br>VVVDLDPEDPEVQISWFVDGKQMQTAKTQPRE<br>EQFNGTYRVVSVLPIGHQDWLKGKQFTCKVNN<br>KALPSPIERTISKARGQAHQPSVYVLPPSREE<br>LSKNTVSLSCAIKDFFPPDIDVEWQSNGQQEP<br>ESKYRTTPPQLDEDGSYFLTSKLSVDKSRWQR<br>GDTFICAVMHEALHNHYTQESLSHSPGK | Exemplary variant canine<br>IgG-B Fc<br>Heterodimer chain 4<br>T(137)S<br>L(139)A<br>Y(180)T |
| 113 | PGCGLLGGPSVFIFPPKPKDILVTARTPTVTC<br>VVVDLDPENPEVQISWFVDSKQVQTANTQPRE<br>EQSNGTYRVVSVLPIGHQDWLSGKQFKCKVNN<br>KALPSPIEEIISKTPGQAHQPNVYVLPPSRDE<br>MSKNTVTLWCLVKDFFPPEIDVEWQSNGQQEP<br>ESKYRMTPPQLDEDGSYFLYSKLSVDKSRWQR<br>GDTFICAVMHEALHNHYTQISLSHSPGK | Exemplary variant canine<br>IgG-C Fc<br>Heterodimer chain 3<br>T(137)W |
| 114 | PGCGLLGGPSVFIFPPKPKDILVTARTPTVTC<br>VVVDLDPENPEVQISWFVDSKQVQTANTQPRE<br>EQSNGTYRVVSVLPIGHQDWLSGKQFKCKVNN<br>KALPSPIEEIISKTPGQAHQPNVYVLPPSRDE<br>MSKNTVTLSCAVKDFFPPEIDVEWQSNGQQEP<br>ESKYRMTPPQLDEDGSYFLTSKLSVDKSRWQR<br>GDTFICAVMHEALHNHYTQISLSHSPGK | Exemplary variant canine<br>IgG-C Fc<br>Heterodimer chain 4<br>T(137)S<br>L(139)A<br>Y(180)T |
| 115 | PVPESLGGPSVFIFPPKPKDILRITRITEITC<br>VVLDLGREDPEVQISWFVDGKEVHTAKTQPRE<br>QQFNSTYRVVSVLPIEHQDWLIGKEEKCRVNH<br>IGLPSPIERTISKARGQAHQPSVYVLPPSPKE | Exemplary variant canine<br>IgG-D Fc<br>Heterodimer chain 3<br>T(138)W |

TABLE 1-continued

Table 1 provides a listing of exemplary sequences referenced herein.
Description of the Sequences

| SEQ ID NO: | SEQUENCE | DESCRIPTION |
|---|---|---|
|  | LSSSDTVTLWCLIKDFFPPEIDVEWQSNGQPE<br>PESKYHTTAPQLDEDGSYFLYSKLSVDKSRWQ<br>QGDTFTCAVMHEALQNHYTDLSLSHSPGK |  |
| 116 | PVPESLGGPSVFIFPPKPKDILRITRITEITC<br>VVLDLGREDPEVQISWFVDGKEVHTAKTQPRE<br>QQFNSTYRVVSVLPIEHQDWLIGKEEKCRVNH<br>IGLPSPIERTISKARGQAHQPSVYVLPPSPKE<br>LSSSDTVTLSCAIKDFFPPEIDVEWQSNGQPE<br>PESKYHTTAPQLDEDGSYFLTSKLSVDKSRWQ<br>QGDTFTCAVMHEALQNHYTDLSLSHSPGK | Exemplary variant canine<br>IgG-D Fc<br>Heterodimer chain 4<br>T(138)S<br>L(140)A<br>Y(181)T |
| 16 | PKTASTIESKTGEGPKCPVPEIPGAPSVFIFP<br>PKPKDTLSISRTPEVICLVVDLGPDDSNVQIT<br>WFVDNTEMHTAKTRPREEQFNSTYRVVSVLPI<br>LHQDWLKGKEFKCKVNSKSLPSAMERTISKAK<br>GQPHEPQVYVLPPTQEELSENKVSVTCLIKGF<br>HPPDIAVEWEITGQPEPENNYQTTPPQLDSDG<br>TYFLYSRLSVDRSHWQRGNTYTCSVSHEALHS<br>HHTQKSLTQSPGK | Exemplary wild-type feline<br>IgG2 Fc<br>Protein A+<br>C1q- |
| 117 | RKTDHPPGPKPCDCPKCPPPEMLGGPSIFIFP<br>PKPKDTLSISRTPEVICLVVDLGPDDSDVQIT<br>WFVDNTQVYTAKTSPREEQFNSTYRVVSVLPI<br>LHQDWLKGKEFKCKVNSKSLPSPIERTISKAK<br>GQPHEPQVYVLPPAQEELSENKVSVTCLIKSF<br>HPPDIAVEWEITGQPEPENNYRTTPPQLDSDG<br>TYFVYSKLSVDRSHWQRGNTYTCSVSHEALHS<br>HHTQKSLTQSPGK | Exemplary wild-type feline<br>IgG1a Fc<br>Protein A+<br>C1q+ |
| 118 | RKTDHPPGPKPCDCPKCPPPEMLGGPSIFIFP<br>PKPKDTLSISRTPEVICLVVDLGPDDSDVQIT<br>WFVDNTQVYTAKTSPREEQFNSTYRVVSVLPI<br>LHQDWLKGKEFKCKVNSKSLPSPIERTISKDK<br>GQPHEPQVYVLPPAQEELSENKVSVTCLIEGF<br>YPSDIAVEWEITGQPEPENNYRTTPPQLDSDG<br>TYFLYSRLSVDRSRWQRGNTYTCSVSHEALHS<br>HHTQKSLTQSPGK | Exemplary wild-type feline<br>IgG1b Fc<br>Protein A+<br>C1q+ |
| 119 | PKTASTIESKTGEGPKCPVPEIPGAPSVFIFP<br>PKPKDTLSISRTPEVICLVVDLGPDDSNVQIT<br>WFVDNTEMHTAKTRPREEQFNSTYRVVSVLPI<br>LHQDWLKGKEFKCKVNSKSLPSAMERTISKAK<br>GQPHEPQVYVLPPTQEELSENKVSVWCLIKGF<br>HPPDIAVEWEITGQPEPENNYQTTPPQLDSDG<br>TYFLYSRLSVDRSHWQRGNTYTCSVSHEALHS<br>HHTQKSLTQSPGK | Exemplary variant feline<br>IgG2 Fc<br>Heterodimer chain 1<br>T(154)W |
| 120 | PKTASTIESKTGEGPKCPVPEIPGAPSVFIFP<br>PKPKDTLSISRTPEVICLVVDLGPDDSNVQIT<br>WFVDNTEMHTAKTRPREEQFNSTYRVVSVLPI<br>LHQDWLKGKEFKCKVNSKSLPSAMERTISKAK<br>GQPHEPQVYVLPPTQEELSENKVSVSCAIKGF<br>HPPDIAVEWEITGQPEPENNYQTTPPQLDSDG<br>TYFLTSRLSVDRSHWQRGNTYTCSVSHEALHS<br>HHTQKSLTQSPGK | Exemplary variant feline<br>IgG2 Fc<br>Heterodimer chain 2<br>T(154)S<br>L(156)A<br>Y(197)T |
| 121 | RKTDHPPGPKPCDCPKCPPPEMLGGPSIFIFP<br>PKPKDTLSISRTPEVICLVVDLGPDDSDVQIT<br>WFVDNTQVYTAKTSPREEQFNSTYRVVSVLPI<br>LHQDWLKGKEFKCKVNSKSLPSPIERTISKAK<br>GQPHEPQVYVLPPAQEELSENKVSVWCLIKSF<br>HPPDIAVEWEITGQPEPENNYRTTPPQLDSDG<br>TYFVYSKLSVDRSHWQRGNTYTCSVSHEALHS<br>HHTQKSLTQSPGK | Exemplary variant feline<br>IgG1a Fc<br>Heterodimer chain 1<br>T(154)W |
| 122 | RKTDHPPGPKPCDCPKCPPPEMLGGPSIFIFP<br>PKPKDTLSISRTPEVICLVVDLGPDDSDVQIT<br>WFVDNTQVYTAKTSPREEQFNSTYRVVSVLPI<br>LHQDWLKGKEFKCKVNSKSLPSPIERTISKAK<br>GQPHEPQVYVLPPAQEELSENKVSSCAIKSF<br>HPPDIAVEWEITGQPEPENNYRTTPPQLDSDG<br>TYFVTSKLSVDRSHWQRGNTYTCSVSHEALHS<br>HHTQKSLTQSPGK | Exemplary variant feline<br>IgG1a Fc<br>Heterodimer chain 2<br>T(154)S<br>L(156)A<br>Y(197)T |

TABLE 1-continued

Table 1 provides a listing of exemplary sequences referenced herein.
Description of the Sequences

| SEQ ID NO: | SEQUENCE | DESCRIPTION |
|---|---|---|
| 123 | RKTDHPPGPKPCDCPKCPPPEMLGGPSIFIFP PKPKDTLSISRTPEVICLVVDLGPDDSDVQIT WFVDNIQVYTAKTSPREEQFNSTYRVVSVLPI LHQDWLKGKEFKCKVNSKSLPSPIERTISKDK GQPHEPQVYVLPPAQEELSENKVSVWCLIEGF YPSDIAVEWEITGQPEPENNYRTIPPQLDSDG TYFLYSRLSVDRSRWQRGNTYTCSVSHEALHS HHTQKSLTQSPGK | Exemplary variant feline IgG1b Fc Heterodimer chain 1 T(154)W |
| 124 | RKTDHPPGPKPCDCPKCPPPEMLGGPSIFIFP PKPKDTLSISRTPEVICLVVDLGPDDSDVQIT WFVDNIQVYTAKTSPREEQFNSTYRVVSVLPI LHQDWLKGKEFKCKVNSKSLPSPIERTISKDK GQPHEPQVYVLPPAQEELSENKVSVSCAIEGF YPSDIAVEWEITGQPEPENNYRTTPPQLDSDG TYFLTSRLSVDRSRWQRGNTYTCSVSHEALHS HHTQKSLTQSPGK | Exemplary variant feline IgG1b Fc Heterodimer chain 2 T(154)S L(156)A Y(197)T |
| 17 | PKTASTIESKTGECPKCPVPEIPGAPSVFIFP PKPKDTLSISRTPEVICLVVDLGPDDSNVQIT WFVDNTEMHTAKTRPREEQENSTYRVVSVLPI LHQDWLKGKEFKCKVNSKSLPSAMERTISKAK GQPHEPQVYVLPPTQEELSENKVSVTCLIKGF HPPDIAVEWEITGQPEPENNYQTTPPQLDSDG TYFLYSRLSVDRSHWQRGNTYTCSVSHEALHS HHTQKSLTQSPGK | Exemplary variant feline IgG2 Fc Hinge Cys G(14)C |
| 125 | *RKTDHPPGPKPCDCPKCPPPEMLGGP*SVFIFP PKPKDTLSISRTPEVTCLVVDLGPDDSNVQIT WFVDNTEMHTAKTRPREEQENSTYRVVSVLPI LHQDWLKGKEFKCKVNSKSLPSAMERTISKAK GQPHEPQVYVLPPTQEELSENKVSVTCLIKGF HPPDIAVEWEITGQPEPENNYQTTPPQLDSDG TYFLYSRLSVDRSHWQRGNTYTCSVSHEALHS HHTQKSLTQSPGK | Exemplary variant feline IgG2 Fc with feline IgG1 hinge |
| 126 | PKTASTIESKTGEGPPCPVPEIPGAPSVFIFP PKPKDTLSISRTPEVTCLVVDLGPDDSNVQIT WFVDNTEMHTAKTRPREEQENSTYRVVSVLPI LHQDWLKGKEFKCKVNSKSLPSAMERTISKAK GQPHEPQVYVLPPTQEELSENKVSVTCLIKGF HPPDIAVEWEITGQPEPENNYQTTPPQLDSDG TYFLYSRLSVDRSHWQRGNTYTCSVSHEALHS HHTQKSLTQSPGK | Exemplary variant feline IgG2 Fc with modified hinge K(16)P |
| 127 | RKTDHPPGPKPCDCPPCPPPEMLGGPSIFIFP PKPKDTLSISRTPEVTCLVVDLGPDDSDVQIT WFVDNIQVYTAKTSPREEQFNSTYRVVSVLPI LHQDWLKGKEFKCKVNSKSLPSPIERTISKAK GQPHEPQVYVLPPAQEELSENKVSVTCLIKSF HPPDIAVEWEITGQPEPENNYRTIPPQLDSDG TYFVYSKLSVDRSHWQRGNTYTCSVSHEALHS HHTQKSLTQSPGK | Exemplary variant feline IgG1a Fc with modified hinge K(16)P |
| 128 | RKTDHPPGPKPCDCPPCPPPEMLGGPSIFIFP PKPKDTLSISRTPEVTCLVVDLGPDDSDVQIT WFVDNIQVYTAKTSPREEQFNSTYRVVSVLPI LHQDWLKGKEFKCKVNSKSLPSPIERTISKDK GQPHEPQVYVLPPAQEELSENKVSVTCLIEGF YPSDIAVEWEITGQPEPENNYRTTPPQLDSDG TYFLYSRLSVDRSRWQRGNTYTCSVSHEALHS HHTQKSLTQSPGK | Exemplary variant feline IgG1b Fc with modified hinge K(16)P |
| 18 | *DMSKCPKCPAPELL*GGPSVFIFPPNPKDALMI SRTPVVTCVVVNLSDQYPDVQFSWYVDNTEVH SAITKQREAQFNSTYRVVSVLPIQHQDWLSGK EFKCSVTNVGVPQPISRAISRGKGPSRVPQVY VLPPHPDELAKSKVSVTCLVKDFYPPDISVEW QSNRWPELEGKYSTTPAQLDGDGSYFLYSKLS LETSRWQQVESFICAVMHEALHNHFIKTDISE SLGK | Exemplary variant equine Fc IgG2 (with equine IgG1 hinge) Protein A+ C1q- |

TABLE 1-continued

Table 1 provides a listing of exemplary sequences referenced herein.
Description of the Sequences

| SEQ ID NO: | SEQUENCE | DESCRIPTION |
|---|---|---|
| 19 | DMSKCPKCPAPELLGGPSVFIFPPNPKDTLMI SRTPVVTCVVVNLSDQYPDVQFSWYVDNTEVH SAITKQREAQFNSTYRVVSVLPIQHQDWLSGK EFKCSVTNVGVPQPISRAISRGKGPSRVPQVY VLPPHPDELAKSKVSVTCLVKDFYPPDISVEW QSNRWPELEGKYSTTPAQLDGDGSYFLYSKLS LETSRWQQVESFICAVMHEALHNHYTKTDISE SLGK | Exemplary variant equine IgG2 Fc (with equine IgG1 hinge) C1q- Protein A+ A(29)T F(217)Y |
| 20 | HXEGTFTSDVSSYLEGQAAKEFIAWLVKG | Exemplary variant GLP1 (7-35) X8 may be G or S |
| 21 | HSQGTFTSDYSKYLDSRRAQDFVQWLMNT | Glucagon (Gluc) |
| 22 | HGEGTFTSDLSKQMEEEAVRLFIEWLKNGGPS SGAPPPS | Extendin-4 |
| 23 | HGEGTFTSDVSSYLEGQAAKEFIAWLVKGGGG SGGGGSGGGGSGGGGSPKTASTIESKTGEGPK CPVPEIPGAPSVFIFPPKPKDTLSISRTPEVT CLVVDLGPDDSNVQITWFVDNTEMHTAKTRPR EEQFNSTYRVVSVLPILHQDWLKGKEFKCKVN SKSLPSAMERTISKAKGQPHEPQVYVLPPTQE ELSENKVSVTCLIKGFHPPDIAVEWEITGQPE PENNYQTTPPQLDSDGTYFLYSRLSVDRSHWQ RGNTYTCSVSHEALHSHHTQKSLTQSPGKGGG GSGGGGHAEGTFTSDVSSYLEGQAAKEFIAWL VKGGG | GLP1-G8/GLP-2G_III_ WTfeIgG2 |
| 24 | HGEGTFTSDVSSYLEGQAAKEFIAWLVKGGGG SGGGGSGGGGSGGGGSPKTASTIESKTGEGPK CPVPEIPGAPSVFIFPPKPKDTLSISRTPEVT CLVVDLGPDDSNVQITWFVDNTEMHTAKTRPR EEQFNSTYRVVSVLPILHQDWLKGKEFKCKVN SKSLPSAMERTISKAKGQPHEPQVYVLPPTQE ELSENKVSVTCLIKGFHPPDIAVEWEITGQPE PENNYQTTPPQLDSDGTYFLYSRLSVDRSHWQ RGNTYTCSVSHEALHSHHTQKSLTQSPGK | GLP1-G8_I_WTfeIgG2 |
| 25 | HGEGTFTSDVSSYLEGQAAKEFIAWLVKGGGG SGGGGSGGGGSGGGGSPKTASTIESKTGECPK CPVPEIPGAPSVFIFPPKPKDTLSISRTPEVT CLVVDLGPDDSNVQITWFVDNTEMHTAKTRPR EEQFNSTYRVVSVLPILHQDWLKGKEFKCKVN SKSLPSAMERTISKAKGQPHEPQVYVLPPTQE ELSENKVSVTCLIKGFHPPDIAVEWEITGQPE PENNYQTTPPQLDSDGTYFLYSRLSVDRSHWQ RGNTYICSVSHEALHSHHTQKSLTQSPGKGGG GSGGGGHAEGTFTSDVSSYLEGQAAKEFIAWL VKGGG | GLP1-G8/GLP1-2G_III_ VARfeIgG2 |
| 26 | HGEGTFTSDVSSYLEGQAAKEFIAWLVKGGGG SGGGGSGGGGSGGGGSPKTASTIESKTGECPK CPVPEIPGAPSVFIFPPKPKDTLSISRTPEVT CLVVDLGPDDSNVQITWFVDNTEMHTAKTRPR EEQFNSTYRVVSVLPILHQDWLKGKEFKCKVN SKSLPSAMERTISKAKGQPHEPQVYVLPPTQE ELSENKVSVTCLIKGFHPPDIAVEWEITGQPE PENNYQTTPPQLDSDGTYFLYSRLSVDRSHWQ RGNTYTCSVSHEALHSHHTQKSLTQSPGK | GLP1-G8_I_VARfeIgG2 |
| 27 | HSEGTFTSDVSSYLEGQAAKEFIAWLVKGGAG GGGGSGGGSGGGGSGGGGSPKTASTIESKTGEGP KCPVPEIPGAPSVFIFPPKPKDTLSISRTPEV TCLVVDLGPDDSNVQITWFVDNTEMHTAKTRP REEQFNSTYRVVSVLPILHQDWLKGKEFKCKV NSKSLPSAMERTISKAKGQPHEPQVYVLPPTQ EELSENKVSVTCLIKGFHPPDIAVEWEITGQP EPENNYQTTPPQLDSDGTYFLYSRLSVDRSHW QRGNTYTCSVSHEALHSHHTQKSLTQSPGKGG GGSGGGGHAEGTFTSDVSSYLEGQAAKEFIAW LVKGGGG | GLP1-S8/GLP1-3G_III_ WTfeIgG2 |

TABLE 1-continued

Table 1 provides a listing of exemplary sequences referenced herein.
Description of the Sequences

| SEQ ID NO: | SEQUENCE | DESCRIPTION |
|---|---|---|
| 28 | HSEGTFTSDVSSYLEGQAAKEFIAWLVKGGAG GGGGSGGGSGGGSGGGSPKTASTIESKTGEGP KCPVPEIPGAPSVFIFPPKPKDTLSISRTPEV TCLVVDLGPDDSNVQITWFVDNTEMHTAKTRP REEQFNSTYRVVSVLPILHQDWLKGKEFKCKV NSKSLPSAMERTISKAKGQPHEPQVYVLPPTQ EELSENKVSVTCLIKGFHPPDIAVEWEITGQP EPENNYQTTPPQLDSDGTYFLYSRLSVDRSHW QRGNTYTCSVSHEALHSHHTQKSLTQSPGK | GLP1-S8_I_WTfeIgG2 |
| 29 | HGEGTFTSDVSSYLEGQAAKEFIAWLVKGGAG GGGGSGGGSGGGSGGGSPKESTSKCISPCPVP ESLGGPSVFIFPPKPKDTLLIARTPEITCVVL DLGREDPEVQISWFVDGKEVHTAKTQPREQQF NSTYRVVSVLPIGHQDWLIGKEEKCRVNHIGL PSPIERTISKARGQAHQPSVYVLPPSPKELSS SDTVTLTCLIKDFFPPEIDVEWQSNGQPEPES KYHTTAPQLDEDGSYFLYSKLSVDKSRWQQGD TFTCAVMHEALHNHYTDLSLSHSPGKGGGGSG GGGHAEGTFTSDVSSYLEGQAAKEFIAWLVKG GGG | GLP1-G8/GLP1-3G_III_ VARcaIgGD |
| 30 | HGEGTFTSDVSSYLEGQAAKEFIAWLVKGGAG GGGGSGGGSGGGSGGGSPKESTCKCISPCPVP ESLGGPSVFIFPPKPKDTLLIARTPEITCVVL DLGREDPEVQISWFVDGKEVHTAKTQPREQQF NSTYRVVSVLPIGHQDWLIGKEEKCRVNHIGL PSPIERTISKARGQAHQPSVYVLPPSPKELSS SDTVTLTCLIKDFFPPEIDVEWQSNGQPEPES KYHTTAPQLDEDGSYFLYSKLSVDKSRWQQGD TFTCAVMHEALHNHYTDLSLSHSPGK | GLP1-G8_I_VARcaIgGD |
| 31 | HSEGTFTSDVSSYLEGQAAKEFIAWLVKGGAG GGGGSGGGSGGGSGGGSPKESTSKCISPCPVP ESLGGPSVFIFPPKPKDTLLIARTPEITCVVL DLGREDPEVQISWFVDGKEVHTAKTQPREQQF NSTYRVVSVLPIGHQDWLTGKEFKCRVNHIGL PSPIERTISKARGQAHQPSVYVLPPSPKELSS SDTVTLTCLIKDFFPPEIDVEWQSNGQPEPES KYHTTAPQLDEDGSYFLYSKLSVDKSRWQQGD TFTCAVMHEALHNHYTDLSLSHSPGKGGGGSG GGGHAEGTFTSDVSSYLEGQAAKEFIAWLVKG GGG | GLP1-88/GLP1-3G_III_ VARcaIgGD |
| 32 | HSEGTFTSDVSSYLEGQAAKEFIAWLVKGGAG GGGGSGGGSGGGSGGGSPKESTCKCISPCPVP ESLGGPSVFIFPPKPKDTLLIARTPEITCVVL DLGREDPEVQISWFVDGKEVHTAKTQPREQQF NSTYRVVSVLPIGHQDWLTGKEFKCRVNHIGL PSPIERTISKARGQAHQPSVYVLPPSPKELSS SDTVTLTCLIKDFFPPEIDVEWQSNGQPEPES KYHTTAPQLDEDGSYFLYSKLSVDKSRWQQGD TFTCAVMHEALHNHYTDLSLSHSPGK | GLP1-S8_I_VARcaIgGD |
| 33 | HGEGTFTSDVSSYLEGQAAKEFIAWLVKGGAG GGGGSGGGSGGGSGGGSDMSKCPKCPAPELLG GPSVFIFPPNPKDTLMISRTPVVICVVVNLSD QYPDVQFSWYVDNTEVHSAITKQREAQFNSTY RVVSVLPIQHQDWLSGKEFKCSVTNVGVPQPI SRAISRGKGPSRVPQVYVLPPHPDELAKSKVS VTCLVKDFYPPDISVEWQSNRWPELEGKYSTT PAQLDGDGSYFLYSKLSLETSRWQQVESFTCA VMHEALHNHYTKTDISESLGKGGGGSGGGGHA EGTFTSDVSSYLEGQAAKEFIAWLVKGGGG | GLP1-G8/GLPL1-3G_III_ VAReqIgG2 |
| 34 | HGEGTFTSDVSSYLEGQAAKEFIAWLVKGGAG GGGGSGGGSGGGSGGGSDMSKCPKCPAPELLG GPSVFIFPPNPKDTLMISRTPVVICVVVNLSD QYPDVQFSWYVDNTEVHSAITKQREAQFNSTY RVVSVLPIQHQDWLSGKEFKCSVTNVGVPQPI SRAISRGKGPSRVPQVYVLPPHPDELAKSKVS VTCLVKDFYPPDISVEWQSNRWPELEGKYSTT PAQLDGDGSYFLYSKLSLETSRWQQVESFTCA VMHEALHNHYTKTDISESLGK | GLP1-G8_I_VAReqIgG2 |

TABLE 1-continued

Table 1 provides a listing of exemplary sequences referenced herein.
Description of the Sequences

| SEQ ID NO: | SEQUENCE | DESCRIPTION |
|---|---|---|
| 35 | HSEGTFTSDVSSYLEGQAAKEFIAWLVKGGAG GGGGSGGGSGGGSGGGSDMSKCPKCPAPELLG GPSVFIFPPNPKDTLMISRTPVVICVVVNLSD QYPDVQFSWYVDNTEVHSAITKQREAQFNSTY RVVSVLPIQHQDWLSGKEFKCSVTNVGVPQPI SRAISRGKGPSRVPQVYVLPPHPDELAKSKVS VICLVKDFYPPDISVEWQSNRWPELEGKYSIT PAQLDGDGSYFLYSKLSLETSRWQQVESFTCA VMHEALHNHYTKTDISESLGKGGGGSGGGGHA EGTFTSDVSSYLEGQAAKEFIAWLVKGGGG | GLP1-88/GLP1-3G_III_VAReqIgG2 |
| 36 | HSEGTFTSDVSSYLEGQAAKEFIAWLVKGGAG GGGGSGGGSGGGSGGGSDMSKCPKCPAPELLG GPSVFIFPPNPKDTLMISRTPVVTCVVVNLSD QYPDVQFSWYVDNTEVHSAITKQREAQFNSTY RVVSVLPIQHQDWLSGKEFKCSVTNVGVPQPI SRAISRGKGPSRVPQVYVLPPHPDELAKSKVS VTCLVKDFYPPDISVEWQSNRWPELEGKYSTT PAQLDGDGSYFLYSKLSLETSRWQQVESFICA VMHEALHNHYTKTDISESLGK | GLP1-S8_I_VAReqIgG2 |
| 37 | MAVLGLLFCLVTFPSCVLSHSEGTFTSDVSSY LEGQAAKEFIAWLVKGGAGGGGGSGGGSGGGS GGGSPKTASTIESKTGEGPKCPVPEIPGAPSV FIFPPPKPKDTLSISRTPEVTCLVVDLGPDDSN VQITWFVDNTEMHTAKTRPREEQFNSTYRVVS VLPILHQDWLKGKEFKCKVNSKSLPSAMERTI SKAKGQPHEPQVYVLPPTQEELSENKVSVTCL IKGFHPPDIAVEWEITGQPEPENNYQTTPPQL DSDGTYFLYSRLSVDRSHWQRGNTYTCSVSHE ALHSHHTQKSLTQSPGKGGGGSGGGGHAEGTF TSDVSSYLEGQAAKEFIAWLVKGGGG | ssGLP1-S8/GLP1-3G_III_WTfeIgG2 |
| 38 | MAVLGLLFCLVTFPSCVLSHGEGTFTSDVSSY LEGQAAKEFIAWLVKGGGGSGGGGSGGGGSGG GGSPKTASTIESKTGECPKCPVPEIPGAPSVF IFPPPKPKDTLSISRTPEVICLVVDLGPDDSNV QITWFVDNTEMHTAKTRPREEQFNSTYRVVSV LPILHQDWLKGKEFKCKVNSKSLPSAMERTIS KAKGQPHEPQVYVLPPTQEELSENKVSVTCLI KGFHPPDIAVEWEITGQPEPENNYQTTPPQLD SDGTYFLYSRLSVDRSHWQRGNTYTCSVSHEA LHSHHTQKSLTQSPGKGGGGSGGGGHAEGTFT SDVSSYLEGQAAKEFIAWLVKGGG | ssGLP1-G8/GLP1-2G_III_VARfeIgG2 |
| 39 | MAVLGLLFCLVTFPSCVLSHGEGTFTSDVSSY LEGQAAKEFIAWLVKGGGGSGGGGSGGGGSGG GGSPKTASTIESKTGECPKCPVPEIPGAPSVF IFPPPKPKDTLSISRTPEVICLVVDLGPDDSNV QITWFVDNTEMHTAKTRPREEQFNSTYRVVSV LPILHQDWLKGKEFKCKVNSKSLPSAMERTIS KAKGQPHEPQVYVLPPTQEELSENKVSVTCLI KGFHPPDIAVEWEITGQPEPENNYQTTPPQLD SDGTYFLYSRLSVDRSHWQRGNTYTCSVSHEA LHSHHTQKSLTQSPGK | ssGLP1-G8_I_VARfeIgG2 |
| 40 | MAVLGLLFCLVTFPSCVLSHSEGTFTSDVSSY LEGQAAKEFIAWLVKGGAGGGGGSGGGSGGGS GGGSPKTASTIESKTGEGPKCPVPEIPGAPSV FIFPPPKPKDTLSISRTPEVTCLVVDLGPDDSN VQITWFVDNTEMHTAKTRPREEQFNSTYRVVS VLPILHQDWLKGKEFKCKVNSKSLPSAMERTI SKAKGQPHEPQVYVLPPTQEELSENKVSVTCL IKGFHPPDIAVEWEITGQPEPENNYQTTPPQL DSDGTYFLYSRLSVDRSHWQRGNTYTCSVSHE ALHSHHTQKSLTQSPGK | ssGLP1-S8_I_WTfeIgG2 |
| 41 | MAVLGLLFCLVTFPSCVLSHGEGIFTSDVSSY LEGQAAKEFIAWLVKGGGGSGGGGSGGGGSGG GGSPKESTCKCISPCPVPESLGGPSVFIFPPK PKDTLLIARTPEITCVVLDGREDPEVQISWF VDGKEVHTAKTQPREQQFNSTYRVVSVLPIGH QDWLTGKEFKCRVNHIGLPSPIERTISKARGQ | ssGLP1-G8/GLP1-2G_III_VARcaIgGD |

TABLE 1-continued

Table 1 provides a listing of exemplary sequences referenced herein.
Description of the Sequences

| SEQ ID NO: | SEQUENCE | DESCRIPTION |
|---|---|---|
|  | AHQPSVYVLPPSPKELSSSDTVTLTCLIKDFF PPEIDVEWQSNGQPEPESKYHTTAPQLDEDGS YFLYSKLSVDKSRWQQGDTFTCAVMHEALHNH YTDLSLSHSPGK*GGGGSGGGG*HAEGTFTSD̲VS SYLEGQAAKEFIAWLVKGGG |  |
| 42 | *MAVLGLLFCLVTFPSCVLS*HGEGIFTSDVSSY LEGQAAKEFIAWLVKGGGG*SGGGGSGGGGSGG GGS*PKESTSKCISPCPVPESLGGPSVFIFPPK PKDTLLIA̲RTPEITCVVLDLGREDPEVQISWF VDGKE̲VHTAKTQPREQQFNSTYRVVSVLPIGH QDWLTGKEFKCRVNHIGLPSPIERTISKARGQ AHQPSVYVLPPSPKELSSSDTVTLTCLIKDFF PPEIDVEWQSNGQPEPESKYHTTAPQLDEDGS YFLYSKLSVDKSRWQQGDTFTCAVMHEALHNH YTDLSLSHSPGK*GGGGSGGGG*HAEGTFTSD̲VS SYLEGQAAKEFIAWLVKGGG | ssGLP1-G8/GLP1-2G_III_ VARcaIgGD |
| 43 | *MAVLGLLFCLVTFPSCVLS*HSEGTFTSDVSSY LEGQAAKEFIAWLVKGGAGG̲GGGSGGGSGGGS GGGSPKESTSKCISPCPVPESLGGPSVFIFPP KPKDTLLIA̲RTPEITCVVLDLGREDPEVQISW FVDGKE̲VHTAKTQPREQQFNSTYRVVSVLPIG HQDWLTGKEFKCRVNHIGLPSPIERTISKARG QAHQPSVYVLPPSPKELSSSDTVTLTCLIKDF FPPEIDVEWQSNGQPEPESKYHTTAPQLDEDG SYFLYSKLSVDKSRWQQGDTFTCAVMHEALHN HYTDLSLSHSPGK*GGGGSGGGG*HAEGTFTSD̲V SSYLEGQAAKEFIAWLVKGGGG | ssGLP1-S8/GLP1-3G_III_ VARcaIgGD |
| 44 | *MAVLGLLFCLVTFPSCVLS*HGEGIFTSDVSSY LEGQAAKEFIAWLVKGGAGG̲GGGSGGGSGGGS GGGSDMSKCPKCPAPELLGGPSVFIFPPNPKD TLMISRIPVVICVVVNLSDQYPDVQFSWYVDN T̲EVHSAITKQREAQFNSTYRVVSVLPIQHQDW LSGKEFKCSVTNVGVPQPISRAISRGKGPSRV PQVYVLPPHPDELAKSKVSVTCLVKDFYPPDI SVEWQSNRWPELEGKYSTTPAQLDGDGSYFLY SKLSLETSRWQQVESFTCAVMHEALHNHYTKT DISESLGK*GGGGSGGGG*HAEGTFTSDVSS̲YLE GQAAKEFIAWLVKGGGG | ssGLP1-G8/GLP1-3G_III_ VAReqIgG2 |
| 45 | *MAVLGLLFCLVTFPSCVLS*HGEGIFTSDVSSY LEGQAAKEFIAWLVKGGAGG̲GGGSGGGSGGGS GGGSSVPKPQCPPYTHSKFLGGPSVFIFPPNP KDTLMISRTPVVICVVVNLSDQYPDVQFSWYV DNT̲EVHSAITKQREAQFNSTYRVVSVLPIQHQ DWLSGKEFKCSVTNVGVPQPISRAISRGKGPS RVPQVYVLPPHPDELAKSKVSVTCLVKDFYPP DISVEWQSNRWPELEGKYSITPAQLDGDGSYF LYSKLSLETSRWQQVESFTCAVMHEALHNHYT̲ KTDISESLGK | ssGLP1-G8_I_VAReqIgG2 |
| 46 | *MAVLGLLFCLVTFPSCVLS*HSEGTFTSDVSSY LEGQAAKEFIAWLVKGGAGG̲GGGSGGGSGGGS GGGSDMSKCPKCPAPELLGGPSVFIFPPNPKD TLMISRIPVVICVVVNLSDQYPDVQFSWYVDN T̲EVHSAITKQREAQFNSTYRVVSVLPIQHQDW LSGKEFKCSVTNVGVPQPISRAISRGKGPSRV PQVYVLPPHPDELAKSKVSVICLVKDFYPPDI SVEWQSNRWPELEGKYSTTPAQLDGDGSYFLY SKLSLETSRWQQVESFTCAVMHEALHNHYTKT DISESLGK*GGGGSGGGG*HAEGTFTSDVSS̲YLE GQAAKEFIAWLVKGGGG | ssGLP1-S8/GLP1-3G_III_ VAReqIgG2 |
| 47 | *MAVLGLLFCLVTFPSCVLS*HSEGIFTSDVSSY LEGQAAKEFIAWLVKGGAGGGGGS*GGGGSGGGS GGGS*S̲VPKPQCPPYTHSKFLGGPSVFIFPPNP KDTLMISRTPVVICVVVNLSDQYPDVQFSWYV DNT̲EVHSAITKQREAQFNSTYRVVSVLPIQHQ DWLSGKEFKCSVTNVGVPQPISRAISRGKGPS RVPQVYVLPPHPDELAKSKVSVICLVKDFYPP DISVEWQSNRWPELEGKYSITPAQLDGDGSYF | ssGLP1-S8_I_VAReqIgG2 |

TABLE 1-continued

Table 1 provides a listing of exemplary sequences referenced herein.
Description of the Sequences

| SEQ ID NO: | SEQUENCE | DESCRIPTION |
|---|---|---|
|  | LYSKLSLETSRWQQVESFTCAVMHEALHNHYTKTDISESLGK |  |
| 48 | MGLVAPVVLLHQDDEEHGQDEGPEDGSGYLLGTLTRFSSDFDSAPEVILAPDDQLQLPHPSSRENFWARTGLCAESFLLRPVGPVGPVMGWSEGFHKRNSRQEFLRRRLFAGGLCAASTQESRNRCSSRGCKSSPADCPELDRTQHLGNSVGPIQAAHQELALGAGGPGDECQCCSVSNSLFIPEPQSTCPYNGYTSWPLEGNLRVACAPPPPPARTLFGGSRRGAVDKKAGGGNRSPGGGAGTGEFGAPGAGGGLGRRPEVGAWTAAEGTNPADLASSPPPPSTRPPAAPRPPCADFCAASPQTTFPIPSP*RRPLPASGGATVSLSETVQKWREYRHQCQRFLTEAPPPATGLFCNRTFDEYACWPDGLPGSFVNVSCPWYLPWASSVLQGHVYRFCTAEGLWLRQDNSSLPWRNLSECEESKRGERSSPEEQLLSFS*IIYTVGYTLSFSALVIASAILLSFRHLHCTRNYIHLNLFASFILRALSVFIRDAVLKWMYSTAPQQHQWDGLLSYQDSLGCRLVFLLMQYCVAANYYWLLVEGVYLYILLAFSVESEQRIFRLYLSIGWGVPLLFVIWGIVKYLYEDEGCWTRNSNMNYWLIIRLPILFAIGVNFLIFVRVICIVVSKLKANLMCKTDIKCRLAKSTLTLIPLLGTHEVVFAFVMDEHARGTLRFIKLFTELSFTSFQGLMVAILYCFVNNEVQMEFRRSWERWRLKHLHIQRDSSMKPLKCPTSSLTSGGTVGSSVYAASCQASCS | Feline glucagon-like peptide 1 receptor (GLP1R) |
| 49 | RPLPASGGATVSLSETVQKWREYRHQCQRFLTEAPPPATGLFCNRTFDEYACWPDGLPGSFVNVSCPWYLPWASSVLQGHVYRFCTAEGLWLRQDNSSLPWRNLSECEESKRGERSSPEEQLLSFS | Mature feline glucagon-like peptide 1 receptor-N-terminal domain (GLP1R-N) |
| 50 | *METDTLLLWVLLLWVPGSTG*RPLPASGGATVSLSETVQKWREYRHQCQRFLTEAPPPATGLFCNRTFDEYACWPDGLPGSFVNVSCPWYLPWASSVLQGHVYRFCTAEGLWLRQDNSSLPWRNLSECEESKRGERSSPEEQLLSFSGSENLYFQGPKSCDKTHTCPPCPAPELLGGPSVFLFPPKPKDTLMISRIPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGKHHHHHH | ssFeGLP1R-N_huFc_PolyHis |
| 51 | *METDTLLLWVLLLWVPGSTG*RPLPASGGATVSLSETVQKWREYRHQCQRFLTEAPPPATGLFCNRTFDEYACWPDGLPGSFVNVSCPWYLPWASSVLQGHVYRFCTAEGLWLRQDNSSLPWRNLSECEESKRGERSSPEEQLLSFSGGGSHHHHHH | ssFeGLP1R-N_PolyHis |
| 52 | HGEGTFTSDVSSYLEGQAAKEFIAWLVKG*GGGSGGGGSGGGGSGGGGS*PKTASTIESKTGEGPKCPVPEIPGAPSVFIFPPKPKDTLSISRTPEVTCLVVDLGPDDSNVQITWFVDNTEMHTAKTRPREEQFNSTYRVVSVLPILHQDWLKGKEFKCKVNSKSLPSAMERTISKAKGQPHEPQVYVLPPTQEELSENKVSVTCLIKGFHPPDIAVEWEITGQPEPENNYQTTPPQLDSDGTYFLYSRLSVDRSHWQRGNTYICSVSHEALHSHHTQKSLTQSPGK*GGGSGGGG*HSQGTFTSDYSKYLDSRRAQDFVQWLMNT*GGG* | GLP1-G8/Gluc-3G_IV_WTfeIgG2 |
| 53 | HSQGTFTSDYSKYLDSRRAQDFVQWLMNT*GGGGSGGGGSGGGGSGGGGS*PKTASTIESKTGEGPKCPVPEIPGAPSVFIFPPKPKDTLSISRTPEVTCLVVDLGPDDSNVQITWFVDNTEMHTAKTRPREEQFNSTYRVVSVLPILHQDWLKGKEFKCKVNSKSLPSAMERTISKAKGQPHEPQVYVLPPTQEELSENKVSVTCLIKGFHPPDIAVEWEITGQPEPENNYQTTPPQLDSDGTYFLYSRLSVDRSHWQRGNTYICSVSHEALHSHHTQKSLTQSPGK*GG* | Gluc/GLP1-2G_V_WTfeIgG2 |

TABLE 1-continued

Table 1 provides a listing of exemplary sequences referenced herein.
Description of the Sequences

| SEQ ID NO: | SEQUENCE | DESCRIPTION |
|---|---|---|
| | *GGSGGGG*HAEGTFTSDVSSYLEGQAAKEFIAW LVKG*GG* | |
| 54 | HG̲EGTFTSDVSSYLEGQAAKEFIAWLVKG*AG GGGGSGGGSGGGSGGGS*PKESTSKCISPCPVP ESLGGPSVFIFPPKPKDTLLIAR̲TPEITCVVL DLGREDPEVQISWFVDGK̲EVHTAKTQPREQQF NSTYRVVSVLPIG̲HQDWLTGKEFKCRVNHIGL PSPIERTISKARG̲QAHQPSVYVLPPSPKELSS SDTVTLTCLIKDFFPPEIDVEWQSNGQPEPES KYHTTAPQLDEDGSYFLYSKLSVDKSRWQQGD TFTCAVMHEALHN̲HYTDLSLSHSPGK*GGGGSG GGG*HSQGTFTSD̲YSKYLDSRRAQDEVQWLMNT *GGGG* | GLP1-G8/Glu-4G_IV_VARcaIgGD |
| 55 | HSQGTFTSDYSKYLDSRRAQDFVQWLMNT*GAG GGGGSGGGSGGGSGGGS*PKESTSKCISPCPVP ESLGGPSVFIFPPKPKDTLLIAR̲TPEITCVVL DLGREDPEVQISWFVDGK̲EVHTAKTQPREQQF NSTYRVVSVLPIG̲HQDWLTGKEFKCRVNHIGL PSPIERTISKARG̲QAHQPSVYVLPPSPKELSS SDTVTLTCLIKDFFPPEIDVEWQSNGQPEPES KYHTTAPQLDEDGSYFLYSKLSVDKSRWQQGD TFTCAVMHEALHN̲HYTDLSLSHSPGK*GGGGSG GGG*HAEGTFTSD̲VSSYLEGQAAKEFIAWLVKG *GGG* | Gluc/GLP1-3G_V_VARcaIgGD |
| 56 | HG̲EGTFTSDVSSYLEGQAAKEFIAWLVKG*AG GGGGSGGGSGGGSGGGS*DMSKCPKCPAPELLG GPSVFIFPPNPKDTLMISRTPVVTCVVVNLSD QYPDVQFSWYVDNT̲EVHSAITKQREAQFNSTY RVVSVLPIQHQDWLSGKEFKCSVTNVGVPQPI SRAISRGKGPSRVPQVYVLPPHPDELAKSKVS VTCLVKDFYPPDISVEWQSNRWPELEGKYSTT PAQLDGDGSYFLYSKLSLETSRWQQVESFICA VMHEALHNHYTK̲TDISESLGK*GGGGSGGGG*HS QGTFTSDYSK̲YLDSRRAQDFVQWLMNT*GGGG* | Gluc/GLP1-3G_V_VAReqIgGD |
| 57 | HSQGTFTSDYSKYLDSRRAQDFVQWLMNT*GAG GGGGSGGGSGGGSGGGS*DMSKCPKCPAPELLG GPSVFIFPPNPKDTLMISRTPVVTCVVVNLSD QYPDVQFSWYVDNT̲EVHSAITKQREAQFNSTY RVVSVLPIQHQDWLSGKEFKCSVTNVGVPQPI SRAISRGKGPSRVPQVYVLPPHPDELAKSKVS VTCLVKDFYPPDISVEWQSNRWPELEGKYSTT PAQLDGDGSYFLYSKLSLETSRWQQVESFICA VMHEALHNHYTK̲TDISESLGK*GGGGSGGGG*HA EGTFTSDVSS̲YLEGQAAKEFIAWLVKG*GGG* | Gluc/GLP1-3G_V_VAReqIgG2 |
| 58 | HG̲EGTFTSDVSSYLEGQAAKEFIAWLVKG*AG GGGGSGGGSGGGSGGGS*ESKYGPPCPPCPAP EFLGGPSVFLFPPKPKDTLMISRTPEVICVVV DVSQEDPEVQFNWYVDGVEVHNAKTKPREEQF NSTYRVVSVLTVLHQDWLNGKEYKCKVSNKGL PSSIEKTISKAKGQPREPQVYTLPPSQEEMTK NQVSLTCLVKGFYPSDIAVEWESNGQPENNYK TTPPVLDSDGSFFLYSRLTVDKSRWQEGNVFS CSVMHEALHNHYTQKSLSLSLGK*GGGGSGGGG* HSQGTFTSDYSKYLDSRRAQDFVQWLMNT*GGG G* | GLP1-G8/Glu-4G_IV_huIgG4 |
| 59 | HSQGTFTSDYSKYLDSRRAQDFVQWLMNT*GGG GGSGGGSGGGSGGGSS*ESKYGPPCPPCPAPEF LGGPSVFLFPPKPKDTLMISRTPEVTCVVVDV SQEDPEVQFNWYVDGVEVHNAKTKPREEQFNS TYRVVSVLTVLHQDWLNGKEYKCKVSNKGLPS SIEKTISKAKGQPREPQVYTLPPSQEEMTKNQ VSLTCLVKGFYPSDIAVEWESNGQPENNYKTT PPVLDSDGSFFLYSRLTVDKSRWQEGNVFSCS VMHEALHNHYTQKSLSLSLGK*GGGGSGGGG*HA EGTFTSDVSSYLEGQAAKEFIAWLVKGGA*GGG G* | Gluc/GLP1-3G_V_huIgG4 |

TABLE 1-continued

Table 1 provides a listing of exemplary sequences referenced herein.
Description of the Sequences

| SEQ ID NO: | SEQUENCE | DESCRIPTION |
|---|---|---|
| 60 | PVPEPLGGPSVLIFPPKPKDTLRITRTPEVIC VVLDLGREDPEVQISWFVDGKEVHTAKTQSRE QQFNGTYRVVSVLPIEHQDWLTGKEFKCRVNH IDLPSPIERTISKARGRAHKPSVYVLPPSPKE LSSSDTVSITCLIKDFYPPDIDVEWQSNGQQE PERKHRMTPPQLDEDGSYFLYSKLSVDKSRWQ QGDPFTCAVMHETLHNHYTDLSLSHSPGK | Exemplary variant canine IgG-A Fc C1q- Protein A+ I(21)T Q(207)H |
| 61 | PGCGLLGGPSVFIFPPKPKDTLVTARTPTVTC VVVDLDPENPEVQISWFVDSKQVQTANTQPRE EQSNGTYRVVSVLPIGHQDWLSGKQFKCKVNN KALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc C1q+ Protein A+ I(21)T |
| 62 | PVPESLGGPSVFIFPPKPKDTLRITRTPEITC VVLDLGREDPEVQISWFVDGKEVHTAKTQPRE QQFNSTYRVVSVLPIEHQDWLTGKEFKCRVNH IGLPSPIERTISKARGQAHQPSVYVLPPSPKE LSSSDTVTLTCLIKDFFPPEIDVEWQSNGQPE PESKYHTTAPQLDEDGSYFLYSKLSVDKSRWQ QGDTFTCAVMHEALHNHYTDLSLSHSPGK | Exemplary variant canine IgG-D Fc C1q- Protein A+ I(21)T Q(207)H |
| 63 | GGPSVFLFPPNPKDILMITRIPEVICVVDVS QENPDVKFNWYMDGVEVRTATTRPKEEQFNST YRVVSVLRIQHQDWLSGKEFKCKVNNQALPQP IERTITKTKGRSQEPQVYVLAPHPDESKKSKV SVTCLVKDFYPPEINIEWSNGQPELETKYST TQAQQDSDGSYFLYSKLSVDRNRWQQGTTFTC GVMHEALHNHYTQKNVSKNPGK | Exemplary wild-type equine IgG1 Fc Protein A+ C1q+ |
| 64 | GGPSVFIFPPNPKDALMISRTPVVTCVVVNLS DQYPDVQFSWYVDNTEVHSAITKQREAQFNST YRVVSVLPIQHQDWLSGKEFKCSVTNVGVPQP ISRAISRGKGPSRVPQVYVLPPHPDELAKSKV SVTCLVKDFYPPDISVEWQSNRWPELEGKYST TPAQLDGDGSYFLYSKLSLETSRWQQVESFTC AVMHEALHNHFTKTDISESLGK | Exemplary wild-type equine IgG2 Fc Protein A- C1q- |
| 65 | GGPSVFIFPPKPKDVLMITRMPEVTCLVVDVS HDSSDVLFTWYVDGTEVKTAKTMPNEEQNNST YRVVSVLRIQHQDWLNGKKFKCKVNNQALPAP VERTISKATGQTRVPQVYVLAPHPDELSKNKV SVTCLVKDFYPPDITVEWQSNEHPEPEGKYRT TEAQKDSDGSYFLYSKLTVEKDRWQQGTTFTC VVMHEALHNHVMQKNISKNPGK | Exemplary wild-type equine IgG3 Fc Protein A+ C1q+ |
| 66 | VGPSVFIFPPKPKDVLMISRTPTVTCVVVDVG HDFPDVQFNWYVDGVETHTATTEPKQEQFNST YRVVSVLPIQHKDWLSGKEFKCKVNNKALPAP VERTISAPTGQPREPQVYVLAPHRDELSKNKV SVTCLVKDFYPPDIDIEWKSNGQPEPETKYST TPAQLDSDGSYFLYSKLTVETNRWQQGTTFTC AVMHEALHNHYTEKSVSKSPGK | Exemplary wild-type equine IgG4 Fc Protein A+ C1q+ |
| 67 | GGPSVFIFPPKPKDVLMISRKPEVTCVVVDLG HDDPDVQFTWFVDGVETHTATTEPKEEQFNST YRVVSVLPIQHQDWLSGKEFKCSVTSKALPAP VERTISKAKGQLRVPQVYVLAPHPDELAKNTV SVTCLVKDFYPPEIDVEWQSNEHPEPEGKYST TPAQLNSDGSYFLYSKLSVETSRWKQGESFTC GVMHEAVENHYTQKNVSHSPGK | Exemplary wild-type equine IgG5 Fc Protein- C1q- |
| 68 | GRPSVFIFPPNPKDTLMISRTPEVTCVVVDVS QENPDVKFNWYVDGVEAHTATTKAKEKQDNST YRVVSVLPIQHQDWRRGKEFKCKVNNRALPAP VERTITKAKGELQDPQVYILAPHPDEVTKNTV SVTCLVKDFYPPDINVEWQSNEEPEPEVKYST TPAQLDGDGSYFLYSKLTVETDRWEQGESFTC VVMHEAIRHTYRQKSITNFPGK | Exemplary wild-type equine IgG6 Fc Protein A- C1q- |

TABLE 1-continued

Table 1 provides a listing of exemplary sequences referenced herein.
Description of the Sequences

| SEQ ID NO: | SEQUENCE | DESCRIPTION |
| --- | --- | --- |
| 69 | VGPSVFIFPPKPKDVLMISRTPTVICVVVDVG HDFPDVQFNWYVDGVETHTATTEPKQEQNNST YRVVSILAIQHKDWLSGKEFKCKVNNQALPAP VQKTISKPTGQPREPQVYVLAPHPDELSKNKV SVTCLVKDFYPPDIDIEWKSNGQPEPETKYST TPAQLDGDGSYFLYSKLTVETNRWQQGTTFTC AVMHEALHNHYTEKSVSKSPGK | Exemplary wild-type equine IgG7 Fc Protein A+ C1q+ |
| 70 | GGPSVFLFPPNPKDILMITRIPEVICVVVDVS QENPDVKFNWYMDGVEVRTATTRPKEEQFNST YRVVSVLRIQHQDWLSGKEFKCSVNNQALPQP IERTITKTKGRSQEPQVYVLAPHPDESKKSKV SVTCLVKDFYPPEINIEWQSNGQPELETKYST TQAQQDSDGSYFLYSKLSVDRNRWQQGTTFTC GVMHEALHNHYTQKNVSKNPGK | Exemplary variant equine IgG1 Fc Protein A+ C1q- K(87)S |
| 71 | GGPSVFIFPPNPKDALMISRTPVVICVVVNLS DQYPDVQFSWYVDNTEVHSAITKQREAQFNST YRVVSVLPIQHQDWLSGKEFKCSVTNVGVPQP ISRAISRGKGPSRVPQVYVLPPHPDELAKSKV SVTCLVKDFYPPDISVEWQSNRWPELEGKYST TPAQLDGDGSYFLYSKLSLETSRWQQESFTC AVMHEALHNHYTKTDISESLGK | Exemplary variant equine IgG2 Fc C1q- Protein A+ F(203)Y |
| 72 | GGPSVFIFPPNPKDTLMISRTPVVICVVVNLS DQYPDVQFSWYVDNTEVHSAITKQREAQFNST YRVVSVLPIQHQDWLSGKEFKCSVTNVGVPQP ISRAISRGKGPSRVPQVYVLPPHPDELAKSKV SVTCLVKDFYPPDISVEWQSNRWPELEGKYST TPAQLDGDGSYFLYSKLSLETSRWQQVESFTC AVMHEALHNHYTKTDISESLGK | Exemplary variant equine IgG2 Fc C1q- Protein A+ A(15)T F(203)Y |
| 129 | PPCVLSAEGVIPIPSVPKPQCPPYTHSKFLGG PSVFIFPPNPKDALMISRTPVVTCVVVNLSDQ YPDVQFSWYVDNTEVHSAITKQREAQFNSTYR VVSVLPIQHQDWLSGKEFKCSVTNVGVPQPIS RAISRGKGPSRVPQVYVLPPHPDELAKSKVSV TCLVKDFYPPDISVEWQSNRWPELEGKYSTTP AQLDGDGSYFLYSKLSLETSRWQQVESFTCAV MHEALHNHFTKTDISESLGK | Exemplary wild-type equine IgG2 Fc with hinge Protein A- C1q- |
| 130 | PPCVLSAEGVIPIPSVPKPPCPPYTHSKFLGG PSVFIFPPNPKDALMISRTPVVTCVVVNLSDQ YPDVQFSWYVDNTEVHSAITKQREAQFNSTYR VVSVLPIQHQDWLSGKEFKCSVTNVGVPQPIS RAISRGKGPSRVPQVYVLPPHPDELAKSKVSV TCLVKDFYPPDISVEWQSNRWPELEGKYSTTP AQLDGDGSYFLYSKLSLETSRWQQVESFTCAV MHEALHNHFTKTDISESLGK | Exemplary variant equine IgG2 Fc with modified hinge Protein A- C1q- Q(20)P |
| 131 | PPSVLSAEGVIPIPSVPKPQCPPYTHSKFLGG PSVFIFPPNPKDALMISRTPVVTCVVVNLSDQ YPDVQFSWYVDNTEVHSAITKQREAQFNSTYR VVSVLPIQHQDWLSGKEFKCSVTNVGVPQPIS RAISRGKGPSRVPQVYVLPPHPDELAKSKVSV TCLVKDFYPPDISVEWQSNRWPELEGKYSTTP AQLDGDGSYFLYSKLSLETSRWQQVESFTCAV MHEALHNHFTKTDISESLGK | Exemplary variant equine IgG2 Fc with modified hinge Protein A- C1q- C(3)S |
| 132 | PPSVLSAEGVIPIPSVPKPPCPPYTHSKFLGG PSVFIFPPNPKDALMISRTPVVTCVVVNLSDQ YPDVQFSWYVDNTEVHSAITKQREAQFNSTYR VVSVLPIQHQDWLSGKEFKCSVTNVGVPQPIS RAISRGKGPSRVPQVYVLPPHPDELAKSKVSV TCLVKDFYPPDISVEWQSNRWPELEGKYSTTP AQLDGDGSYFLYSKLSLETSRWQQVESFICAV MHEALHNHFTKTDISESLGK | Exemplary variant equine IgG2 Fc with modified hinge Protein A- C1q- C(3)S Q(20)P |
| 133 | PPCVLSAEGVIPIPSVPKPQCPPYTHSKFLGG PSVFIFPPNPKDTLMISRTPVVICVVVNLSDQ YPDVQFSWYVDNTEVHSAITKQREAQFNSTYR VVSVLPIQHQDWLSGKEFKCSVTNVGVPQPIS RAISRGKGPSRVPQVYVLPPHPDELAKSKVSV | Exemplary variant equine IgG2 Fc with hinge Protein A+ C1q- A(45)T |

TABLE 1-continued

Table 1 provides a listing of exemplary sequences referenced herein.
Description of the Sequences

| SEQ ID NO: | SEQUENCE | DESCRIPTION |
|---|---|---|
|  | TCLVKDFYPPDISVEWQSNRWPELEGKYSTTP<br>AQLDGDGSYFLYSKLSLETSRWQQVESFICAV<br>MHEALHNHYTKTDISESLGK | F(233)Y |
| 134 | PPCVLSAEGVIPIPSVPKPPCPPYTHSKFLGG<br>PSVFIFPPNPKDTLMISRTPVVTCVVVNLSDQ<br>YPDVQFSWYVDNTEVHSAITKQREAQFNSTYR<br>VVSVLPIQHQDWLSGKEFKCSVTNVGVPQPIS<br>RAISRGKGPSRVPQVYVLPPHPDELAKSKVSV<br>TCLVKDFYPPDISVEWQSNRWPELEGKYSTTP<br>AQLDGDGSYFLYSKLSLETSRWQQVESFICAV<br>MHEALHNHYTKTDISESLGK | Exemplary variant equine<br>IgG2 Fc with modified hinge<br>Protein A+<br>C1q-<br>Q(20)P<br>A(45)T<br>F(233)Y |
| 135 | PPSVLSAEGVIPIPSVPKPPCPPYTHSKFLGG<br>PSVFIFPPNPKDTLMISRTPVVTCVVVNLSDQ<br>YPDVQFSWYVDNTEVHSAITKQREAQFNSTYR<br>VVSVLPIQHQDWLSGKEFKCSVTNVGVPQPIS<br>RAISRGKGPSRVPQVYVLPPHPDELAKSKVSV<br>TCLVKDFYPPDISVEWQSNRWPELEGKYSTTP<br>AQLDGDGSYFLYSKLSLETSRWQQVESFICAV<br>MHEALHNHYTKTDISESLGK | Exemplary variant equine<br>IgG2 Fc with modified hinge<br>Protein A+<br>C1q-<br>C(3)S<br>Q(20)P<br>A(45)T<br>F(233)Y |
| 73 | GGPSVFIFPPKPKDVLMITRMPEVTCLVVDVS<br>HDSSDVLFTWYVDGTEVKTAKTMPNEEQNNST<br>YRVVSVLRIQHQDWLNGKKFKCSVNNQALPAP<br>VERTISKATGQTRVPQVYVLAPHPDELSKNKV<br>SVTCLVKDFYPPDITVEWQSNEHPEPEGKYRT<br>TEAQKDSDGSYFLYSKLTVEKDRWQQGTTFTC<br>VVMHEALHNHVMQKNISKNPGK | Exemplary variant equine<br>IgG3 Fc<br>Protein A+<br>C1q-<br>K(87)S |
| 74 | VGPSVFIFPPKPKDVLMISRTPTVTCVVVDVG<br>HDFPDVQFNWYVDGVETHTATTEPKQEQFNST<br>YRVVSVLPIQHKDWLSGKEFKCSVNNKALPAP<br>VERTISAPTGQPREPQVYVLAPHRDELSKNKV<br>SVTCLVKDFYPPDIDIEWKSNGQPEPETKYST<br>TPAQLDSDGSYFLYSKLTVETNRWQQGTTFTC<br>AVMHEALHNHYTEKSVSKSPGK | Exemplary variant equine<br>IgG4 Fc<br>Protein A+<br>C1q-<br>K(87)S |
| 75 | GGPSVFIFPPKPKDVLMISRKPEVTCVVVDLG<br>HDDPDVQFTWFVDGVETHTATTEPKEEQFNST<br>YRVVSVLPIQHQDWLSGKEFKCSVTSKALPAP<br>VERTISKAKGQLRVPQVYVLAPHPDELAKNTV<br>SVTCLVKDFYPPEIDVEWQSNEHPEPEGKYST<br>TPAQLNSDGSYFLYSKLSVETSRWKQGESFTC<br>GVMHEALHNHYTQKNVSHSPGK | Exemplary variant equine<br>IgG5 Fc<br>C1q-<br>Protein A+<br>V(199)L<br>E(200)H |
| 76 | GRPSVFIFPPNPKDTLMISRTPEVTCVVVDVS<br>QENPDVKFNWYVDGVEAHTATTKAKEKQDNST<br>YRVVSVLPIQHQDWRRGKEFKCKVNNRALPAP<br>VERTITKAKGELQDPQVYILAPHPDEVTKNTV<br>SVTCLVKDFYPPDINVEWQSNEEPEPEVKYST<br>TPAQLDGDGSYFLYSKLTVETDRWEQGESFTC<br>VVMHEALHNHYRQKSITNFPGK | Exemplary variant equine<br>IgG6 Fc<br>C1q-<br>Protein A+<br>I(199)L<br>R(200)H<br>H(201)N<br>T(202)H |
| 77 | VGPSVFIFPPKPKDVLMISRTPTVTCVVVDVG<br>HDFPDVQFNWYVDGVETHTATTEPKQEQNNST<br>YRVVSILAIQHKDWLSGKEFKCSVNNQALPAP<br>VQKTISKPTGQPREPQVYVLAPHPDELSKNKV<br>SVTCLVKDFYPPDIDIEWKSNGQPEPETKYST<br>TPAQLDGDGSYFLYSKLTVETNRWQQGTTFTC<br>AVMHEALHNHYTEKSVSKSPGK | Exemplary variant equine<br>IgG7 Fc<br>Protein A+<br>C1q-<br>K(87)S |
| 78 | PAPEMLGGPSVFIFPPKPKDTLLIARTPEVTC<br>VVVDLDPEDPEVQISWFVDGKQMQTAKTQPRE<br>EQFNGTYRVVSVLPIGHQDWLKGKQFTCRVNN<br>KALPSPIERTISKARGQAHQPSVYVLPPSREE<br>LSKNTVSLTCLIKDFFPPDIDVEWQSNGQQEP<br>ESKYRTTPPQLDEDGSYFLYSKLSVDKSRWQR<br>GDTFICAVMHEALHNHYTQESLSHSPGK | Exemplary variant canine<br>IgG-B Fc<br>Protein A+<br>C1q-<br>K(93)R |
| 79 | PGCGLLGGPSVFIFPPKPKDILVTARTPTVTC<br>VVVDLDPENPEVQISWFVDSKQVQTANTQPRE<br>EQSNGTYRVVSVLPIGHQDWLSGKQFKCRVNN | Exemplary variant canine<br>IgG-C Fc<br>Protein A- |

TABLE 1-continued

Table 1 provides a listing of exemplary sequences referenced herein.
Description of the Sequences

| SEQ ID NO: | SEQUENCE | DESCRIPTION |
|---|---|---|
| | KALPSPIEEIISKTPGQAHQPNVYVLPPSRDE<br>MSKNTVTLTCLVKDFFPPEIDVEWQSNGQQEP<br>ESKYRMTPPQLDEDGSYFLYSKLSVDKSRWQR<br>GDTFICAVMHEALHNHYTQISLSHSPGK | C1q-<br>K(93)R |
| 80 | RKTDHPPGPKTGEGPKCPPPEMLGGPSIFIFP<br>PKPKDTLSISRTPEVTCLVVDLGPDDSDVQIT<br>WFVDNTQVYTAKTSPREEQFNSTYRVVSVLPI<br>LHQDWLKGKEEKCKVNSKSLPSPIERTISKAK<br>GQPHEPQVYVLPPAQEELSENKVSVTCLIKSF<br>HPPDIAVEWEITGQPEPENNYRTIPPQLDSDG<br>TYFVYSKLSVDRSHWQRGNTYTCSVSHEALHS<br>HHTQKSLTQSPGK | Exemplary wild-type feline<br>IgG1a Fc<br>Protein A+<br>C1q+ |
| 81 | RKTDHPPGPKTGEGPKCPPPEMLGGPSIFIFP<br>PKPKDTLSISRTPEVICLVVDLGPDDSDVQIT<br>WFVDNIQVYTAKTSPREEQFNSTYRVVSVLPI<br>LHQDWLKGKEEKCKVNSKSLPSPIERTISKDK<br>GQPHEPQVYVLPPAQEELSENKVSVTCLIEGF<br>YPSDIAVEWEITGQPEPENNYRTIPPQLDSDG<br>TYFLYSRLSVDRSRWQRGNTYTCSVSHEALHS<br>HHTQKSLTQSPGK | Exemplary wild-type feline<br>IgG1b Fc<br>Protein A+<br>C1q+ |
| 136 | RKTDHPPGPKPCDCPKCPPPEMLGGPSIFIFP<br>PKPKDTLSISRTPEVICLVVDLGPDDSDVQIT<br>WFVDNIQVYTAKTSPREEQFNSTYRVVSVLPI<br>LHQDWLKGKEEKCKVNSKSLPSPIERTISKAK<br>GQPHEPQVYVLPPAQEELSENKVSVICLIKSF<br>HPPDIAVEWEITGQPEPENNYRTIPPQLDSDG<br>TYFVYSKLSVDRSHWQRGNTYTCSVSHEALHS<br>HHTQKSLTQSPGK | Exemplary variant feline<br>IgG1a Fc<br>Protein A+<br>C1q-<br>P(198)A |
| 82 | RKTDHPPGPKTGEGPKCPPPEMLGGPSIFIFP<br>PKPKDTLSISRTPEVICLVVDLGPDDSDVQIT<br>WFVDNIQVYTAKTSPREEQFNSTYRVVSVLPI<br>LHQDWLKGKEEKCKVNSKSLPSPIERTISKAK<br>GQPHEPQVYVLPPAQEELSENKVSVICLIKSF<br>HPPDIAVEWEITGQPEPENNYRTIPPQLDSDG<br>TYFVYSKLSVDRSHWQRGNTYTCSVSHEALHS<br>HHTQKSLTQSPGK | Exemplary variant feline<br>IgG1a Fc<br>Protein A+<br>C1q-<br>P(198)A |
| 137 | RKTDHPPGPKPCDCPKCPPPEMLGGPSIFIFP<br>PKPKDTLSISRTPEVICLVVDLGPDDSDVQIT<br>WFVDNIQVYTAKTSPREEQFNSTYRVVSVLPI<br>LHQDWLKGKEEKCKVNSKSLPSPIERTISKDK<br>GQPHEPQVYVLPPAQEELSENKVSVTCLIEGF<br>YPSDIAVEWEITGQPEPENNYRTIPPQLDSDG<br>TYFLYSRLSVDRSRWQRGNTYTCSVSHEALHS<br>HHTQKSLTQSPGK | Exemplary variant feline<br>IgG1b Fc<br>Protein A+<br>C1q-<br>P(198)A |
| 83 | RKTDHPPGPKTGEGPKCPPPEMLGGPSIFIFP<br>PKPKDTLSISRTPEVICLVVDLGPDDSDVQIT<br>WFVDNIQVYTAKTSPREEQFNSTYRVVSVLPI<br>LHQDWLKGKEEKCKVNSKSLPSPIERTISKDK<br>GQPHEPQVYVLPPAQEELSENKVSVTCLIEGF<br>YPSDIAVEWEITGQPEPENNYRTIPPQLDSDG<br>TYFLYSRLSVDRSRWQRGNTYTCSVSHEALHS<br>HHTQKSLTQSPGK | Exemplary variant feline<br>IgG1b Fc<br>Protein A+<br>C1q-<br>P(198)A |
| 84 | PGCGLLGGPSVFIFPPKPKDTLLIARTPTVTC<br>VVVDLDPENPEVQISWFVDSKQVQTANTQPRE<br>EQSNGTYRVVSVLPIGHQDWLSGKQEKCRVNN<br>KALPSPIEEIISKTPGAHQPNVYVLPPSRDE<br>MSKNTVTLTCLVKDFFPPEIDVEWQSNGQQEP<br>ESKYRMTPPQLDEDGSYFLYSKLSVDKSRWQR<br>GDTFICAVMHEALHNHYTQISLSHSPGK | Exemplary variant canine<br>IgG-C Fc<br>C1q-<br>K(93)R<br>Protein A+<br>I(21)T<br>V(23)L<br>T(24)I |
| 85 | HAEGTFTSDVSSYLEGQAAKEFIAWLVKGAG | Wild-type GLP1 (7-37) |
| 86 | HSEGTFTSDVSSYLEGQAAKEFIAWLVKG | GLP1-S8 (7-35) |
| 87 | HGEGTFTSDVSSYLEGQAAKEFIAWLVKG | GLP1-G8 (7-35) |

TABLE 1-continued

Table 1 provides a listing of exemplary sequences referenced herein.
Description of the Sequences

| SEQ ID NO: | SEQUENCE | DESCRIPTION |
|---|---|---|
| 88 | G | 1G extension |
| 89 | GG | 2G extension |
| 90 | GGG | 3G extension |
| 91 | GGGG | 4G extension |
| 92 | GGGGG | 5G extension |
| 93 | GGGGGG | 6G extension |
| 94 | GGGGGGG | 7G extension |
| 95 | GGGGGGGG | 8G extension |
| 96 | *MAVLGLLFCLVTFPSCVLSH*GEGIFTSDVSSY LEGQAAKEFIAWLVKG*GAGGGGGSGGGSGGGS GGGS*PKTASTIESKTGEGPKCPVPEIPGAPSV FIFPPPKPKDTLSISRTPEVTCLVVDLGPDDSN VQITWFVDNTEMHTAKTRPREEQFNSTYRVVS VLPILHQDWLKGKEFKCKVNSKSLPSAMERTI SKAKGQPHEPQVYVLPPTQEELSENKVSVTCL IKGFHPPDIAVEWEITGQPEPENNYQTTPPQL DSDGTYFLYSRLSVDRSHWQRGNTYTCSVSHE ALHSHHTQKSLTQSPGK | ssGLP1-G8_I_WTfeIgG2 |
| 97 | *MAVLGLLFCLVTFPSCVLSH*GEGIFTSDVSSY LEGQAAKEFIAWLVKG*GAGGGGGSGGGSGGGS GGGS*PKTASTIESKTGEGPKCPVPEIPGAPSV FIFPPPKPKDTLSISRTPEVTCLVVDLGPDDSN VQITWFVDNTEMHTAKTRPREEQFNSTYRVVS VLPILHQDWLKGKEFKCKVNSKSLPSAMERTI SKAKGQPHEPQVYVLPPTQEELSENKVSVTCL IKGFHPPDIAVEWEITGQPEPENNYQTTPPQL DSDGTYFLYSRLSVDRSHWQRGNTYTCSVSHE ALHSHHTQKSLTQSPGK*GGGGSGGGG*HAEGTF TSDVSSYLEGQAAKEFIAWLVKG*GGG* | ssGLP1-G8/GLP1-3G_III_WTfeIgG2 |
| 98 | HAEGTFTSDVSSYLEGQAAKEFIAWLVKGA | Variant GLP1 (7-36) |
| 99 | HAEGTFTSDVSSYLEGQAAKEFIAWLVKG | Variant GLP1 (7-35) |
| 100 | *VPKPQCPPYTHSKFL*GGPSVFIFPPNPKDALM ISRTPVVTCVVVNLSDQYPDVQFSTNYVDNTEV HSAITKQREAQFNSTYRVVSVLPIQHQDWLSG KEFKCSVTNVGVPQPISRAISRGKGPSRVPQV YVLPPHPDELAKSKVSVTCLVKDFYPPDISVE WQSNRWPELEGKYSTTPAQLDGDGSYFLYSKL SLETSRWQQVESFTCAVMHEALHNHFIKTDIS ESLGK | Exemplary wild-type equine Fc IgG2 (including equine IgG2 hinge) Protein-C1q- |
| 101 | DMSKCPKCPAPELL | Exemplary wild-type equine IgG1 hinge |
| 102 | VPKPQCPPYTHSKFL | Exemplary wild-type equine IgG2 hinge |
| 138 | PPCVLSAEGVIPIPSVPKPQCPPYTHSKFL | Exemplary wild-type equine IgG2 hinge |
| 103 | HGEGTFTSDVSSYLEGQAAKEFIAWLVKG*AG GGGGSGGGSGGGSGGGS*DMSKCPKCPAPELLG GPSVFIFPPNPKDTLMISRTPVVICVVVNLSD QYPDVQFSWYVDNTEVHSAITKQREAQFNSTY RVVSVLPIQHQDWLSGKEFKCSVTNVGVPQPI SRAISRGKGPSRVPQVYVLPPHPDELAKSKVS VTCLVKDFYPPDISVEWQSNRWPELEGKYSTT PAQLDGDGSYFLYSKLSLETSRWQQVESFTCA VMHEALHNHYTKTDISESLGK*GGGGSGGGG*HA EGTFTSDVSSYLEGQAAKEFIAWLVKG*GGG* | GLP1-G8/GLP1-3G_III_VAReqIgG2 |
| 104 | HGEGTFTSDVSSYLEGQAAKEFIAWLVKG*AG GGGSGGGSGGGSGGGSS*VPKPQCPPYTHSKF | GLP1-G8_I_VAReqIgG2 |

TABLE 1-continued

Table 1 provides a listing of exemplary sequences referenced herein.
Description of the Sequences

| SEQ ID NO: | SEQUENCE | DESCRIPTION |
|---|---|---|
| | LGGPSVFIFPPNPKDTLMISRTPVVTCVVVNL SDQYPDVQFSWYVDNTEVHSAITKQREAQFNS TYRVVSVLPIQHQDWLSGKEFKCSVTNVGVPQ PISRAISRGKGPSRVPQVYVLPPHPDELAKSK VSVTCLVKDFYPPDISVEWQSNRWPELEGKYS TTPAQLDGDSYFLYSKLSLETSRWQQVESFT CAVMHEALHNHYTKTDISESLGK | |
| 105 | HGEGTFTSDVSSYLEGQAAKEFIAWLVKGGGG SGGGGSGGGGSGGGGSPKESTCKCISPCPVPE SLGGPSVFIFPPPKPKDTLLIARTPEITCVVLD LGREDPEVQISWFVDGKEVHTAKTQPREQQFN STYRVVSVLPIGHQDWLTGKEFKCRVNHIGLP SPIERTISKARGQAHQPSVYVLPPSPKELSSS DTVTLTCLIKDFFPPEIDVEWQSNGQPEPESK YHTTAPQLDEDGSYFLYSKLSVDKSRWQQGDT FTCAVMHEALHNHYTDLSLSHSPGK*GGGGSGG GG*HAEGTFTSDVSSYLEGQAAKEFIAWLVKGG G | GLP1-G8/GLP1-2G_III_ VARcaIgGD |
| 106 | HGEGTFTSDVSSYLEGQAAKEFIAWLVKGGGG SGGGGSGGGGSGGGGSPKESTSKCISPCPVPE SLGGPSVFIFPPPKPKDTLLIARTPEITCVVLD LGREDPEVQISWFVDGKEVHTAKTQPREQQFN STYRVVSVLPIGHQDWLTGKEFKCRVNHIGLP SPIERTISKARGQAHQPSVYVLPPSPKELSSS DTVTLTCLIKDFFPPEIDVEWQSNGQPEPESK YHTTAPQLDEDGSYFLYSKLSVDKSRWQQGDT FTCAVMHEALHNHYTDLSLSHSPGK*GGGGSGG GG*HAEGTFTSDVSSYLEGQAAKEFIAWLVKGG G | GLP1-G8/GLP1-2G_III_ VARcaIgGD |
| 139 | PAPEPLGGPSVFIFPPKPKDTLLTARTPEVIC VVVDLDPEDPEVQISWFVDGKQMQTAKTQPRE EQFNGTYRVVSVLPIGHQDWLKGKQFTCKVNN KALPSPIERTISKARGQAHQPSVYVLPPSREE LSKNTVSLTCLIKDFFPPDIDVEWQSNGQQEP ESKYRTTPPQLDEDGSYFLYSKLSVDKSRWQR GDTFICAVMHEALHNHYTQESLSHSPGK | Exemplary variant canine IgG-B Fc Protein A+ C1q+ CD16- M(5)P |
| 140 | PAPEMLGGPSVFIFPPKPKDILLIARTPEVIC VVVDLDREDPEVQISWFVDGKQMQTAKTQPRE EQFNGTYRVVSVLPIGHQDWLKGKQFTCKVNN KALPSPIERTISKARGQAHQPSVYVLPPSREE LSKNTVSLTCLIKDFFPPDIDVEWQSNGQQEP ESKYRTIPPQLDEDGSYFLYSKLSVDKSRWQR GDTFICAVMHEALHNHYTQESLSHSPGK | Exemplary variant canine IgG-B Fc Protein A+ C1q+ CD16- P(39)R |
| 141 | PAPEMLGGPSVFIFPPKPKDILLIARTPEVIC VVVDLGPEDPEVQISWFVDGKQMQTAKTQPRE EQFNGTYRVVSVLPIGHQDWLKGKQFTCKVNN KALPSPIERTISKARGQAHQPSVYVLPPSREE LSKNTVSLTCLIKDFFPPDIDVEWQSNGQQEP ESKYRTIPPQLDEDGSYFLYSKLSVDKSRWQR GDTFICAVMHEALHNHYTQESLSHSPGK | Exemplary variant canine IgG-B Fc Protein A+ C1q+ CD16- D(38)G |
| 142 | PAPEMLGGPSVFIFPPKPKDILLIARTPEVIC VVVDLDPEDPEVQISWFVDGKQMQTAKTQPRE EQFNGTYRVVSVLPIGHQDWLKGKQFTCKVNN IALPSPIERTISKARGQAHQPSVYVLPPSREE LSKNTVSLTCLIKDFFPPDIDVEWQSNGQEP ESKYRTIPPQLDEDGSYFLYSKLSVDKSRWQR GDTFICAVMHEALHNHYTQESLSHSPGK | Exemplary variant canine IgG-B Fc Protein A+ C1q+ CD16- K(97)I |
| 143 | PAPEMLGGPSVFIFPPKPKDILLIARTPEVIC VVVDLDPEDPEVQISWFVDGKQMQTAKTQPRE EQFNGTYRVVSVLPIGHQDWLKGKQFTCKVNN KGLPSPIERTISKARGQAHQPSVYVLPPSREE LSKNTVSLTCLIKDFFPPDIDVEWQSNGQQEP ESKYRTIPPQLDEDGSYFLYSKLSVDKSRWQR GDTFICAVMHEALHNHYTQESLSHSPGK | Exemplary variant canine IgG-B Fc Protein A+ C1q+ CD16- A(98)G |
| 144 | PAPEMLGGPSVFIFPPKPKDILLIARTPEVIC VVVDLGPEDPEVQISWFVDGKQMQTAKTQPRE | Exemplary variant canine IgG-B Fc |

TABLE 1-continued

Table 1 provides a listing of exemplary sequences referenced herein.
Description of the Sequences

| SEQ ID NO: | SEQUENCE | DESCRIPTION |
|---|---|---|
| | EQFNGTYRVVSVLPIGHQDWLKGKQFTCKVNN IGLPSPIERTISKARGQAHQPSVYVLPPSREE LSKNTVSLTCLIKDFFPPDIDVEWQSNGQQEP ESKYRTIPPQLDEDGSYFLYSKLSVDKSRWQR GDTFICAVMHEALHNHYTQESLSHSPGK | Protein A+ C1q+ CD16- D(38)G K(97)I A(98)G |
| 145 | PAPEMLGGPSVFIFPPKPKDILLIARTPEVIC VVVDLGPEDPEVQISWFVDGKQMQTAKTQPRE EQFNGTYRVVSVLPIGHQDWLKGKQFTCRVNN IGLPSPIERTISKARGQAHQPSVYVLPPSREE LSKNTVSLTCLIKDFFPPDIDVEWQSNGQQEP ESKYRTIPPQLDEDGSYFLYSKLSVDKSRWQR GDTFICAVMHEALHNHYTQESLSHSPGK | Exemplary variant canine IgG-B Fc Protein A+ C1q- CD16- D(38)G K(93)R K(97)I A(98)G |
| 146 | PAPEPLGGPSVFIFPPKPKDILLIARTPEVIC VVVDLDREDPEVQISWFVDGKQMQTAKTQPRE EQFNGTYRVVSVLPIGHQDWLKGKQFTCKVNN KALPSPIERTISKARGQAHQPSVYVLPPSREE LSKNTVSLTCLIKDFFPPDIDVEWQSNGQQEP ESKYRTTPPQLDEDGSYFLYSKLSVDKSRWQR GDTFICAVMHEALHNHYTQESLSHSPGK | Exemplary variant canine IgG-B Fc Protein A+ C1q+ CD16- M(5)P P(39)R |
| 147 | PAPEPLGGPSVFIFPPKPKDILLIARTPEVIC VVVDLDREDPEVQISWFVDGKQMQTAKTQPRE EQFNGTYRVVSVLPIGHQDWLKGKQFTCRVNN KALPSPIERTISKARGQAHQPSVYVLPPSREE LSKNTVSLTCLIKDFFPPDIDVEWQSNGQQEP ESKYRTIPPQLDEDGSYFLYSKLSVDKSRWQR GDTFICAVMHEALHNHYTQESLSHSPGK | Exemplary variant canine IgG-B Fc Protein A+ C1q- CD16- M(5)P P(39)R K(93)R |
| 148 | PGCGPLGGPSVFIFPPKPKDILVTARTPTVIC VVVDLDPENPEVQISWFVDSKQVQTANTQPRE EQSNGTYRVVSVLPIGHQDWLSGKQFKCKVNN KALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q+ CD16- L(5)P |
| 149 | PGCGLLGGPSVFIFPPKPKDILVTARTPTVIC VVVDLDRENPEVQISWFVDSKQVQTANTQPRE EQSNGTYRVVSVLPIGHQDWLSGKQFKCKVNN KALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q+ CD16- P(39)R |
| 150 | PGCGLLGGPSVFIFPPKPKDILVTARTPTVIC VVVDLGPENPEVQISWFVDSKQVQTANTQPRE EQSNGTYRVVSVLPIGHQDWLSGKQFKCKVNN KALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q+ CD16- D(38)G |
| 151 | PGCGLLGGPSVFIFPPKPKDILVTARTPTVIC VVVDLDPENPEVQISWFVDSKQVQTANTQPRE EQSNGTYRVVSVLPIGHQDWLSGKQFKCKVNN IALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q+ CD16- K(97)I |
| 152 | PGCGLLGGPSVFIFPPKPKDILVTARTPTVIC VVVDLDPENPEVQISWFVDSKQVQTANTQPRE EQSNGTYRVVSVLPIGHQDWLSGKQFKCKVNN KGLPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q+ CD16- A(98)G |

TABLE 1-continued

Table 1 provides a listing of exemplary sequences referenced herein.
Description of the Sequences

| SEQ ID NO: | SEQUENCE | DESCRIPTION |
|---|---|---|
| 153 | PGCGLLGGPSVFIFPPKPKDILVTARTPTVTC VVVDLDPENPEVQISWFVDSKVQTANTQPRE EQSNGTYRVVSVLPIGHQDWLSGKQFKCRVNN KALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q- CD16+ K(93)R |
| 154 | PGCGLLGGPSVFIFPPKPKDILVTARTPTVTC VVVDLGPENPEVQIWFVDSKVQTANTQPRE EQSNGTYRVVSVLPIGHQDWLSGKQFKCKVNN IGLPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q+ CD16- D(38)G K(97)I A(98)G |
| 155 | PGCGLLGGPSVFIFPPKPKDILVTARTPTVTC VVVDLGPENPEVQISWFVDSKVQTANTQPRE EQSNGTYRVVSVLPIGHQDWLSGKQFKCRVNN IGLPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q- CD16- D(38)G K(93)R K(97)I A(98)G |
| 156 | PGCGPLGGPSVFIFPPKPKDILVTARTPTVTC VVVDLDRENPEVQISWFVDSKVQTANTQPRE EQSNGTYRVVSVLPIGHQDWLSGKQFKCKVNN KALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q+ CD16- L(5)P P(39)R |
| 157 | PGCGPLGGPSVFIFPPKPKDILVTARTPTVTC VVVDLDRENPEVQISWFVDSKVQTANTQPRE EQSNGTYRVVSVLPIGHQDWLSGKQFKCRVNN KALPSPIEEIISKTPGQAHQPNVYVLPPSRDE MSKNTVTLTCLVKDFFPPEIDVEWQSNGQQEP ESKYRMTPPQLDEDGSYFLYSKLSVDKSRWQR GDTFICAVMHEALHNHYTQISLSHSPGK | Exemplary variant canine IgG-C Fc Protein A+ C1q- CD16- M(5)P P(39)R K(93)R |
| 158 | PVPEPLGGPSVLIFPPKPKDILRITRTPEVIC VVLDLGREDPEVQISWFVDGKEVHTAKTQSRE QQFX₁GTYRVVSVLPIEHQDWLIGKEFKCRVNH IDLPSPIERTISKARGRAHKPSVYVLPPSPKE LSSSDTVSITCLIKDFYPPDIDVEWQSNGQQE PERKHRMTPPQLDEDGSYFLYSKLSVDKSRWQ QGDPFTCAVMHETLQNHYTDLSLSHSPGK | Exemplary aglycosyl variant canine IgG-A Fc N(68)X₁ X₁ = any amino acid except N |
| 159 | PVPEPLGGPSVLIFPPKPKDILRITRTPEVIC VVLDLGREDPEVQISWFVDGKEVHTAKTQSRE QQFNPTYRVVSVLPIEHQDWLTGKEFKCRVNH IDLPSPIERTISKARGRAHKPSVYVLPPSPKE LSSSDTVSITCLIKDFYPPDIDVEWQSNGQQE PERKHRMTPPQLDEDGSYFLYSKLSVDKSRWQ QGDPFTCAVMHETLQNHYTDLSLSHSPGK | Exemplary aglycosyl variant canine IgG-A Fc G(69)13 |
| 160 | PVPEPLGGPSVLIFPPKPKDILRITRTPEVIC VVLDLGREDPEVQISWFVDGKEVHTAKTQSRE QQFNGX₂YRVVSVLPIEHQDWLTGKEFKCRVNH IDLPSPIERTISKARGRAHKPSVYVLPPSPKE LSSSDTVSITCLIKDFYPPDIDVEWQSNGQQE PERKHRMTPPQLDEDGSYFLYSKLSVDKSRWQ QGDPFTCAVMHETLQNHYTDLSLSHSPGK | Exemplary aglycosyl variant canine IgG-A Fc T(70)X₂ X₂ = any amino acid except T or S |
| 161 | PAPEMLGGPSVFIFPPKPKDILLIARTPEVIC VVVDLDPEDPEVQISWFVDGKQMQTAKTQPRE EQFX₁GTYRVVSVLPIGHQDWLKGKQFTCKVNN | Exemplary aglycosyl variant canine IgG-B Fc N(68)X₁ |

TABLE 1-continued

Table 1 provides a listing of exemplary sequences referenced herein.
Description of the Sequences

| SEQ ID NO: | SEQUENCE | DESCRIPTION |
|---|---|---|
|  | KALPSPIERTISKARGQAHQPSVYVLPPSREE<br>LSKNTVSLTCLIKDFFPPDIDVEWQSNGQQEP<br>ESKYRTTPPQLDEDGSYFLYSKLSVDKSRWQR<br>GDTFICAVMHEALHNHYTQESLSHSPGK | $X_1$ = any amino acid except N |
| 162 | PAPEMLGGPSVFIFPPKPKDILLIARTPEVIC<br>VVVDLDPEDPEVQISWFVDGKQMQTAKTQPRE<br>EQFNPTYRVVSVLPIGHQDWLKGKQFTCKVNN<br>KALP<u>S</u>PIERTISKARGQAHQPSVYVLPPSREE<br>LSKNTVSLTCLIKDFFPPDIDVEWQSNGQQEP<br>ESKYRTTPPQLDEDGSYFLYSKLSVDKSRWQR<br>GDTFICAVMHEALHNHYTQESLSHSPGK | Exemplary aglycosyl variant canine IgG-B Fc<br>G(69)13 |
| 163 | PAPEMLGGPSVFIFPPKPKDILLIARTPEVIC<br>VVVDLDPEDPEVQISWFVDGKQMQTAKTQPRE<br>EQFNG$X_2$YRVVSVLPIGHQDWLKGKQFTCKVNN<br>KALPSPIERTISKARGQAHQPSVYVLPPSREE<br>LSKNTVSLTCLIKDFFPPDIDVEWQSNGQQEP<br>ESKYRTTPPQLDEDGSYFLYSKLSVDKSRWQR<br>GDTFICAVMHEALHNHYTQESLSHSPGK | Exemplary aglycosyl variant canine IgG-B Fc<br>T(70)$X_2$<br>$X_2$ = any amino acid except T or S |
| 164 | PGCGLLGGPSVFIFPPKPKDILVTARTPTVTC<br>VVVDLDPENPEVQISWFVDSKQVQTANTQPRE<br>EQS$X_1$GTYRVVSVLPIGHQDWLSGKQFKCKVNN<br>KALP<u>S</u>PIEEIISKTPGQAHQPNVYVLPPSRDE<br>MSKNTVTLTCLVKDFFPPEIDVEWQSNGQQEP<br>ESKYRMTPPQLDEDGSYFLYSKLSVDKSRWQR<br>GDTFICAVMHEALHNHYTQISLSHSPGK | Exemplary aglycosyl variant canine IgG-C Fc<br>N(68)$X_1$<br>$X_1$ = any amino acid except N |
| 165 | PGCGLLGGPSVFIFPPKPKDILVTARTPTVTC<br>VVVDLDPENPEVQISWFVDSKQVQTANTQPRE<br>EQSNPTYRVVSVLPIGHQDWLSGKQFKCKVNN<br>KALP<u>S</u>PIEEIISKTPGQAHQPNVYVLPPSRDE<br>MSKNTVTLTCLVKDFFPPEIDVEWQSNGQQEP<br>ESKYRMTPPQLDEDGSYFLYSKLSVDKSRWQR<br>GDTFICAVMHEALHNHYTQISLSHSPGK | Exemplary aglycosyl variant canine IgG-C Fc<br>G(69)13 |
| 166 | PGCGLLGGPSVFIFPPKPKDILVTARTPTVTC<br>VVVDLDPENPEVQISWFVDSKQVQTANTQPRE<br>EQSNG$X_2$YRVVSVLPIGHQDWLSGKQFKCKVNN<br>KALPSPIEEIISKTPGQAHQPNVYVLPPSRDE<br>MSKNTVTLTCLVKDFFPPEIDVEWQSNGQQEP<br>ESKYRMTPPQLDEDGSYFLYSKLSVDKSRWQR<br>GDTFICAVMHEALHNHYTQISLSHSPGK | Exemplary aglycosyl variant canine IgG-C Fc<br>T(70)$X_2$<br>$X_2$ = any amino acid except T or S |
| 167 | PVPESLGGPSVFIFPPKPKDILRITRTPEITC<br>VVLDLGREDPEVQISWFVDGKEVHTAKTQPRE<br>QQF$X_1$STYRVVSVLPIEHQDWLTGKEFKCRVNH<br>IGLPSPIERTISKARGQAHQPSVYVLPPSPKE<br>LSSSDTVTLTCLIKDFFPPEIDVEWQSNGQPE<br>PESKYHTTAPQLDEDGSYFLYSKLSVDKSRWQ<br>QGDTFTCAVMHEALQNHYTDLSLSHSPGK | Exemplary aglycosyl variant canine IgG-D Fc<br>N(68)$X_1$<br>$X_1$ = any amino acid except N |
| 168 | PVPESLGGPSVFIFPPKPKDILRITRTPEITC<br>VVLDLGREDPEVQISWFVDGKEVHTAKTQPRE<br>QQFNPTYRVVSVLPIEHQDWLTGKEFKCRVNH<br>IGLP<u>S</u>PIERTISKARGQAHQPSVYVLPPSPKE<br>LSSSDTVTLTCLIKDFFPPEIDVEWQSNGQPE<br>PESKYHTTAPQLDEDGSYFLYSKLSVDKSRWQ<br>QGDTFTCAVMHEALQNHYTDLSLSHSPGK | Exemplary aglycosyl variant canine IgG-D Fc<br>S(69)P |
| 169 | PVPESLGGPSVFIFPPKPKDILRITRTPEITC<br>VVLDLGREDPEVQISWFVDGKEVHTAKTQPRE<br>QQFNS$X_2$YRVVSVLPIEHQDWLTGKEFKCRVNH<br>IGLPSPIERTISKARGQAHQPSVYVLPPSPKE<br>LSSSDTVTLTCLIKDFFPPEIDVEWQSNGQPE<br>PESKYHTTAPQLDEDGSYFLYSKLSVDKSRWQ<br>QGDTFTCAVMHEALQNHYTDLSLSHSPGK | Exemplary aglycosyl variant canine IgG-D Fc<br>T(70)$X_2$<br>$X_2$ = any amino acid except T or S |
| 170 | RKTDHPPGPKPCDCPKCPPPEMLGGPSIFIFP<br>PKPKDTLSISRTPEVTCLVVDLGPDDSDVQIT<br>WFVDNTQVYTAKTSPREEQF$X_1$STYRVVSVLPI<br>LHQDWLKGKEFKCKVNSKSLPSPIERTISKAK<br>GQPHEPQVYVLPPAQEELSENKVSVTCLIKSF | Exemplary aglycosyl variant feline IgG1a Fc<br>N(85)$X_1$<br>$X_1$ = any amino acid except N |

TABLE 1-continued

Table 1 provides a listing of exemplary sequences referenced herein.
Description of the Sequences

| SEQ ID NO: | SEQUENCE | DESCRIPTION |
|---|---|---|
|  | HPPDIAVEWEITGQPEPENNYRTTPPQLDSDG<br>TYFVYSKLSVDRSHWQRGNTYTCSVSHEALHS<br>HHTQKSLTQSPGK |  |
| 171 | RKTDHPPGPKPCDCPKCPPPEMLGGPSIFIFP<br>PKPKDTLSISRTPEVTCLVVDLGPDDSDVQIT<br>WFVDNTQVYTAKTSPREEQFNPTYRVVSVLPI<br>LHQDWLKGKEFKCKVNSKSLPSPIERTISKAK<br>GQPHEPQVYVLPPAQEELSENKVSVTCLIKSF<br>HPPDIAVEWEITGQPEPENNYRTTPPQLDSDG<br>TYFVYSKLSVDRSHWQRGNTYTCSVSHEALHS<br>HHTQKSLTQSPGK | Exemplary aglycosyl variant feline IgG1a Fc<br>S(86)P |
| 172 | RKTDHPPGPKPCDCPKCPPPEMLGGPSIFIFP<br>PKPKDTLSISRTPEVTCLVVDLGPDDSDVQIT<br>WFVDNTQVYTAKTSPREEQFNSX$_2$YRVVSVLPI<br>LHQDWLKGKEFKCKVNSKSLPSPIERTISKAK<br>GQPHEPQVYVLPPAQEELSENKVSVTCLIKSF<br>HPPDIAVEWEITGQPEPENNYRTTPPQLDSDG<br>TYFVYSKLSVDRSHWQRGNTYTCSVSHEALHS<br>HHTQKSLTQSPGK | Exemplary aglycosyl variant feline IgG1a Fc<br>T(87)X$_2$<br>X$_2$ = any amino acid except T or S |
| 173 | RKTDHPPGPKPCDCPKCPPPEMLGGPSIFIFP<br>PKPKDTLSISRTPEVTCLVVDLGPDDSDVQIT<br>WFVDNTQVYTAKTSPREEQFX$_1$STYRVVSVLPI<br>LHQDWLKGKEFKCKVNSKSLPSPIERTISKDK<br>GQPHEPQVYVLPPAQEELSENKVSVTCLIEGF<br>YPSDIAVEWEITGQPEPENNYRTTPPQLDSDG<br>TYFLYSRLSVDRSRWQRGNTYTCSVSHEALHS<br>HHTQKSLTQSPGK | Exemplary aglycosyl variant feline IgG1b Fc<br>N(85)X$_1$<br>X$_1$ = any amino acid except N |
| 174 | RKTDHPPGPKPCDCPKCPPPEMLGGPSIFIFP<br>PKPKDTLSISRTPEVTCLVVDLGPDDSDVQIT<br>WFVDNTQVYTAKTSPREEQFNPTYRVVSVLPI<br>LHQDWLKGKEFKCKVNSKSLPSPIERTISKDK<br>GQPHEPQVYVLPPAQEELSENKVSVTCLIEGF<br>YPSDIAVEWEITGQPEPENNYRTTPPQLDSDG<br>TYFLYSRLSVDRSRWQRGNTYTCSVSHEALHS<br>HHTQKSLTQSPGK | Exemplary aglycosyl variant feline IgG1b Fc<br>S(86)P |
| 175 | RKTDHPPGPKPCDCPKCPPPEMLGGPSIFIFP<br>PKPKDTLSISRTPEVTCLVVDLGPDDSDVQIT<br>WFVDNTQVYTAKTSPREEQENSX$_2$YRVVSVLPI<br>LHQDWLKGKEFKCKVNSKSLPSPIERTISKDK<br>GQPHEPQVYVLPPAQEELSENKVSVTCLIEGF<br>YPSDIAVEWEITGQPEPENNYRTTPPQLDSDG<br>TYFLYSRLSVDRSRWQRGNTYTCSVSHEALHS<br>HHTQKSLTQSPGK | Exemplary aglycosyl variant feline IgG1b Fc<br>T(87)X$_2$<br>X$_2$ = any amino acid except T or S |
| 176 | PKTASTIESKTGEGPKCPVPEIPGAPSVFIFP<br>PKPKDTLSISRTPEVTCLVVDLGPDDSNVQIT<br>WFVDNTEMHTAKTRPREEQEX$_1$STYRVVSVLPI<br>LHQDWLKGKEFKCKVNSKSLPSAMERTISKAK<br>GQPHEPQVYVLPPTQEELSENKVSVTCLIKGF<br>HPPDIAVEWEITGQPEPENNYQTTPPQLDSDG<br>TYFLYSRLSVDRSHWQRGNTYTCSVSHEALHS<br>HHTQKSLTQSPGK | Exemplary aglycosyl variant feline IgG2 Fc<br>N(85)X$_1$<br>X$_1$ = any amino acid except N |
| 177 | PKTASTIESKTGEGPKCPVPEIPGAPSVFIFP<br>PKPKDTLSISRTPEVTCLVVDLGPDDSNVQIT<br>WFVDNTEMHTAKTRPREEQFNPTYRVVSVLPI<br>LHQDWLKGKEFKCKVNSKSLPSAMERTISKAK<br>GQPHEPQVYVLPPTQEELSENKVSVTCLIKGF<br>HPPDIAVEWEITGQPEPENNYQTTPPQLDSDG<br>TYFLYSRLSVDRSHWQRGNTYTCSVSHEALHS<br>HHTQKSLTQSPGK | Exemplary aglycosyl variant feline IgG2 Fc<br>S(86)P |
| 178 | PKTASTIESKTGEGPKCPVPEIPGAPSVFIFP<br>PKPKDTLSISRTPEVTCLVVDLGPDDSNVQIT<br>WFVDNTEMHTAKTRPREEQENSX$_2$YRVVSVLPI<br>LHQDWLKGKEFKCKVNSKSLPSAMERTISKAK<br>GQPHEPQVYVLPPTQEELSENKVSVTCLIKGF<br>HPPDIAVEWEITGQPEPENNYQTTPPQLDSDG | Exemplary aglycosyl variant feline IgG2 Fc<br>T(87)X$_2$<br>X$_2$ = any amino acid except T or S |

TABLE 1-continued

Table 1 provides a listing of exemplary sequences referenced herein.
Description of the Sequences

| SEQ ID NO: | SEQUENCE | DESCRIPTION |
|---|---|---|
|  | TYFLYSRLSVDRSHWQRGNTYTCSVSHEALHS HHTQKSLTQSPGK |  |
| 179 | GGPSVFLEPPNPKDILMITRIPEVICVVVDVS QENPDVKFNWYMDGVEVRTATTRPKEEQFX$_1$ST YRVVSVLRIQHQDWLSGKEFKCKVNNQALPQP IERTITKTKGRSQEPQVYVLAPHPDESKKSKV SVTCLVKDFYPPEINIEWQSNGQPELETKYST TQAQQDSDGSYFLYSKLSVDRNRWQQGTTFTC GVMHEALHNHYTQKNVSKNPGK | Exemplary aglycosyl variant equine IgG1 Fc N(62)X$_1$ X$_1$ = any amino acid except N |
| 180 | GGPSVFLEPPNPKDILMITRIPEVICVVVDVS QENPDVKFNWYMDGVEVRTATTRPKEEQFNPT YRVVSVLRIQHQDWLSGKEFKCKVNNQALPQP IERTITKTKGRSQEPQVYVLAPHPDESKKSKV SVTCLVKDFYPPEINIEWQSNGQPELETKYST TQAQQDSDGSYFLYSKLSVDRNRWQQGTTFTC GVMHEALHNHYTQKNVSKNPGK | Exemplary aglycosyl variant equine IgG1 Fc S(63)P |
| 181 | GGPSVFLFPPNPKDILMITRIPEVICVVVDVS QENPDVKFNWYMDGVEVRTATTRPKEEQFNSX$_2$ YRVVSVLRIQHQDWLSGKEFKCKVNNQALPQP IERTITKTKGRSQEPQVYVLAPHPDESKKSKV SVTCLVKDFYPPEINIEWQSNGQPELETKYST TQAQQDSDGSYFLYSKLSVDRNRWQQGTTFTC GVMHEALHNHYTQKNVSKNPGK | Exemplary aglycosyl variant equine IgG1 Fc T(64)X$_2$ X$_2$ = any amino acid except T or S |
| 182 | GGPSVFIFPPNPKDALMISRTPVVTCVVVNLS DQYPDVQFSWYVDNTEVHSAITKQREAQFX$_1$ST YRVVSVLPIQHQDWLSGKEFKCSVTNVGVPQP ISRAISRGKGPSRVPQVYVLPPHPDELAKSKV SVTCLVKDFYPPDISVEWQSNRWPELEGKYST TPAQLDGDGSYFLYSKLSLETSRWQQVESFTC AVMHEALHNHFTKTDISESLGK | Exemplary aglycosyl variant equine IgG2 Fc N(62)X$_1$ X$_1$ = any amino acid except N |
| 183 | GGPSVFIFPPNPKDALMISRTPVVTCVVVNLS DQYPDVQFSWYVDNTEVHSAITKQREAQFNPT YRVVSVLPIQHQDWLSGKEFKCSVTNVGVPQP ISRAISRGKGPSRVPQVYVLPPHPDELAKSKV SVTCLVKDFYPPDISVEWQSNRWPELEGKYST TPAQLDGDGSYFLYSKLSLETSRWQQVESFTC AVMHEALHNHFTKTDISESLGK | Exemplary aglycosyl variant equine IgG2 Fc S(63)P |
| 184 | GGPSVFIFPPNPKDALMISRTPVVTCVVVNLS DQYPDVQFSWYVDNTEVHSAITKQREAQFNSX$_2$ YRVVSVLPIQHQDWLSGKEFKCSVTNVGVPQP ISRAISRGKGPSRVPQVYVLPPHPDELAKSKV SVTCLVKDFYPPDISVEWQSNRWPELEGKYST TPAQLDGDGSYFLYSKLSLETSRWQQVESFTC AVMHEALHNHFTKTDISESLGK | Exemplary aglycosyl variant equine IgG2 Fc T(64)X$_2$ X$_2$ = any amino acid except T or S |
| 185 | GGPSVFIFPPKPKDVLMITRMPEVTCLVVDVS HDSSDVLFTWYVDGTEVKTAKTMPNEEQNX$_1$ST YRVVSVLRIQHQDWLNGKKFKCKVNNQALPAP VERTISKATGQTRVPQVYVLAPHPDELSKNKV SVTCLVKDFYPPDITVEWQSNEHPEPEGKYRT TEAQKDSDGSYFLYSKLTVEKDRWQQGTTFTC VVMHEALHNHVMQKNISKNPGK | Exemplary aglycosyl variant equine IgG3 Fc N(62)X$_1$ X$_1$ = any amino acid except N |
| 186 | GGPSVFIFPPKPKDVLMITRMPEVTCLVVDVS HDSSDVLFTWYVDGTEVKTAKTMPNEEQNNPT YRVVSVLRIQHQDWLNGKKFKCKVNNQALPAP VERTISKATGQTRVPQVYVLAPHPDELSKNKV SVTCLVKDFYPPDITVEWQSNEHPEPEGKYRT TEAQKDSDGSYFLYSKLTVEKDRWQQGTTFTC VVMHEALHNHVMQKNISKNPGK | Exemplary aglycosyl variant equine IgG3 Fc S(63)P |
| 187 | GGPSVFIFPPKPKDVLMITRMPEVTCLVVDVS HDSSDVLFTWYVDGTEVKTAKTMPNEEQNNSX$_2$ YRVVSVLRIQHQDWLNGKKFKCKVNNQALPAP VERTISKATGQTRVPQVYVLAPHPDELSKNKV SVTCLVKDFYPPDITVEWQSNEHPEPEGKYRT TEAQKDSDGSYFLYSKLTVEKDRWQQGTTFTC VVMHEALHNHVMQKNISKNPGK | Exemplary aglycosyl variant equine IgG3 Fc T(64)X$_2$ X$_2$ = any amino acid except T or S |

TABLE 1-continued

Table 1 provides a listing of exemplary sequences referenced herein.
Description of the Sequences

| SEQ ID NO: | SEQUENCE | DESCRIPTION |
|---|---|---|
| 188 | VGPSVFIFPPKPKDVLMISRTPTVTCVVVDVG HDFPDVQFNWYVDGVETHTATTEPKQEQFX$_1$ST YRVVSVLPIQHKDWLSGKEFKCKVNNKALPAP VERTISAPTGQPREPQVYVLAPHRDELSKNKV SVTCLVKDFYPPDIDIEWKSNGQPEPETKYST IPAQLDSDGSYFLYSKLTVETNRWQQGTTFTC AVMHEALHNHYTEKSVSKSPGK | Exemplary aglycosyl variant equine IgG4 Fc N(62)X$_1$ X$_1$ = any amino acid except N |
| 189 | VGPSVFIFPPKPKDVLMISRTPTVTCVVVDVG HDFPDVQFNWYVDGVETHTATTEPKQEQFNPT YRVVSVLPIQHKDWLSGKEFKCKVNNKALPAP VERTISAPTGQPREPQVYVLAPHRDELSKNKV SVTCLVKDFYPPDIDIEWKSNGQPEPETKYST TPAQLDSDGSYFLYSKLTVETNRWQQGTTFTC AVMHEALHNHYTEKSVSKSPGK | Exemplary aglycosyl variant equine IgG4 Fc S(63)P |
| 190 | VGPSVFIFPPKPKDVLMISRTPTVTCVVVDVG HDFPDVQFNWYVDGVETHTATTEPKQEQFNSX$_2$ YRVVSVLPIQHKDWLSGKEFKCKVNNKALPAP VERTISAPTGQPREPQVYVLAPHRDELSKNKV SVTCLVKDFYPPDIDIEWKSNGQPEPETKYST TPAQLDSDGSYFLYSKLTVETNRWQQGTTFTC AVMHEALHNHYTEKSVSKSPGK | Exemplary aglycosyl variant equine IgG4 Fc T(64)X$_2$ X$_2$ = any amino acid except T or S |
| 191 | GGPSVFIFPPKPKDVLMISRKPEVTCVVVDLG HDDPDVQFTWFVDGVETHTATTEPKEEQFX$_1$PT YRVVSVLPIQHQDWLSGKEFKCSVTSKALPAP VERTISKAKGQLRVPQVYVLAPHPDELAKNTV SVTCLVKDFYPPEIDVEWQSNEHPEPEGKYST TPAQLNSDGSYFLYSKLSVETSRWKQGESFTC GVMHEAVENHYTQKNVSHSPGK | Exemplary aglycosyl variant equine IgG5 Fc N(62)X$_1$ X$_1$ = any amino acid except N |
| 192 | GGPSVFIFPPKPKDVLMISRKPEVTCVVVDLG HDDPDVQFTWFVDGVETHTATTEPKEEQFNPT YRVVSVLPIQHQDWLSGKEFKCSVTSKALPAP VERTISKAKGQLRVPQVYVLAPHPDELAKNTV SVTCLVKDFYPPEIDVEWQSNEHPEPEGKYST TPAQLNSDGSYFLYSKLSVETSRWKQGESFTC GVMHEAVENHYTQKNVSHSPGK | Exemplary aglycosyl variant equine IgG5 Fc S(63)P |
| 193 | GGPSVFIFPPKPKDVLMISRKPEVTCVVVDLG HDDPDVQFTWFVDGVETHTATTEPKEEQFNSX$_2$ YRVVSVLPIQHQDWLSGKEFKCSVTSKALPAP VERTISKAKGQLRVPQVYVLAPHPDELAKNTV SVTCLVKDFYPPEIDVEWQSNEHPEPEGKYST TPAQLNSDGSYFLYSKLSVETSRWKQGESFTC GVMHEAVENHYTQKNVSHSPGK | Exemplary aglycosyl variant equine IgG5 Fc T(64)X$_2$ X$_2$ = any amino acid except T or S |
| 194 | GRPSVFIFPPNPKDTLMISRTPEVTCVVVDVS QENPDVKFNWYVDGVEAHTATTKAKEKQDX$_1$ST YRVVSVLPIQHQDWRRGKEFKCKVNNRALPAP VERTITKAKGELQDPQVYILAPHPDEVTKNTV SVTCLVKDFYPPDINVEWQSNEEPEPEVKYST TPAQLDGDGSYFLYSKLTVETDRWEQGESFTC VVMHEAIRHTYRQKSITNFPGK | Exemplary aglycosyl variant equine IgG6 Fc N(62)X$_1$ X$_1$ = any amino acid except N |
| 195 | GRPSVFIFPPNPKDTLMISRTPEVTCVVVDVS QENPDVKFNWYVDGVEAHTATTKAKEKQDNPT YRVVSVLPIQHQDWRRGKEFKCKVNNRALPAP VERTITKAKGELQDPQVYILAPHPDEVTKNTV SVTCLVKDFYPPDINVEWQSNEEPEPEVKYST IPAQLDGDGSYFLYSKLTVETDRWEQGESFTC VVMHEAIRHTYRQKSITNFPGK | Exemplary aglycosyl variant equine IgG6 Fc S(63)P |
| 196 | GRPSVFIFPPNPKDTLMISRTPEVTCVVVDVS QENPDVKFNWYVDGVEAHTATTKAKEKQDNSX$_2$ YRVVSVLPIQHQDWRRGKEFKCKVNNRALPAP VERTITKAKGELQDPQVYILAPHPDEVTKNTV SVTCLVKDFYPPDINVEWQSNEEPEPEVKYST TPAQLDGDGSYFLYSKLTVETDRWEQGESFTC VVMHEAIRHTYRQKSITNFPGK | Exemplary aglycosyl variant equine IgG6 Fc T(64)X$_2$ X$_2$ = any amino acid except T or S |
| 197 | VGPSVFIFPPKPKDVLMISRTPTVTCVVVDVG HDFPDVQFNWYVDGVETHTATTEPKQEQNX$_1$ST | Exemplary aglycosyl variant equine IgG7 Fc |

TABLE 1-continued

Table 1 provides a listing of exemplary sequences referenced herein.
Description of the Sequences

| SEQ ID NO: | SEQUENCE | DESCRIPTION |
|---|---|---|
|  | YRVVSILAIQHKDWLSGKEFKCKVNNQALPAP VQKTISKPTGQPREPQVYVLAPHPDELSKNKV SVTCLVKDFYPPDIDIEWKSNGQPEPETKYST TPAQLDGDGSYFLYSKLTVETNRWQQGTTFTC AVMHEALHNHYTEKSVSKSPGK | N(62)$X_1$ $X_1$ = any amino acid except N |
| 198 | VGPSVFIFPPKPKDVLMISRTPTVTCVVVDVG HDFPDVQFNWYVDGVETHTATTEPKQEQNNPT YRVVSILAIQHKDWLSGKEFKCKVNNQALP$\overline{AP}$ VQKTISKPTGQPREPQVYVLAPHPDELSKNKV SVTCLVKDFYPPDIDIEWKSNGQPEPETKYST TPAQLDGDGSYFLYSKLTVETNRWQQGTTFTC AVMHEALHNHYTEKSVSKSPGK | Exemplary aglycosyl variant equine IgG7 Fc S(63)P |
| 199 | VGPSVFIFPPKPKDVLMISRTPTVTCVVVDVG HDFPDVQFNWYVDGVETHTATTEPKQEQNNS$X_2$ YRVVSILAIQHKDWLSGKEFKCKVNNQALPAP VQKTISKPTGQPREPQVYVLAPHPDELSKNKV SVTCLVKDFYPPDIDIEWKSNGQPEPETKYST TPAQLDGDGSYFLYSKLTVETNRWQQGTTFTC AVMHEALHNHYTEKSVSKSPGK | Exemplary aglycosyl variant equine IgG7 Fc T(64)$X_2$ $X_2$ = any amino acid except T or S |

DESCRIPTION OF THE EMBODIMENTS

Variant IgG Fc polypeptides from companion animals, such as canine, equine, and feline, are described. In some embodiments, the variant igG Fc polypeptides have increased binding to Protein A, decreased binding to C1q, decreased binding to CD16, increased stability, increased recombinant production, increased hinge disulfide formation, and/or form heterodimeric polypeptides. In some embodiments, antibodies, antibody fragments, or fusion proteins comprise a variant IgG Fc polypeptide. Methods of producing or purifying variant IgG Fc polypeptides and methods of administering variant IgG Fc polypeptides to companion animals are also provided assay.

Also provided are various embodiments relating to contiguous polypeptides and heterodimeric polypeptides comprising one or more variant GLP1 polypeptide(s) having improved serum half-life. In some embodiments, the contiguous polypeptides or heterodimeric polypeptides comprise a GLP1 polypeptide and a glucagon polypeptide as a dual GLP1 receptor and glucagon receptor agonist. In some embodiments, such polypeptides may be used to treat, for example, diabetes, obesity, or related indications, in companion animals, such as canines, felines, and equines.

For the convenience of the reader, the following definitions of terms used herein are provided.

As used herein, numerical terms such as $K_D$ are calculated based upon scientific measurements and, thus, are subject to appropriate measurement error. In some instances, a numerical term may include numerical values that are rounded to the nearest significant figure.

As used herein, "a" or "an" means "at least one" or "one or more" unless otherwise specified. As used herein, the term "or" means "and/or" unless specified otherwise. In the context of a multiple dependent claim, the use of "or" when referring back to other claims refers to those claims in the alternative only.

Exemplary Variant IgG Fc Polypeptides

Novel variant IgG Fc polypeptides are provided, for example, variant IgG Fc polypeptides for increased binding to Protein A, for decreased binding to C1q, for decreased binding to CD16, for increased stability, for increased recombinant production, for increased hinge disulfide formation, and/or for forming heterodimeric proteins assay.

"Amino acid sequence," means a sequence of amino acids residues in a peptide or protein. The terms "polypeptide" and "protein" are used interchangeably to refer to a polymer of amino acid residues, and are not limited to a minimum length. Such polymers of amino acid residues may contain natural or unnatural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "fragment crystallizable polypeptide" or "Fc polypeptide" is the portion of an antibody molecule that interacts with effector molecules and cells. It comprises the C-terminal portions of the immunoglobulin heavy chains. As used herein, an Fc polypeptide includes fragments of the Fc domain having one or more biological activities of an entire Fc polypeptide. In some embodiments, a biological activity of an Fc polypeptide is the ability to bind FcRn. In some embodiments, a biological activity of an Fc polypeptide is the ability to bind C1q. In some embodiments, a biological activity of an Fc polypeptide is the ability to bind CD16. In some embodiments, a biological activity of an Fc polypeptide is the ability to bind protein A. An "effector function" of the Fc polypeptide is an action or activity performed in whole or in part by any antibody in response to a stimulus and may include complement fixation and/or ADCC (antibody-dependent cellular cytotoxicity) induction.

"IgX Fc" refers to an Fc polypeptide derived from a particular antibody isotype (e.g., IgG, IgA, IgD, IgE, IgM, etc.), where "X" denotes the antibody isotype. Thus, "IgG Fc" denotes that the Fc polypeptide is derived from a γ chain, "IgA Fc" denotes that the Fc polypeptide is derived from an α chain, "IgD Fc" denotes that the Fc polypeptide is derived from a δ chain, "IgE Fc" denotes that the Fc polypeptide is derived from a ε chain, "IgM Fc" denotes that the Fc polypeptide is derived from a μ chain, etc. In some embodiments, the IgG Fc polypeptide comprises the hinge, CH2, and CH3, but does not comprise CH1 or CL. In some embodiments, the IgG Fc polypeptide comprises CH2 and CH3, but does not comprise CH1, the hinge, or CL. In some embodiments, the IgG Fc polypeptide comprises CH1, hinge, CH2, CH3, with or without CL. "IgX-N Fc" or "IgXN Fc" denotes that the Fc polypeptide is derived from a particular subclass of antibody isotype (such as canine IgG subclass IgG-A, IgG-B, IgG-C, or IgG-D; feline IgG subclass IgG1a, IgG1b, or IgG2; or equine IgG subclass IgG1, IgG2, IgG3, IgG4, IgG5, IgG6, or IgG7, etc.), where "N" denotes the subclass.

"Hinge" refers to any portion of an Fc polypeptide or variant Fc polypeptide that is proline-rich and comprises at least one cysteine residue located between CH1 and CH2 of a full-length heavy chain constant region.

In some embodiments, a hinge is capable of forming a disulfide linkage within the same hinge region, within the same Fc polypeptide, with a hinge region of a separate Fc polypeptide, or with a separate Fc polypeptide. In some embodiments, a hinge comprises at least one, at least two, at least three, at least four, at least five, at least six, at least seven, at least eight, at least nine, or at least ten proline residues.

The term "companion animal species" refers to an animal suitable to be a companion to humans. In some embodiments, a companion animal species is a canine (or dog), a feline (or cat), or an equine (or horse). In some embodiments, a companion animal species is a small mammal, such as a canine, feline, dog, cat, rabbit, ferret, guinea pig, rodent, etc. In some embodiments, a companion animal species is a farm animal, such as a horse, cow, pig, etc.

In some embodiments, an IgX Fc polypeptide or an IgX-N Fc polypeptide is derived from a companion animal, such as a dog, a cat, or a horse. In some embodiments, IgG Fc polypeptides are isolated from canine γ heavy chains, such as IgG-A, IgG-B, IgG-C, or IgG-D. In some instances, IgG Fc polypeptides are isolated from feline γ heavy chains, such as IgG1a, IgG1b, or IgG2. In other instances, IgG Fc polypeptides are isolated from equine γ heavy chains, such as IgG1, IgG2, IgG3, IgG4, IgG5, IgG6, or IgG7.

The terms "IgX Fc" and "IgX Fc polypeptide" include wild-type IgX Fc polypeptides and variant IgX Fc polypeptides, unless indicated otherwise.

"Wild-type" refers to a non-mutated version of a polypeptide that occurs in nature, or a fragment thereof. A wild-type polypeptide may be produced recombinantly.

In some embodiments, a wild-type IgG Fc polypeptide comprises the amino acid sequence of SEQ ID NO: 1, SEQ ID NO: 2, SEQ ID NO: 3, SEQ ID NO: 4, SEQ ID NO: 16, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 80, SEQ ID NO: 81, SEQ ID NO: 100, SEQ ID NO: 107, SEQ ID NO: 108, SEQ ID NO: 117, SEQ ID NO: 118.

A "variant" is a polypeptide that differs from a reference polypeptide by single or multiple non-native amino acid substitutions, deletions, and/or additions. In some embodiments, a variant retains at least one biological activity of the reference polypeptide. In some embodiments, a variant (e.g., a variant canine IgG-A Fc, a variant canine IgG-C Fc, a variant canine IgG-D Fc, variant equine IgG2 Fc, variant equine IgG5 Fc, or variant equine IgG6 Fc) has an activity that the reference polypeptide substantially lacks. For example, in some embodiments, a variant canine IgG-A Fc, a variant canine IgG-C Fc, a variant canine IgG-D Fc, variant equine IgG2 Fc, variant equine IgG5 Fc, or variant equine IgG6 Fc binds Protein A.

As used herein, "percent (%) amino acid sequence identity" and "homology" with respect to a nucleic acid molecule or polypeptide sequence are defined as the percentage of nucleotide or amino acid residues in a reference sequence that are identical with the nucleotide or amino acid residues in the specific nucleic acid molecule or polypeptide sequence, after aligning the sequences and introducing gaps, if necessary to achieve the maximum percent sequence identity, and not considering any conservative substitutions as part of the sequence identity. Alignment for purposes of determining percent sequence identity can be achieved in various ways that are within the skill in the art, for instance, using publicly available computer software such as BLAST, BLAST-2, ALIGN, or MEGALINE™ (DNASTAR) software. Those skilled in the art can determine appropriate parameters for measuring alignment, including any algorithms needed to achieve maximal alignment over the full length of sequences being compared.

In some embodiments, a variant has at least about 50% sequence identity with the reference nucleic acid molecule or polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, deleted, at the N- or C-terminus of the polypeptide. In some embodiments, a variant has at least about 50% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 95% sequence identity, at least about 97% sequence identity, at least about 98% sequence identity, or at least about 99% sequence identity with the sequence of the reference nucleic acid or polypeptide.

A "point mutation" is a mutation that involves a single amino acid residue. The mutation may be the loss of an amino acid, substitution of one amino acid residue for another, or the insertion of an additional amino acid residue.

An "amino acid substitution" refers to the replacement of one amino acid in a polypeptide with another amino acid. In some embodiments, an amino acid substitution is a conservative substitution. Nonlimiting exemplary conservative amino acid substitutions are shown in Table 2. Amino acid substitutions may be introduced into a molecule of interest and the products screened for a desired activity, for example, retained/improved antigen binding, decreased immunogenicity, or improved ADCC or CDC or enhanced pharmacokinetics.

TABLE 2

| Original Residue | Exemplary Substitutions |
| --- | --- |
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions entail exchanging a member of one of these classes with another class.

A "variant IgG Fc" as used herein is an IgG Fc polypeptide that differs from a reference IgG Fc polypeptide by single or multiple amino acid substitutions, deletions, and/or additions and substantially retains at least one biological activity of the reference IgG Fc polypeptide.

An "amino acid derivative," as used herein, refers to any amino acid, modified amino acid, and/or amino acid analogue, that is not one of the 20 common natural amino acids found in humans. Exemplary amino acid derivatives include natural amino acids not found in humans (e.g., selenocysteine and pyrolysine, which may be found in some microorganisms) and unnatural amino acids. Exemplary amino acid derivatives, include, but are not limited to, amino acid derivatives commercially available through chemical product manufacturers (e.g., sigmaaldrich.com/chemistry/chemistry-products.html?TablePage=16274965, accessed on May 6, 2017, which is incorporated herein by reference). One or more amino acid derivatives may be incorporated into a polypeptide at a specific location using a translation system that utilizes host cells, orthogonal aminoacyl-tRNA synthetases derived from eubacterial synthetases, orthogonal tRNAs, and an amino acid derivative. For further descriptions, see, e.g., U.S. Pat. No. 9,624,485.

In some embodiments, a variant IgG Fc polypeptide comprises an amino acid substitution with an amino acid derivative. In some embodiments, the amino acid derivative is an alanine derivative, a cysteine derivative, an aspartic acid derivative, a glutamic acid derivative, a phenylalanine derivative, a glycine derivative, a histidine derivative, an isoleucine derivative, a lysine derivative, a leucine derivative, a methionine derivative, an asparagine derivative, a proline derivative, a glutamine derivative, an arginine derivative, a serine derivative, a threonine derivative, a valine derivative, a tryptophan derivative, or a tyrosine derivative.

In some embodiments, a variant IgG Fc polypeptide comprises a variant IgG Fc polypeptide of a companion animal species. In some embodiments, a variant IgG Fc polypeptide comprises a variant canine IgG Fc polypeptide, a variant equine IgG Fc polypeptide, or a feline IgG Fc polypeptide.

Exemplary Variant IgG Fc Polypeptides with Modified Protein a Binding

In some embodiments, a variant IgG Fc polypeptide has modified Protein A binding affinity. In some embodiments, a variant IgG Fc polypeptide has increased binding affinity to Protein A. In some embodiments, a variant IgG Fc polypeptide may be purified using Protein A column chromatography.

In some embodiments, a variant IgG Fc polypeptide comprises an amino acid substitution at a position corresponding to position 21, position 23, position 25, position 80, position 205, and/or position 207 of SEQ ID NO: 1. In some embodiments, a variant IgG Fc polypeptide comprises an amino acid substitution at a position corresponding to position 21, position 23, and/or position 24 of SEQ ID NO: 3. In some embodiments, a variant IgG Fc polypeptide comprises an amino acid substitution at a position corresponding to position 21, position 23, position 25, position 80, and/or position 207 of SEQ ID NO: 4.

In some embodiments, a variant IgG Fc polypeptide comprises an amino acid substitution at a position corresponding to position 15, and/or position 203 of SEQ ID NO: 64. In some embodiments, a variant IgG Fc polypeptide comprises an amino acid substitution at a position corresponding to position 199 and/or position 200 of SEQ ID NO: 67. In some embodiments, a variant IgG Fc polypeptide comprises an amino acid substitution at a position corresponding to position 199, position 200, position 201, and/or 202 of SEQ ID NO: 68.

In some embodiments, a variant IgG Fc polypeptide comprises an amino acid substitution at position 21, position 23, position 25, position 80, position 205, and/or position 207 of SEQ ID NO: 1. In some embodiments, a variant IgG Fc polypeptide comprises an amino acid substitution at position 21, position 23, and/or position 24 of SEQ ID NO: 3. In some embodiments, a variant IgG Fc polypeptide comprises an amino acid substitution at position 21, position 23, position 25, position 80, and/or position 207 of SEQ ID NO: 3.

In some embodiments, a variant IgG Fc polypeptide comprises an amino acid substitution at position 15 and/or position 203 of SEQ ID NO: 64. In some embodiments, a variant IgG Fc polypeptide comprises an amino acid substitution at position 199 and/or position 200 of SEQ ID NO: 67. In some embodiments, a variant IgG Fc polypeptide comprises an amino acid substitution at position 199, position 200, position 201, and/or position 202 of SEQ ID NO: 68.

In some embodiments, a variant IgG Fc polypeptide comprises a threonine at a position corresponding to position 21 of SEQ ID NO: 1, a leucine at a position corresponding to position 23 of SEQ ID NO: 1, an alanine at a position corresponding to position 25 of SEQ ID NO: 1, a glycine at a position corresponding to position 80 of SEQ ID NO: 1, an alanine at a position corresponding to position 205 of SEQ ID NO: 1, and/or a histidine at a position corresponding to position 207 of SEQ ID NO: 1. In some embodiments, a variant IgG Fc polypeptide comprises a threonine at a position corresponding to position 21 of SEQ ID NO: 3, a leucine at a position corresponding to position 23 of SEQ ID NO: 3, and/or an isoleucine at a position corresponding to position 24 of SEQ ID NO: 3. In some embodiments, a variant IgG Fc polypeptide comprises a threonine at a position corresponding to position 21 of SEQ ID NO: 4, a leucine at a position corresponding to position 23 of SEQ ID NO: 4, an alanine at a position corresponding to position 25 of SEQ ID NO: 4, a glycine at a position corresponding to position 80 of SEQ ID NO: 3, and/or a histidine at a position corresponding to position 207 of SEQ ID NO: 4.

In some embodiments, a variant IgG Fc polypeptide comprises a threonine or a valine at a position corresponding to position 15 of SEQ ID NO: 64, and/or a tyrosine or a valine at a position corresponding to position 203 of SEQ ID NO: 64. In some embodiments, a variant IgG Fc polypeptide comprises a leucine at a position corresponding to position 199 of SEQ ID NO: 67, and/or a histidine at a position corresponding to position 200 of SEQ ID NO: 67. In some embodiments, a variant IgG Fc polypeptide comprises an isoleucine at a position corresponding to position 199 of SEQ ID NO: 68, a histidine at a position corresponding to position 200 of SEQ ID NO: 68, an asparagine at a position corresponding to position 201 of SEQ ID NO: 68, and/or a histidine at a position corresponding to position 202 of SEQ ID NO: 68.

In some embodiments, a variant IgG Fc polypeptide comprises a threonine at position 21 of SEQ ID NO: 1, a leucine at position 23 of SEQ ID NO: 1, an alanine at position 25 of SEQ ID NO: 1, a glycine at position 80 of SEQ ID NO: 1, an alanine at position 205 of SEQ ID NO: 1, and/or a histidine at position 207 of SEQ ID NO: 1. In some embodiments, a variant IgG Fc polypeptide comprises a threonine at position 21 of SEQ ID NO: 3, a leucine at position 23 of SEQ ID NO: 3, and/or an isoleucine at position 24 of SEQ ID NO: 3. In some embodiments, a variant IgG Fc polypeptide comprise a threonine at a position 21 of SEQ ID NO: 4, a leucine at position 23 of SEQ ID NO: 4, an alanine at position 25 of SEQ ID NO: 4, a glycine at position 80 of SEQ ID NO: 4, and/or a histidine at position 207 of SEQ ID NO: 4.

In some embodiments, a variant IgG Fc polypeptide comprises a threonine or a valine at position 15 of SEQ ID NO: 64, and/or a tyrosine or a valine at position 203 of SEQ ID NO: 64. In some embodiments, a variant IgG Fc polypeptide comprises a leucine at position 199 of SEQ ID NO: 67, and/or a histidine at position 200 of SEQ ID NO: 67. In some embodiments, a variant IgG Fc polypeptide comprises an isoleucine at position 199 of SEQ ID NO: 68, a histidine at position 200 of SEQ ID NO: 68, an asparagine at position 201 of SEQ ID NO: 68, and/or a histidine at position 202 of SEQ ID NO: 68.

In some embodiments, a variant IgG Fc polypeptide comprises an amino acid sequence of SEQ ID NO: 5, SEQ ID NO: 6, SEQ ID NO: 7, SEQ ID NO: 60, SEQ ID NO: 61, SEQ ID NO: 62, or SEQ ID NO: 84. In some embodiments, a variant IgG Fc polypeptide comprises SEQ ID NO: 19, SEQ ID NO: 71, SEQ ID NO: 72, SEQ ID NO: 75, or SEQ ID NO: 76.

Exemplary Variant IgG Fc Polypeptides with Modified CD16 Binding

In some embodiments, a variant IgG Fc polypeptide has modified CD16 binding affinity. In some embodiments, a variant IgG Fc polypeptide has decreased binding affinity to CD16. In some embodiments, a variant IgG Fc may have a reduced ADCC immune response.

In some embodiments, a variant IgG Fc polypeptide comprises an amino acid substitution at a position corresponding to position 5, position 38, position 39, position 97, and/or position 98 of SEQ ID NO: 2. In some embodiments, a variant IgG Fc polypeptide comprises an amino acid substitution at a position corresponding to position 5, position 38, position 39, position 97, and/or position 98 of SEQ ID NO: 3.

In some embodiments, a variant IgG Fc polypeptide comprises an amino acid substitution at position 5, position 38, position 39, position 97, and/or position 98 of SEQ ID NO: 2. In some embodiments, a variant IgG Fc polypeptide comprises an amino acid substitution at position 5, position 38, position 39, position 97, and/or position 98 of SEQ ID NO: 3.

In some embodiments, a variant IgG Fc polypeptide comprises a proline at a position corresponding to position 5, a glycine at a position corresponding to position 38, an arginine at a position corresponding to position 39, a isoleucine at a position corresponding to position 97, and/or a glycine at a position corresponding to position 98 of SEQ ID NO: 2. In some embodiments, a variant IgG Fc polypeptide comprises a proline at a position corresponding to position 5, a glycine at a position corresponding to position 38, an arginine at a position corresponding to position 39, a isoleucine at a position corresponding to position 97, and/or a glycine at a position corresponding to position 98 of SEQ ID NO: 3.

In some embodiments, a variant IgG Fc polypeptide comprises a proline at position 5, a glycine at position 38, an arginine at position 39, a isoleucine at position 97, and/or a glycine at position 98 of SEQ ID NO: 2. In some embodiments, a variant IgG Fc polypeptide comprises a proline at position 5, a glycine at position 38, an arginine at position 39, a isoleucine at position 97, and/or a glycine at position 98 of SEQ ID NO: 3.

In some embodiments, a variant IgG Fc polypeptide comprises an amino acid sequence of SEQ ID NO: 139, SEQ ID NO: 140, SEQ ID N: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 154, SEQ ID NO: 155, SEQ ID NO: 156, or SEQ ID NO: 157.

Exemplary Variant IgG Fc Polypeptides with Modified C1q Binding

In some embodiments, a variant IgG Fc polypeptide has modified C1q binding affinity. In some embodiments, a variant IgG Fc polypeptide has reduced binding affinity to C1q. In some embodiments, a variant IgG Fc polypeptide may have reduced complement fixation. In some embodiments, a variant IgG Fc may have a reduced complement-mediated immune response.

In some embodiments, a variant IgG Fc polypeptide comprises an amino acid substitution at a position corresponding to position 93 of SEQ ID NO: 2. In some embodiments, a variant IgG Fc polypeptide comprises an amino acid substitution at a position corresponding to position 93 of SEQ ID NO: 3. In some embodiments, a variant IgG Fc polypeptide comprises an amino acid substitution at a position corresponding to position 87 of SEQ ID NO: 63. In some embodiments, a variant IgG Fc polypeptide comprises an amino acid substitution at a position corresponding to position 87 of SEQ ID NO: 65. In some embodiments, a variant IgG Fc polypeptide comprises an amino acid substitution at a position corresponding to position 87 of SEQ ID NO: 66. In some embodiments, a variant IgG Fc polypeptide comprises an amino acid substitution at a position corresponding to position 198 of SEQ ID NO: 80. In some embodiments, a variant IgG Fc polypeptide comprises an amino acid substitution at a position corresponding to position 198 of SEQ ID NO: 81.

In some embodiments, a variant IgG Fc polypeptide comprises an amino acid substitution at position 93 of SEQ ID NO: 2. In some embodiments, a variant IgG Fc polypeptide comprises an amino acid substitution at position 93 of SEQ ID NO: 3. In some embodiments, a variant IgG Fc polypeptide comprises an amino acid substitution at position 87 of SEQ ID NO: 63. In some embodiments, a variant IgG Fc polypeptide comprises an amino acid substitution at position 87 of SEQ ID NO: 65. In some embodiments, a variant IgG Fc polypeptide comprises or an amino acid substitution at position 87 of SEQ ID NO: 66. In some embodiments, a variant IgG Fc polypeptide comprises an amino acid substitution at position 198 of SEQ ID NO: 80. In some embodiments, a variant IgG Fc polypeptide comprises an amino acid substitution at position 198 of SEQ ID NO: 81.

In some embodiments, a variant IgG Fc polypeptide comprises an arginine at a position corresponding to position 93 of SEQ ID NO: 2. In some embodiments, a variant IgG Fc polypeptide comprises an arginine at a position corresponding to position 93 of SEQ ID NO: 3. In some embodiments, a variant IgG Fc polypeptide comprises a serine at a position corresponding to position 87 of SEQ ID NO: 63. In some embodiments, a variant IgG Fc polypeptide comprises a serine substitution at a position corresponding to position 87 of SEQ ID NO: 65. In some embodiments, a variant IgG Fc polypeptide comprises a serine at a position corresponding to position 87 of SEQ ID NO: 66. In some embodiments, a variant IgG Fc polypeptide comprises an alanine at a position corresponding to position 198 of SEQ ID NO: 80. In some embodiments, a variant IgG Fc polypeptide comprises an alanine at a position corresponding to position 198 of SEQ ID NO: 81.

In some embodiments, a variant IgG Fc polypeptide comprises an arginine at position 93 of SEQ ID NO: 2. In some embodiments, a variant IgG Fc polypeptide comprises an amino acid substitution at position 93 of SEQ ID NO: 3. In some embodiments, a variant IgG Fc polypeptide comprises a serine at position 87 of SEQ ID NO: 63. In some embodiments, a variant IgG Fc polypeptide comprises a serine at position 87 of SEQ ID NO: 65. In some embodiments, a variant IgG Fc polypeptide comprises a serine at position 87 of SEQ ID NO: 66. In some embodiments, a variant IgG Fc polypeptide comprises an alanine at position 198 of SEQ ID NO: 80. In some embodiments, a variant IgG Fc polypeptide comprises an alanine at position 198 of SEQ ID NO: 81.

In some embodiments, a variant IgG Fc polypeptide comprises the amino acid sequence of SEQ ID NO: 78, SEQ ID NO: 79, or SEQ ID NO: 84. In some embodiments, a variant IgG Fc polypeptide comprises the amino acid sequence of SEQ ID NO: 70, SEQ ID NO: 73, SEQ ID NO: 74, or SEQ ID NO: 77. In some embodiments, a variant IgG Fc polypeptide comprises the amino acid sequence of SEQ ID NO: 82 or SEQ ID NO: 83.

Exemplary Variant IgG Fc Polypeptides with a Modified Inter-Chain Disulfide Linkage In some embodiments, a variant feline IgG Fc polypeptide has at least one additional inter-chain disulfide linkage relative to the wild-type feline IgG Fc polypeptide. In some embodiments, a variant feline IgG Fc polypeptide has at least one additional inter-chain disulfide linkage in the hinge region. In some embodiments, a variant feline IgG2 Fc polypeptide with at least one additional inter-chain disulfide linkage has increased inter-chain stability relative to the wild-type feline IgG Fc polypeptide. In some embodiments, a variant IgG polypeptide has at least one amino acid modification to a hinge region relative to a wild-type IgG Fc polypeptide. In some embodiments, the wild-type IgG Fc polypeptide is a wild-type feline or equine IgG Fc polypeptide. In some embodiments, the variant IgG Fc polypeptide comprises a hinge region or a portion of a hinge region from an IgG Fc polypeptide of a different isotype. In some embodiments, the variant IgG Fc polypeptide comprises a hinge region from a wild-type feline IgG-1a Fc polypeptide, from a wild-type feline IgG-1b Fc polypeptide, or from a wild-type equine IgG1 Fc polypeptide. In some embodiments, a variant IgG2 Fc polypeptide has increased recombinant production and/or increased hinge disulfide formation relative to the wild-type IgG Fc polypeptide. In some embodiments, the increased recombinant production and/or increased hinge disulfide formation can be determined by SDS-PAGE analysis under reducing and/or non-reducing conditions.

In some embodiments, a variant IgG Fc polypeptide comprises a cysteine at a position corresponding to position 8, position 9, position 10, position 11, position 12, position 13, position 14, position 15, or position 16 of SEQ ID NO: 16. In some embodiments, a variant IgG Fc polypeptide comprises a cysteine at position 8, position 9, position 10, position 11, position 12, position 13, position 14, position 15, or position 16 of SEQ ID NO: 16. In some embodiments, a variant IgG Fc polypeptide comprises SEQ ID NO: 17.

In some embodiments, a variant IgG Fc polypeptide comprises an amino acid substitution at a position corresponding to position 16 of SEQ ID NO: 16, SEQ ID NO: 80, SEQ ID NO: 81, SEQ ID NO: 117, or SEQ ID NO: 118. In some embodiments, a variant IgG Fc polypeptide comprises an amino acid substitution at a position corresponding to position 3 and/or at a position corresponding to position 20 of SEQ ID NO: 129.

In some embodiments, a variant IgG Fc polypeptide comprises an amino acid substitution at position 16 of SEQ ID NO: 16, SEQ ID NO: 80, SEQ ID NO: 81, SEQ ID NO: 117, or SEQ ID NO: 118. In some embodiments, a variant IgG Fc polypeptide comprises an amino acid substitution at position 3 and/or at a position corresponding to position 20 of SEQ ID NO: 129.

In some embodiments, a variant IgG Fc polypeptide comprises a proline at a position corresponding to position 16 of SEQ ID NO: 16, SEQ ID NO: 80, SEQ ID NO: 81, SEQ ID NO: 117, or SEQ ID NO: 118. In some embodiments, a variant IgG Fc polypeptide comprises a serine at a position corresponding to position 3 and/or a proline at a position corresponding to position 20 of SEQ ID NO: 129.

In some embodiments, a variant IgG Fc polypeptide comprises a proline at position 16 of SEQ ID NO: 16, SEQ ID NO: 80, SEQ ID NO: 81, SEQ ID NO: 117, or SEQ ID NO: 118. In some embodiments, a variant IgG Fc polypeptide comprises a serine at position 3 and/or a proline at position 20 of SEQ ID NO: 129.

In some embodiments, the variant IgG Fc polypeptide comprises SEQ ID NO: 19, SEQ ID NO: 125 or SEQ ID NO: 126, SEQ ID NO: 127, SEQ ID NO: 128, SEQ ID NO: SEQ ID NO: 129, SEQ ID NO: 130, SEQ ID NO: 131, SEQ ID NO: 132, SEQ ID NO: 133, SEQ ID N: 134, SEQ ID NO: 135.

Exemplary Variant IgG Fc Polypeptides for Heterodimeric Polypeptides

In certain embodiments, a heterodimeric polypeptide provided herein is a a bispecific antibody. A bispecific antibody has a binding specificity for two different epitopes or target molecules. In some embodiments, a bispecific antibody binds to two different epitopes of the same target molecule. Bispecific antibodies may be full length antibodies or antibody fragments.

In some embodiments, the heterodimeric polypeptide comprises a first variant IgG Fc polypeptide comprising a "knob" mutation and a second variant IgG Fc polypeptide comprising a "hole" mutation. Nonlimiting exemplary knob and hole mutations are described, for example, in Merchant, A. M. et al. An efficient route to human bispecific IgG. Nat Biotechnol, 16(7):677-81 (1998).

In some embodiments, a variant canine or variant feline IgG Fc polypeptide comprises a knob mutation. In some embodiments, a variant IgG Fc polypeptide comprises a tyrosine or a tryptophan at a position corresponding to position 138 of SEQ ID NO: 1. In some embodiments, a variant IgG Fc polypeptide comprises a tyrosine or a tryptophan at a position corresponding to position 137 of SEQ ID NO: 2. In some embodiments, a variant IgG Fc polypeptide comprises a tyrosine or a tryptophan at a position corresponding to position 137 of SEQ ID NO: 3. In some embodiments, a variant IgG Fc polypeptide comprises a tyrosine or a tryptophan at a position corresponding to position 138 of SEQ ID NO: 4. In some embodiments, a variant IgG Fc polypeptide comprises a tryptophan at a position corresponding to position 154 of SEQ ID NO: 16, SEQ ID NO: 80, SEQ ID NO: 81, SEQ ID NO: 117, or SEQ ID NO: 118.

In some embodiments, a variant IgG Fc polypeptide comprises a tyrosine or a tryptophan at position 138 of SEQ ID NO: 1. In some embodiments, a variant IgG Fc polypeptide comprises a tyrosine or a tryptophan at position 137 of SEQ ID NO: 2. In some embodiments, a variant IgG Fc polypeptide comprises a tyrosine or a tryptophan at position 137 of SEQ ID NO: 3. In some embodiments, a variant IgG Fc polypeptide comprises a tyrosine or a tryptophan at position 138 of SEQ ID NO: 4. In some embodiments, a variant IgG Fc polypeptide comprises a tryptophan at position 154 of SEQ ID NO: 16, SEQ ID NO: 80, SEQ ID NO: 81, SEQ ID NO: 117, or SEQ ID NO: 118.

In some embodiments, a variant IgG Fc polypeptide comprising a knob mutation comprises an amino acid sequence of SEQ ID NO: 8, SEQ ID NO: 10, SEQ ID NO: 12, SEQ ID NO: 14, SEQ ID NO: 109, SEQ ID NO: 111, SEQ ID NO: 113, SEQ ID NO: 115, SEQ ID NO: 119, SEQ ID NO: 121, or SEQ ID NO: 123.

In some embodiments, a variant canine or a variant feline IgG Fc polypeptide comprises a hole mutation. In some embodiments, a variant IgG Fc polypeptide comprises a serine at a position corresponding to position 138, an alanine at a position corresponding to position 140, and/or a threonine at a position corresponding to position 181 of SEQ ID NO: 1. In some embodiments, a variant IgG Fc polypeptide comprises a serine at a position corresponding to position 137, an alanine at a position corresponding to position 139, and/or a threonine at a position corresponding to position 180 of SEQ ID NO: 2. In some embodiments, a variant IgG Fc polypeptide comprises a serine at a position corresponding to position 137, an alanine at a position corresponding to position 139, and/or a threonine at a position corresponding to position 180 of SEQ ID NO: 3. In some embodiments, a variant IgG Fc polypeptide comprises a serine at a position corresponding to position 138, an alanine at a position corresponding to position 140, and/or a threonine at a position corresponding to position 181 of SEQ ID NO: 4. In some embodiments, a variant IgG Fc polypeptide comprises a serine at a position corresponding to position 154, an alanine at a position corresponding to position 156, and/or a threonine at a position corresponding to position 197 of SEQ ID NO: 16, SEQ ID NO: 80, SEQ ID NO: 81, SEQ ID NO: 117, or SEQ ID NO: 118.

In some embodiments, a variant IgG Fc polypeptide comprises a serine at position 138, an alanine at position 140, and/or a threonine at position 181 of SEQ ID NO: 1. In some embodiments, a variant IgG Fc polypeptide comprises a serine at position 137, an alanine at position 139, and/or a threonine at position 181 of SEQ ID NO: 2. In some embodiments, a variant IgG Fc polypeptide comprises a serine at position 137, an alanine at position 139, and/or a threonine at position 181 of SEQ ID NO: 3. In some embodiments, a variant IgG Fc polypeptide comprises a serine at position 138, an alanine at position 140, and/or a threonine at position 181 of SEQ ID NO: 4. In some embodiments, a variant IgG Fc polypeptide comprises a serine at position 154, an alanine at position 156, and/or a threonine at position 197 of SEQ ID NO: 16, SEQ ID NO: 80, SEQ ID NO: 81, SEQ ID NO: 117, or SEQ ID NO: 118.

In some embodiments, a variant IgG Fc polypeptide comprising a hole mutation comprises an amino acid sequence of SEQ ID NO: 9, SEQ ID NO: 11, SEQ ID NO: 13, SEQ ID NO: 15, SEQ ID NO: 110, SEQ ID NO: 112, SEQ ID NO: 114, SEQ ID NO: 116, SEQ ID NO: 120, SEQ ID NO: 122, or SEQ ID NO: 124.

In some embodiments, a contiguous polypeptide comprises a GLP1 polypeptide and a variant canine or feline IgG Fc polypeptide comprising a knob mutation. In some embodiments, a contiguous polypeptide comprises a glucagon polypeptide and a variant canine or feline IgG Fc polypeptide comprising a knob mutation. In some embodiments, a contiguous polypeptide comprises a GLP1 polypeptide and a variant canine or feline IgG Fc polypeptide comprising a hole mutation. In some embodiments, a contiguous polypeptide comprises a glucagon polypeptide and a variant canine or feline IgG Fc polypeptide comprising a hole mutation.

In some embodiments, the heterodimeric polypeptide comprises a first contiguous polypeptide comprises a GLP1 polypeptide and a variant canine or feline IgG Fc polypeptide comprising a knob mutation, and a second contiguous polypeptide comprises a glucagon polypeptide and a variant canine or feline IgG Fc polypeptide comprising a hole mutation. In some embodiments, the heterodimeric polypeptide comprises a first contiguous polypeptide comprises a glucagon polypeptide and a variant canine or feline IgG Fc polypeptide comprising a knob mutation, and a second contiguous polypeptide comprises a GLP1 polypeptide and a variant canine or feline IgG Fc polypeptide comprising a hole mutation.

Exemplary GLP1 Polypeptides and Glucagon Polypeptides

"GLP1" or a "GLP1 polypeptide," as used herein, is a polypeptide comprising the entirety or a fragment of glucagon-like peptide-1 that binds to a glucagon-like peptide 1 receptor (GLP1R).

For example, "GLP1" refers to a GLP1 polypeptide from any vertebrate source, including mammals such as primates (e.g., humans and cynomolgus monkeys), rodents (e.g., mice and rats), and companion animals (e.g., dogs, cats, and equine), unless otherwise indicated. In some embodiments, a GLP1 polypeptide is a wild-type GLP1 polypeptide, such as GLP1 (7-37) (SEQ ID N: 85). In some embodiments, a GLP1 polypeptide is a variant GLP1 polypeptide, such as GLP1 (7-36) (SEQ ID NO: 98), GLP1 (7-35) (SEQ ID NO: 99), GLP1-S8 (7-35) (SEQ ID NO: 86), or GLP1-G8 (7-35) (SEQ ID NO: 87). In some embodiments, GLP1 comprises the amino acid sequence of SEQ ID NO: 20.

"GLP1R," as used herein, is a polypeptide comprising the entirety or a fragment of a glucagon-like peptide 1 receptor that is capable of binding to a wild-type GLP1.

For example, "GLP1R" refers to a GLP1R polypeptide from any vertebrate source, including mammals such as primates (e.g., humans and cynomolgus monkeys), rodents (e.g., mice and rats), and companion animals (e.g., dogs, cats, and equine), unless otherwise indicated. In some embodiments, GLP1R is an extracellular domain fragment that binds a wild-type GLP1 polypeptide. In some embodiments, a feline GLP1R comprises the amino acid sequence of SEQ ID NO: 49. In some embodiments, a feline GLP1R comprises the amino acid sequence of SEQ ID NO: 48.

An "extracellular domain" ("ECD") is the portion of a polypeptide that extends beyond the transmembrane domain into the extracellular space. The term "extracellular domain," as used herein, may comprise a complete extracellular domain or may comprise a truncated extracellular domain missing one or more amino acids, that binds to its ligand. The composition of the extracellular domain may depend on the algorithm used to determine which amino acids are in the membrane. Different algorithms may predict, and different systems may express, different extracellular domains for a given protein.

"Glucagon" or a "glucagon polypeptide," as used herein, is a polypeptide comprising the entirety or a fragment of glucagon that binds to a glucagon receptor.

For example, "glucagon" refers to a glucagon polypeptide from any vertebrate source, including mammals such as primates (e.g., humans and cynomolgus monkeys), rodents (e.g., mice and rats), and companion animals (e.g., dogs, cats, and equine), unless otherwise indicated. In some embodiments, a glucagon polypeptide is a wild-type glucagon polypeptide, such as SEQ ID NO: 21.

Exemplary Variant IgG Fc Polypeptides and Fusion Molecules

Polypeptides and other molecules may comprise a variant IgG Fc polypeptide. In some embodiments, a fusion molecule comprises a variant IgG Fc polypeptide, such as the variant IgG Fc polypeptides described herein. In some embodiments, an antibody or an antibody fragment comprises a variant IgG Fc polypeptide, such as the variant IgG Fc polypeptides described herein.

A "fusion molecule," as used herein, refers to a molecule comprising one or more "fusion partners." In some embodiments, the fusion partners are covalently linked ("fused"). If two fusion partners are both polypeptides, the fusion partner polypeptides may be part of a contiguous amino acid sequence (i.e., a contiguous polypeptide). A first fusion partner polypeptide may be linked to either the N-terminus or the C-terminus of a second fusion partner. In some embodiments, the fusion partners are translated as a single polypeptide from a coding sequence that encodes both fusion partners. Fusion partners may be covalently linked through other means, such as, for example, a chemical linkage other than a peptide bond. Many known methods of covalently linking polypeptides to other molecules (for example, fusion partners) may be used. In other embodiments, the fusion partners are fused through a "linker," which is comprised of at least one amino acid or chemical moiety. In some embodiments, fusion partners are noncovalently linked. In some such embodiments, they may be linked, for example, using binding pairs. Exemplary binding pairs include, but are not limited to, biotin and avidin or streptavidin, an antibody and its antigen, etc.

In some embodiments, the fusion partners include an IgG Fc polypeptide and at least one GLP1 polypeptide. In some embodiments, the fusion partners include an IgG Fc polypeptide, a GLP1 polypeptide, and a glucagon polypeptide. In some embodiments, a GLP1 polypeptide may be linked to either the N-terminus or the C-terminus of an IgG Fc polypeptide. In some embodiments, a glucagon polypeptide may be linked to either the N-terminus or the C terminus of an IgG Fc polypeptide.

The term "contiguous polypeptide" herein is used to mean an uninterrupted sequence of amino acids. A contiguous polypeptide is typically translated from a single continuous DNA sequence. It can be made by genetic engineering, for example, by removing the stop codon from the DNA sequence of the first protein, then appending the DNA sequence of the second protein in frame, so that the DNA sequence is expressed as a single protein. Typically, this is accomplished by cloning a cDNA into an expression vector in frame with an existing gene.

A "linker" refers to one or more amino acid residues that connects a first polypeptide with a second polypeptide.

In some embodiments, the linker is a flexible, non-structural linker. In some embodiments, the linker is a glycine-rich, serine-rich, or glycine- and serine-rich linker. In some embodiments, a linker comprises 100%, at least 95%, at least 90%, or at least 85% serine and/or glycine amino acid residues.

An "extension," as used herein, refers to one or more amino acid residues that are connected to a polypeptide at its C-terminus or at its N-terminus.

In some embodiments, an extension is flexible. In some embodiments, the extension adds flexibility to the polypeptide without interfering with the biological activity of the polypeptide. In some embodiments, the extension increases solubility of the polypeptide. In some embodiments, the extension comprises one or more glycine residues. In some embodiments, the extension comprises a glycine residue (SEQ ID NO: 88), two glycine residues (SEQ ID NO: 89), a three glycine residues (SEQ ID NO: 90), four glycine residues (SEQ ID NO: 91), five glycine residues (SEQ ID NO: 92), six glycine residues (SEQ ID NO: 93), seven glycine residues (SEQ ID NO: 94), eight glycine residues (SEQ ID NO: 95), or more glycine residues.

In some embodiments, the contiguous polypeptide comprises an IgG Fc polypeptide comprising an amino acid sequence of any one of SEQ ID NOs: 1, 2, 3, 4, 5, 6, 7, 8, 9, 10, 11, 12, 13, 14, 15, 16, 17, 18, 19, 60, 61, 62, 63, 64, 65, 66, 67, 68, 69, 70, 71, 72, 73, 74, 75, 76, 77, 78, 79, 80, 81, 82, 83, 84, 100, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 167, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 and a GLP1 polypeptide comprising an amino acid sequence of SEQ ID NO: 85. In some embodiments, the contiguous polypeptide comprises an IgG Fc polypeptide comprising an amino acid sequence of any one of SEQ ID NOs: 1, 2, 3, 4, 5, 6, 7, 8, 9, 10, 11, 12, 13, 14, 15, 16, 17, 18, 19, 60, 61, 62, 63, 64, 65, 66, 67, 68, 69, 70, 71, 72, 73, 74, 75, 76, 77, 78, 79, 80, 81, 82, 83, 84, 100, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 167, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 and a GLP1 polypeptide comprising an amino acid sequence of SEQ ID NO: 86. In some embodiments, the contiguous polypeptide comprises an IgG Fc polypeptide comprising an amino acid sequence of any one of SEQ ID NOs: 1, 2, 3, 4, 5, 6, 7, 8, 9, 10, 11, 12, 13, 14, 15, 16, 17, 18, 19, 60, 61, 62, 63, 64, 65, 66, 67, 68, 69, 70, 71, 72, 73, 74, 75, 76, 77, 78, 79, 80, 81, 82, 83, 84, 100, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 167, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 and a GLP1 polypeptide comprising an amino acid sequence of SEQ ID NO: 87. In some embodiments, the contiguous polypeptide comprises an IgG Fc polypeptide comprising an amino acid sequence of any one of SEQ ID NOs: 1, 2, 3, 4, 5, 6, 7, 8, 9, 10, 11, 12, 13, 14, 15, 16, 17, 18, 19, 60, 61, 62, 63, 64, 65, 66, 67, 68, 69, 70, 71, 72, 73, 74, 75, 76, 77, 78, 79, 80, 81, 82, 83, 84, 100, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 167, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 and a GLP1 polypeptide comprising an amino acid sequence of SEQ ID NO: 98. In some embodiments, the contiguous polypeptide comprises an IgG Fc polypeptide comprising an amino acid sequence of any one of SEQ ID NOs: 1, 2, 3, 4, 5, 6, 7, 8, 9, 10, 11, 12, 13, 14, 15, 16, 17, 18, 19, 60, 61, 62, 63, 64, 65, 66, 67, 68, 69, 70, 71, 72, 73, 74, 75, 76, 77, 78, 79, 80, 81, 82, 83, 84, 100, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 167, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 and a GLP1 polypeptide comprising an amino acid sequence of SEQ ID NO: 99.

In some embodiments, the contiguous polypeptide comprises an IgG Fc polypeptide comprising an amino acid sequence of any one of SEQ ID NOs: 1, 2, 3, 4, 5, 6, 7, 8, 9, 10, 11, 12, 13, 14, 15, 16, 17, 18, 19, 60, 61, 62, 63, 64, 65, 66, 67, 68, 69, 70, 71, 72, 73, 74, 75, 76, 77, 78, 79, 80, 81, 82, 83, 84, 100, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 167, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 and a glucagon polypeptide comprising an amino acid sequence of SEQ ID NO: 21.

In some embodiments, a contiguous polypeptide comprises a first GLP1 polypeptide (GLP1A), a first linker (L1), an Fc polypeptide of a companion animal species, optionally a second linker (L2), and optionally a second GLP1 polypeptide (GLP1B). In some embodiments, the contiguous polypeptide comprises:

| | |
|---|---|
| GLP1A-L1-Fc; | Formula (I): |
| Fc-L1-GLP1A; or | Formula (II): |
| GLP1A-L1-Fc-L2-GLP1B. | Formula (III): |

In some embodiments, a contiguous polypeptide comprises a GLP1 polypeptide, a first linker (L1), an Fc polypeptide, a second linker (L2), and a glucagon polypeptide (Gluc). In some embodiments, the contiguous polypeptide comprises:

| | |
|---|---|
| GLP1-L1-Fc-L2-Gluc; or | Formula (IV): |
| Gluc-L1-Fc-L2-GLP1. | Formula (V): |

In some embodiments, the GLP1 fusion molecule has an increased serum half-life compared to a wild-type GLP1 polypeptide. The increased half-life of the GLP1 fusion molecules described herein may require lower doses and less-frequent dosing regimen than wild-type GLP1 polypeptides.

In some embodiments, GLP1B, if present, comprises the same amino acid sequence as GLP1A.

In some embodiments, GLP1, GLP1A, or GLP1B, if present, comprises a wild-type GLP1 polypeptide. In some embodiments, GLP1, GLP1A, or GLP1B, if present, comprises a variant GLP1 polypeptide. In some embodiments, GLP1, GLP1A, or GLP1B, if present, comprises an amino acid sequence of SEQ ID NO: 85, SEQ ID NO: 86, SEQ ID NO: 87, SEQ ID NO: 98, or SEQ ID NO: 99.

In some embodiments, the glucagon polypeptide comprises a wild-type glucagon polypeptide. In some embodiments, the glucagon polypeptide comprises an amino acid sequence of SEQ ID NO: 21. In some embodiments, the glucagon polypeptide comprises a variant glucagon polypeptide.

In some embodiments, the Fc polypeptide is a human IgG Fc. In some embodiments, the Fc polypeptide is a human IgG1 Fc, a human IgG2 Fc, a human IgG3 Fc, or a human IgG4 Fc. In some embodiments, the Fc polypeptide is a variant human IgG Fc.

In some embodiments, the Fc polypeptide is an IgG Fc from a companion animal. In some embodiments, the Fc polypeptide is a canine IgG-A Fc, a canine IgG-B Fc, a canine IgG-C Fc, a canine IgG-D Fc. In some embodiments, the Fc is an equine IgG1 Fc, an equine IgG2 Fc, an equine IgG3 Fc, an equine IgG4 Fc, an equine IgG5 Fc, an equine IgG6 Fc, or an equine IgG7 Fc. In some embodiments, the Fc is a feline IgG1a Fc, a feline IgG1b Fc, or a feline IgG2 Fc.

In some embodiments, the Fc polypeptide is a variant IgG Fc. In some embodiments, the FC polypeptide is a variant canine IgG-A Fc, a variant canine IgG-B Fc, a variant canine IgG-C Fc, a variant canine IgG-D Fc. In some embodiments, the Fc is a variant equine IgG1 Fc, a variant equine IgG2 Fc, a variant equine IgG3 Fc, a variant equine IgG4 Fc, a variant equine IgG5 Fc, a variant equine IgG6 Fc, or a variant equine IgG7 Fc. In some embodiments, the Fc is a variant feline IgG1a Fc, a variant feline IgG1b Fc, or a variant feline IgG2 Fc.

In some embodiments, L1 and L2, if present, each independently is a flexible linker. In some embodiments, the amino acid sequence of L1 and L2, if present, each independently comprises 100%, at least 95%, at least 90%, at least 85% serine and/or glycine amino acid residues.

In some embodiments, the contiguous polypeptide comprises an extension at its C-terminus. In some embodiments, the contiguous polypeptide comprises a glycine residue, two glycine residues, three glycine residues, four glycine residues, five glycine residues, six glycine residues, seven glycine residues, eight glycine residues, or greater than eight glycine residues at its C-terminus. In some embodiments, the contiguous polypeptide comprises an amino acid sequence of SEQ ID NO: 88, SEQ ID NO: 89, SEQ ID NO: 90, SEQ ID NO: 91, SEQ ID NO: 92, SEQ ID NO: 93, SEQ ID NO: 94, or SEQ ID NO: 95 at its C-terminus.

In some embodiments, the contiguous polypeptide comprises the amino acid sequence of SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47, SEQ ID NO: 96; SEQ ID NO: 97, SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 103; SEQ ID NO: 104; SEQ ID NO: 105; or SEQ ID NO: 106.

A nucleotide sequence encoding a polypeptide of interest, such as a variant IgG Fc polypeptide or other polypeptide described herein, can be inserted into an expression vector suitable for expression in a selected host cell. A variant IgG Fc polypeptide or other polypeptide described herein may be expressed by culturing a host cell transfected with an expression vector comprising the nucleotide sequence.

A "vector" is a plasmid that can be used to transfer DNA sequences from one organism to another or to express a gene of interest. A vector typically includes an origin of replication and regulatory sequences which regulate the expression of the gene of interest, and may or may not carry a selective marker gene, such as an antibiotic resistance gene. A vector is suitable for the host cell in which it is to be expressed. A vector may be termed a "recombinant vector" when the gene of interest is present in the vector.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NS0 cells, PER.C6® cells (Crucell), 293 cells, and CHO cells, and their derivatives, such as 293-6E, DG44, CHO-S, and CHO-K cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) encoding an amino acid sequence(s) provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated."

A "signal sequence" refers to a sequence of amino acid residues or polynucleotides encoding such, which facilitates secretion of a polypeptide of interest and is typically cleaved upon export of the polypeptide to the outside of the cell surface membrane.

In some embodiments, a variant IgG Fc polypeptide or a contiguous polypeptide comprising a variant Fc polypeptide is isolated using chromatography, such as size exclusion chromatography, ion exchange chromatography, protein A column chromatography, hydrophobic interaction chromatography, and CHT chromatography.

A label can be attached to a variant IgG Fc polypeptides or a contiguous polypeptide comprising a variant Fc polypeptide. A "label" means a moiety attached to a molecule to render it detectable. In some embodiments, a variant IgG Fc polypeptide or a contiguous polypeptide comprising a variant Fc polypeptide is labeled with a detectable moiety including but not limited to radioisotopes, fluorescent labels, and various enzyme-substrate labels known in the art. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, p-galactosidase, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety. General techniques to be used in performing the various immunoassays noted above are known to those of ordinary skill in the art.

Exemplary Variant IgG Fc Polypeptide Affinity to Protein A and/or C1q and/or CD16

The variant IgG Fc polypeptides described herein may have altered binding affinity to Protein A and/or C1q and/or CD16. In some embodiments, a variant IgG Fc polypeptide has increased binding affinity to Protein A relative to the wild-type IgG Fc polypeptide. Such variant IgG Fc polypeptides may be purified by Protein A column chromatography. In some embodiments, a variant IgG Fc polypeptide has reduced binding affinity to C1q relative to the wild-type IgG Fc polypeptide. Such variant IgG Fc polypeptides may have reduced complement-mediated immune responses. In some embodiments, a variant IgG Fc polypeptide has reduced binding affinity to CD16 relative to the wild-type IgG Fc polypeptide. Such variant IgG Fc polypeptides may have reduced ADCC immune responses. In some embodiments, a variant IgG Fc polypeptide has increased binding affinity to Protein A relative to the wild-type IgG Fc polypeptide and/or has reduced binding affinity to C1q relative to the wild-type IgG Fc polypeptide and/or has reduced binding affinity to CD16 relative to the wild-type IgG Fc polypeptide.

"Protein A," as used herein, is a polypeptide comprising the entirety or a portion of Protein A that is capable of binding a wild-type canine IgG-B Fc, a wild-type equine IgG1 Fc, a wild-type equine IgG3 Fc, a wild-type equine IgG4 Fc, a wild-type equine IgG7 Fc, a wild-type feline IgG1a Fc, a wild-type feline IgG1b Fc, or a wild-type feline IgG2 Fc.

"C1q" or "C1q complex" is used interchangeably to refer to a protein complex involved in the complement system, or a portion thereof, that can bind a wild-type canine IgG-B Fc, a wild-type canine IgG-C Fc, a wild-type equine IgG1 Fc, a wild-type equine IgG3 Fc, a wild-type equine IgG4 Fc, a wild-type equine IgG7 Fc, a wild-type feline IgG1a Fc, or a wild-type feline IgG1b Fc.

"CD16," as used herein, is a polypeptide comprising the entirety or a portion of CD16 that is capable of binding a wild-type canine IgG-A Fc or a wild-type canine IgG-D Fc. The term "binds" to a substance is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA, KinEx A, biolayer interferometry (BLI), surface plasmon resonance devices, or etc.

"Protein A+," as used herein, means that the Fc polypeptide has Protein A binding affinity. In some embodiments, a Protein A+ Fc polypeptide comprises at least one an amino acid modification that increases Protein A binding affinity.

"Protein A−," as used herein, means that the Fc polypeptide has low or no Protein A binding affinity.

"C1q+," as used herein, means that the Fc polypeptide has C1q binding affinity.

"C1q−," as used herein, means that the Fc polypeptide has low or no C1q binding affinity. In some embodiments, a C1q− Fc polypeptide has at least one an amino acid modification that reduces C1q binding affinity.

"CD16+," as used herein, means that the Fc polypeptide has CD16 binding affinity.

"CD16−," as used herein, means that the Fc polypeptide has low or no CD16 binding affinity. In some embodiments, a CD16− Fc polypeptide has at least one an amino acid modification that reduces CD16 binding affinity.

The term "affinity" means the strength of the sum total of noncovalent interactions between a single binding site of a molecule (for example, a receptor) and its binding partner (for example, a ligand). The affinity of a molecule X for its partner Y can generally be represented by the dissociation constant (Ku). Affinity can be measured by common methods known in the art, such as, for example, immunoblot, ELISA, KinEx A, biolayer interferometry (BLI), or surface plasmon resonance devices.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51: 19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is an Octet® system (Pall ForteBio LLC). See, e.g., Abdiche et al., 2008, *Anal. Biochem.* 377: 209-277.

The terms "$K_D$," "$K_d$," "Kd" or "Kd value" as used interchangeably to refer to the equilibrium dissociation constant of a receptor-ligand interaction or antibody-antigen interaction.

In some embodiments, a variant IgG Fc polypeptide binds to Protein A with a dissociation constant ($K_D$) of less than $5 \times 10^{-6}$ M, less than $1 \times 10^{-6}$ M, less than $5 \times 10^{-7}$ M, less than $1 \times 10^{-7}$ M, less than $5 \times 10^{-8}$ M, less than $1 \times 10^{-8}$ M, less than $5 \times 10^{-9}$ M, less than $1 \times 10^{-9}$ M, less than $5 \times 10^{-10}$ M, less than $1 \times 10^{-10}$ M, less than $5 \times 10^{-11}$ M, less than $1 \times 10^{-11}$ M, less than $5 \times 10^{-12}$ M, or less than $1 \times 10^{-12}$ M, as measured by biolayer interferometry.

In some embodiments, a variant IgG Fc polypeptide binds to C1q or CD16 with a dissociation constant ($K_D$) of greater than $5 \times 10^{-6}$ M, greater than $1 \times 10^{-5}$ M, greater than $5 \times 10^{-5}$ M, greater than $1 \times 10^{-4}$ M, greater than $5 \times 10^{-4}$ M, or greater than $1 \times 10^{-3}$ M, as measured by biolayer interferometry.

In some embodiments, the $K_D$ of an IgG Fc polypeptide, such as a variant IgG Fc polypeptide, to Protein A or to C1q or to CD16 is measured by using biolayer interferometry assays using a biosensor, such as an Octet® System (Pall ForteBio LLC, Fremont, CA) according to the supplier's instructions. In brief, biotinylated Protein A or C1q or CD16 is bound to the sensor tip and the association of IgG Fc polypeptide is monitored for a specified time or until steady state is reached. Dissociation may be monitored for a specified time or until steady state is reached. A buffer only blank curve is subtracted to correct for any drift. The data are fit to a 2:1 binding model using ForteBio data analysis software to determine association rate constant ($k_{on}$), dissociation rate constant ($k_{off}$), and the $K_d$. The equilibrium dissociation constant ($K_D$) is calculated as the ratio of $k_{off}/k_{on}$. The term "$k_{on}$" refers to the rate constant for association of a molecule X to its partner Y and the term "$k_{off}$" refers to the rate constant for dissociation of a molecule X or partner Y from the molecule X/partner Y complex.

To "increase" or "stimulate" means to increase, improve, or augment an activity, function, or amount as compared to a reference. In some embodiments, by "increase" or "stimulate" is meant the ability to cause an overall increase of about 5% or greater, of about 10% or greater, of about 20% or greater, of about 30% or greater, of about 40% or greater, of about 50% or greater, of about 60% or greater, of about 70% or greater, of about 80% or greater, of about 90% or greater, of about 100% or greater, of about 125% or greater, of about 200% or greater relative to a reference value. In some embodiments, by "increase" or "stimulate" is meant the ability to cause an overall increase of about 5% to about 50%, of about 10% to about 20%, of about 50% to about 100%, of about 25% to about 70% relative to a reference value. In some embodiments, by "increase" or "stimulate" is meant the ability to cause an overall increase of 50% or greater. In some embodiments, by "increase" or "stimulate" is meant the ability to cause an overall increase of 75%, 85%, 90%, 95%, or greater. In some embodiments, the amount noted above is stimulated or increased over a period of time, relative to a control dose (such as a placebo) over the same period of time.

In some embodiments, a variant IgG Fc polypeptide is capable of binding to Protein A with an increased affinity of about 5% or greater, of about 10% or greater, of about 20% or greater, of about 30% or greater, of about 40% or greater, of about 50% or greater, of about 60% or greater, of about 70% or greater, of about 80% or greater, of about 90% or greater, of about 100% or greater, of about 125% or greater, of about 150% or greater, of about 200% or greater relative to a reference IgG Fc polypeptide. In some embodiments, a variant IgG Fc polypeptide is capable of binding to Protein A with an increased affinity of about 5% to about 50%, of about 10% to about 20%, of about 50% to about 100%, of about 25% to about 70% relative to a reference IgG Fc polypeptide. In some embodiments, the reference IgG Fc polypeptide is a wild-type IgG Fc polypeptide. In some embodiments, the reference IgG Fc polypeptide is a different variant IgG Fc polypeptide.

To "reduce" or "inhibit" means to decrease, reduce, or arrest an activity, function, or amount as compared to a reference. In some embodiments, by "reduce" or "inhibit" is meant the ability to cause an overall decrease of about 5% or greater, of about 10% or greater, of about 20% or greater, of about 30% or greater, of about 40% or greater, of about 50% or greater, of about 60% or greater, of about 70% or greater, of about 80% or greater, or of about 90% or greater relative to a reference IgG Fc polypeptide. In some embodiments, by "reduce" or "inhibit" is meant the ability to cause an overall decrease of about 5% to about 50%, of about 10% to about 20%, of about 50% to about 100%, of about 25% to about 70% relative to a reference value. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time.

In some embodiments, a variant IgG Fc polypeptide is capable of binding to C1q or CD16 with a decreased affinity of about 5% or greater, of about 10% or greater, of about 20% or greater, of about 30% or greater, of about 40% or greater, of about 50% or greater, of about 60% or greater, of about 70% or greater, of about 80% or greater, of about 90% or greater relative to a reference IgG Fc polypeptide. In some embodiments, a variant IgG Fc polypeptide is capable of binding to C1q or CD16 with a decreased affinity of about 5% to about 50%, of about 10% to about 20%, of about 50% to about 100%, of about 25% to about 70% relative to a reference IgG Fc polypeptide. In some embodiments, the reference IgG Fc polypeptide is a wild-type IgG Fc polypeptide. In some embodiments, the reference IgG Fc polypeptide is a different variant IgG Fc polypeptide.

A "reference" as used herein, refers to any sample, standard, or level that is used for comparison purposes. A reference may be a wild-type reference or a variant reference. A reference may be obtained from a healthy or non-diseased sample. In some examples, a reference is obtained from a non-diseased or non-treated sample of a companion animal. In some examples, a reference is obtained from one or more healthy animals of a particular species, which are not the animal being tested or treated.

Exemplary Biological Activity of Variant GLP1 Fusion Molecules

In some embodiments, a GLP1 fusion molecule binds to GLP1R and activates cAMP production. In some embodiments, a GLP1 fusion polypeptide increases production of cAMP in a cell by at least 10%, at least 15%, at least 20%, at least 25%, at least 30%, at least 35%, at least 40%, at least 45%, at least 50%, at least 60%, at least 70%, at least 80%, at least 90%, or 100% compared to signaling function in the absence of the GLP1 fusion polypeptide.

Exemplary Pharmaceutical Compositions

The terms "pharmaceutical formulation" and "pharmaceutical composition" refer to a preparation which is in such form as to permit the biological activity of the active ingredient(s) to be effective, and which contains no additional components that are unacceptably toxic to a subject to which the formulation would be administered.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. Examples of pharmaceutically acceptable carriers include alumina; aluminum stearate; lecithin; serum proteins, such as human serum albumin, canine or other animal albumin; buffers such as phosphate, citrate, tromethamine or HEPES buffers; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts, colloidal silica, or magnesium trisilicate; polyvinyl pyrrolidone, cellulose-based substances; polyethylene glycol; sucrose; mannitol; or amino acids including, but not limited to, arginine.

The pharmaceutical composition can be stored in lyophilized form. Thus, in some embodiments, the preparation process includes a lyophilization step. The lyophilized composition may then be reformulated, typically as an aqueous composition suitable for parenteral administration, prior to administration to the dog, cat, or horse. In other embodiments, particularly where a variant IgG Fc polypeptide or other polypeptide described herein is highly stable to thermal and oxidative denaturation, the pharmaceutical composition can be stored as a liquid, i.e., as an aqueous composition, which may be administered directly, or with appropriate dilution, to the dog, cat, or horse. A lyophilized composition can be reconstituted with sterile Water for Injection (WFI). Bacteriostatic reagents, such benzyl alcohol, may be included. Thus, the invention provides pharmaceutical compositions in solid or liquid form.

The pH of the pharmaceutical compositions may be in the range of from about pH 5 to about pH 8, when administered. The compositions of the invention are sterile if they are to be used for therapeutic purposes. Sterility can be achieved by any of several means known in the art, including by filtration through sterile filtration membranes (e.g., 0.2 micron membranes). Sterility may be maintained with or without anti-bacterial agents.

Certain Uses of Fc Polypeptides and Pharmaceutical Compositions

A polypeptide comprising a variant Fc polypeptide, such as a variant IgG Fc polypeptide, of the invention or pharmaceutical compositions comprising a variant Fc polypeptide of the invention may be useful for extending product half-life in vivo in a companion animal, including, but not limited to, canine, feline, or equine.

As used herein, "treatment" is an approach for obtaining beneficial or desired clinical results. "Treatment" as used herein, covers any administration or application of a therapeutic for disease in a mammal, including a companion animal. For purposes of this disclosure, beneficial or desired clinical results include, but are not limited to, any one or more of: alleviation of one or more symptoms, diminishment of extent of disease, preventing or delaying spread of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

A "therapeutically effective amount" of a substance/molecule, agonist or antagonist may vary according to factors such as the type of disease to be treated, the disease state, the severity and course of the disease, the type of therapeutic purpose, any previous therapy, the clinical history, the response to prior treatment, the discretion of the attending veterinarian, age, sex, and weight of the animal, and the ability of the substance/molecule, agonist or antagonist to elicit a desired response in the animal. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic or prophylactic result.

In some embodiments, a variant IgG Fc polypeptide or other polypeptide described herein, or a pharmaceutical composition comprising such is administered parenterally, by subcutaneous administration, intravenous infusion, or intramuscular injection. In some embodiments, a variant IgG Fc polypeptide or other polypeptide described herein, or a pharmaceutical composition comprising such is administered as a bolus injection or by continuous infusion over a period of time. In some embodiments, a variant IgG Fc polypeptide or other polypeptide described herein, or a pharmaceutical composition comprising such is administered by an intramuscular, an intraperitoneal, an intracerebrospinal, a subcutaneous, an intra-arterial, an intrasynovial, an intrathecal, or an inhalation route.

In some embodiments, a GLP1 fusion polypeptide or pharmaceutical compositions comprising it can be utilized in accordance with the methods herein to treat high blood glucose-related conditions. In some embodiments, an GLP1 fusion polypeptide or pharmaceutical compositions is administered to a companion animal, such as a canine, a feline, or equine, to treat high blood glucose-related condition.

In some embodiments, a variant IgG Fc polypeptide or other polypeptide described herein, or a pharmaceutical composition comprising such is administered in an amount in the range of 0.0001 mg/kg body weight to 100 mg/kg body weight per dose. In some embodiments, GLP1 analog may be administered in an amount in the range of 0.005 mg/kg body weight to 20 mg/kg body weight per dose. In some embodiments, GLP1 analog may be administered in an amount in the range of 1 mg/kg body weight to 10 mg/kg body weight per dose. In some embodiments, GLP1 analog may be administered in an amount in the range of 0.5 mg/kg body weight to 100 mg/kg body, in the range of 1 mg/kg body weight to 100 mg/kg body weight, in the range of 5 mg/kg body weight to 100 mg/kg body weight, in the range of 10 mg/kg body weight to 100 mg/kg body weight, in the range of 20 mg/kg body weight to 100 mg/kg body weight, in the range of 50 mg/kg body weight to 100 mg/kg body weight, in the range of 1 mg/kg body weight to 10 mg/kg body weight, in the range of 5 mg/kg body weight to 10 mg/kg body weight, in the range of 0.5 mg/kg body weight to 10 mg/kg body weight, or in the range of 5 mg/kg body weight to 50 mg/kg body weight.

In some embodiments, a variant IgG Fc polypeptide or other polypeptide described herein, or a pharmaceutical composition comprising such is administered to a companion animal at one time or over a series of treatments. In some embodiments, the dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

In some embodiments, the dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

In some embodiments, the method comprises administering in combination with a GLP1 fusion polypeptide insulin, a DPP4 inhibitor, a SGLT2 inhibitor, a biguanides sulfonylurea, a meglitinide derivative, an alpha-glucosidase inhibitor, a thiazolidinedione (TZD), an amylinomimetic, a bile acid sequestrant, a dopamine agonist.

The following examples illustrate particular aspects of the disclosure and are not intended in any way to limit the disclosure.

EXAMPLES

Example 1

Variant Canine IgG Fc Polypeptides for Increased Protein a Binding and/or Decreased Complement Binding and/or Decreased CD16 Binding Purification of antibodies using Protein A affinity is a well-developed process. However, among four subtypes of canine IgG, only IgG-B Fc (e.g., SEQ ID NO: 2 or SEQ ID NO: 107) has Protein A binding affinity. Canine IgG-A Fc (e.g., SEQ ID NO: 1), IgG-C Fc (e.g., SEQ ID NO: 3 or SEQ ID NO: 108), and IgG-D Fc (e.g., SEQ ID NO: 4) have weak or no measurable Protein A binding affinity. Variant canine IgG-A Fc, IgG-C Fc, and IgG-D Fc polypeptides were designed for altered Protein A binding.

In addition, canine IgG-B Fc and IgG-C Fc have complement activity and bind to C1q, while canine IgG-A Fc and IgG-D Fc have weak or no measurable binding affinity to C1q. To potentially reduce the C1q binding and/or potentially reduce complement-mediated immune responses, variant canine IgG-B Fc and IgG-C Fc polypeptides were designed.

Furthermore, canine IgG-B Fc and IgG-C Fc have CD16 binding activity. To potentially reduce the binding of CD16 to IgG-B Fc and IgG-C Fc, and/or potentially reduce ADCC, variant canine IgG-B Fc and IgG-C Fc polypeptides were designed.

Table 3, below summarizes the Protein A and C1q binding characteristics of canine IgG Fc subtypes. Notably, none of the wild-type canine IgG Fc subtypes lacks C1q binding and binds Protein A.

TABLE 3

| Wild-type Canine IgG Fc | Protein A Binding | C1q Binding | CD16 Binding |
|---|---|---|---|
| IgG-A Fc | − | − | − |
| IgG-B Fc | + | + | + |
| IgG-C Fc | − | + | + |
| IgG-D Fc | − | − | − |

(−) denotes low or no measurable binding activity.

Using three-dimensional protein modeling and protein sequence analysis, the sequences of canine IgG-B Fc that are likely in contact with Protein A were identified. FIG. 1 shows an alignment of canine IgG-A, B, C, and D Fc sequences. The boxes indicate the regions likely in contact with Protein A.

Two approaches were used to design variant canine IgG-A, IgG-C, and IgG-D Fc polypeptides for increased Protein A binding. For the first approach, variant canine IgG-A, IgG-C, and IgG-D Fc polypeptides were designed to have the same Protein A binding motif sequences as canine IgG-B Fc (e.g., SEQ ID NO: 5, SEQ ID NO: 6, and SEQ ID NO: 7, respectively). For the second approach, variant canine IgG-A Fc I(21)T/Q(207)H (SEQ ID NO: 60), variant canine IgG-C Fc I(21)T (SEQ ID NO: 61), and variant canine IgG-D Fc I(21)T/Q(207)H (SEQ ID NO: 62) were designed with one or two amino acid substitutions in the Protein A binding region to correspond with the canine IgG-B Fc sequence.

In addition, variant canine IgG-A Fc, IgG-C Fc, and IgG-D Fc polypeptides with increased Protein A binding may be prepared having one or more of the amino acid substitutions listed in Table 4.

TABLE 4

| Variant Canine IgG Fc Amino Acid Substitutions* (Protein A +) | | |
|---|---|---|
| Canine IgG-A Fc (SEQ ID NO: 1) | Canine IgG-C Fc (SEQ ID NO: 3) | Canine IgG-D Fc (SEQ ID NO: 4) |
| Ile (21) Thr | Ile (21) Thr | Ile (23) Thr |
| Arg (23) Leu | Val (23) Leu | Arg (23) Leu |
| Thr (25) Ala | Thr (24) Ile | Thr (25) Ala |
| Glu (80) Gly | | Glu (80) Gly |
| Thr (205) Ala | | Gln (207) His |
| Gln (207) His | | |

*The amino acid positions listed are relative to the SEQ ID NO. indicated.

To potentially reduce the binding of C1q to canine IgG-B Fc and IgG-C Fc, and/or potentially reduce complement-mediated immune responses, variant canine IgG-B Fc and IgG-C Fc polypeptides may be prepared having an amino acid substitution of Lys with any amino acid except Lys at an amino acid position corresponding to position 93 of SEQ ID NO: 2 or of SEQ ID NO: 3, respectively. These amino acid substitutions were identified after analysis of the protein sequence and 3-D structure modeling of canine IgG-B Fc and IgG-C Fc compared to canine IgG-A Fc and IgG-D Fc, which are understood to not exhibit complement activity. For example, variant canine IgG-B Fc K(93)R (SEQ ID NO: 78) and variant canine IgG-C Fc K(93)R (SEQ ID NO: 79) may be prepared. Reduced binding between human C1q and a fusion protein comprising variant canine IgG-B Fc K(93)R was observed when compared to a fusion protein comprising wild-type canine IgG-B Fc.

To potentially reduce the binding of CD16 to IgG-B Fc and IgG-C Fc, and/or potentially reduce ADCC, variant canine IgG-B Fc and IgG-C Fc polypeptides may be prepared having one or more of the amino acid substitutions listed in Table 5. The amino acid substitution(s) were identified after analysis of the protein sequence and 3-D structure modeling of canine IgG-B and IgG-C compared to IgG-A and IgG-D, which are understood to not exhibit ADCC activity.

TABLE 5

| Original residue position* | | |
|---|---|---|
| Canine IgG-B Fc (SEQ ID NO: 2) | Canine IgG-C Fc (SEQ ID NO: 3) | Substitution(s) |
| Met (5) | Leu (5) | Any amino acid except original residue, such as Pro |
| Asp (38) | Asp (38) | Any amino acid except original residue, such as Gly |
| Pro (39) | Pro (39) | Any amino acid except original residue, such as Arg |
| Lys (97) | Lys (97) | Any amino acid except original residue, such as Ile |
| Ala (98) | Ala (98) | Any amino acid except original residue, such as Gly |

*The amino acid positions listed are relative to the SEQ ID NO. indicated.

Since wild-type canine IgG-C Fc lacks Protein A binding and has C1q binding, a double variant canine IgG-C Fc that binds Protein A and has reduced binding to C1q may be prepared by combining one or more of the amino acid substitutions listed in Table 4 with a K(93)R substitution or K(93)X substitution, wherein X is any amino acid except Lys. A double variant canine IgG-B Fc or double variant canine IgG-C Fc with reduced binding to C1q and reduced binding to CD16 may be prepared by combining one or more of the amino acid substitutions listed in Table 5 with a K(93)R substitution or K(93)X substitution, wherein X is any amino acid except Lys. A triple variant canine-IgG-C Fc that binds Protein A and has reduced binding to C1q and CD16 may be prepared by combining one or more of the amino acid substitutions listed in Table 4 and one or more of the amino acid substitutions listed in Table 5 with a K(93)R substitution or K(93)X substitution, wherein X is any amino acid except Lys.

The binding of any variant canine IgG Fc to Protein A, CD16, and/or C1q may be determined and compared to the binding of another IgG Fc to Protein A, CD16, and/or C1q (e.g., the corresponding wild-type canine IgG Fc, another wild-type or variant canine IgG Fc, or a wild-type or variant IgG Fc of another companion animal, etc.).

Binding analysis may be performed using an Octet biosensor. Briefly, the target molecule (e.g., Protein A, C1q, CD16, etc.) may be biotinylated and free unreacted biotin removed (e.g., by dialysis). The biotinylated target molecule is captured on streptavidin sensor tips. Association of the target molecule with various concentrations (e.g., 10 μg/mL) of IgG Fc polypeptide is monitored for a specified time or until steady state is reached. Dissociation is monitored for a specified time or until steady state is reached. A buffer only blank curve may be subtracted to correct for any drift. The data are fit to a 1:1 binding model using ForteBio™ data analysis software to determine the $k_{on}$, $k_{off}$, and the $K_d$.

Example 2

Variant Equine IgG Fc Polypeptides for Increased Protein a Binding and/or Decreased Complement Binding Of the seven subtypes of equine IgG, IgG1 Fc (e.g., SEQ ID NO: 63), IgG3 Fc (e.g., SEQ ID NO: 65), IgG4 Fc (e.g., SEQ ID NO: 66), IgG7 Fc (e.g., SEQ ID NO: 69) have Protein A binding affinity. Equine IgG2 Fc (e.g., SEQ ID NO: 18, SEQ ID NO: 64), IgG5 Fc (e.g., SEQ ID NO: 67), and IgG6 Fc (e.g., SEQ ID NO: 68) have weak or no measurable Protein A binding affinity. Variant equine IgG2 Fc, IgG5 Fc, and IgG6 Fc polypeptides were designed for altered Protein A binding.

In addition, equine IgG2 Fc, IgG5 Fc, and IgG6 Fc have weak or no measurable binding affinity to C1q, while equine IgG1 Fc, IgG3 Fc, IgG4 Fc, and IgG7 Fc bind to C1q. To potentially reduce the C1q binding and/or potentially reduce complement-mediated immune responses, variant equine IgG1 Fc, IgG3 Fc, IgG4 Fc, and IgG7 Fc polypeptides were designed.

Table 6, below summarizes the Protein A and C1q binding characteristics of equine IgG Fc subtypes. Notably, none of the wild-type equine IgG Fc subtypes lacks C1q binding and binds Protein A.

TABLE 6

| Wild-type Equine IgG Fc | Protein A Binding | C1q Binding |
|---|---|---|
| IgG1 Fc | + | + |
| IgG2 Fc | − | − |
| IgG3 Fc | + | + |
| IgG4 Fc | + | + |
| IgG5 Fc | − | − |
| IgG6 Fc | − | − |
| IgG7 Fc | + | + |

(−) denotes low or no measurable binding activity.

Using three-dimensional protein modeling and protein sequence analysis, the sequences of equine IgG1 Fc, IgG3 Fc, IgG4 Fc, and IgG7 Fc that are likely in contact with Protein A were identified. Variant equine IgG2 Fc, IgG5 Fc, and IgG6 Fc polypeptides with increased Protein A binding may be prepared having one or more of the amino acid substitutions listed in Table 7.

TABLE 7

| Variant Equine IgG Fc Amino Acid Substitutions* (Protein A +) | | |
|---|---|---|
| Equine IgG2 Fc (SEQ ID NO: 64) | Equine IgG5 Fc (SEQ ID NO: 67) | Equine Ig6 Fc (SEQ ID NO: 68) |
| Ala (15) Thr Phe (203) Tyr | Val (199) Leu Glu (200) Tyr | Ile (199) Leu Arg (200) His His (201) Asn Thr (202) His |

*The amino acid positions listed are relative to the SEQ ID NO. indicated

For example, variant equine IgG2 Fc, IgG5 Fc, and IgG6 Fc polypeptides were designed with one or multiple amino acid substitutions in the Protein A binding region to correspond with the sequence of wild-type equine IgG Fc, which does bind Protein A. Variant equine IgG2 Fc F(203)Y (SEQ ID NO: 71); variant equine IgG2 Fc A(15)T/F(203)Y (SEQ ID NO: 72); variant equine IgG5 Fc V(199)L/E(200)Y (SEQ ID NO: 75); and variant equine IgG6 Fc I(199)L/R(200)H/H(201)N/T(202)H (SEQ ID NO: 76) with increased Protein A binding may be prepared.

To potentially reduce the binding of C1q to equine IgG1 Fc, IgG3 Fc, IgG4 Fc, and IgG7 Fc, and/or potentially reduce complement-mediated immune responses, variant canine IgG1 Fc, IgG3 Fc, IgG4 Fc, and IgG7 Fc polypeptides may be prepared having an amino acid substitution of Lys with any amino acid except Lys at an amino acid position corresponding to position 87 of SEQ ID NO: 63, of SEQ ID NO: 65, of SEQ ID NO: 66, of SEQ ID NO: 69, respectively. These amino acid substitutions were identified after analysis of the protein sequence and 3-D structure modeling of equine IgG1 Fc, IgG3 Fc, IgG4 Fc, and IgG7 Fc compared to equine IgG2 Fc, IgG5 Fc, and IgG6 Fc, which are understood to not exhibit complement activity. For example, variant equine IgG1 Fc K(87)S (SEQ ID NO: 70), variant equine IgG 3 Fc K(87)S (SEQ ID NO: 73), variant equine IgG4 Fc K(87)S (SEQ ID NO: 74), and variant equine IgG7 Fc K(87)S (SEQ ID NO: 77) may be prepared.

The binding of any variant equine IgG Fc to Protein A and/or C1q may be determined and compared to the binding of another IgG Fc to Protein A and/or C1q (e.g., the corresponding wild-type equine IgG Fc, another wild-type or variant equine IgG Fc, or a wild-type or variant IgG Fc of another companion animal, etc.). The binding assay described in Example 1 may be used.

Example 3

Variant Feline IgG Fc Polypeptides for Decreased Complement Binding

Each of the three subtypes of feline IgG, IgG1a Fc (SEQ ID NO: 80 or SEQ ID NO: 117), IgG1b Fc (SEQ ID NO: 81 or SEQ ID NO: 118), and IgG2 Fc (SEQ ID NO: 16) have Protein A binding affinity. However, only feline IgG2 Fc has weak or no measurable binding affinity to C1q, while feline IgG1a Fc, IgG1b Fc bind to C1q. To potentially reduce the C1q binding and/or potentially reduce complement-mediated immune responses, variant feline IgG1a Fc and IgG1b Fc polypeptides were designed.

Table 8, below summarizes the Protein A and C1q binding characteristics of feline IgG Fc subtypes. Notably, none of the wild-type equine IgG Fc subtypes lacks C1q binding and binds Protein A.

TABLE 8

| Wild-type Feline IgG Fc | Protein A Binding | C1q Binding |
|---|---|---|
| IgG1a Fc | + | + |
| IgG1b Fc | + | + |
| IgG2 Fc | + | − |

(−) denotes low or no measurable binding activity.

To potentially reduce the binding of C1q to feline IgG1a Fc and IgG1b Fc, and/or potentially reduce complement-mediated immune responses, variant feline IgG1a Fc and IgG1b Fc polypeptides may be prepared having an amino acid substitution of Pro with any amino acid except Pro at an amino acid position corresponding to position 198 of SEQ ID NO: 80 or of SEQ ID NO: 81, respectively. These amino acid substitutions were identified after analysis of the protein sequence and 3-D structure modeling of feline IgG1a Fc and IgG1b Fc compared to feline IgG2 Fc, which is understood to not exhibit complement activity. For example, variant feline IgG1a Fc P(198)A (SEQ ID NO: 82) and variant feline IgG1b Fc P(198)A (SEQ ID NO: 83) may be prepared.

The binding of any variant feline IgG Fc to C1q may be determined and compared to the binding of another IgG Fc to C1q (e.g., the corresponding wild-type feline IgG Fc, another wild-type or variant feline IgG Fc, or a wild-type or variant IgG Fc of another companion animal, etc.). The binding assay described in Example 1 may be used.

Example 4

Variant Canine and Feline IgG Fc Polypeptides for Heterodimeric Proteins

To enable the preparation of a bispecific canine or feline antibody or a bifunctional canine or feline Fc fusion protein using a knob-in-hole heterodimerization approach, pairing of variant canine IgG Fc polypeptides and variant feline IgG Fc polypeptides was investigated.

An amino acid substitution of threonine at a position corresponding to position 138 of canine IgG-A (SEQ ID NO: 1), at a position corresponding to position 137 of canine IgG-B Fc (SEQ ID NO: 2), at a position corresponding to position 137 of canine IgG-C Fc (SEQ ID NO: 3), or at a position corresponding to position 138 of canine IgG-D Fc (SEQ ID NO: 4) to tyrosine (T138Y or T137Y) can be introduced to one Fc chain (heterodimer chain 1). Examples of amino acid sequences of variant canine IgG-A Fc, IgG-B Fc, IgG-C Fc, and IgG-D Fc heterodimer chain 1 are SEQ ID NO: 8, SEQ ID NO: 10, SEQ ID NO: 12, and SEQ ID NO: 14, respectively.

An amino acid substitution of tyrosine at a position corresponding to position 181 of canine IgG-A (SEQ ID NO: 1), at a position corresponding to position 180 of canine IgG-B Fc (SEQ ID NO: 2), at a position corresponding to position 180 of canine IgG-C Fc (SEQ ID NO: 3), or at a position corresponding to position 181 of canine IgG-D Fc (SEQ ID NO: 4) to threonine (Y181T or Y180T) can be introduced to a second Fc chain (heterodimer chain 2). Examples of amino acid sequences of variant canine IgG-A Fc, IgG-B Fc, IgG-C Fc, and IgG-D Fc heterodimer chain 2 are SEQ ID NO: 9, SEQ ID NO: 11, SEQ ID NO: 13, and SEQ ID NO: 15, respectively.

A second pairing of variant canine IgG Fc heterodimer chains 3 and 4 was also investigated. An amino acid substitution of threonine to tryptophan at a position corresponding to position 138 of canine IgG-A (SEQ ID NO: 1) or of canine IgG-D (SEQ ID NO: 4) (T138W), or at a position corresponding to position 137 of canine IgG-B Fc (SEQ ID NO: 2) or of canine IgG-C Fc (SEQ ID NO: 3) (T137W) can be introduced to one Fc chain (heterodimer chain 3). Examples of amino acid sequences of variant canine IgG-A Fc, IgG-B Fc, IgG-C Fc, and IgG-D Fc heterodimer chain 3 are SEQ ID NO: 109, SEQ ID NO: 111, SEQ ID NO: 113, and SEQ ID NO: 115.

An amino acid substitution of threonine to serine at a position corresponding to position 138, of leucine to alanine at a position corresponding to position 140, and of tyrosine to threonine at a position corresponding to position 181 of canine IgG-A (SEQ ID NO: 1) or of IgG-D (SEQ ID NO: 4) (T138S, L140A, Y181T), or of threonine to serine at a position corresponding to position 137, of leucine to alanine at a position corresponding to position 139, and of tyrosine to threonine at a position corresponding to position 180 of canine IgG-B Fc (SEQ ID NO: 2) or of IgG-C(SEQ ID NO: 3) (T137S, L139A, Y180T) can be introduced to a second Fc chain (heterodimer chain 4). Examples of amino acid sequences of variant canine IgG-A Fc, IgG-B Fc, IgG-C Fc, and IgG-D Fc heterodimer chain 4 are SEQ ID NO: 110, SEQ ID NO: 112, SEQ ID NO: 114, and SEQ ID NO: 116.

An amino acid substitution of threonine to tryptophan at a position corresponding to position 154 of feline IgG2 (SEQ ID NO: 16), of feline IgG1a Fc (SEQ ID NO: 80 or SEQ ID NO: 117), or of feline IgG1b Fc (SEQ ID NO: 81 or SEQ ID NO: 118) (T154W) can be introduced to one Fc chain (heterodimer chain 1). Examples of amino acid sequences of variant feline IgG2 Fc, IgG1a Fc, and IgG1b Fc heterodimer chain 1 are SEQ ID NO: 119, SEQ ID NO: 121, and SEQ ID NO: 123, respectively.

An amino acid substitution of threonine to serine at a position corresponding to position 154, of leucine to alanine at a position corresponding to position 156, and of tyrosine to threonine at a position corresponding to position 197 of feline IgG2 Fc (SEQ ID NO: 16), of IgG-1a (SEQ ID NO: 80 or SEQ ID NO: 117), or of IgG-1b Fc (SEQ ID NO: 81 or SEQ ID NO: 118) (T154S, L156A, Y197T) can be introduced to a second Fc chain (heterodimer chain 4). Examples of amino acid sequences of variant feline IgG2 Fc, IgG1a Fc, and IgG1b Fc heterodimer chain 4 are SEQ ID NO: 120, SEQ ID NO: 122, and SEQ ID NO: 124.

The pairing of variant canine IgG Fc heterodimer chains 1 and 2, the pairing of variant canine IgG Fc heterodimer chains 3 and 4, or the pairing of variant feline IgG Fc heterodimer chains 1 and 2 may allow for Fc heterodimerization and prevent or reduce Fc homodimerization. A heterodimer chain 1 of one canine IgG subtype may be combined with a heterodimer chain 2 of the same or a different canine IgG subtype. A heterodimer chain 3 of one canine IgG subtype may be combined with a heterodimer chain 4 of the same or a different canine IgG subtype. A heterodimer chain 1 of one feline IgG subtype may be combined with a heterodimer chain 2 of the same or a different feline IgG subtype. The design can enable dimerization of bispecific canine or feline antibodies. In addition, two different peptides or proteins or a combination of different proteins can be fused to the heterodimeric Fc chains. For example, a dual GLP1 and glucagon molecule can be created using variant canine IgG Fc heterodimer chains or variant feline IgG Fc heterodimer chains, such as a GLP1 polypeptide (e.g., SEQ ID NO: SEQ ID NO: 85, SEQ ID NO: 86, SEQ ID NO: 87, SEQ ID NO: 88, SEQ ID NO: 89, SEQ ID NO: 90, or SEQ ID NO: 91) fused to a variant canine IgG-D Fc heterodimer chain 1 (e.g., SEQ ID NO: 14) and a glucagon polypeptide (e.g., SEQ ID NO: 92, SEQ ID NO: 93, SEQ ID NO: 94, or SEQ ID NO: 95) fused to a variant canine IgG-D Fc heterodimer chain 2 (e.g., SEQ ID NO: 15).

Example 5

GLP1 Fusion Proteins

The amino acid sequence of GLP1 is conserved among human, feline, canine, and equine, among other species. GLP1 proteolytic products (e.g., GLP1 (amino acids 7-37) (SEQ ID NO: 85) are rapidly degraded by dipeptidyl peptidase-4 (DPP-4) and are understood to have a short serum half-life of a couple minutes.

The design of contiguous polypeptides comprising at least one GLP1 polypeptide and feline, canine, or equine IgG Fc polypeptides was investigated to generate long-acting GLP1 fusion proteins. The following constructs were designed:

GLP1A-L1-Fc;      Formula (I):

Fc-L1-GLP1A; or      Formula (II):

GLP1A-L1-Fc-L2-GLP1B.      Formula (III):

wherein GLP1A is a first GLP1 polypeptide, GLP1B is a second GLP1 polypeptide, L1 and L2 are linkers; and Fc is an IgG Fc polypeptide of a companion animal species.

GLP1 was modified to be DPP-4 resistant by replacing alanine with either glycine or serine at a position corresponding to position 8 of wild-type GLP1 (7-37) (SEQ ID NO: 85). A minimal sequence of wild-type GLP1 (7-37) (SEQ ID NO:87) for binding to the N-terminal domain of mature feline GLP1R (SEQ ID NO: 49) was analyzed by three-dimensional protein modeling of the complex. Based on this modeling, the two C-terminal amino acids were removed from the DPP-4 resistant GLP1 to generate GLP1-S8 (7-35) (SEQ ID NO: 86) and GLP1-G8 (7-35) (SEQ ID NO: 87) polypeptides.

GLP1 polypeptides when positioned at the C-terminus of a construct, such as in formulas II and III, are not susceptible to DPP-4 degradation. Therefore, the alanine to glycine or serine substitution is not necessary for GLP1 polypeptides positioned at the C-terminus. Accordingly, wild-type GLP1 (7-37) (SEQ ID NO: 85) may be used at the C-terminus.

The linker may be a flexible, non-structural linker, such as a glycine- and serine-rich linker. A flexible extension may be added to the C-terminus of the contiguous polypeptide. The extension may comprise a glycine residue (SEQ ID NO: 88), two glycine residues (SEQ ID NO: 89), a three glycine residues (SEQ ID NO: 90), four glycine residues (SEQ ID NO: 91), five glycine residues (SEQ ID NO: 92), six glycine residues (SEQ ID NO: 93), seven glycine residues (SEQ ID NO: 94), eight glycine residues (SEQ ID NO: 95), or more glycine residues.

Example 6

GLP1 and Feline IgG Fc Fusion Proteins

Nucleotide sequences encoding (1) a contiguous polypeptide of Formula I having a signal sequence, GLP1-G8 (7-35) (SEQ ID NO: 87), a flexible linker, and wildtype feline IgG2 Fc (ssGLP1-G8_I_WTfeIgG2; SEQ ID NO: 96); and (2) a contiguous polypeptide of Formula III having a signal sequence, GLP1-G8 (7-35) (SEQ ID NO: 87), GLP1 (7-35) (SEQ ID NO: 89), two flexible linkers, a 2G C-terminal extension, and wildtype feline IgG2 Fc (ssGLP1-G8/GLP1-2G_III_WTfeIgG2; SEQ ID NO: 97) were synthesized and cloned into separate mammalian expression vectors. Wild-type feline IgG2 Fc (SEQ ID NO: 16) was chosen based on its low or no C1Q binding for reduced complement activity and Protein A binding for ease of purification.

The resulting vectors were separately transfected to CHO cells. The supernatant containing the contiguous polypeptides without the signal peptide (SEQ ID NOs: 24 and 23) was collected and filtered. Both proteins were affinity purified using a Protein A column (CaptivA® Protein A Affinity Resin, Repligen). The proteins were determined to be monomeric as assessed by HPLC gel filtration. However, the SDS-PAGE analysis showed that a percentage of both continuous polypeptides migrated to the same position in the gel in the absence and presence of reducing agent (DTT) (FIG. 2A). This result suggests that the hinge of wild-type feline IgG2 Fc, which has only one pair of cysteine residues, may not be enough to form an effective disulfide linkage.

Three-dimensional protein modeling analysis of several ortholog hinge structures was used to determine the approximate locations for modifying the feline IgG2 hinge to increase disulfide formation. To increase disulfide formation at the feline IgG2 hinge, the hinge sequence may be modified by substituting an amino acid with cysteine. For example, a variant feline IgG2 Fc (SEQ ID NO: 17) having a modified hinge was prepared by substituting Gly with Cys at an amino acid position corresponding to position 14 of SEQ ID NO: 16. The corresponding contiguous polypeptides ssGLP1-G8_I_VARfeIgG2 (SEQ ID NO: 39) and ssGLP1-G8/GLP1-2G_III_WTfeIgG2 (SEQ ID NO: 38) comprising variant feline IgG Fc of SEQ ID NO: 17 were designed, expressed in CHO cells, and purified by Protein A chromatography. The amino acid sequences of the secreted proteins after cleavage of the signal sequence are SEQ ID NOs 26 and 25, respectively. The SDS-PAGE analysis of the variant feline IgG2 constructs showed a decrease in the amount of protein in the lower molecular weight band in absence of reducing agent compared to the wild-type feline IgG2 constructs (compare FIG. 2 B to FIG. 2A). These results suggest that the Fc covalent pairing was improved for both variant feline IgG2 constructs.

Furthermore, differential scanning fluorimetry was used to assess the stability of the contiguous polypeptides at various pH, as reflected by mean melting point temperature (n=3) (Table 9, below). The increased stability of the variant feline IgG2 hinge is most evident at pH 6. For example, the constructs having variant feline IgG2 (SEQ ID NOs: 25 and 26) exhibited a higher Tm at pH 6 (56.9 and 59.7° C.) than the corresponding constructs having wild-type feline IgG2 (SEQ ID NOs: 23 and 24), which had a Tm of 55.2 and 56.9° C., respectively.

TABLE 9

| Construct (10 µg) | Mean Melting Point Temperature (Tm ° C.) (n = 3) | | | | | |
|---|---|---|---|---|---|---|
| | pH 3 | pH 4 | pH 5 | pH 6 | pH 7 | pH 8 |
| GLP1-G8/ GLP1-2G_III_WTfeIgG2 (SEQ ID NO: 23) | NC | NC | NC | 55.2 | 55.7 | 54.2 |
| GLP1-G8_I_WTfeIgG2 (SEQ ID NO: 24) | NC | NC | 48.5 | 56.9 | 59.9 | 59 |
| GLP1-G8/ GLP1-2G_III_WTfeIgG2 (SEQ ID NO: 25) | NC | NC | NC | 56.9 | 55 | 52.5 |
| GLP1-G8_I_VARfeIgG2 (SEQ ID NO: 26) | NC | NC | 53.1 | 59.7 | 59.9 | 58.2 |

NC = no curve because no distinct transition point was observed.

Contiguous polypeptides of Formulas I, II, and III comprising GLP1-S8 (7-35) (SEQ ID NO: 86) instead of GLP1-G8 (7-35) (SEQ ID NO: 87) may be similarly designed and prepared. For example, ssGLP1-S8_I_WTfeIgG2 (SEQ ID NO: 40), GLP1-S8_I_WTfeIgG2 (SEQ ID NO: 28), ssGLP1-S8/GLP1-3G_III_WTfeIgG2 (SEQ ID NO: 37), and GLP1-S8/GLP1-3G_III_WTfeIgG2 (SEQ ID NO: 27) may be prepared. Similar constructs having variant instead of wild-type feline IgG Fc, such as GLP1-S8_I_VARfeIgG2, GLP1-S8_VARfeIgG2, GLP1-S8/GLP1-2G_III_VARfeIgG2, and GLP1-S8/GLP1-3G_III_VARfeIgG2, may also be prepared.

While feline IgG2 Fc was used in this example, contiguous polypeptides of Formulas I, II, and III comprising feline IgG1a Fc or IgG1b Fc instead of IgG2 may be designed and prepared. For example, similar contiguous polypeptides having wild-type feline IgG1a Fc, wild-type feline IgG1b Fc, variant feline IgG1a Fc, or variant feline IgG1b Fc (SEQ ID NOs: 80 to 83, respectively), may be designed and prepared.

Example 7

GLP1 and Canine IgG Fc Fusion Proteins

Various Formula I, II, and III contiguous polypeptides comprising a variant GLP1 and a canine IgG Fc may be designed and prepared. For example, a variant canine IgGD Fc (e.g., SEQ ID NO: 7 or SEQ ID NO: 62) may be chosen based on its low or no C1q binding for reduced complement activity and Protein A binding for ease of purification. In addition, a flexible, non-structural linker, such as a glycine- and/or serine-rich linker, may be used.

GLP1-G8_I_VARcaIgGD (SEQ ID NO: 30) and GLP1-S8_I_VARcaIgGD (SEQ ID NO: 32) are examples of Formula I contiguous polypeptides comprising (1) either GLP1-G8 (7-35) or GLP1-S8 (7-35), (2) a flexible linker, and (3) a variant canine IgGD Fc (e.g., SEQ ID NO: 7). GLP1-G8/ GLP1-3G_III_VARcaIgGD (SEQ ID NO: 29) and GLP1-S8/GLP1-3G_III_VARcaIgGD (SEQ ID NO: 31) are examples of Formula III contiguous polypeptides comprising (1) either GLP1-G8 (SEQ ID NO: 87) or GLP1-S8 (SEQ ID NO: 86), (2) GLP1 (7-35) (SEQ ID NO: 61), (3) two flexible linkers, (4) a 3G C-terminal extension, and (5) a variant canine IgGD Fc.

The contiguous polypeptides may be designed with a signal sequence, a different GLP1 polypeptide (e.g., SEQ ID NO: 85, 86, 87, 98, or 99), or different modifications to the canine IgG Fc. Examples with such variations include ssGLP1-S8/GLP1-2G_III_VARcaIgGD (SEQ ID NO: 41), ssGLP1-G8/GLP1-2G_III_VARcaIgGD (SEQ ID NO: 42), ssGLP1-S8/GLP1-3G_III_VARcaIgGD (SEQ ID NO: 43), GLP1-S8/GLP1-2G_III_VARcaIgGD (SEQ ID NO: 105), and GLP1-G8/GLP1-2G_III_VARcaIgGD (SEQ ID NO: 106).

Furthermore, contiguous polypeptides of Formulas I, II, and III may comprise a wild-type canine IgGD, or a wild-type or variant canine IgGA, IgGB, or IgGC, instead of a variant canine IgGD. For example, similar contiguous polypeptides may be designed and prepared having a wild-type canine IgGA Fc, IgGB Fc, IgGC Fc, or IgGD Fc (e.g., SEQ ID NO: 1, 2, 3, or 4, respectively). Additional examples include contiguous polypeptides comprising a variant canine IgGA Fc (e.g., SEQ ID NO: 5 or 60), a variant canine IgGB Fc (e.g., SEQ ID NO: 78), or a variant canine IgGC Fc (e.g., SEQ ID NO: 6, 61, 79, or 84).

GLP1-G8/GLP1-3G_III_VARcaIgGD (SEQ ID NO: 29) and GLP1-G8_I_VARcaIgGD (SEQ ID NO: 30) were expressed separately in CHO cells and the supernatants containing the proteins collected and filtered. Both contiguous polypeptides were affinity purified by Protein A chromatography. The SDS-PAGE profiles of the two contiguous polypeptides in the absence and presence of reducing agent (DTT) were compared and the results suggested that the Fc disulfide bond was effectively formed for both polypeptides (data not shown).

Example 8

GLP1 and Equine IgG Fc Fusion Proteins

Various Formula I, II, and III contiguous polypeptides comprising a variant GLP1 and an equine IgG Fc may be designed and prepared. For example, a variant canine IgG2 Fc (e.g., SEQ ID NO: 19, 71, or 72) may be chosen based on its low or no C1q binding for reduced complement activity and Protein A binding for ease of purification. In addition, a flexible, non-structural linker, such as a glycine- and/or serine-rich linker, may be used.

GLP1-G8_I_VAReqIgG2 (SEQ ID NO: 34) and GLP1-S8_I_VAReqIgG2 (SEQ ID NO: 36) are examples of Formula I contiguous polypeptides comprising (1) either GLP1-G8 or GLP1-S8, (2) a flexible linker, and (3) a variant equine IgG2 Fc (e.g., SEQ ID NO: 19). GLP1-G8/GLP1-3G_III_

VAReqIgG2 (SEQ ID NO: 33) and GLP1-S8/GLP1-3G_III_VAReqIgG2 (SEQ ID NO: 35) are examples of Formula III contiguous polypeptides comprising (1) either GLP1-G8 (7-35) (SEQ ID NO: 87) or GLP1-S8 (7-35) (SEQ ID NO: 86), (2) GLP1 (7-35) (SEQ ID NO: 61), (3) two flexible linkers, (4) a 3G C-terminal extension, and (5) a variant equine IgGD Fc.

The contiguous polypeptides may be designed with a signal sequence, a different GLP1 analog (e.g., SEQ ID NO: 86, 87, 98, or 99), a glycine extension (e.g., SEQ ID NO: 88 to 95) or additional modifications to the equine IgG Fc. Examples with such variations include ssGLP1-G8/GLP1-3G_III_VAReqIgG2 (SEQ ID NO: 44), ssGLP1-G8_I_VAReqIgG2 (SEQ ID NO: 45), ssGLP1-S8/GLP1-3G_III_VAReqIgG2 (SEQ ID NO: 46), and ssGLP1-S8_I_VAReqIgG2 (SEQ ID NO: 47).

Furthermore, contiguous polypeptides of Formulas I, II, and III may comprise a wild-type equine IgG2, or a wild-type or variant equine IgG1, IgG3, IgG4, IgG5, IgG6, IgG7, instead of a variant equine IgG2. For example, similar contiguous polypeptides may be designed and prepared having a wild-type equine IgG1 Fc (e.g., SEQ ID NO: 63), IgG2 Fc (e.g., SEQ ID NO: 18 or 64), IgG3 Fc (e.g., SEQ ID NO: 65), IgG4 Fc (e.g., SEQ ID NO: 66), IgG5 Fc (e.g., SEQ ID NO: 67), IgG6 Fc (e.g., SEQ ID NO: 68), or IgG7 Fc (e.g., SEQ ID NO: 69). Additional examples include contiguous polypeptides comprising a variant equine IgG1Fc (e.g., SEQ ID NO: 70), a variant equine IgG3 Fc (e.g., SEQ ID NO: 73), a variant equine IgG4 Fc (e.g., SEQ ID NO: 74), a variant equine IgG5 Fc (e.g., SEQ ID NO: 75), a variant equine IgG6 Fc (e.g., SEQ ID NO: 76), or a variant equine IgG7 Gc (e.g., SEQ ID NO: 77).

The nucleotide sequences encoding ssGLP1-G8/GLP1-3G_III_VAReqIgG2 (SEQ ID NO: 44) and ssGLP1-G8_I_VAReqIgG2 (SEQ ID NO: 45) were synthesized and cloned into separate mammalian expression vectors. The resulting vectors were separately transfected to CHO cells. The supernatant containing the contiguous polypeptides following cleavage of the signal peptide (SEQ ID NOs: 103 and 104) was collected and filtered. Both proteins were affinity purified using a Protein A column (CaptivA® Protein A Affinity Resin, Repligen). were expressed separately in CHO cells and the supernatants containing the proteins collected and filtered. Both contiguous polypeptides were affinity purified by Protein A chromatography. The SDS-PAGE profiles of the two contiguous polypeptides in the absence and presence of reducing agent (DTT) were compared and the results suggested that the Fc disulfide bond was effectively formed for both polypeptides (data not shown).

Example 9

Expression and Purification of Feline GLP1R N-Terminal Soluble Domain

The N-terminal domain of mature feline GLP1R (SEQ ID NO: 49) responsible for binding GLP1 to GLP1R was identified from the full-length feline GLP1R amino acid sequence (SEQ ID NO: 48). Nucleotide sequences encoding (1) a signal sequence, feline N-terminal GLP1R, human Fc, and a poly-His tag (ssFeGLP1R-N-huFc_PolyHis; SEQ ID NO: 50) and (2) a signal sequence, feline N-terminal GLP1R, and a poly-His tag (ssFeGLP1R-N_polyHis; SEQ ID NO: 51) were synthesized and cloned into separate mammalian expression vectors. The resulting vectors were separately transfected to CHO cells. The supernatant containing the polypeptides was collected and filtered. The proteins were affinity purified using a Ni-Sepharose column or Protein A column (CaptivA® Protein A Affinity Resin, Repligen) for the huFc construct. Both proteins were used for GLP1 functional binding and ELISAs.

Example 10

GLP1 Fusion Protein Binding Kinetics

The binding affinity of GLP1-G8_I_VARfeIgG2 (SEQ ID NO: 26) to FeGLP1R-N-huFc_PolyHis was assessed using biolayer interferometry (Octet). Briefly, FeGLP1R-N-huFc_PolyHis was biotinylated, the free unreacted biotin was removed, and the biotinylated protein was captured to streptavidin sensor tips. The association of different concentrations GLP1-G8_I_VARfeIgG2 was monitored for ninety seconds. Dissociation was monitored for 600 seconds. A buffer only blank curve was subtracted to correct for any drift. The data were fit to a 1:1 binding model using ForteBio™ data analysis software to determine the $k_{on}$, $k_{off}$, and the $K_d$. The buffer for dilutions and all binding steps was: 20 mM phosphate, 150 mM NaCl, pH 7.2. The $K_d$ between Feline GLP1RN-terminal domain and GLP1-G8_I_VARfeIgG2 was between $8.0 \times 10^{-9}$ and $16 \times 10^{-9}$ M.

Example 11

GLP1 Fusion Protein Bioactivity in a Cell-Based Assay

CHOK-1-GL1R cell line (Discoverx, cat #95-0062C2), a hamster ovarian cell line which overexpresses Gs-coupled human glucagon ligand peptide-1 receptors (GLP1R) on the cell surface, was used to measure GLP1 cellular activity with a cAMP Hunter Bioassay kit (Discoverx, Cat #95-0062Y2). Cells were plated in a 96-well plate and incubated at 37° C., 5% $CO_2$ for 24 hours. Cells were then treated with a control agonist—either GLP1 human (37 a.a.) (Prospec, Cat #HOR-236) or Extendin-4 (Discoverx, Cat #92-1115)—or a contiguous polypeptide comprising a variant GLP1 at a series of 3-fold dilutions followed by incubation at 37° C. for 30 min. The contiguous polypeptides tested were GLP1-G8/GLP1-2G_III_VARfeIgG2 (SEQ ID NO: 25) and GLP1-G8_I_VARfeIgG2 (SEQ ID NO: 26).

Upon GLP1 binding to the Gs-coupled GLP1R receptor, Gs stimulates adenylate cyclase to generate cAMP. At the end of incubation, cAMP Antibody Reagent and cAMP Working Detection Solution, which contains lysis buffer, β-galactosidase (β-gal) small fragment conjugated cAMPs, and substrates, were added to the cells. The cells were incubated in the dark for 1 hour at room temperature to allow the immunocompetition reaction to occur between endogenously generated cAMPs and β-gal small fragment conjugated cAMPs for cAMP antibody binding.

At the end of the 1 hour incubation, cAMP Solution A containing β-gal large fragments, which can complement with the free (non-antibody binding) β-gal small fragment-cAMPs to form functional enzymes, were added to the cell lysate. The lysate was incubated for 3 to 6 hours in the dark at room temperature to allow the β-gal to hydrolyze the substrate and generate luminescent signals.

The more unbound free β-gal small fragment-cAMPs that remain, the more functional β-gal enzymes form. Therefore, the amount of signal produced is directly proportional to the amount of cAMP in the cell lysate. At the end of incubation, luminescence was read on a Synergy HT microplate reader (Biotek, Winooski, VT). The EC50s were calculated with a software GraphPad Prism (GraphPad Software, Inc. La Jolla, USA).

Figure 3:
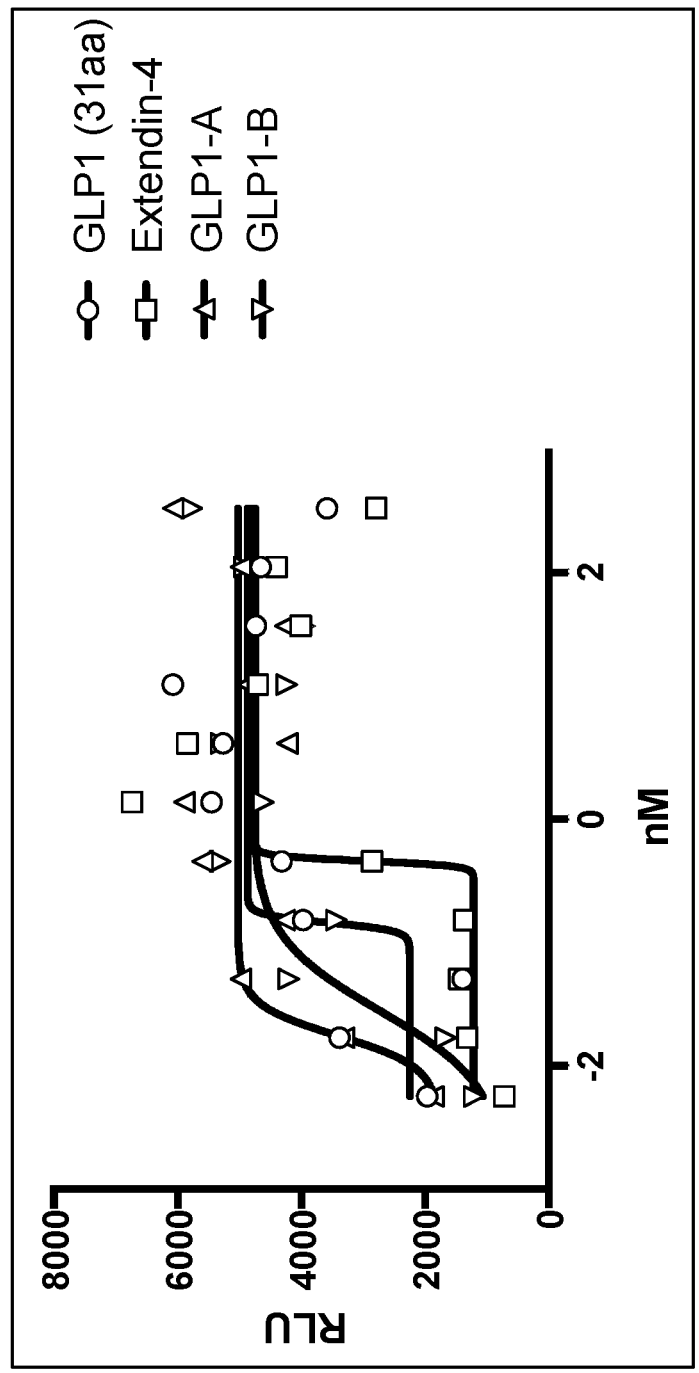
FIG. 3 shows a cAMP CHO-K1 GLP1R Bioassay to evaluate activity of GLP1-G8/GLP1-2G_III_VARfeIgG2 (SEQ ID NO: 25) and GLP1-G8_I_VARfeIgG2 (SEQ ID NO: 26) compared to controls (GLP1 (7-37) and Extendin-4).

FIG. 3 shows a plot of the relative light units (RLU) versus concentration for each sample tested. The EC50s are listed in Table 10, below. Both GLP1-G8/GLP1-2G_III_VARfeIgG2 (SEQ ID NO: 25) and GLP1-G8_I_VARfeIgG2 (SEQ ID NO: 26) are more active than GLP1 (7-37) and Extendin-4. GLP1-G8/GLP1-2G_III_VARfeIgG2 (SEQ ID NO: 25) is more potent than GLP1-G8_I_VARfeIgG2 (SEQ ID NO: 26), suggesting that the C-terminal GLP1 may contribute additional activity.

TABLE 10

| Sample | EC 50 (nM) |
| --- | --- |
| GLP1 (7-37) | 0.1449 |
| Extendin-4 | 0.4596 |
| GLP1-G8/GLP1-2G_III_VARfeIgG2 (SEQ ID NO: 25) | 0.01751 |
| GLP1-G8_I_VARfeIgG2 (SEQ ID NO: 26) | 0.02806 |

Example 12

GLP1 Fusion Protein Long-Term Stability

GLP1-G8_I_VARfeIgG2 (SEQ ID NO: 26) was stored in PBS, pH7.2 at a concentration of 1.3 mg/mL, placed in 1.5 mL Eppendorf tube, and stored at 2-8° C. for one year (Lot 2-29-2016). GLP1-G8_I_VARfeIgG2 (SEQ ID NO: 26) was also stored in PBS, pH7.2 at a concentration of 10 mg/mL, placed in 1.5 mL Eppendorf tube, and stored at 2-8° C. for one day (Lot 2-2-2017). To evaluate stability, the stored sample were analyzed by cell-based assay using the same CHOK-1-GL1R cell line (Discoverx, cat #95-0062C2) described in Example 11, but cellular activity was assessed using a cAMP-Glo™ Max Assay (Promega, Cat #PAV1682).

CHOK-1-GL1R cells were plated in a 96-well plate (Corning, Cat #3610) at a density of 20,000 cells per well in F-12K Medium (ATCC, Cat #ATCC® 30-2004) supplemented with 10% Fetal Bovine Serum, heat inactivated (Sigma, Cat #2868) and incubated at 37° C., 5% CO2 for 24 hours. Cells were then stimulated with a control agonist GLP1 human (37 a.a.) (Prospec, Cat #HOR-236), Lot 2-20-2016, or Lot 2-2-2017 at a series of 3-fold dilutions with serum-free medium followed by addition of Complete Induction Buffer which contains $MgCl_2$ to a final concentration 20 mM, isobutyl-1-methylxanthine (IBMX) (Sigma-Aldrich Cat. #17018) to a final concentration 500 μM and Ro 20-1724 [4-(3-butoxy-4-methoxy-benzyl) imidazolidone] (Sigma Aldrich, Cat. #B8279) to a final concentration 100 μL.

The cells were incubated at room temperature for 30 minutes. In this process, upon GLP1 binding to the Gs-coupled GLP1R receptor, Gs stimulates adenylate cyclase to generate cAMP. At the end of incubation, cAMP Detection Solution, which contains an inactive protein kinase A holoenzyme, protein kinase A substrate, and lysis buffer, was added to the cells. The plates placed on an orbital shaker for 1-2 minutes and then incubated at room temperature (23° C.) for 20 minutes. Cellular cAMP will activate protein kinase A by binding its regulatory-inhibitory subunits and releasing the catalytic subunits. The free catalytic subunits catalyze the transfer of the terminal phosphate of ATP to the protein kinase A substrate, consuming cellular ATP in the process. At the end of incubation, a luciferase-based Kinase-Glo® Reagent was added to the cell lysates and the plates were shaken on an orbital shaker for 2 min followed by incubation in the dark at room temperature for 10 min.

Mono-oxygenation of luciferin was catalyzed by luciferase in the presence of $Mg^{2+}$ and ATP that presented in the cell lysate, resulting in a luminescent signal proportional to the amount of ATP in the cells. At the end of 10 min incubation, the plate was read on a Synergy HT microplate reader (Biotek, Winooski, VT). Luminescence is proportional to ATP levels but inversely proportional to cAMP levels. Thus, as cAMP concentration increases, luminescence decreases.

Figure 4:
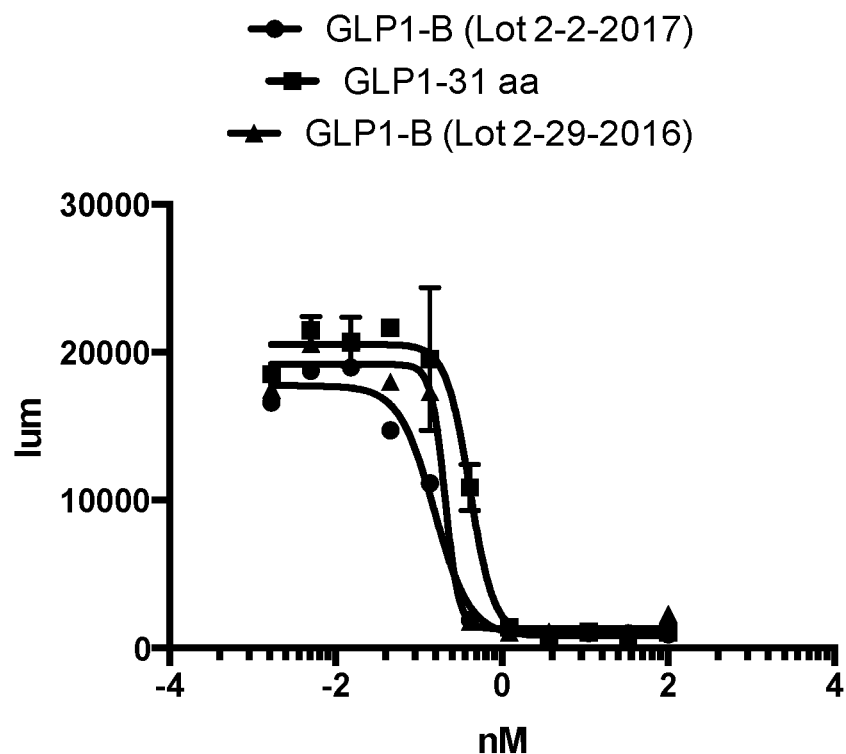
FIG. 4 shows a cell-based bioassay to evaluate activity of GLP1-G8_I_VARfeIgG2 (SEQ ID NO: 26) ("GLP1-B" in this figure) after 1 year of storage with CHOK1-GLP1R cells and cAMP-glo (n=2).

FIG. 4 shows the results of the cell-based assay as a plot of luminescence versus concentration for Lot 2-29-2016 compared to Lot 2-2-2017 and GLP1 (31 a.a.). The GLP1-G8_I_VARfeIgG2 sample maintained cellular activity after storage in PBS at 2-8° C. for one year.

Example 13

GLP1 Fusion Protein Serum Stability

Figure 5:
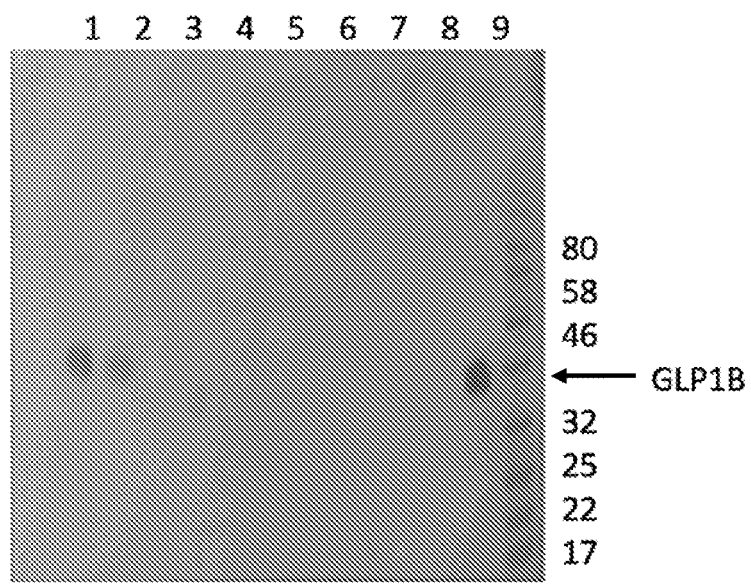
FIG. 5 shows a Western Blot analysis of GLP1-G8_I_VARfeIgG2 (SEQ ID NO: 26) ("GLP1B" in this figure) after incubation in serum for 24 hours at 37° C. (lane 1), in PBS for 24 hours at 37° C. (lane 2), in PBS for 24 hours at 4° C. (lane 9). A mouse anti-GLP1 antibody was used.

GLP1-G8_I_VARfeIgG2 (SEQ ID NO: 26) was stored in PBS, pH7.2 with feline serum at 37° C. for 24 hours to test in vitro serum stability. The cell-based assay was performed as described in Example 12 and results suggested that the activity was maintained (data not shown). In addition, no visible degradations were observed by Western blot analysis (FIG. 5).

Example 14

GLP1 Fusion Protein In Vivo Pharmacokinetics

Figure 6:
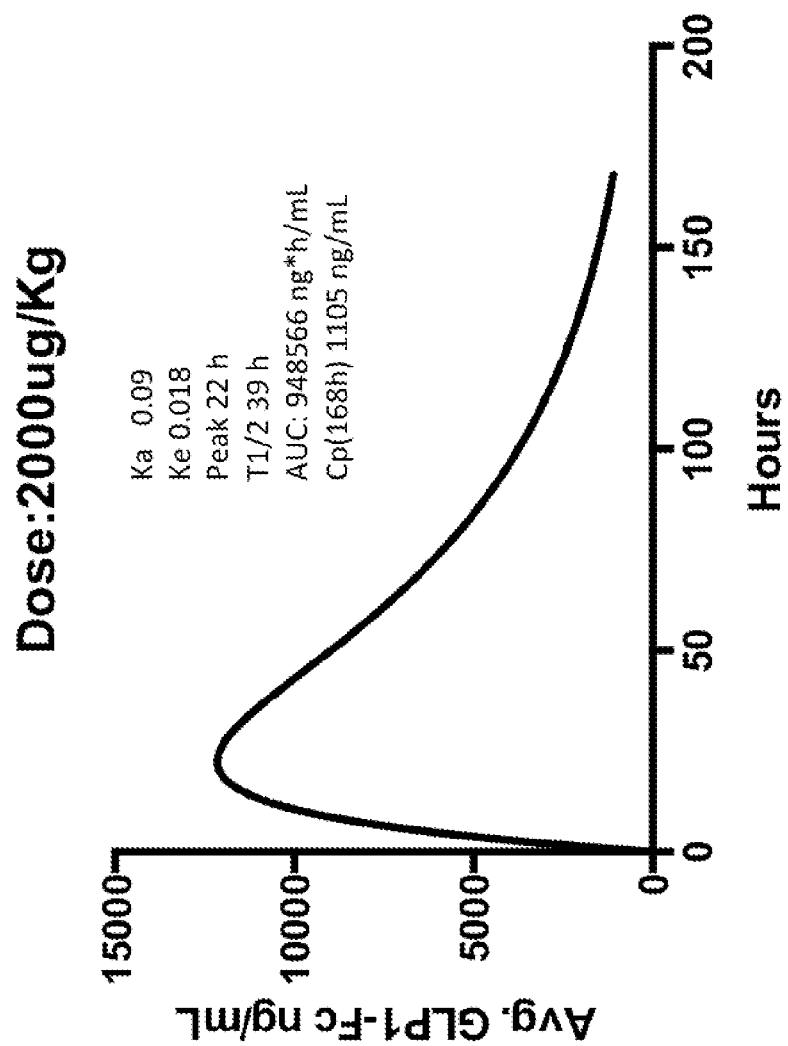
FIG. 6 is a plot of GLP1-G8_I_VARfeIgG2 (SEQ ID NO:26) concentration in the serum over time after subcutaneous administration to 5 cats, as measured by quantitative ELISA.

GLP1-G8_I_VARfeIgG2 (SEQ ID NO: 26) was administered as a single dose (2 mg/kg) by subcutaneous injection to 5 cats. Serum samples were taken before dosing (time 0) and at 4 hours, 8 hours, 12 hours, 24 hours, 48 hours, 72 hours, and 168 hours. The concentration of GLP1-G8_I_VARfeIgG2 in the serum samples was measured by quantitative ELISA. GLP1-G8_I_VARfeIgG2 polypeptide with a detection limit of 4 ng/mL was used as a reference. The serum concentration of GLP1-G8_I_VARfeIgG2 was plotted against time (FIG. 6). The mean serum half-life ($t_{1/2}$) of GLP1-G8_I_VARfeIgG2 was 39 hours. The average $T_{max}$ was 22 hours, the average $C_{max}$ was 12 μg/mL, and the mean area under the curve (AUC) was about 950 m(h)/mL.

The quantitative ELISA used an anti-GLP1 antibody (4F3, Novus Biologicals, Catalog No. NBP1-97413) and a goat anti-cat IgG-Fc, HRP conjugated antibody (Bethyl Laboratories, Inc., Catalog No. A20-117P) for quantification of GLP1-G8_I_VARfeIgG2 in feline serum samples from the in vivo pharmacokinetics study. A 96-well plate was coated with anti-GLP1 antibody (5 μg/mL in coating buffer, 100 μl/well). The plate was sealed and incubated overnight at 4° C. The plate was washed in triplicate with 1×TBST (10×TBST, Teknova, Catalog No. T9511) and blocking buffer was added. After removing the blocking buffer, serial dilutions of reference standard and samples in blocking buffer were added (100 μl/well) and the plate was incubated for 2 hours at room temperature. The plate was washed in triplicate with 1×TBST and goat anti-cat IgG Fc antibody was added (0.1 μg/mL in blocking buffer, 100 μl/well). After incubation for 1 hour at room temperature, the plate was washed 5 times with 1×TBST. TMB substrate (ScyTek, Catalog No. TM1999) was added (100 μl/well) and allowed to incubate at room temperature for 1 minute. The reaction was stopped by the addition of 2M $H_2SO_4$ (50 μl/well).

Absorbance at 450 nm was measured and the concentration of GLP1-G8_I_VARfeIgG2 in the serum samples calculated.

Figure 7:
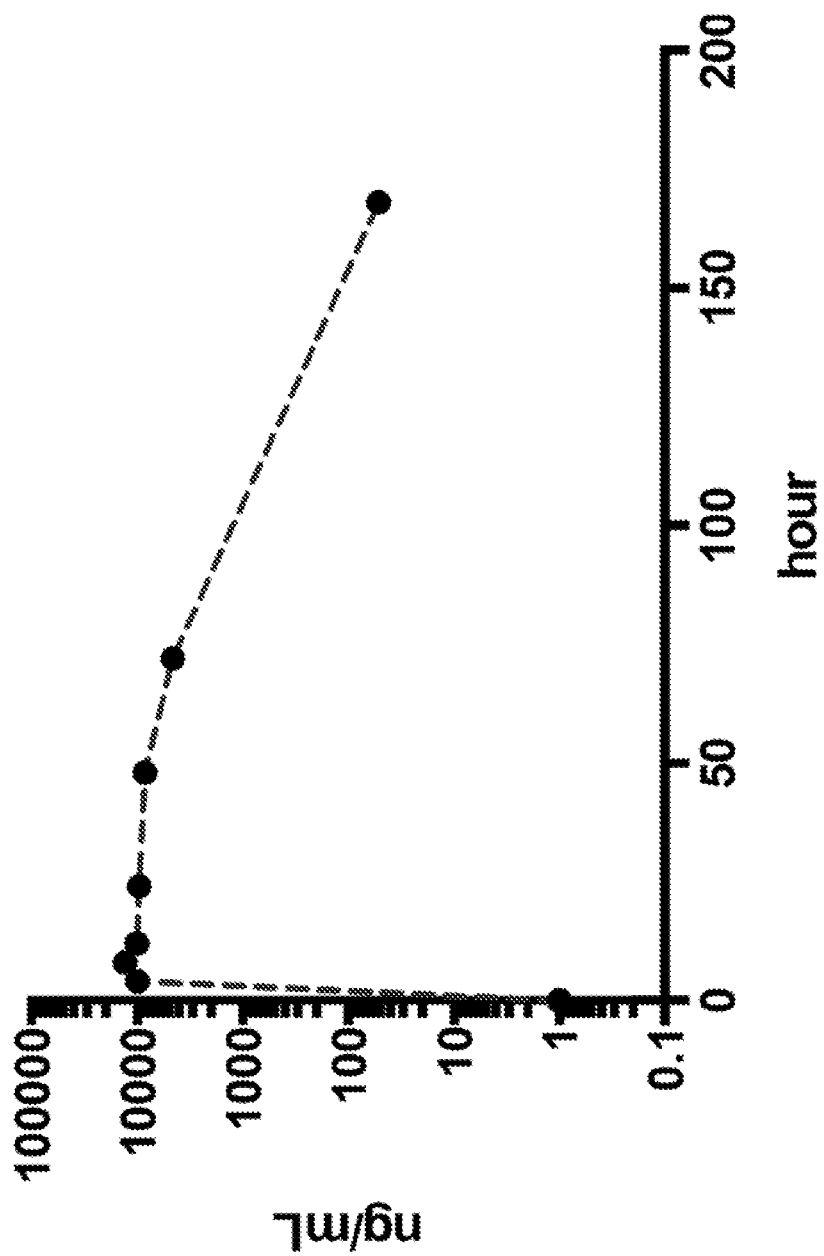
FIG. 7 shows a plot of GLP1-G8_I_VARfeIgG2 (SEQ ID NO:26) concentration in the serum over time after subcutaneous administration to 5 cats, as measured by cell-based activity assay. The mean AUC from 0 to 168 hours was about 840 μg(h)/mL and the mean $t_{1/2}$ was 36 hours.

Furthermore, GLP1-G8_I_VARfeIgG2 concentration in the same serum samples (no DPP-4 inhibitor added) was assessed using a cell-based activity assay. The same CHOK-1-GL1R cell line (Discoverx, cat #95-0062C2) and cAMP-Glo™ Max Assay (Promega, Cat #PAV1682) described in Example 12 was used. In this Example, however, the cells were stimulated with a control agonist GLP1 human (37 a.a.) (Prospec, Cat #HOR-236) or samples of cat serum taken before dosing (time 0) and at at 4 hours, 8 hours, 12 hours, 24 hours, 48 hours, 72 hours, and 168 hours diluted in serum-free medium (5%, 0.5%, and 0.05% dilutions). The concentration of GLP1-G8_I_VARfeIgG2 in each sample was calculated using SoftMax pro 7 (Molecular Devices, Sunnyvale, CA). The mean concentration of GLP1-G8_I_VARfeIgG2 for the 5 cats was plotted against time (FIG. 7). The mean AUC was about 840 μg(h)/mL and the mean $t_{1/2}$ was 36 hours. The concentrations calculated from the cell-based activity assay are consistent with the concentrations obtained from the ELISA, which suggests that the variant GLP1 detected by ELISA is biologically active.

Example 15

GLP1, Glucagon, and IgG Fc Fusion Proteins

To investigate a long acting GLP1 receptor and Glucagon receptor dual agonist, contiguous polypeptides comprising a GLP1 polypeptide, a glucagon polypeptide, and an IgG Fc polypeptide having the following constructs were designed:

GLP1-L1-Fc-L2-Gluc; and                 Formula (IV):

Gluc-L1-Fc-L2-GLP1,                 Formula (V):

wherein GLP1 is a GLP1 polypeptide, Gluc is a glucagon polypeptide, L1 and L2 are linkers, and Fc is an Fc polypeptide.

As discussed above, GLP1 was modified to be DPP-4 resistant by replacing alanine with either glycine or serine at a position corresponding to position 8 of wild-type GLP1 (7-37) (SEQ ID NO: 85). In addition, the DPP-4 resistant GLP1 was further modified by removing the two C-terminal amino acids to generate variant GLP1-S8 (7-35) (SEQ ID NO: 86) and variant GLP1-G8 (7-35) (SEQ ID NO: 87) polypeptides.

GLP1 polypeptides when positioned at the C-terminus of a construct, such as in Formula (V), are not susceptible to DPP-4 degradation. Therefore, the alanine to glycine or serine substitution is not necessary for GLP1 polypeptides positioned at the C-terminus. Accordingly, wild-type GLP1 (7-37) (SEQ ID NO: 85) may be used at the C-terminus.

The linker may be a flexible, non-structural linker, such as a glycine- and serine-rich linker. A flexible extension may be added to the C-terminus of the contiguous polypeptide. The extension may comprise a glycine residue (SEQ ID NO: 88), two glycine residues (SEQ ID NO: 89), a three glycine residues (SEQ ID NO: 90), four glycine residues (SEQ ID NO: 91), five glycine residues (SEQ ID NO: 92), six glycine residues (SEQ ID NO: 93), seven glycine residues (SEQ ID NO: 94), eight glycine residues (SEQ ID NO: 95), or more glycine residues.

The contiguous polypeptide may comprise a wildtype glucagon polypeptide (e.g., SEQ ID NO: 21) or a variant glucagon polypeptide.

The contiguous polypeptide may comprise a human IgG Fc or an IgG Fc of a companion animal species, such as canine, feline, or equine. The subtype of IgG Fc used may be based on having low or no C1q binding activity and/or having Protein A binding capacity. For example, a wild-type or variant human, canine, equine, or feline IgG Fc having low or no C1q binding and/or having Protein A binding capacity may be used (e.g., SEQ ID NO: 1, 2, 3, 4, 5, 6, 7, 8, 9, 10, 11, 12, 13, 14, 15, 16, 17, 18, 19, 60, 61, 62, 63, 64, 65, 66, 67, 68, 69, 70, 71, 72, 73, 74, 75, 76, 77, 78, 79, 80, 81, 82, 83, or 84).

Exemplary contiguous polypeptides comprising a GLP1 polypeptide, a Glucagon polypeptide, and a feline IgG Fc polypeptide include GLP1-G8/Gluc-3G_IV_WTfeIgG2 (SEQ ID NO: 52) and Gluc/GLP1-2G_V_WTfeIgG2 (SEQ ID NO: 53).

Exemplary contiguous polypeptides comprising a GLP1 polypeptide, a Glucagon polypeptide, and a canine IgG Fc polypeptide include GLP1-G8/Gluc-4G_IV_VARcaIgGD (SEQ ID NO: 54) and Gluc/GLP1-3G_V_VARcaIgGD (SEQ ID NO: 55).

Exemplary contiguous polypeptides comprising a GLP1 polypeptide, a Glucagon polypeptide, and an equine IgG Fc polypeptide include GLP1-G8/Gluc-4G_IV_VAReqIgGD (SEQ ID NO: 56) and Gluc/GLP1-3G_V_VAReqIgG2 (SEQ ID NO: 57).

Exemplary contiguous polypeptides comprising a GLP1 polypeptide, a Glucagon polypeptide, and a human IgG Fc polypeptide include GLP1-G8/Gluc-4G_IV_huIgG4 (SEQ ID NO: 8) and Gluc/GLP1-3G_V_huIgG4 (SEQ ID NO: 59).

Example 16

Variant IgG Fc Polypeptides for Enhanced Hinge Disulfide Formation

Additional three-dimensional protein modeling analysis of several ortholog hinge structures was used to modify feline and equine IgG hinges to enhance disulfide formation. To enhance disulfide formation at the feline IgG hinge, the hinge sequence may be modified by substituting lysine with proline at a position corresponding to position 16 of feline IgG2 (SEQ ID NO: 16), of feline IgG1a (SEQ ID NO: 80 or SEQ ID NO: 117), or of feline IgG1b (SEQ ID NO: 81 or SEQ ID NO: 118) (e.g., K16P). Examples of amino acid sequences of variant feline IgG polypeptides having a modified hinge include SEQ ID NO: 125, SEQ ID NO: 126, and SEQ ID NO: 127.

To enhance disulfide formation at the equine IgG hinge, the hinge sequence may be modified by substitution cysteine with serine at a position corresponding to position 3 of an equine IgG (e.g., IgG2 Fc (SEQ ID NO: 129)) and/or substituting glutamine with proline at a position corresponding to position 20 of an equine IgG (e.g., IgG2 Fc (SEQ ID NO: 129) (e.g., C3S, Q20P). Examples of amino acid sequences of variant equine IgG polypeptides having a modified hinge include SEQ ID NO: 130, SEQ ID NO: 131, SEQ ID NO: 132, SEQ ID NO: 134, and SEQ ID NO: 135.

Example 17

Variant IgG Fc Polypeptides for Enhanced Recombinant Production and/or Enhanced Hinge Disulfide Formation Three-dimensional protein modeling was used to design feline and equine variant IgG Fc polypeptides comprising sequences from the hinge region from a different IgG isotype for enhanced recombinant production and improved hinge disulfide formation. Variant feline IgG2 Fc polypeptides may be prepared that comprise sequences from the hinge region of feline IgG1a or IgG1b (e.g., SEQ ID NO: 125). In addition, variant equine IgG2 Fc polypeptides may be prepared that comprise sequences from the hinge region of equine IgG1 (e.g., SEQ ID NO: 19).

Levels of recombinant production of variant IgG Fc polypeptides and/or levels of hinge disulfide formation may be determined and compared to that of another IgG Fc by SDS-PAGE analysis under reducing and non-reducing conditions (e.g., the corresponding wild-type IgG Fc of the same or different isotype, or a wild-type or variant IgG Fc of another companion animal, etc.).

The invention claimed is:
1. A variant IgG Fc polypeptide comprising:
   (a) the polypeptide of SEQ ID NO: 1 having an amino acid substitution consisting of a threonine at position 21 and optionally at least one amino acid substitution selected from the group consisting of: a leucine at position 23, an alanine at position 25, a glycine at position 80, an alanine at position 205, and a histidine at position 207, or
   (b) a polypeptide that is at least 97% identical to SEQ ID NO: 1, wherein the polypeptide has a threonine at the position corresponding to position 21 of SEQ ID NO: 1 and optionally at least one amino acid substitution selected from the group consisting of: a leucine at the position corresponding to position 23 of SEQ ID NO: 1, an alanine at the position corresponding to position 25 of SEQ ID NO: 1, a glycine at the position corresponding to position 80 of SEQ ID NO: 1, an alanine at the position corresponding to position 205 of SEQ ID NO: 1, and a histidine at the position corresponding to position 207 of SEQ ID NO: 1.

2. The polypeptide of claim 1, wherein the polypeptide is an antibody, an antibody fusion, or a fusion polypeptide.

3. An isolated nucleic acid encoding the variant IgG Fc polypeptide of claim 1.

4. A host cell comprising the nucleic acid of claim 3.

5. A method of producing a variant IgG Fc polypeptide comprising providing a host cell comprising a nucleic acid encoding the variant IgG Fc polypeptide of claim 1, culturing the host cell, and isolating the variant IgG Fc polypeptide produced.

6. A pharmaceutical composition comprising the polypeptide of claim 1 and a pharmaceutically acceptable carrier.

7. The pharmaceutical composition of claim 6, wherein the pharmaceutically acceptable carrier comprises one or more of alumina, aluminum stearate, lecithin, one or more serum protein, human serum albumin, canine or other animal albumin, one or more buffer, glycine, sorbic acid, potassium sorbate, one or more partial glyceride mixtures of saturated vegetable fatty acids, water, one or more salt, one or more electrolyte, protamine sulfate, disodium hydrogen phosphate, potassium hydrogen phosphate, sodium chloride, zinc salts, colloidal silica, magnesium trisilicate, polyvinyl pyrrolidone, one or more cellulose-based substances, polyethylene glycol, sucrose, mannitol, or one or more amino acids.

8. The pharmaceutical composition of claim 7, wherein (i) the one or more buffer comprises one or more of phosphate buffer, citrate buffer, tromethamine buffer, or HEPES buffer; (ii) the one or more amino acids comprises arginine; or both (i) and (ii).

9. A method of delivering a polypeptide to a subject comprising administering the variant IgG Fc polypeptide of claim 1 parenterally.

10. The polypeptide of claim 1, wherein the variant IgG Fc polypeptide binds to Protein A with a dissociation constant ($K_d$) of less than $5\times10^{-6}$ M, less than $1\times10^{-6}$ M, less than $5\times10^{-7}$ M, less than $1\times10^{-7}$ M, less than $5\times10^{-8}$ M, less than $1\times10^{-8}$ M, less than $5\times10^{-9}$ M, less than $1\times10^{-9}$ M, less than $5\times10^{-10}$ M, less than $1\times10^{-10}$ M, less than $5\times10^{-11}$ M, less than $1\times10^{-11}$ M, less than $5\times10^{-12}$ M, or less than $1\times10^{-12}$ M, as measured by biolayer interferometry.

11. A method of delivering a polypeptide to a subject comprising administering the variant IgG Fc polypeptide of claim 1 via by an intramuscular, an intraperitoneal, an intracerebrospinal, a subcutaneous, an intra-arterial, an intrasynovial, an intrathecal, or an inhalation route.

12. A method of delivering a polypeptide to a subject comprising administering the variant IgG Fc polypeptide of claim 1 via subcutaneous administration, intravenous infusion, or intramuscular injection.

13. The polypeptide of claim 1, wherein the polypeptide sequence comprises SEQ ID NO: 5 or SEQ ID NO: 60.

14. The polypeptide of claim 1, wherein the polypeptide has increased binding affinity to Protein A and/or reduced binding affinity to C1q and CD16 relative to SEQ ID NO: 1.

15. The polypeptide of claim 1, wherein the polypeptide of (a) further comprises an amino acid substitution consisting of a leucine at position 23.

16. The polypeptide of claim 1, wherein the polypeptide of (a) further comprises an amino acid substitution consisting of a glycine at position 80.

17. The polypeptide of claim 1, wherein the polypeptide of (a) further comprises an amino acid substitution consisting of an alanine at position 25.

18. The polypeptide of claim 1, wherein the polypeptide of (a) further comprises an amino acid substitution consisting of a histidine at position 207.

19. The polypeptide of claim 1, wherein the polypeptide of (a) has at least one amino acid substitution selected from the group consisting of: a leucine at position 23, an alanine at position 25, a glycine at position 80, an alanine at position 205, and a histidine at position 207.

20. The polypeptide of claim 1, wherein the polypeptide of (b) has at least one amino acid substitution selected from the group consisting of: a leucine at the position corresponding to position 23 of SEQ ID NO: 1, an alanine at the position corresponding to position 25 of SEQ ID NO: 1, a glycine at the position corresponding to position 80 of SEQ ID NO: 1, an alanine at the position corresponding to position 205 of SEQ ID NO: 1, and a histidine at the position corresponding to position 207 of SEQ ID NO: 1.

21. The polypeptide of claim 1, wherein the polypeptide of (a) further comprises an amino acid substitution consisting of an alanine at position 205.

22. A variant IgG Fc polypeptide comprising:
   (a) an amino acid sequence at least 97% identical to the amino acid sequence of SEQ ID NO: 3, wherein the polypeptide comprises a threonine at the position corresponding to position 21 of SEQ ID NO: 3 and optionally at least one amino acid substitution selected from the group consisting of a leucine at the position corresponding to position 23 of SEQ ID NO: 3 and an isoleucine at the position corresponding to position 24 of SEQ ID NO: 3; or
   (b) the polypeptide of SEQ ID NO: 3 having an amino acid substitution consisting of a threonine at position 21 of SEQ ID NO: 3 and optionally at least one amino acid substitution selected from the group consisting of a leucine at position 23 and an isoleucine at position 24.

23. The polypeptide of claim 22, wherein the polypeptide sequence comprises SEQ ID NO: 6, SEQ ID NO: 61, or SEQ ID NO: 84.

24. The polypeptide of claim 22, wherein the polypeptide has increased binding affinity to Protein A and/or reduced binding affinity to C1q and CD16 relative to SEQ ID NO: 3.

25. The polypeptide of claim 22, wherein the polypeptide of (a) has at least one amino acid substitution selected from the group consisting of a leucine at the position corresponding to position 23 of SEQ ID NO: 3 and an isoleucine at the position corresponding to position 24 of SEQ ID NO: 3.

26. The polypeptide of claim 22, wherein the polypeptide of (b) has at least one amino acid substitution selected from the group consisting of a leucine at position 23 and an isoleucine at position 24.

27. A variant IgG Fc polypeptide comprising:
   (a) an amino acid sequence at least 97% identical to the amino acid sequence of SEQ ID NO: 4, wherein the polypeptide comprises a threonine at the position corresponding to position 21 of SEQ ID NO: 4 and optionally at least one amino acid substitution selected from the group consisting of: a leucine at the position corresponding to position 23 of SEQ ID NO: 4, an alanine at the position corresponding to position 25 of SEQ ID NO: 4, a glycine at the position corresponding to position 80 of SEQ ID NO: 4, and a histidine at the position corresponding to position 207 of SEQ ID NO: 4; or
   (b) the polypeptide of SEQ ID NO: 4 having an amino acid substitution consisting of a threonine at position 21 of SEQ ID NO: 4 and optionally at least one amino acid substitution selected from the group consisting of: a leucine at position 23, an alanine at position 25, a glycine at position 80, and a histidine at position 207.

28. The polypeptide of claim 27, wherein the polypeptide sequence comprises SEQ ID NO: 7 or SEQ ID NO: 62.

29. The polypeptide of claim 27, wherein the polypeptide has increased binding affinity to Protein A and/or reduced binding affinity to C1q and CD16 relative to SEQ ID NO: 4.

30. The polypeptide of claim 27, wherein the polypeptide of (a) has at least one amino acid substitution selected from the group consisting of: a leucine at the position corresponding to position 23 of SEQ ID NO: 4, an alanine at the position corresponding to position 25 of SEQ ID NO: 4, a glycine at the position corresponding to position 80 of SEQ ID NO: 4, and a histidine at the position corresponding to position 207 of SEQ ID NO: 4.

31. The polypeptide of claim 27, wherein the polypeptide of (b) has at least one amino acid substitution selected from the group consisting of: a leucine at position 23, an alanine at position 25, a glycine at position 80, and a histidine at position 207.

* * * * *